US009458514B2

(12) United States Patent
Barry et al.

(10) Patent No.: US 9,458,514 B2

(45) Date of Patent: Oct. 4, 2016

(54) NUCLEIC ACIDS PROBES FOR DETECTION OF YEAST AND FUNGAL

(75) Inventors: Thomas Gerard Barry, Kinvara (IE); Terence James Smith, Galway (IE); Majella Maher, Moycullen (IE)

(73) Assignee: National University of Ireland, Galway, Galway (IE)

(*) Notice: Subject to any disclaimer, the term of this patent is extended or adjusted under 35 U.S.C. 154(b) by 1074 days.

(21) Appl. No.: 12/516,973

(22) PCT Filed: Dec. 14, 2007

(86) PCT No.: PCT/IE2007/000123

§ 371 (c)(1), (2), (4) Date: Nov. 18, 2009

(87) PCT Pub. No.: WO2008/072217

PCT Pub. Date: Jun. 19, 2008

(65) Prior Publication Data

US 2010/0143910 A1 Jun. 10, 2010

(30) Foreign Application Priority Data

Dec. 15, 2006 (IE) .................................... 2006/0925

(51) Int. Cl.

*C12Q 1/68* (2006.01)
*C12P 19/34* (2006.01)
*C07H 21/04* (2006.01)

(52) U.S. Cl.

CPC .................................. *C12Q 1/6895* (2013.01)

(58) Field of Classification Search

USPC ................................... 435/6.12, 91.2, 24.33
See application file for complete search history.

(56) References Cited

U.S. PATENT DOCUMENTS

| | | | | |
|---|---|---|---|---|
| 5,426,026 | A | 6/1995 | Jordan | |
| 5,658,726 | A | 8/1997 | Lemontt | |
| 5,958,693 | A | 9/1999 | Sandhu | |
| 6,017,366 | A | 1/2000 | Berman | |
| 6,017,699 | A | 1/2000 | Jordan | |
| 6,387,652 | B1 | 5/2002 | Haugland | |
| 6,747,137 | B1 | 6/2004 | Weinstock | |
| 7,504,490 | B1 * | 3/2009 | Weinstock et al. | 536/23.1 |
| 2002/0058293 | A1 * | 5/2002 | Takesako et al. | 435/7.31 |
| 2003/0148519 | A1 * | 8/2003 | Engelke et al. | 435/455 |
| 2004/0044193 | A1 | 3/2004 | Schroppel | |
| 2004/0229367 | A1 | 11/2004 | Berka | |
| 2005/0048509 | A1 | 3/2005 | Han | |

FOREIGN PATENT DOCUMENTS

| | | |
|---|---|---|
| EP | 0422869 | 4/1991 |
| EP | 0422872 | 4/1991 |
| WO | 0183824 | 11/2001 |
| WO | 2008072217 | 6/2008 |

OTHER PUBLICATIONS

Lowe et al. Nucleic acid research, 1990, vol. 18(7), p. 1757-1761.*
The nucleic acid sequences search reports for SEQ ID No: 415, 418-419, (AC AWP40937), searched Jan. 30, 2013.*
Rychlik et al., Nucleic acid research, 1989, vol. 17(21), p. 8543-8551.*
"Stakeholder Insight: Invasive fungal infections," Datamonitor. Jan. 2004.
"Stakeholder Opinions: Sepsis, Under reaction to an overraction," Datamonitor. Mar. 2006.
Atkins, et al., "Fungal Molecular Diagnostics; A Mini review," J. Appl. Genet. 2004, vol. 45, No. 1; pp. 3-15.
Delbruck, et al., "Characterization and Regulation of the Genes Encoding Ribosomal Proteins L39 and S7 of the Human Pathogen Candida albicans," Yeast. 1997, vol. 13, pp. 1199-1210.
Synetos, et al., "The Yeast Ribosomal Protein S7 and its Genes," Journal of Biological Chemistry. 1992, vol. 267, pp. 3008-3013.
Gurpreet, et al., "Molecular Probes for Diagnosis of Fungal Infections," Journal of Clinical Microbiology, Nov. 1995, vol. 33, No. 11; pp. 2913-2919.
International Search Report for international application No. PCT/IE07/000123 issued by the International Searching Authority mailed on Jan. 9, 2008.
International Preliminary Report on Patentability and Written Opinion for international application No. PCT/IE07/000123 issued by the International Searching Authority mailed on Jun. 16, 2009.

* cited by examiner

*Primary Examiner* — Kenneth R. Horlick
*Assistant Examiner* — Joyce Tung
(74) *Attorney, Agent, or Firm* — Leason Ellis LLP

(57) ABSTRACT

The present invention use of to a portion of the RPS7 gene or its corresponding mRNA in a diagnostic assay for fungal and yeast species and sequences for use in such assays and methods.

28 Claims, 4 Drawing Sheets

Figure 1A and B:
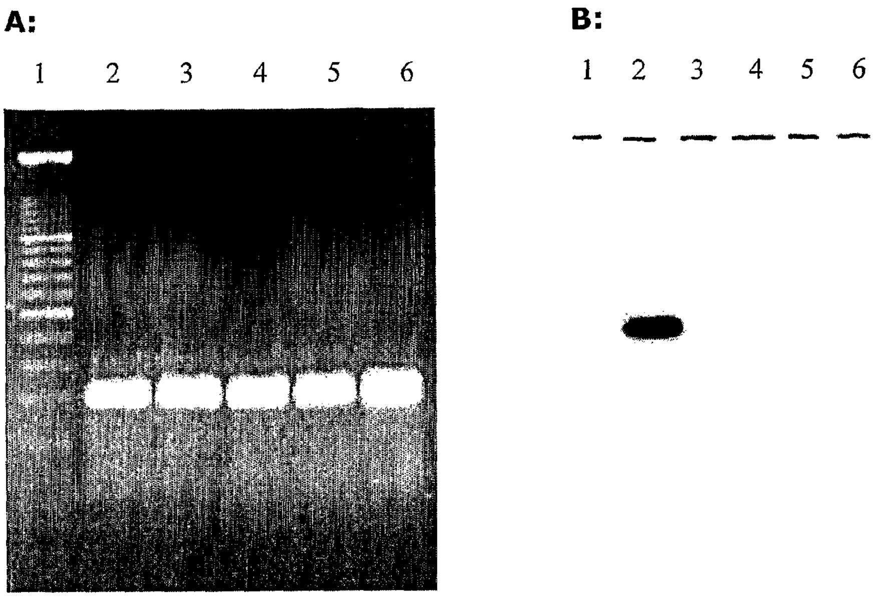
Figure 2:
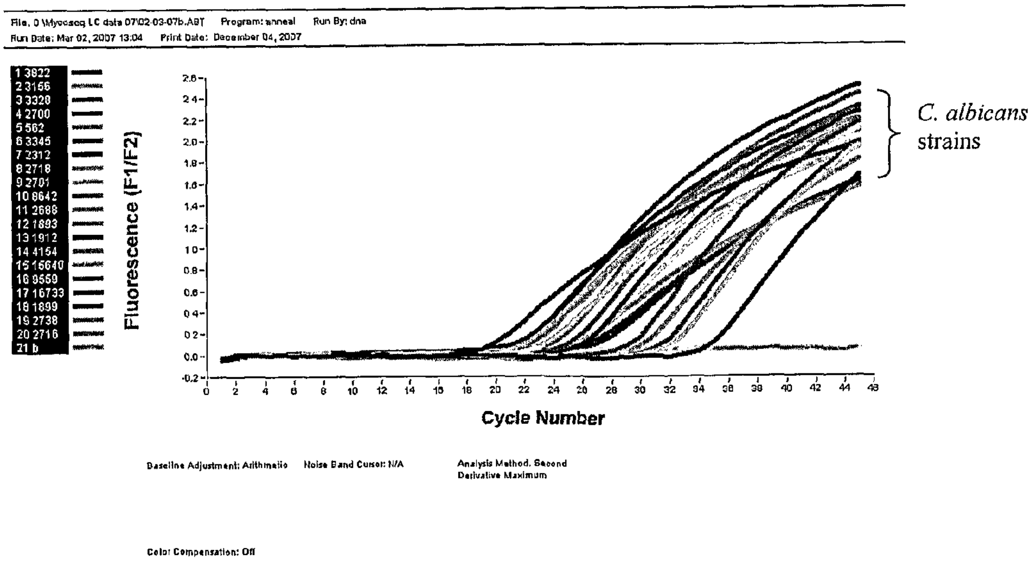

NUCLEIC ACIDS PROBES FOR DETECTION OF YEAST AND FUNGAL

FIELD OF THE INVENTION

The present invention relates to ribosomal protein genes, the corresponding mRNA, and specific probes, primers and oligonucleotides related thereto and their use in diagnostic assays to detect and/or discriminate yeast and fungal species. In particular, the present invention relates to the gene corresponding to the ribosomal protein RPS7 and its corresponding mRNA.

BACKGROUND TO THE INVENTION

Detection and identification of yeast and fungi as the cause of infections has never been more important. The numbers of immunocompromised patients at risk for yeast and fungal infection continues to increase, as does the spectrum of fungal agents causing disease. Mortality from fungal infections, particularly invasive fungal infections, is 30% or greater in certain at risk patient groups ("*Stakeholder Insight: Invasive fungal infections*", Datamonitor, January 2004). The array of available antifungal agents is growing; however, so too is the recognition of both intrinsic and emerging resistance to antifungal drugs. These factors are contributing to the increased need for cost containment in laboratory testing and has led to laboratory consolidation in testing procedures.

Invasive fungal infections are on the increase. In 2003, it was estimated that there were 9 million at risk patients of which 1.2 million developed infection. Immunocompromised patients including transplant and surgical patients, neonates, cancer patients, diabetics and those with HIV/AIDs are at high risk of developing invasive fungal infections (Datamonitor report: Stakeholder opinion—Invasive fungal infections, options outweigh replacements 2004). A large number of severe sepsis are reported each year. Despite improvements in its medical management, sepsis still constitutes one of the greatest challenges in intensive care medicine. Micro-organisms (bacteria, fungi and yeast) responsible for causing sepsis are traditionally detected in hospital laboratories with the aid of microbiological culture methods with poor sensitivity (25-82%), which are very time-consuming, generally taking from two to five days to complete, and up to eight days for the diagnosis of fungal infections Definitive diagnosis is usually based on either the recovery and identification of a specific agent from clinical specimens or microscopic demonstration of fungi with distinct morphological features.

However, there are numerous cases where these methods fail to provide conclusive proof as to the infecting agent. In these instances, the detection of specific host antibody responses can be used, although again this can be affected by the immune status of the patient. Time is critical in the detection and identification of bloodstream infections typically caused by bacteria and fungi. Effective treatment depends on finding the source of infection and making appropriate decisions about antibiotics or antifungals quickly and efficiently. Only after pathogens are correctly identified can targeted therapy using a specific antibiotic begin. Many physicians would like to see the development of better in vitro amplification and direct detection diagnostic techniques for the early diagnosis of yeast and fungi ("*Stakeholder Insight: Invasive fungal infections*", Datamonitor, January 2004). Recently Roche™ launched a real time PCR based assay (Septifast™), for the detection of bacterial, fungal and yeast DNA in clinical samples. Therefore there is a clear need for the development of novel rapid diagnostic tests for clinically significant bacterial and fungal pathogens for bioanalysis applications in the clinical sector. This has led us to the search and identify novel fungal and yeast nucleic acid targets for application in Nucleic Acid Diagnostisc (NAD) tests.

*Candida* spp. and *Aspergillus* spp. now rank as the most prominent pathogens infecting immunosupressed patients. In particular, infections are common in the urinary tract, the respiratory system and the bloodstream, at the site of insertion of stents, catheters and orthopaedic joints. Approximately, 10% of the known *Candida* spp. have been implicated in human infection. Invasive candidiasis occurs when candida enters the bloodstream and it is estimated to occur at a frequency of 8/100,000 population in the US with a mortality rate of 40%. *Candida albicans* is the $4^{th}$ most common cause of bloodstream infection. Aspergillosis usually begins as a pulmonary infection that can progress to a life-threatening invasive infection in some patients and has a mortality rate of greater than 90%. Emerging mycoses agents include *Fusarium, Scedosporium*, Zygomycetes and *Trichosporon* spp. ("*Stakeholder Insight: Invasive fungal infections*", Datamonitor, January 2004).

Fungal and yeast nucleic acid based diagnostics have focused heavily on the ribosomal RNA (rRNA) genes, RNA transcripts, and their associated DNA/RNA regions. The rRNA genes are highly conserved in all fungal species and they also contain divergent and distinctive intergenic transcribed spacer regions. Ribosomal rRNA comprises three genes: the large sub-unit gene (28S), the small sub-unit gene (18S) and the 5.8S gene. The 28S and 18S rRNA genes are separated by the 5.8S rRNA and two internal transcribed spacers (ITS1 and ITS2). Because the ITS region contains a high number of sequence polymorphisms, numerous researchers have concentrated their efforts on these as targets (Atkins and Clark, 2004). rRNA genes are also multicopy genes with >10 copies within the fungal genome.

A number of groups are working on developing new assays for fungal and yeast infections. US2004044193 relates to, amongst a number of other aspects, the transcription factor CaTEC1 of *Candida albicans*; inhibitors thereof, and methods for the diagnosis and therapy of diseases which are connected with a *Candida* infection; and also diagnostic and pharmaceutical compositions which contain the nucleotide sequences, proteins, host cells and/or antibodies. WO0183824 relates to hybridization assay probes and accessory oligonucleotides for detecting ribosomal nucleic acids from *Candida albicans* and/or *Candida dubiniensis*. U.S. Pat. Nos. 6,017,699 and 5,426,026 relate to a set of DNA primers which can be used to amplify and speciate DNA from five medically important *Candida* species. U.S. Pat. No. 6,747,137 discloses sequences useful for diagnosis of *Candida* infections. EP 0422872 and U.S. Pat. No. 5,658,726 disclose probes based on 18S rRNA genes, and U.S. Pat. No. 5,958,693 discloses probes based on 28S rRNA, for diagnosis of a range of yeast and fungal species. U.S. Pat. No. 6,017,366 describes sequences based on chitin synthase gene for use in nucleic acid based diagnostics for a range of *Candida* species.

It is clear though, that development of faster, more accurate diagnostic methods are required, particularly in light of the selection pressure caused by modern antimicrobial treatments which give rise to increased populations of resistant virulent strains with mutated genome sequences. Methods that enable early diagnosis of microbial causes of infection enable the selection of a specific narrow spectrum antibiotic or antifungal to treat the infection (Datamonitor report: Stakeholder opinion—Invasive fungal infections, options outweigh replacements 2004; Datamonitor report: Stakeholder Opinion-Sepsis, under reaction to an overreaction, 2006).

RPS7 is one of more than 70 ribosomal proteins. It is found in prokaryotes and eukaryotes and functions in the small ribosomal subunit in the folding of rRNA which forms the head of the small ribosomal subunit. The rps7 gene encodes an essential protein which has a conserved function within the ribosome. In yeasts, for example *Saccharomyces cerevisiae* RPS7 is encoded by two genes differing at 14 base pair positions with each gene having 1 intron. Synetos et al. (1992) showed that *Saccharomyces* could survive with one copy of the gene but that deletion of both was lethal. Delbrück et al. (1997) cloned and sequenced the rps7 gene in *C. albicans* (GenBank Accession number U37009), determining that rps7 in *C. albicans* lacked an intron and shared 83% homology at an amino acid level with the RPS7 protein in *S. cerevisiae*. This group also showed that the rps7 gene was up-regulated during hyphal formation with expression levels 3-6 fold higher than rRNA. This suggests that the gene is clinically relevant as morphogenesis from yeast form to hyphal formation is important in *Candida* spp. infections. In *Aspergillus* spp. in particular *A. fumigatus*, the rps7 gene contains 3 exons and 2 introns and therefore the structure of the gene is different from those found in yeasts.

It is therefore an object of the invention to provide sequences and/or diagnostic assays that may be used in detection and identification of one or more yeast or fungal species. The present inventors have exploited the structural organization of the rps7 gene to design *Candida* and *Aspergillus* gene-specific primers. This has an advantage over the prior art in that if one wants to identify a fungal pathogen in a sample which contains *Candida* as a commensal, the approach of using universal primers may not be successful. There is a strong possibility that the *Candida* will outcompete the fungal pathogen in the amplification process and will be preferentially amplified, resulting in failure to detect the disease-causing pathogen. Furthermore, it has been suggested by Delbrück et al. 1997 that the sequence differences between different alleles of the rps7 gene on different chromosomes in one species may be even greater than differences between genes in different related asexual species. This would lead the skilled person away from selecting this gene as a target for molecular diagnostics. Also, different sequence types exist for some species, such as *Candida albicans*, which would also lead one away from selecting this gene as a target gene for molecular diagnostics.

DEFINITIONS

As used herein, the following terms have the given meanings unless expressly stated to the contrary.

“Synthetic oligonucleotide” refers to molecules of nucleic acid polymers of 2 or more nucleotide bases that are not derived directly from genomic DNA or live organisms. The term synthetic oligonucleotide is intended to encompass DNA, RNA, and DNA/RNA hybrid molecules that have been manufactured chemically, or synthesized enzymatically in vitro.

An “oligonucleotide” is a nucleotide polymer having two or more nucleotide subunits covalently joined together. Oligonucleotides are generally about 10 to about 100 nucleotides. The sugar groups of the nucleotide subunits may be ribose, deoxyribose, or modified derivatives thereof such as OMe. The nucleotide subunits may be joined by linkages such as phosphodiester linkages, modified linkages or by non-nucleotide moieties that do not prevent hybridization of the oligonucleotide to its complementary target nucleotide sequence. Modified linkages include those in which a standard phosphodiester linkage is replaced with a different linkage, such as a phosphorothioate linkage, a methylphosphonate linkage, or a neutral peptide linkage. Nitrogenous base analogs also may be components of oligonucleotides in accordance with the invention.

A “target nucleic acid” is a nucleic acid comprising a target nucleic acid sequence. A “target nucleic acid sequence,” “target nucleotide sequence” or “target sequence” is a specific deoxyribonucleotide or ribonucleotide sequence that can be hybridized to a complementary oligonucleotide.

An “oligonucleotide probe” is an oligonucleotide having a nucleotide sequence sufficiently complementary to its target nucleic acid sequence to be able to form a detectable hybrid probe:target duplex under high stringency hybridization conditions. An oligonucleotide probe is an isolated chemical species and may include additional nucleotides outside of the targeted region as long as such nucleotides do not prevent hybridization under high stringency hybridization conditions. Non-complementary sequences, such as promoter sequences, restriction endonuclease recognition sites, or sequences that confer a desired secondary or tertiary structure such as a catalytic active site can be used to facilitate detection using the invented probes. An oligonucleotide probe optionally may be labelled with a detectable moiety such as a radioisotope, a fluorescent moiety, a chemiluminescent, a nanoparticle moiety, an enzyme or a ligand, which can be used to detect or confirm probe hybridization to its target sequence. Oligonucleotide probes are preferred to be in the size range of from about 10 to about 100 nucleotides in length, although it is possible for probes to be as much as and above about 500 nucleotides in length, or below 10 nucleotides in length.

A “hybrid” or a “duplex” is a complex formed between two single-stranded nucleic acid sequences by Watson-Crick base pairings or non-canonical base pairings between the complementary bases. “Hybridization” is the process by which two complementary strands of nucleic acid combine to form a double-stranded structure (“hybrid” or “duplex”).

A “fungus” or “yeast” is meant any organism of the kingdom Fungi, and preferably, is directed towards any organism of the phylum Ascomycota and most preferably is directed towards any organism of the class Hemiascomycetes.

“Complementarity” is a property conferred by the base sequence of a single strand of DNA or RNA which may form a hybrid or double-stranded DNA:DNA, RNA:RNA or DNA:RNA through hydrogen bonding between Watson-Crick base pairs on the respective strands. Adenine (A) ordinarily complements thymine (T) or uracil (U), while guanine (G) ordinarily complements cytosine (C).

The term “stringency” is used to describe the temperature, ionic strength and solvent composition existing during hybridization and the subsequent processing steps. Those skilled in the art will recognize that “stringency” conditions may be altered by varying those parameters either individually or together. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency conditions are chosen to maximize the difference in stability between the hybrid formed with the target and the non-target nucleic acid.

With “high stringency” conditions, nucleic acid base pairing will occur only between nucleic acid fragments that have a high frequency of complementary base sequences (for example, hybridization under “high stringency” conditions, may occur between homologs with about 85-100% identity, preferably about 70-100% identity). With medium stringency conditions, nucleic acid base pairing will occur between nucleic acids with an intermediate frequency of complementary base sequences (for example, hybridization under “medium stringency” conditions may occur between homologs with about 50-70% identity). Thus, conditions of “weak” or “low” stringency are often required with nucleic acids that are derived from organisms that are genetically diverse, as the frequency of complementary sequences is usually less.

‘High stringency’ conditions are those equivalent to binding or hybridization at 42° C. in a solution consisting of 5×SSPE (43.8 g/l NaCl, 6.9 g/l $NaH_2PO_4H_2O$ and 1.85 g/l EDTA, ph adjusted to 7.4 with NaOH), 0.5% SDS, 5×Denhardt’s reagent and 100 μg/ml denatured salmon sperm DNA followed by washing in a solution comprising 0.1× SSPE, 1.0% SDS at 42° C. when a probe of about 500 nucleotides in length is used.

“Medium stringency’ conditions are those equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt’s reagent and 100 μg/ml denatured salmon sperm DNA followed by washing in a solution comprising 1.0× SSPE, 1.0% SDS at 42° C., when a probe of about 500 nucleotides in length is used.

‘Low stringency’ conditions are those equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt’s reagent [50×Denhardt’s contains per 500 ml: 5 g Ficoll (Type 400, Pharamcia), 5 g BSA (Fraction V; Sigma)] and 100 μg/ml denatured salmon sperm DNA followed by washing in a solution comprising 5×SSPE, 0.1% SDS at 42° C., when a probe of about 500 nucleotides in length is used.

In the context of nucleic acid in-vitro amplification based technologies, “stringency” is achieved by applying temperature conditions and ionic buffer conditions that are particular to that in-vitro amplification technology. For example, in the context of PCR and real-time PCR, “stringency” is achieved by applying specific temperatures and ionic buffer strength for hybridisation of the oligonucleotide primers and, with regards to real-time PCR hybridisation of the probe/s, to the target nucleic acid for in-vitro amplification of the target nucleic acid.

“High stringency” when used in reference to in vitro amplification based detection systems, for example in PCR and real-time PCR, comprise conditions of a hybridisation (annealing) temperature in the range of 55° C. to 65° C. in a buffer environment containing $MgCl_2$ at a concentration of 1.5-8 mM.

“Medium stringency” when used in reference to in vitro amplification based detection systems for example in PCR and real-time PCR, comprise conditions of a hybridisation (annealing) temperature in the range of 45° C. to 54° C. in a buffer environment containing $MgCl_2$ at a concentration of 1.5-8 mM.

“Low stringency” when used in reference to in vitro amplification based detection systems for example in PCR and real-time PCR, comprise conditions of a hybridisation (annealing) temperature in the range of 40° C. to 44° C. in a buffer environment containing $MgCl_2$ at a concentration of 1.5-8 mM.

One skilled in the art will understand that substantially corresponding probes of the invention can vary from the referred-to sequence and still hybridize to the same target nucleic acid sequence. This variation from the nucleic acid may be stated in terms of a percentage of identical bases within the sequence or the percentage of perfectly complementary bases between the probe and its target sequence. Probes of the present invention substantially correspond to a nucleic acid sequence if these percentages are from about 100% to about 80% or from 0 base mismatches in about 10 nucleotide target sequence to about 2 bases mismatched in an about 10 nucleotide target sequence. In preferred embodiments, the percentage is from about 100% to about 85%. In more preferred embodiments, this percentage is from about 90% to about 100%; in other preferred embodiments, this percentage is from about 95% to about 100%

By “sufficiently complementary” or “substantially complementary” is meant nucleic acids having a sufficient amount of contiguous complementary nucleotides to form, under high stringency hybridization conditions, a hybrid that is stable for detection.

By “nucleic acid hybrid” or “probe:target duplex” is meant a structure that is a double-stranded, hydrogen-bonded structure, preferably about 10 to about 100 nucleotides in length, more preferably 14 to 50 nucleotides in length, although this will depend to an extent on the overall length of the oligonucleotide probe. The structure is sufficiently stable to be detected by means such as chemiluminescent or fluorescent light detection, autoradiography, electrochemical analysis or gel electrophoresis. Such hybrids include RNA:RNA, RNA:DNA, or DNA:DNA duplex molecules.

“RNA and DNA equivalents” refer to RNA and DNA molecules having the same complementary base pair hybridization properties. RNA and DNA equivalents have different sugar groups (i.e., ribose versus deoxyribose), and may differ by the presence of uracil in RNA and thymine in DNA. The difference between RNA and DNA equivalents do not contribute to differences in substantially corresponding nucleic acid sequences because the equivalents have the same degree of complementarity to a particular sequence.

By “preferentially hybridize” is meant that under high stringency hybridization conditions oligonucleotide probes can hybridize their target nucleic acids to form stable probe:target hybrids (thereby indicating the presence of the target nucleic acids) without forming stable probe:non-target hybrids (that would indicate the presence of non-target nucleic acids from other organisms). Thus, the probe hybridizes to target nucleic acid to a sufficiently greater extent than to non-target nucleic acid to enable one skilled in the art to accurately detect the presence of (for example *Candida*) and distinguish these species from other organisms. Preferential hybridization can be measured using techniques known in the art and described herein.

By “theranostics” is meant the use of diagnostic testing to diagnose the disease, choose the correct treatment regime and monitor the patient response to therapy. The theranostics of the invention may be based on the use of an NAD assay of this invention on samples, swabs or specimens collected from the patient.

SUMMARY OF THE INVENTION

The present invention provides a diagnostic kit for detection and identification of yeast and/or fungal species comprising an oligonucleotide probe capable of binding to at least a portion of the RPS7 gene or its corresponding mRNA. The oligonucleotide probe may have a sequence substantially homologous to or substantially complementary to a portion of the RPS7 gene or its corresponding mRNA. It will thus be capable of binding or hybridizing with a complementary DNA or RNA molecule. The RPS7 gene may be a fungal RPS7 gene. The RPS7 gene may be a yeast RPS7 gene. The nucleic acid molecule may be synthetic. The kit may comprise more than one such probe. In particular the kit may comprise a plurality of such probes. In addition the kit may comprise additional probes for other organisms, such as, for example, bacterial species or viruses.

The RPS7 gene codes for the ribosomal protein S7 which is a protein component of the small ribosomal subunit in yeast and fungi. It is required for ribosomal biogenesis and hence for protein synthesis. RPS7 is involved in the initiation of assembly of the 18S rRNA.

The present invention has identified high copy number mRNAs for use in yeast and fungal diagnostics. The identified sequences are suitable not only for in vitro DNA/RNA amplification based detection systems but also for signal amplification based detection systems.

Furthermore the sequences of the invention identified as suitable targets provide the advantages of having significant intragenic sequence heterogeneity in some regions, which is advantageous and enables aspects of the invention to be directed towards group or species-specific targets, and also having significant sequence homogeneity in some regions, which enables aspects of the invention to be directed towards genus-specific yeast and fungal primers and probes for use in direct nucleic acid detection technologies, signal amplification nucleic acid detection technologies, and nucleic acid in vitro amplification technologies for yeast and fungal diagnostics. The RPS7 sequences allow for multi-test capability and automation in diagnostic assays.

One of the advantages of the sequences of the present invention is that the intragenic RPS7 nucleotide sequence diversity between closely related yeast and fungal species enables specific primers and probes for use in diagnostics assays for the detection of yeast and fungi to be designed. The RPS7 nucleotide sequences, both DNA and RNA can be used with direct detection, signal amplification detection and in vitro amplification technologies in diagnostics assays. The RPS7 sequences allow for multi-test capability and automation in diagnostic assays.

The high copy number of the RPS7 mRNA provides an advantage for its use in diagnostics assays in combination with signal amplification detection technologies. Moreover, the labile nature of the RPS7 transcript allows this diagnostic target to be used in viability diagnostics assays.

The kit may further comprise a primer for amplification of at least a portion of the RPS7 gene. Suitably the kit comprises a forward and a reverse primer for a portion of the RPS7 gene. The portion of the RPS7 gene may be a portion of exon 3 of the *Aspergillus* RPS7 gene. Alternatively, the portion of the RPS7 gene may be equivalent to a portion of the region of the gene from base pair position 508 to base pair position 711 of the *C. albicans* RPS7 gene. Particularly preferred are kits comprising a probe for a portion of exon 3 of the *Aspergillus* RPS7 gene and a probe for a portion of the region of the gene equivalent to base pair position 508 to base pair position 711 of the *C. albicans* RPS7 gene. Equivalent regions to base pair position 508 to base pair position 711 can be found in other organisms, such as *Saccharomyces species* and *Cryptococcus neoformans*, but not necessarily at position 508 to 711. The kit may also comprise additional probes.

The probe may have a sequence selected from the group the SEQ ID NO 1 through to SEQ ID NO 7, SEQ ID No 176 through to SEQ ID NO 189 and SEQ ID NO 378 through to SEQ ID NO 413 and SEQ ID NO 419 through to SEQ ID NO 448 or a sequence substantially homologous to or substantially complementary to those sequences which can also act as a probe for the RPS7 gene.

The kit may comprise at least one forward in vitro amplification primer and at least one reverse in vitro amplification primer, the forward amplification primer having a sequence selected from the group consisting of SEQ ID NO 8 through to SEQ 40, SEQ ID NO 414, SEQ ID NO 417, SEQ ID NO 418 or a sequence being substantially homologous or complementary thereto which can also act as a forward amplification primer, and the reverse amplification primer having a sequence selected from the group consisting of SEQ ID NO 3, SEQ ID NO 22 through to SEQ 49, SEQ ID NO 415 and SEQ ID NO 416 or a sequence being substantially homologous or complementary thereto which can also act as a reverse amplification primer. The diagnostic kit may be based on direct nucleic acid detection technologies, signal amplification nucleic acid detection technologies, and nucleic acid in vitro amplification technologies is selected from one or more of Polymerase Chain Reaction (PCR), Ligase Chain Reaction (LCR), Nucleic Acids Sequence Based Amplification (NASBA), Strand Displacement Amplification (SDA), Transcription Mediated Amplification (TMA), Branched DNA technology (bDNA) and Rolling Circle Amplification Technology (RCAT)), or other in vitro enzymatic amplification technologies.

The invention also provides a nucleic acid molecule selected from the group consisting of SEQ ID NO 1 through to SEQ ID NO 466 and sequences substantially homologous thereto, or substantially complementary to a portion thereof and having a function in diagnostics based on the RPS7 gene. The nucleic acid molecule may comprise an oligonucleotide having a sequence substantially homologous to or substantially complementary to a portion of a nucleic acid molecule of SEQ ID NO 1 through to SEQ ID NO 466.

The invention also provides a method of detecting a target organism in a test sample comprising the steps of:

(i) Mixing the test sample with at least one oligonucleotide probe as defined above under appropriate conditions; and (ii) hybridizing under high stringency conditions any nucleic acid that may be present in the test sample with the oligonucleotide to form a probe:target duplex; and (iii) determining whether a probe:target duplex is present; the presence of the duplex positively identifying the presence of the target organism in the test sample.

The probe may have a sequence selected from the group consisting of SEQ ID NO 1 through to SEQ ID NO 49, SEQ ID NO 176 through to SEQ ID NO 189 and SEQ ID NO 378 through to SEQ ID NO 448 or a sequence substantially homologous to or substantially complementary to those sequences which can also act as a probe for the RPS7 gene.

The nucleic acid molecule and kits of the present invention may be used in a diagnostic assay to detect the presence of one or more yeast and/or fungal species, to measure yeast and/or fungal titres in a patient or in a method of assessing the efficacy of a treatment regime designed to reduce yeast and/or fungal titre in a patient or to measure yeast and/or fungal contamination in an environment. The environment may be a hospital, or it may be a food sample, an environmental sample e.g. water, an industrial sample such as an in-process sample or an end product requiring bioburden or quality assessment.

The kits and the nucleic acid molecule of the invention may be used in the identification and/or characterization of one or more disruptive agents that can be used to disrupt the RPS7 gene function. The disruptive agent may be selected from the group consisting of antisense RNA, PNA, and siRNA.

In some embodiments, the RPS7 gene is an *E. gossypil* gene. In some such embodiments, the RPS7 gene may be selected from the group consisting of: SEQ ID NO 54, SEQ ID NO 194, SEQ ID NO 212, or their respective mRNA equivalents, SEQ ID NO 55, SEQ ID NO 195, SEQ ID NO 213 or a portion thereof, or a sequence substantially homologous thereto, or substantially complementary to a portion of one or more sequences.

In some embodiments, the RPS7 gene is a *K. lactis* gene. In some such embodiments, the RPS7 gene may be selected from the group consisting of: SEQ ID NO 56, SEQ ID NO 196, SEQ ID NO 210, or their respective mRNA equivalents, SEQ ID NO 57, SEQ ID NO 197, SEQ ID NO 211 or a portion thereof, or a sequence substantially homologous thereto, or substantially complementary to a portion of one or more sequences.

In some embodiments, the RPS7 gene is a *D. hansenil* gene. In some such embodiments, the RPS7 gene may be selected from the group consisting of: SEQ ID NO 60, SEQ ID NO 200, SEQ ID NO 214, or their respective mRNA equivalents, SEQ ID NO 61, SEQ ID NO 201, SEQ ID NO 215 or a portion thereof, or a sequence substantially homologous thereto, or substantially complementary to a portion of one or more sequences.

In some embodiments of the invention, a nucleic acid molecule comprising a species-specific probe can be used to discriminate between species of the same genus.

For example, *Candida albicans* species specific probes may comprise oligonucleotides comprising sequences SEQ ID NO 6, SEQ ID NO 7 and SEQ ID NO 378 through SEQ ID NO 385 or a portion thereof, or a sequence substantially homologous thereto, or substantially complementary to a portion of one or more sequences.

The oligonucleotides of the invention may be provided in a composition for detecting the nucleic acids of yeast and fungal target organisms. Such a composition may also comprise buffers, enzymes, detergents, salts and so on, as appropriate to the intended use of the compositions. It is also envisioned that the compositions, kits and methods of the invention, while described herein as comprising at least one synthetic oligonucleotide, may also comprise natural oligonucleotides with substantially the same sequences as the synthetic nucleotide fragments in place of, or alongside synthetic oligonucleotides.

The invention also provides for an in vitro amplification diagnostic kit for a target yeast and/or fungal organism comprising at least one forward in vitro amplification primer and at least one reverse in vitro amplification primer, the forward amplification primer being selected from the group consisting of one or more of SEQ ID NO 8-40, SEQ ID NO 414, SEQ ID NO 417, SEQ ID NO 418 or a sequence being substantially homologous or complementary thereto which can also act as a forward amplification primer, and the reverse amplification primer being selected from the group consisting of one or more of SEQ ID NO 3, SEQ ID NO 22 through to SEQ ID NO 49, SEQ ID NO 415 and SEQ ID NO 416 or a sequence being substantially homologous or complementary thereto which can also act as a reverse amplification primer.

The invention also provides for a diagnostic kit for detecting the presence of a candidate yeast and/or fungal species, comprising one or more DNA probes comprising a sequence substantially complementary to, or substantially homologous to the sequence of the RPS7 gene of the candidate yeast and/or fungal species. The present invention also provides for one or more synthetic oligonucleotides having a nucleotide sequence substantially homologous to or substantially complementary to one or more of the group consisting of the RPS7 gene or mRNA transcript thereof, the yeast and or fungal RPS7 gene or mRNA transcript thereof, the yeast RPS7 gene or mRNA transcript thereof, one or more of SEQ ID NO 1-SEQ ID NO 466.

The nucleotide may comprise DNA. The nucleotide may comprise RNA. The nucleotide may comprise a mixture of DNA, RNA and PNA. The nucleotide may comprise synthetic nucleotides. The sequences of the invention (and the sequences relating to the methods, kits compositions and assays of the invention) may be selected to be substantially homologous to a portion of the coding region of the RPS 7 gene. The gene may be a gene from a target yeast or fungal organism. The sequences of the invention are preferably sufficient so as to be able form a probe:target duplex to the portion of the sequence.

The invention also provides for a diagnostic kit for a target yeast or fungal organism comprising an oligonucleotide probe substantially homologous to or substantially complementary to an oligonucleotide of the invention (which may be synthetic). It will be appreciated that sequences suitable for use as in vitro amplification primers may also be suitable for use as oligonucleotide probes: while it is preferable that amplification primers may have a complementary portion of between about 15 nucleotides and about 30 nucleotides (more preferably about 15-about 23, most preferably about 20 to about 23), oligonucleotide probes of the invention may be any suitable length. The skilled person will appreciate that different hybridization and or annealing conditions will be required depending on the length, nature & structure (eg. Hybridization probe pairs for LightCycler, Taqman 5' exonuclease probes, hairpin loop structures etc. and sequence of the oligonucleotide probe selected. Kits and assays of the invention may also be provided wherein the oligonucleotide probe is immobilized on a surface. Such a surface may be a bead, a membrane, a column, dipstick, a nanoparticle, the interior surface of a reaction chamber such as the well of a diagnostic plate or inside of a reaction tube, capillary or vessel or the like.

The target yeast or fungal organism may be selected from the group consisting of *C. albicans, C. glabrata, C. tropicalis, C. krusei, C. parapsilosis, C. dubliniensis, C. guillermondii, C. norvegiensis, C. lusitaniae, C. lipolytica, C. rugosa, C. catenulata, C. cifferi, C. famata, C. haemulonii, C. pulcherrima, C. utilis, C. kefyr, C. viswanthii, C. zealanoides. S. cerevisiae, C. neoformans, E. gossypii, K. Lactis, D. hansenii, Aspergillus nidulans, Aspergillus fumigatus Aspergillus terreus, A. versicolor, A. flavus, A. niger, A. candidus, A. clavatus, A. glaucus, Neosartorya fischeri* and *A. fischeri.*

The target yeast organisms may be a *Candida* species for the given set of primers already experimentally demonstrated, and more preferably, selected from the group consisting of *C. albicans, C. glabrata, C. tropicalis, C. krusei, C. parapsilosis, C. dubliniensis, C. guillermondii, C. norvegiensis, C. lusitaniae, C. lipolytica, C. rugosa, C. catenu-*

*lata, C. cifferi, C. famata, C. haemulonii, C. pulcherrima, C. utilis, C. kefyr, C. viswanthii, C. zealanoides*. Under these circumstances, the amplification primers and oligonucleotide probes of the invention may be designed to a gene specific or genus specific region so as to be able to identify one or more, or most, or substantially all of the desired organisms of the target yeast organism grouping. Suitable forward amplification primers may be selected from the group consisting of: Can1F: 5'-AGC TGG TTT CAT GGA TGT-3' (SEQ ID NO 40), SEQ ID NO 36, and SEQ ID NO 37, and/or, a mixture of SEQ ID NO 38 and 39. Suitable reverse amplification primer may be selected from the group consisting of Can2R: 5'-TCT GGG TAT CTG AT(A/G) GTT CT-3' (SEQ ID NO 3), SEQ ID NO 2 and or a mixture of SEQ ID NOs 4 and 5, or indeed, oligonucleotides substantially complementary to one or more of SEQ ID NO 41, SEQ ID NO 42, SEQ ID NO 46, SEQ ID NO 47 and/or a mixture of SEQ ID NO 43-45, and/or a mixture of SEQ ID NO 48-49. Suitable genus-specific oligonucleotide probes are: CASP: 5'-TAA CAT CGT AGG CTA ATC-3' (SEQ ID NO. 1), SEQ ID NO 6, or SEQ ID NO 7. *Candida* species specific probes may be selected from the group consisting of SEQ ID NO 378 through to SEQ ID NO 413.

The target fungal organisms may be an *Aspergillus* species for given set of primers already experimentally demonstrated, and more preferably, selected from the group consisting of *Aspergillus nidulans, Aspergillus fumigatus Aspergillus terreus, A. versicolor, A. flavus, A. niger, A. candidus, A. clavatus, A. glaucus, Neosartorya fischeri* and *A. fischeri*. Suitable forward amplification primers may be SEQ ID NO 414, SEQ ID NO 417 and SEQ ID NO 418 with reverse primers selected may be SEQ ID NO 415 or SEQ ID NO 416. *Aspergillus* species specific probes may be selected from the group consisting of SEQ ID NO 419 through to SEQ ID NO 448.

The test sample may comprise cells of the target yeast and/or fungal organism. The method may also comprise a step for releasing nucleic acid from any cells of the target yeast or fungal organism that may be present in said test sample. Ideally, the test sample is a lysate of an obtained sample from a patient (such as a swab, or blood, urine, saliva, a bronchial lavage dental specimen, skin specimen, scalp specimen, transplant organ biopsy, stool, mucus, or discharge sample). The test samples may be a food sample, a water sample an environmental sample, an end product, end product or in-process industrial sample.

The invention also provides for the use of any one of SEQ ID NOs: 1-466 in a diagnostic assay for the presence of one or more yeast or fungal species. The species may be selected from the group consisting of *C. albicans, C. glabrata, C. tropicalis, C. krusei, C. parapsilosis, C. dubliniensis, C. guillermondii, C. norvegiensis, C. lusitaniae, C. lipolytica, C. rugosa, C. catenulata, C. cifferi, C. famata, C. haemulonii, C. pulcherrima, C. utilis, C. kefyr, C. viswanthii, C. zealanoides. S. cerevisiae, C. neoformans, E. gossypii, K. Lactis, D. hansenii, Aspergillus nidulans, Aspergillus fumigatus Aspergillus terreus, A. versicolor, A. flavus, A. niger, A. candidus, A. clavatus, A. glaucus, Neosartorya fischeri* and *A. fischeri*.

The invention also provides for kits for use in theranostics, food safety diagnostics, industrial microbiology diagnostics, environmental monitoring, veterinary diagnostics, bio-terrorism diagnostics comprising one or more of the synthetic oligonucleotides of the invention. The kits may also comprise one or more articles selected from the group consisting of appropriate sample collecting instruments, reagent containers, buffers, labelling moieties, solutions, detergents and supplementary solutions. The invention also provides for use of the sequences, compositions, nucleotide fragments, assays, and kits of the invention in theranostics, Food safety diagnostics, Industrial microbiology diagnostics, Environmental monitoring, Veterinary diagnostics, Bio-terrorism diagnostics.

The nucleic acid molecules, composition, kits or methods may be used in a diagnostic nucleic acid based assay for the detection of yeast and/or fungal species.

The nucleic acid molecules, composition, kits or methods may be used in a diagnostic assay to measure yeast and/or fungal titres in a patient. The titres may be measured in vitro.

The nucleic acid molecules, composition, kits or methods may be used in a method of assessing the efficacy of a treatment regime designed to reduce yeast and/or fungal titre in a patient comprising assessing the yeast and/or fungal titre in the patient (by in vivo methods or in vitro methods) at one or more key stages of the treatment regime. Suitable key stages may include before treatment, during treatment and after treatment. The treatment regime may comprise an antifungal agent, such as a pharmaceutical drug.

The nucleic acid molecules, composition, kits or methods may be used in a diagnostic assay to measure potential yeast and/or fungal contamination, for example, in a hospital.

The nucleic acid molecules, composition, kits or methods may be used in the identification and/or characterization of one or more disruptive agents that can be used to disrupt the RPS7 gene function. Suitable disruptive agents may be selected from the group consisting of antisense RNA, PNA, siRNA.

BRIEF DESCRIPTION OF THE FIGURES

FIG. 1: a: Gel electrophoresis of *Candida* species RT-PCR partial RPS7 sequence amplified using primers Can1F and Can2R; b: Autoradiograph demonstrating the specificity of the *C. albicans* species specific probe, CASP. A and B: lane 1: Marker XIV; 2: *Candida albicans* partial RPS7 RT-PCR product; 3: *C. tropicalis* partial RPS7 RT-PCR product; 4: *C. parapsilosis* partial RPS7 RT-PCR product; 5: *C. glabrata* partial RPS7 RT-PCR product; 6: *C. dubliniensis* partial RPS7 RT-PCR product. These in vitro amplified products were generated using the *Candida* genus specific primers Can1F: 5'-AGC TGG TTT CAT GGA TGT-3': SEQ ID NO: 40. and Can2R: 5'-TCT GGG TAT CTG AT(A/G) GTT CT-3': SEQ ID NO: 3.

FIG. 2: Inclusivity testing of the real-time PCR assay for *C. albicans* based on rps7 gene and incorporating primers SEQ ID No 40 and SEQ ID NO 3 and TaqMan probe SEQ ID NO 384—all 20 *C. albicans* strains detected.

DETAILED DESCRIPTION OF THE INVENTION

Materials and Methods

Figure 3:
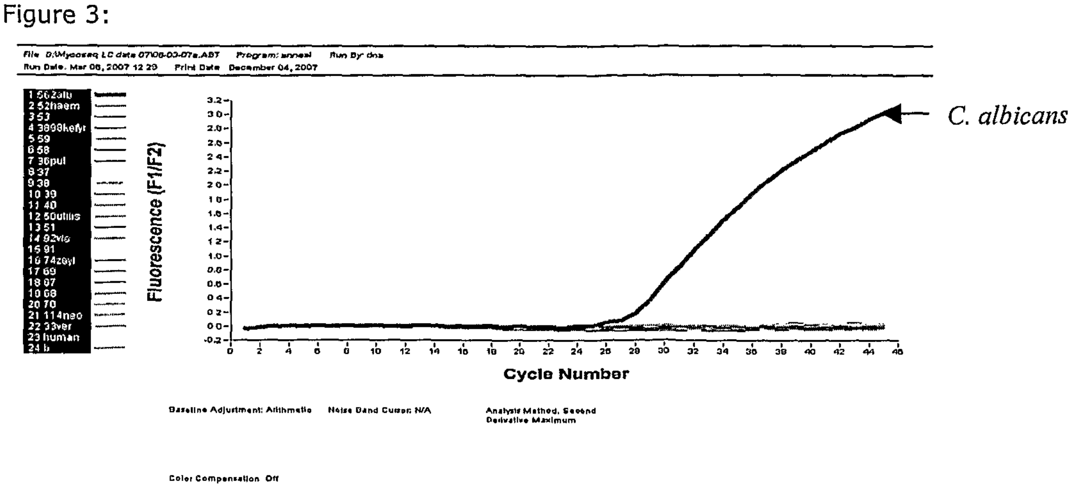
FIG. 3: Specificity of the real-time PCR assay for *C. albicans* based on rps7 gene and incorporating primers SEQ ID No 40 and SEQ ID NO 3 and TaqMan probe SEQ ID NO 384. Cross-check of other *Candida* species related to pathology including *C. haemuloni, C. kefyr, C. pulcherrima, C. utilis, C. viswanthii, C. zeylanoides* and human DNA—no cross reaction observed.

Organism and growth conditions: *Candida* species (CBS 562) were grown on Sabouraud agar (4% wt/vol glucose, 1% wt/vol peptone, 1.5% agar) overnight at 37° C. @ 180 rpm. A single colony was used to inoculate 10 ml of Sabouraud broth (Oxoid™) and grown overnight @ 37° C. 1 ml of overnight culture was used to inoculate 100 ml Sabouraud broth (Oxoid™) and allowed to grow to exponential and stationary phases, 8 hrs and 16 hrs respectively. *Aspergillus niger* was grown on Sabouraud agar for 48 hrs @ 30° C. A hypodermic needle was used to stab the agar and transferred to 100 ml Sabouraud broth and allowed to grow for 48 hours. *Aspergillus* species from slope or dessicated stocks were also grown in Sabouraud agar at 25° C. for 1-7 days.

Total RNA isolation: RNA extraction from *C. albicans* was carried out following growth to exponential phase using the RNeasy™ Mini Kit™ (Qiagen™). 1 ml of culture was centrifuged @ 10,000 rpm and the pellet was resuspended in 100 μl of YI lysis buffer (0.1M EDTA, 1M sorbitol, 0.1% β-Mercaptoethanol and 1000 U lyticase) and incubated @ 30° C. for 20 mins. The quality of total RNA was assessed by gel electrophoresis on 1.2% MOPS denaturing gel and quantified by fluoroimetry using a TBS-380™ minifluorometer (Turner Systems™).

RPS7 Fungal/Yeast genus specific in vitro amplification primer design: Total RNA was isolated from five *Candida* species, *C. albicans, C. glabrata, C. tropicalis, C. parapsilosis* and *C. dubliniensis* using the Ambion™ Yeast total RNA isolation kit and this was carried out according to the manufacturers instructions. An in vitro RT-PCR amplification was then carried out on all five isolated total RNA's to demonstrate the use of Can 1F (SEQ ID NO. 40) and Can2R (SEQ ID NO. 3) for generating sequences from uncharacterized yeast species (*C. tropicalis, C. parapsilosis* and *C. dubliniensis*). RT-PCR amplification was carried out on the isolated total RNAs from all *Candida* species examined using the Titan One Tube™ RT-PCR System (Roche) according to the manufacturers instructions using the in vitro amplification primers SEQ ID NO. 3 and SEQ ID NO. 40. The resultant RT-PCR in vitro amplified products were then electrophoresed on 1.2% agarose gels to determine the success of in vitro amplification and subsequently Southern blotted (FIG. 1A). The remainder of the RT-PCR in vitro amplified products from the uncharacterized *Candida* RPS7 sequences were then purified using the Roche High Pure™ PCR product purification kit according to the manufacturers instructions and subsequently sequenced using SEQ ID NO. 40 as a sequencing primer to generate novel RPS7 partial sequence data for these organisms (SEQ ID 64 and 65, 66 and 67, 68 and 69, 70 and 71).

```
                                          SEQ ID NO: 40
CanlF: 5'-AGC TGG TTT CAT GGA TGT-3':.

                                          SEQ ID NO: 3
Can2R: 5'-TCT GGG TAT CTG AT(A/G) GTT CT-3':.
```

Determination of *Candida, S. cerevisiae* and *C. neoformans* species partial RPS7 sequences using the in vitro PCR amplification—primers CanF1 (SEQ NO: 40) and CanR2 (SEQ ID NO: 3): In order to determine and expand the nucleotide sequence database for the *Candida* species partial RPS7 sequences and also to further demonstrate the broad use of the in vitro PCR amplification primers CanF1 (SEQ ID NO 40) and Can2R(SEQ ID NO 3) a series of PCR in vitro amplifications were carried out on the following *Candida strains, C. albicans* strains, 178, 180, 320, 369, 765, 16733, 1560, 9559, 4154, 2700, 562, 3822, 3156, 3345, 3328, *C. dubliniensis* 3949, *C. glabrata* strains, 9087, 4692, 205444, 10269, 9556, 5563, 3959, 138, 3605, 3897, 8018, 3863, 3902, 604, *C. parapsilosis* strains, 3902, 604, 2194, 2196, 1001, 1716, 9557, 5579, *C. krusei* strains 5579, 9560, 6055, 17518, 573, 3165, 3922, 3847, and *C. tropicalis* strains 3895, 94, 4225, 5557, 15902, 4139, 3873, 3870, 8157, 2311. Total genomic DNA was isolated from each of these strains using the Edge Biosystems Genomic DNA purification kit and the integrity of the purified DNA was determined by electrophoresis of each of the isolated DNA samples on a 1.2% agarose gel. Each DNA sample was then subjected to in vitro PCR amplification using Taq DNA polymerase (Roche) in combination with CanF1 and CanR2 according to the manufacturers instructions. The PCR product amplified from each *Candida* strain genomic DNA was then purified using the Roche High Pure PCR product purification kit. The purified PCR products were then subjected to nucleotide sequencing using CanF1 as a sequencing primer. This resulted in the generation of novel partial RPS7 nucleotide sequences for all *Candida* strains tested. Sequences represented by SEQ ID 62 through SEQ ID NO. 175 represents the partial RPS7 nucleotide sequence generated for *Candida* strains tested for and described above. In addition, PCR amplification primers SEQ ID NO 40 and SEQ ID NO 3 were used to amplify DNA extracted from *Candida* species (n=20 species n=120 strains). These primers amplify at 204 by region of the rps7 gene equivalent to position 508 to 711 of the rps7 gene in *C. albicans* (Accession no: U37009). DNA was extracted on the MagNA Pure System (Roche Molecular Systems) using the MagNA pure Yeast and Bacterial isolation kit III following a pre-treatment of the *Candida* spp. cells with lyticase enzyme. Some DNA extracts were obtained using the EasyMag system (BioMerieux). PCR amplification was performed using the reagents and conditions outlined in Table 1. The PCR products for DNA sequencing were cleaned up using the ExoSAP-IT kit (USB) or the High Pure PCR purification kit (Roche). DNA sequencing of PCR products for *Candida* spp. was undertaken by an external sequence service provider, Sequiserve (Germany) using the SEQ ID NO 40 primer. In addition, PCR primers SEQ ID NO 40 and SEQ ID NO 3 were used to amplify DNA from *C. neoformans* and *S. cerevisiae* species. The PCR products were also sequenced by the external sequence provider, Sequiserve (Germany) using the SEQ ID NO 40 primer. Sequences ID NO 222 through to SEQ ID NO 325 represent the *Candida* spp. rps 7 gene (204 bp) sequences. SEQ ID NO 449 represents the *S. cerevisiae* rps 7 gene (204 bp) sequence and SEQ ID NO 451 represents the *C. neoformans* rps 7 gene sequence.

TABLE 1

PCR reagents and conditions used to amplify the rps7 gene in *Candida* spp. *S. cerevisiae* and *C. neoformans*.

| PCR conditions: | Reaction conditions | Cycle parameters: |
|---|---|---|
| ICycler (50 μL) | 1 μL each primer @ 17 μM | 94° C. 1 min |
| | 5 μl 10X Buffer (Roche) - [100 mM Tris-HCl, 15 mM $MgCl_2$, 500 mM KCl, pH 8.3]. | 30 × 45° C. 1 min<br>72° C. 1 min |
| | 1 μl (IU) Taq Polymerase (Roche) | 72° C. 7 min |
| | 1 μl of stock dNTP mix (10 mM of each dNTP) | |
| | 2-5 μl DNA template | |
| LightCycler (20 μL) | 1 μL each primer @ 10 μM | 1 × 40° C. 10 min |
| | 2 μL FastStart Mix (HybProbe kit) | 1 × 95° C. 10 min |
| | 2.4 μL (4 mM) $MgCl_2$ | |
| | 0.5 μL (1 U) LightCycler UNG | 95° C. −10 sec |
| | 2 μL DNA template | 45 × 55° C. −30 sec<br>72° C. −1 min<br>Cooling 40° C. |

Generation of RPS7 Gene Exon 3 Sequence Information for *Aspergillus* Species.

PCR primers forward primer SEQ ID NO 414 and reverse primer SEQ ID NO SEQ 415 were designed to amplify exon 3 (317 bp) from position 664-980 in RPS7 in *A. fumigatus* GenBank Accession no: XM_749453 in *Aspergillus* spp. DNA from 8 species (n=67 strains-Table 2) were PCR amplified with these primers and sequence information of the exon 3 fragment was successfully obtained for these strains. An independent set of primers, forward primer SEQ ID NO 417 and reverse primer SEQ ID NO 416 were designed and applied to amplify RPS7 gene (exon 3-317 bp) in *A. niger* strains (n=10-Table 2). PCR amplification of the RPS7 exon 3-317 by in the *Aspergillus* spp. was performed with these primers on the iCycler (BioRad) using the conditions described in Table 3. PCR products for DNA sequencing were cleaned up using the High Pure PCR purification kit (Roche). DNA sequencing was performed by an external sequence service provider, Sequiserve (Germany) using the SEQ ID NO 414 and SEQ ID NO 417 (forward) primers.

TABLE 2

*Aspergillus* species and strains for which exon 3 of the RPS7 gene was sequenced.

| Species name | Number of strains sequenced |
|---|---|
| *A. fumigatus* | 20 |
| *A. terreus* | 10 |
| *A. versicolor* | 5 |
| *A. nidulans* | 7 |
| *A. flavus* | 10 |
| *A. niger* | 10 |
| *A. candidus* | 5 |
| *A. clavatus* | 5 |
| *A. glaucus* | 5 |

TABLE 3

PCR reagents and PCR conditions used for PCR amplification of the 317 bp region of exon 3 of the RPS7 gene in *Apergillus* spp. for DNA sequencing.

| PCR conditions: | Reaction conditions | Cycle parameters: |
|---|---|---|
| ICycler (50 μL) | 1 μL each primer @ 10 μM | 94° C. 1 min |
| | 5 μl 10X Buffer (Roche) - [100 mM Tris-HCl, 15 mM $MgCl_2$, 500 mM KCl, pH 8.3]. | 30 × 50/52° C. 1 min<br>72° C. 1 min |
| | 1 μl (IU) Taq Polymerase (Roche) | 72° C. 7 min |
| | 1 μl of stock dNTP mix (10 mM of each dNTP) | |
| | 2-5 μl DNA template | |

Development of prototype species specific *C. albicans* Nucleic Acid Diagnostics (NAD) assay based on the RPS7 gene sequence: The new and already existing RPS7 sequence data (SEQ ID NO 62-SEQ ID NO 175) were then examined and a *C. albicans* species specific oligonucleotide probe (CASP, SEQ ID NO. 1) was identified and then synthesised for use in hybridizing to the Southern blot as described above. The CASP (SEQ ID NO. 1) oligonucleotide probe was radioactively 5' end labelled with gamma $P^{32}$ using T4 Polynucleotide Kinase (Roche) and was then hybridised to the Southern blot for 2 hours at 55° C. The hybridisation fluid was removed and the blot was then washed twice in 6×SSC, 0.1% SDS at room temperature for 10 minutes followed by a high stringency wash in 6×SSC, 0.1% SDS at 55° C. for 1 minute. The blot was exposed to X-Ray film and autoradiography was carried out for 2 hours at −70° C. FIG. 1B shows that CASP species specific oligonucleotide probe only hybridises to the *C. albicans* RT-PCR in vitro amplified product, thus demonstrating the use and potential of the RPS7 nucleic acid sequence as a target for the detection of a yeast species of interest.

```
CASP: 5'-TAA CAT CGT AGG CTA ATC-3': SEQ ID NO. 1
```

Design of Oligonucleotide Probes for *Candida* Spp.

The sequence information obtained for the rps7 gene 204 by target region in *Candida* spp. representing the different sequence types obtained for each species (SEQ ID NO 222 through to SEQ ID NO 325) were aligned and analysed using bioinformatics tools, including Clustal W and BLAST programs and oligonucleotide probes were designed for the identification of different *Candida* species. For *C. albicans* identification, oligonucleotide probes SEQ ID NO 378 through to SEQ ID NO 385 were designed. For *C. krusei* identification, oligonucleotide probes SEQ ID NO 386 through to SEQ ID NO 389 were designed. For *C. parapsilosis* identification, oligonucleotide probes SEQ ID NO 390 through to SEQ ID NO 393 were designed. For identification of *C. tropicalis*, oligonucleotide probes, SEQ ID NO 394 through to SEQ ID NO 405 were designed. For *C. glabrata* identification, oligonucleotide probes SEQ ID NO 406 through to SEQ ID NO 413 were designed.

Figure 4:
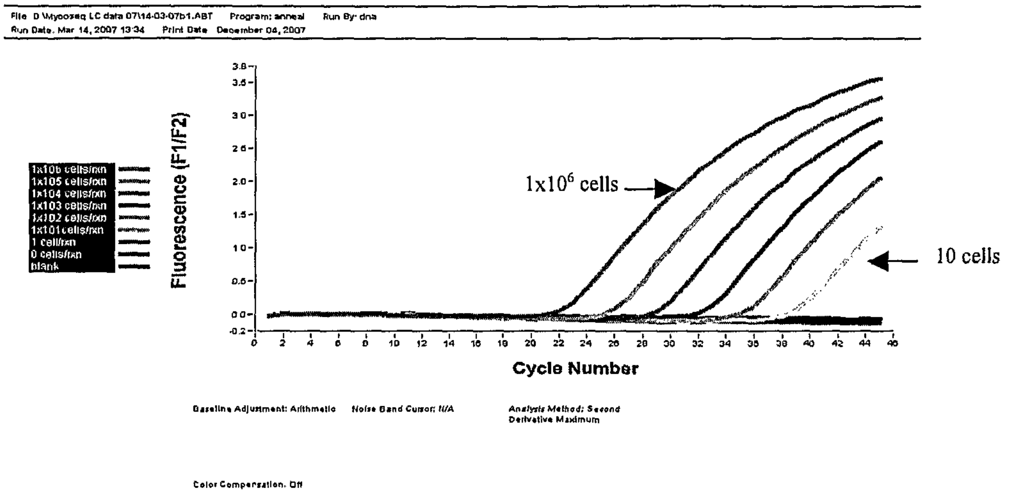
FIG. 4: Limit of detection of the real-time PCR assay for *C. albicans* based on rps7 gene and incorporating primers SEQ ID No 40 and SEQ ID NO 3 and TaqMan probe SEQ ID NO 384 and including serial dilutions ($10^6$-1 cell equivalent) of *C. albicans* genomic DNA —Detection limit 10 cells.

Nucleic acid diagnostics assays were designed for *Candida* spp using the primers SEQ ID NO 40 and SEQ ID NO 3 and oligonucleotide probes SEQ ID NO 378-SEQ ID NO 413. Examples of the assays developed include real-time PCR TaqMan assays for 5 *Candida* species including *C. albicans, C. krusei, C. tropicalis, C. glabrata* and *C. parapsilosis*. An example of the *C. albicans* assay includes primers SEQ ID NO 40 and SEQ ID NO 3 and oligonucleotide probe SEQ ID NO 384 (FIG. 2). An example of assay for *C. krusei* includes primers SEQ ID NO 40 and SEQ ID NO 3 and probe SEQ ID NO 386. An example of an assay for *C. glabrata* includes primers SEQ ID NO 40 and SEQ ID NO 3 and probe SEQ ID NO 412. An example of an assay for *C. tropicalis* includes primers SEQ ID NO 40 and SEQ ID NO 3 and probe SEQ ID NO 400. An example of an assay for *C. parapsilosis* includes primers SEQ ID NO 40 and SEQ ID NO 3 and probe SEQ ID NO 392. These species-specific assays were configured on the LightCycler real-time PCR machine and performed using the conditions and reagents described in Table 4. Each species assay was tested for inclusivity with 20 strains of the species and for each species assay the relevant strains (n=20) were detected. Each species assay was tested for cross-reactivity against a panel of species including 19 species of *Candida,* 24 species of other yeasts and dermatophytes, 9 species of *Aspergillus,* 15 bacterial species and human DNA (Table 5). Each species assay only detected strains of the species it was designed to detect and there was no cross-reaction with DNA from other *Candida* spp., *Aspergillus* species, other yeasts, dermatophytes, bacteria or human DNA. FIG. 3 shows an example of a specificity study with the *C. albicans* species-specific assay. The limits of detection (LOD) or sensitivities of the assays were determined using 10-serial dilutions ($10^6$-1 cell equivalent) of genomic DNA from the relevant species. Detection limits of 10 cell equivalents were established for each species assay. FIG. 4 shows the detection limit obtained for the *C. albicans* assay.

TABLE 4

| PCR reagents and thermocycling conditions: | | |
|---|---|---|
| PCR reagents | Reaction Mix per 20 µl reaction | |
| | FastStart mix 2 µL(Roche LightCycler DNA Master HybProbe kit Cat no 12239272001) | |
| | $MgCl_2$ 3.2 µl | |
| | Probe 2 µL (Final 0.2 µM) | |
| | Primer 1 µL (Final 0.5 µM) | |
| | Primer 1 µL (Final 0.5 µM) | |
| | UNG 0.5 µL (Optional) | |
| | $H_2O$ 8.3 µL (8.8 µL if UNG not being used) | |
| | DNA template 2 µL | |
| Thermocycling conditions | 40° C. 600 sec | −1 cycle |
| | 95° C. 600 sec | −1 cycle |
| | 95° C. 10 sec | 45 cycles |
| | 62° C. 60 sec | |
| | 40° C. −10 sec | −1 cycle |

Panel of species included for cross-reactivity testing in the *Candida species* and *A. fumigatus* assays.

| | | |
|---|---|---|
| *A. fumigatus* | *A. terreus* | *A. candidus* |
| *A. versicolor* | *A. nidulans* | *A. flavus* |
| *A. glaucus* | *A. niger* | *A. clavatus* |
| *C. albicans* | *C. glabrata* | *C. krusei* |
| *C. parapsilosis* | *C. tropicalis* | *C. dubliniensis* |
| *C. guillermondii* | *C. lipolytica* | *C. lusitanie* |
| *C. norvegensis* | *C. rugosa* | *C. catenulata* |
| *C. cifferii* | *C. famata* | *C. haemuloni* |
| *C. keyfr* | *C. pulcherrima* | *C. utilis* |
| *C. viswanthii* | *C. zeylanoides* | *Cryptococcus neoformans* |
| *S. cerevisiae* | *T. asahii* | *R. mucilaginosa* |
| *M. furfur* | *B. capitatus* | *Acremonium spp.* |
| *B australiensis* | *B hawiiensis* | *C lunata* |
| *F solani* | *M circillenoides* | *M ramoissimus* |
| *P. variotti* | *P lilicinus* | *Penicillium chry* |
| *R oryzae* | *Sced. apiosporum* | *Sced. prolificans* |
| *Scop. Brevicaulis* | *H. capsulatum* | *M. canis* |
| *T. quickeanum* | *T. rubrum* | *S. aureus* |
| *P. mirabilis* | *E. coli* | *S. marcescens* |

-continued

| | | |
|---|---|---|
| *P. aeruginosa* | *E. cloacae* | *C. freundii* |
| *E. faecalis* | *S. pneumoniae* | *S. maltophilia* |
| *K. pneumoniae* | *E. aerogenes* | *A. baumani* |
| *K. oxytoca* | *E. faecium* | Human DNA |

Design of Oligonucleotide Primers and Probes for *Aspergillus* Spp.

Following DNA sequencing, the exon 3 RPS7 317 bp, sequence information generated for PCR products amplified from *Aspergillus* spp. representing the different sequence types obtained for each species (SEQ ID NO 326 through to SEQ ID NO 377) were aligned and analysed using bioinformatics tools, including Clustal W and BLAST programs. PCR primer SEQ ID NO 418 was designed for amplification of a 125 by region of the RPS7 gene in *A. fumigatus* and other *Aspergillus* spp. in combination with PCR primer SEQ ID NO 415. For the identification of *A. fumigatus*, oligonucleotide probes SEQ ID NO 419 through to SEQ ID NO 424 were designed. For the identification of *A. candidus*, oligonucleotide probes SEQ ID NO 425 through to SEQ ID NO 428 were designed. For the identification of *A. terreus*, oligonucleotide probes SEQ ID NO 429 through to SEQ ID NO 432 were designed. For the identification of *A. versicolor*, oligonucleotide probes SEQ ID NO 433 through to SEQ ID NO 436 were designed. For the identification of *A. nidulans*, oligonucleotide probes SEQ ID NO 437 through to SEQ ID NO 440 were designed. For the identification of *A. flavus* and oligonucleotide probes SEQ ID NO 441 and SEQ ID NO 442 were designed. Oligonucleotide probes SEQ ID NO 443 through SEQ ID NO 448 were designed for the identification of *A. clavatus.*

Nucleic Acid Based Diagnostic Assay for *Aspergillus* species, *A. fumigatus:*

Figure 5:
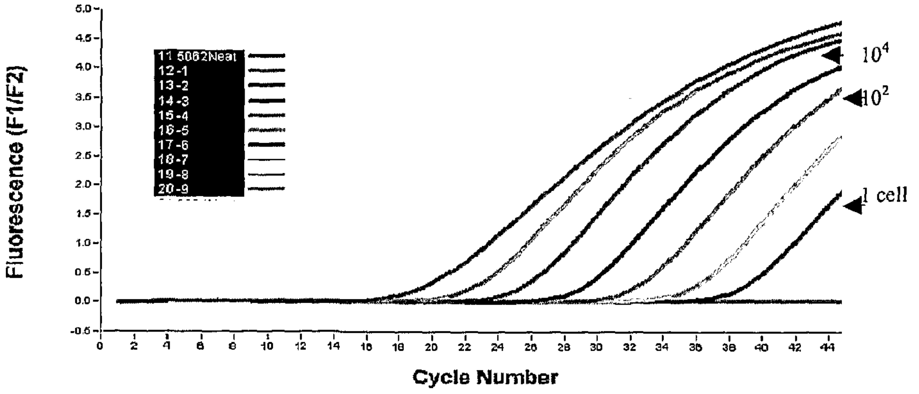
FIG. 5: Limit of detection of the real-time PCR assay for *A. fumigatus* based on rps7 gene and incorporating primers SEQ ID No 418 and SEQ ID NO 415 and TaqMan probe SEQ ID NO 419 and including serial dilutions ($10^6$-1 cell equivalent) of *A. fumigatus* genomic DNA 5062-Detection limit 1 cell equivalent.
Figure 6:
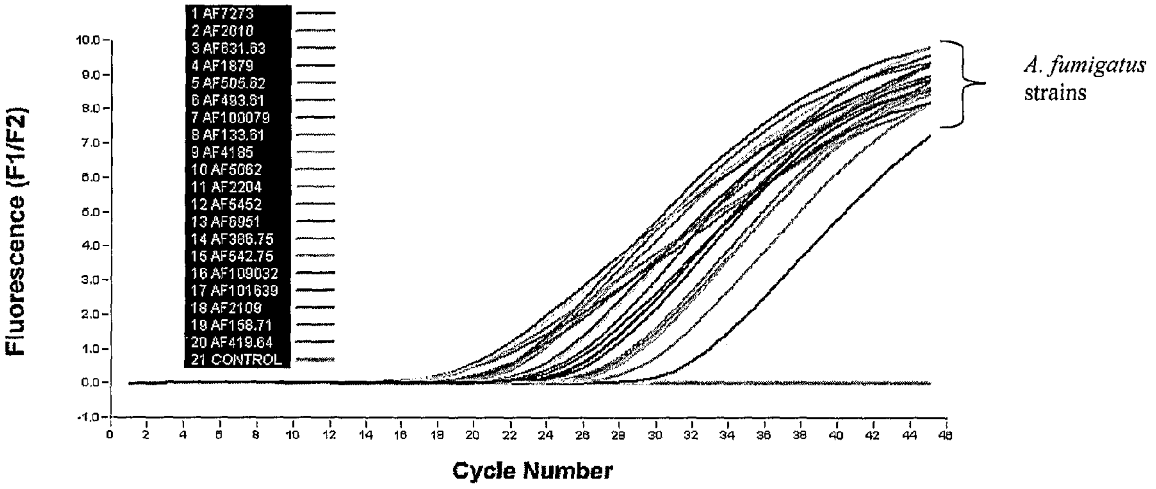
FIG. 6: Inclusivity testing of the real-time PCR assay for *A. fumigatus*(20 strains of *A. fumigatus*) based on rps7 gene and incorporating primers SEQ ID No 418 and SEQ ID NO 415 and TaqMan probe SEQ ID NO 419—all *A. fumigatus* strains detected.
Figure 7:
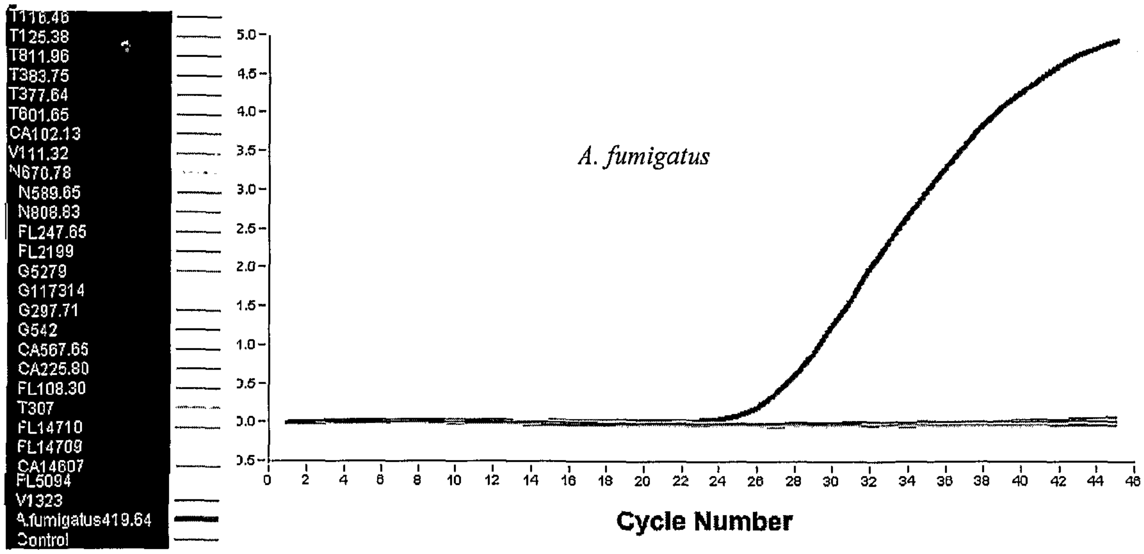
FIG. 7: Specificity testing of the real-time PCR assay for *A. fumigatus* based on rps7 gene and incorporating primers SEQ ID No 418 and SEQ ID NO 415 and TaqMan probe SEQ ID NO 419. Cross-reactivity testing panel included a range of *Aspergillus* species-no cross reaction detected.

Nucleic acid diagnostics assays were designed for *Aspergillus* spp using the primers SEQ ID NO 414 through to SEQ ID NO 418 and oligonucleotide probes SEQ ID 419 through to SEQ ID NO 448. One example of the assays developed is a real-time PCR TaqMan assay for *A. fumigatus* including primer sequences SEQ ID NO 418 and SEQ ID NO 415 and DNA oligonucleotide probe SEQ ID NO 419. This assay was configured on the LightCycler real-time PCR machine and performed using the conditions and reagents described in Table 4. The limit of detection (LOD) or sensitivity of the assay was determined using 10-serial dilutions ($10^6$-1 cell equivalent) of genomic DNA from *A. fumigatus* strain number 5062. FIG. 5 shows the LOD for the *A. fumigatus* assay as 1 genome equivalent. The specificity of the *A. fumigatus* assay was confirmed by testing the *A. fumigatus* assay for inclusivity using 20 strains of *A. fumigatus*. All 20 strains were detected in the assay (FIG. 6). The *A. fumigatus* assay was checked for cross-reactivity against a panel including 20 species of *Candida,* 24 species dermatophytes, 8 species of *Aspergillus* spp. 15 bacterial species and human DNA. There was no cross-reaction of these strains/species or human DNA (Table 5) in the *A. fumigatus* assay. FIG. 7 shows an example of cross-reactivity study performed using a panel of *Aspergillus* species DNA.

In so far as any sequence disclosed herein differs from its counterpart in the attached sequence listing in PatentIn3.3 software, the sequences within this body of text are to be considered as the correct version.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

SEQ IDs

Sites of probes, oligonucleotides etc. are shown in bold and underlined.

N or x=any nucleotide; w=a/t, m=a/c, r=a/g, k=g/t, s=c/g, y=c/t, h=a/t/c, v=a/g/c, d=a/g/t, b=g/t/c.

In some cases, specific degeneracy options are indicated in parenthesis: e.g.: (a/g) is either A or G.

| | | |
|---|---|---|
| SEQ ID NO 1 | TAACATCGTAGGCTAATC | CASP |
| SEQ ID NO 2 | TCTGGGTATCTGATGTTCT | Can2R-n15 |
| SEQ ID NO 3 | TCTGGGTATCTGAT(a/g)GTTCT | Can2R-d15: |
| SEQ ID NO 4 | TCTGGGTATCTGATAGTTCT | Can2R-A15: |
| SEQ ID NO 5 | TCTGGGTATCTGATGGTTCT | Can2R-G15: |
| SEQ ID NO 6 | TAACATCGTAGGCTAATC | *C. albicans* antisense probe |
| SEQ ID NO 7 | GATTAGCCTACGATGTTA | *C. albicans* specific probe |
| RPS7 primer (i) | | |
| SEQ ID NO 8 | ATGGnTAGAGGnCCAAAGAAnCA | |
| SEQ ID NO 9 | ATGG(c/g)TAGAGG(a/t)CCAAAGAA(g/a)CA | |
| SEQ ID NO 10 | ATGGCTAGAGGnCCAAAGAAGCA | |
| SEQ ID NO 11 | ATGGCTAGAGGnCCAAAGAAACA | |
| SEQ ID NO 12 | ATGGGTAGAGGnCCAAAGAAGCA | |
| SEQ ID NO 13 | ATGGGTAGAGGnCCAAAGAAACA | |
| SEQ ID NO 14 | ATGGCTAGAGGACCAAAGAAGCA | |
| SEQ ID NO 15 | ATGGCTAGAGGACCAAAGAAACA | |
| SEQ ID NO 16 | ATGGCTAGAGGTCCAAAGAAGCA | |
| SEQ ID NO 17 | ATGGCTAGAGGTCCAAAGAAACA | |
| SEQ ID NO 18 | ATGGGTAGAGGACCAAAGAAGCA | |
| SEQ ID NO 19 | ATGGGTAGAGGACCAAAGAAACA | |
| SEQ ID NO 20 | ATGGGTAGAGGTCCAAAGAAGCA | |
| SEQ ID NO 21 | ATGGGTAGAGGTCCAAAGAAACA | |
| RPS7 primer (ii) | | |
| SEQ ID NO 22 | GCnCCAAGACCATCnGCTGGTCCnCACA | |
| SEQ ID NO 23 | GC(c/t/a)CCAAGACCATC(t/c)GCTGGTCC(a/t)CACA | |
| SEQ ID NO 24 | GCCCCAAGACCATCTGCTGGTCCACACA | |
| SEQ ID NO 25 | GCTCCAAGACCATCTGCTGGTCCACACA | |
| SEQ ID NO 26 | GCACCAAGACCATCTGCTGGTCCACACA | |
| SEQ ID NO 27 | GCCCCAAGACCATCCGCTGGTCCACACA | |
| SEQ ID NO 28 | GCTCCAAGACCATCCGCTGGTCCACACA | |
| SEQ ID NO 29 | GCACCAAGACCATCCGCTGGTCCACACA | |
| SEQ ID NO 30 | GCCCCAAGACCATCTGCTGGTCCTCACA | |
| SEQ ID NO 31 | GCTCCAAGACCATCTGCTGGTCCTCACA | |
| SEQ ID NO 32 | GCACCAAGACCATCTGCTGGTCCTCACA | |
| SEQ ID NO 33 | GCCCCAAGACCATCCGCTGGTCCTCACA | |

-continued

SEQ ID NO 34 GCTCCAAGACCATCCGCTGGTCCTCACA

SEQ ID NO 35 GCACCAAGACCATCCGCTGGTCCTCACA

RPS7 primer (iii)
SEQ ID NO 36 CCAGCTGGTTTCATGGATGTnATCA

SEQ ID NO 37 CCCAGCTGGTTTCATGGATGT(c/t)ATCA

SEQ ID NO 38 CCCAGCTGGTTTCATGGATGTCATCA

SEQ ID NO 39 CCCAGCTGGTTTCATGGATGTTATCA

SEQ ID NO 40 AGCTGGTTTCATGGATGT Can1F genus specific primer

RPS7 primer (iv)
SEQ ID NO 41 AGAACnATCAGATACCCAGAnCCA

SEQ ID NO 42 AGAAC(c/t)ATCAGATACCCAGA(c/t)CCA

SEQ ID NO 43 AGAACTATCAGATACCCAGACCCA

SEQ ID NO 44 AGAACTATCAGATACCCAGATCCA

SEQ ID NO 45 AGAACCATCAGATACCCAGACCCA

SEQ ID NO 46 AGAACnATCAGATACCCAGA

SEQ ID NO 47 AGAAC(c/t)ATCAGATACCCAGA degen.3'-5'genus spec. primer

SEQ ID NO 48 AGAACCATCAGATACCCAGA

SEQ ID NO 49 AGAACTATCAGATACCCAGA

SEQ ID NO: 50: *S. cerevisiae*
AGCTGGTTTC ATGGATGTCT AGATGCCACC AATGAAAACT TCAGATTGGT CTACGATGTC AAGGGTAGAT

TCGCTGTCCA CCGTATCACC GATGAAGAAG CTTCTTACAA GTTGGGTAAG GTCAAGAAGG TTCAATTAGG

TAAGAAGGGT GTTCCATACG TTGTTACCCA CGATGGTAGA ACTATCAGAT ACCCAGA

SEQ ID NO: 51:
AGCUGGUUUC AUGGAUGUCU AGAUGCCACC AAUGAAAACU UCAGAUUGGU CUACGAUGUC AAGGGUAGAU

UCGCUGUCCA CCGUAUCACC GAUGAAGAAG CUUCUUACAA GUUGGGUAAG GUCAAGAAGG UUCAAUUAGG

UAAGAAGGGU GUUCCAUACG UUGUUACCCA CGAUGGUAGA ACUAUCAGAU ACCCAGA

SEQ ID NO: 52; *C. glabrata*
AGCTGGTTTC ATGGATGTTT GGAAGCTACC AACGAAAACT TCAGATTGGT CTACGACGTC AAGGGTAGAT

TCGCTGTCCA CCGTATCACT GACGAAGAAG CTTCCTACAA GTTGGGTAAG GTCAAGAAGG TCCAATTGGG

TAAGAAGGGT GTTCCATACG TTGTCACTGA CGATGGTAGA ACTATCAGAT ACCCAGA

SEQ ID NO: 53; *C. glabrata*
AGCUGGUUUC AUGGAUGUUU GGAAGCUACC AACGAAAACU UCAGAUUGGU CUACGACGUC AAGGGUAGAU

UCGCUGUCCA CCGUAUCACU GACGAAGAAG CUUCCUACAA GUUGGGUAAG GUCAAGAAGG UCCAAUUGGG

UAAGAAGGGU GUUCCAUACG UUGUCACUGA CGAUGGUAGA ACUAUCAGAU ACCCAGA

SEQ ID NO: 54; *E. gossypii*
AGCTGGTTTC ATGGATGTCT AGAGGCTACC AACGAGAACT TCAGATTGGT ATACGATGTC AAGGGCAGAT

TTGCTGTCCA CCGTATCACC GATGAGGAGG CTACTTACAA GTTGGGTAAG GTTAAGCGCG TTCAGCTAGG

TAAGAAGGGT GTCCCATACG TGGTCACTCA CGACGGCAGA ACCATCAGAT ACCCAGA

SEQ ID NO: 55; *E. gossypii*
AGCUGGUUUC AUGGAUGUCU AGAGGCUACC AACGAGAACU UCAGAUUGGU AUACGAUGUC AAGGGCAGAU

UUGCUGUCCA CCGUAUCACC GAUGAGGAGG CUACUUACAA GUUGGGUAAG GUUAAGCGCG UUCAGCUAGG

UAAGAAGGGU GUCCCAUACG UGGUCACUCA CGACGGCAGA ACCAUCAGAU ACCCAGA

-continued

SEQ ID NO: 56; *K. lactis*
AGCTGGTTTC ATGGATGTTT GGAAGCTACC AACGAAAACT TCAGATTGGT CTACGATGTT AAGGGTAGAT

TCGCTGTCCA CCGTATCACT GATGAAGAAG CTTCCTACAA GTTGGCTAAG GTCAAGAAGG TTCAACTAGG

TAAGAAGGGT ATTCCATACG TCGTTACCCA CGACGGTAGA ACCATCAGAT ACCCAGA

SEQ ID NO: 57; *K. lactis*
AGCUGGUUUC AUGGAUGUUU GGAAGCUACC AACGAAAACU UCAGAUUGGU CUACGAUGUU AAGGGUAGAU

UCGCUGUCCA CCGUAUCACU GAUGAAGAAG CUUCCUACAA GUUGGCUAAG GUCAAGAAGG UUCAACUAGG

UAAGAAGGGU AUUCCAUACG UCGUUACCCA CGACGGUAGA ACCAUCAGAU ACCCAGA

SEQ ID NO: 58; *C. albicans* RPS7
AGCTGGTTTC ATGGATGTCT GGAAGCTACC AACGAACATT TCAGATTAGC CTACGATGTT AAAGGTAAAT

TCGCCGTTCA CAGAATTTCT GCTGAAGAAG CTGTCTACAA ATTGGGTAAA GTCAAGAAAG TCCAATTAGG

TAAGAAAGGT GTTCCATACG TTGTTACCCA CGACGGTAGA ACTATCAGAT ACCCAGA

SEQ ID NO: 59; *C. albicans* RPS7
AGCUGGUUUC AUGGAUGUCU GGAAGCUACC AACGAACAUU UCAGAUUAGC CUACGAUGUU AAAGGUAAAU

UCGCCGUUCA CAGAAUUUCU GCUGAAGAAG CUGUCUACAA AUUGGGUAAA GUCAAGAAAG UCCAAUUAGG

UAAGAAAGGU GUUCCAUACG UUGUUACCCA CGACGGUAGA ACUAUCAGAU ACCCAGA

SEQ ID NO: 60; *D. hansenii*
AGCTGGTTTC ATGGATGTCT AGAAGCTACC AACGAACACT TCAGATTAAT CTATGATGTC AAGGGTAGAT

TCACTGTCCA CAGAATCACT GCTGAAGAAG CTTCTTACAA GTTAGCTAAG GTCAAGAAGG TCCAATTAGG

TAAGAGAGGT ATTCCATACG TTGTCACCCA CGACGGTAGA ACTATCAGAT ACCCAGA

SEQ ID NO: 61; *D. hansenii*
AGCUGGUUUC AUGGAUGUCU AGAAGCUACC AACGAACACU UCAGAUUAAU CUAUGAUGUC AAGGGUAGAU

UCACUGUCCA CAGAAUCACU GCUGAAGAAG CUUCUUACAA GUUAGCUAAG GUCAAGAAGG UCCAAUUAGG

UAAGAGAGGU AUUCCAUACG UUGUCACCCA CGACGGUAGA ACUAUCAGAU ACCCAGA

SEQ ID NO: 62; *C. albicans*
ACCTACCCAGCTGGTTTCATGGATGTCATCACCTTGGAAGCTACCAACGAACATTTCAGA 300

TTAGCCTACGATGTTAAAGGTAAATTCGCCGTTCACAGAATTTCTGCTGAAGAAGCTGTC 360

TACAAATTGGGTAAAGTCAAGAAAGTCCAATTAGGTAAGAAAGGTGTTCCATACGTTGTT 420

ACCCACGACGGTAGAACTATCAGATACCCAGATCCATTGATCAGAGCTAACGATACCGTT 480

SEQ ID NO: 63; *C. albicans*
ACCUACCCAGCUGGUUUCAUGGAUGUCAUCACCUUGGAAGCUACCAACGAACAUUUCAGA 300

UUAGCCUACGAUGUUAAAGGUAAAUUCGCCGUUCACAGAAUUUCUGCUGAAGAAGCUGUC 360

UACAAAUUGGGUAAAGUCAAGAAAGUCCAAUUAGGUAAGAAAGGUGUUCCAUACGUUGUU 420

ACCCACGACGGUAGAACUAUCAGAUACCCAGAUCCAUUGAUCAGAGCUAACGAUACCGUU 480

SEQ ID NO: 64; *C. glabrata*
ACCTACCCAGCTGGTTTCATGGATGTTATCACCTTGGAAGCTACCAACGAAAACTTCAGA 300

TTGGTCTACGACGTCAAGGGTAGATTCGCTGTCCACCGTATCACTGACGAAGAAGCTTCC 360

TACAAGTTGGGTAAGGTCAAGAAGGTCCAATTGGGTAAGAAGGGTGTTCCATACGTTGTC 420

ACTGACGATGGTAGAACTATCAGATACCCAGACCCAAACATCAAGGTCAATGACACCGTC 480

SEQ ID NO: 65; *C. glabrata*
ACCUACCCAGCUGGUUUCAUGGAUGUUAUCACCUUGGAAGCUACCAACGAAAACUUCAGA 300

UUGGUCUACGACGUCAAGGGUAGAUUCGCUGUCCACCGUAUCACUGACGAAGAAGCUUCC 360

UACAAGUUGGGUAAGGUCAAGAAGGUCCAAUUGGGUAAGAAGGGUGUUCCAUACGUUGUC 420

ACUGACGAUGGUAGAACUAUCAGAUACCCAGACCCAAACAUCAAGGUCAAUGACACCGUC 480

-continued

SEQ ID NO: 66; *C. tropicalis*
-----------------------------------GGAAGCTACCAACGAACACTTCAGA 25

TTGATTTACGATGTTAAAGGTAAATTCGCTGTTCACAGAATTTCTGCTGAAGAAGCTTCT 85

TACAAATTAGGTAAAGTCAAGAAGGTTCAATTAGGTAAAAAAGGTGTTCCATACGTTGTC 145

ACCCACGATGGTAGAACCATCAGATACCCAGA---------------------------- 177

SEQ ID NO: 67; *C. Tropicalis*
-----------------------------------GGAAGCUACCAACGAACACUUCAGA 25

UUGAUUUACGAUGUUAAAGGUAAAUUCGCUGUUCACAGAAUUUCUGCUGAAGAAGCUUCU 85

UACAAAUUAGGUAAAGUCAAGAAGGUUCAAUUAGGUAAAAAAGGUGUUCCAUACGUUGUC 145

ACCCACGAUGGUAGAACCAUCAGAUACCCAGA---------------------------- 177

SEQ ID NO: 68; *C. parapsilosis*
-----------------------------------GGAAGCCACCAATGAAAACTTTAGA 25

TTGATTTACGATGTCAAAGGTAGATTTGCTGTCCACAGAATCTCAGCTGAAGAAGCCACT 85

TACAAATTGGGTAAAGTCAAGAGAGTCCAATTGGGTAAGAAGGGAATCCCATACGTTGTC 145

ACCCACGATGGTAGAACCATCAGATACCCAGA---------------------------- 177

SEQ ID NO: 69; *C. parapsilosis*
-----------------------------------GGAAGCCACCAAUGAAAACUUUAGA 25

UUGAUUUACGAUGUCAAAGGUAGAUUUGCUGUCCACAGAAUCUCAGCUGAAGAAGCCACU 85

UACAAAUUGGGUAAAGUCAAGAGAGUCCAAUUGGGUAAGAAGGGAAUCCCAUACGUUGUC 145

ACCCACGAUGGUAGAACCAUCAGAUACCCAGA---------------------------- 177

SEQ ID NO: 70; *C. dubliniensis*
-----------------------------------GGAAGCTACCAACGAAAACTTCAGA 25

TTGGTCTACGACGTCAAGGGTAGATTCGCTGTCCACCGTATCACTGACGAAGAAGCTTCC 85

TACAAGTTGGGTAAGGTCAAGAAGGTCCAATTGGGTAAGAAGGGTGTTCCATACGTTGTC 145

ACTGACGATGGTAGAACYATCAGATACCCAGA---------------------------- 177

SEQ ID NO: 71; *C. dubliniensis*
-----------------------------------GGAAGCUACCAACGAAAACUUCAGA 25

UUGGUCUACGACGUCAAGGGUAGAUUCGCUGUCCACCGUAUCACUGACGAAGAAGCUUCC 85

UACAAGUUGGGUAAGGUCAAGAAGGUCCAAUUGGGUAAGAAGGGUGUUCCAUACGUUGUC 145

ACUGACGAUGGUAGAACYAUCAGAUACCCAGA---------------------------- 177

SEQ ID NO: 72; >*C. albicans*369
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

SEQ ID NO: 73; >*C. albicans*369
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 74; >*C. albicans*178
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

-continued

SEQ ID NO: 75; >*C. albicans*178
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 76; >*C. albicans*180
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

SEQ ID NO: 77; >*C. albicans*180
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 78; >*C. albicans*320
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

SEQ ID NO: 79; >*C. albicans*320
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 80; >*C. albicans*765
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

SEQ ID NO: 81; >*C. albicans*765
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 82; >*C. albicans*16733
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

SEQ ID NO: 83; >*C. albicans*16733
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 84; >*C. albicans*15640
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

SEQ ID NO: 85; >*C. albicans*15640
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

-continued

SEQ ID NO: 86; >*C. albicans*9559
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

SEQ ID NO: 87; >*C. albicans*9559
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 88; >*C. albicans*4154
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

SEQ ID NO: 89; >*C. albicans*4154
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 90; >*C. albicans*2700
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

SEQ ID NO: 91; >*C. albicans*2700
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 92; >*C. albicans*562
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

SEQ ID NO: 93; >*C. albicans*562
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 94; >*C. albicans*3822
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

SEQ ID NO: 95; >*C. albicans*3822
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 96; >*C. albicans*3156
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

-continued

SEQ ID NO: 97; >*C. albicans*3156
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 98; >*C. albicans*3345
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

SEQ ID NO: 99; >*C. albicans*3345
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 100; >*C. albicans*3328
CATCACCTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAG

SEQ ID NO: 101; >*C. albicans*3328
CAUCACCUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAG

SEQ ID NO: 102; >*C. glabrata*90876
CATCACCTTGGAAGCTACCAACGAAAACTTCAGATTGGTCTACGACGTCAAGGGTAGATTCGCTGTCCACCGTATCACTG

ACGAAGAAGCTTCCTACAAGTTGGGTAAGGTCAAGAAGGTCCAATTGGGTAAGAAGGGTGTTCCATACGTTGTCACTGAC

GATGGTAGAACYATCAGATACCCAG

SEQ ID NO: 103; >*C. glabrata*90876
CAUCACCUUGGAAGCUACCAACGAAAACUUCAGAUUGGUCUACGACGUCAAGGGUAGAUUCGCUGUCCACCGUAUCACUG

ACGAAGAAGCUUCCUACAAGUUGGGUAAGGUCAAGAAGGUCCAAUUGGGUAAGAAGGGUGUUCCAUACGUUGUCACUGAC

GAUGGUAGAACYAUCAGAUACCCAG

SEQ ID NO: 104; >*C. glabrata*4692
CATCACCTTGGAAGCTACCAACGAAAACTTCAGATTGGTCTACGACGTCAAGGGTAGATTCGCTGTCCACCGTATCACTG

ACGAAGAAGCTTCCTACAAGTTGGGTAAGGTCAAGAAGGTCCAATTGGGTAAGAAGGGTGTTCCATACGTTGTCACTGAC

GATGGTAGAACYATCAGATACCCAG

SEQ ID NO: 105; >*C. glabrata*4692
CAUCACCUUGGAAGCUACCAACGAAAACUUCAGAUUGGUCUACGACGUCAAGGGUAGAUUCGCUGUCCACCGUAUCACUG

ACGAAGAAGCUUCCUACAAGUUGGGUAAGGUCAAGAAGGUCCAAUUGGGUAAGAAGGGUGUUCCAUACGUUGUCACUGAC

GAUGGUAGAACYAUCAGAUACCCAG

SEQ ID NO: 106; >*C. glabrata*205444
CATCACCTTGGAAGCTACCAACGAAAACTTCAGATTGGTCTACGACGTCAAGGGTAGATTCGCTGTCCACCGTATCACTG

ACGAAGAAGCTTCCTACAAGTTGGGTAAGGTCAAGAAGGTCCAATTGGGTAAGAAGGGTGTTCCATACGTTGTCACTGAC

GATGGTAGAACYATCAGATACCCAG

SEQ ID NO: 107; >*C. glabrata*205444
CAUCACCUUGGAAGCUACCAACGAAAACUUCAGAUUGGUCUACGACGUCAAGGGUAGAUUCGCUGUCCACCGUAUCACUG

ACGAAGAAGCUUCCUACAAGUUGGGUAAGGUCAAGAAGGUCCAAUUGGGUAAGAAGGGUGUUCCAUACGUUGUCACUGAC

GAUGGUAGAACYAUCAGAUACCCAG

-continued

SEQ ID NO: 108; >*C. glabrata*10269
CATCACCTTGGAAGCTACCAACGAAAACTTCAGATTGGTCTACGACGTCAAGGGTAGATTCGCTGTCCACCGTATCACTG

ACGAAGAAGCTTCCTACAAGTTGGGTAAGGTCAAGAAGGTCCAATTGGGTAAGAAGGGTGTTCCATACGTTGTCACTGAC

GATGGTAGAACYATCAGATACCCAG

SEQ ID NO: 109; >*C. glabrata*10269
CAUCACCUUGGAAGCUACCAACGAAAACUUCAGAUUGGUCUACGACGUCAAGGGUAGAUUCGCUGUCCACCGUAUCACUG

ACGAAGAAGCUUCCUACAAGUUGGGUAAGGUCAAGAAGGUCCAAUUGGGUAAGAAGGGUGUUCCAUACGUUGUCACUGAC

GAUGGUAGAACYAUCAGAUACCCAG

SEQ ID NO: 110; >*C. glabrata*9556
CATCACCTTGGAAGCTACCAACGAAAACTTCAGATTGGTCTACGACGTCAAGGGTAGATTCGCTGTCCACCGTATCACTG

ACGAAGAAGCTTCCTACAAGTTGGGTAAGGTCAAGAAGGTCCAATTGGGTAAGAAGGGTGTTCCATACGTTGTCACTGAC

GATGGTAGAACYATCAGATACCCAG

SEQ ID NO: 111; >*C. glabrata*9556
CAUCACCUUGGAAGCUACCAACGAAAACUUCAGAUUGGUCUACGACGUCAAGGGUAGAUUCGCUGUCCACCGUAUCACUG

ACGAAGAAGCUUCCUACAAGUUGGGUAAGGUCAAGAAGGUCCAAUUGGGUAAGAAGGGUGUUCCAUACGUUGUCACUGAC

GAUGGUAGAACYAUCAGAUACCCAG

SEQ ID NO: 112; >*C. glabrata*5563
CATCACCTTGGAAGCTACCAACGAAAACTTCAGATTGGTCTACGACGTCAAGGGTAGATTCGCTGTCCACCGTATCACTG

ACGAAGAAGCTTCCTACAAGTTGGGTAAGGTCAAGAAGGTCCAATTGGGTAAGAAGGGTGTTCCATACGTTGTCACTGAC

GATGGTAGAACYATCAGATACCCAG

SEQ ID NO: 113; >*C. glabrata*5563
CAUCACCUUGGAAGCUACCAACGAAAACUUCAGAUUGGUCUACGACGUCAAGGGUAGAUUCGCUGUCCACCGUAUCACUG

ACGAAGAAGCUUCCUACAAGUUGGGUAAGGUCAAGAAGGUCCAAUUGGGUAAGAAGGGUGUUCCAUACGUUGUCACUGAC

GAUGGUAGAACYAUCAGAUACCCAG

SEQ ID NO: 114; >*C. glabrata*3959
CATCACCTTGGAAGCTACCAACGAAAACTTCAGATTGGTCTACGACGTCAAGGGTAGATTCGCTGTCCACCGTATCACTG

ACGAAGAAGCTTCCTACAAGTTGGGTAAGGTCAAGAAGGTCCAATTGGGTAAGAAGGGTGTTCCATACGTTGTCACTGAC

GATGGTAGAACYATCAGATACCCAG

SEQ ID NO: 115; >*C. glabrata*3959
CAUCACCUUGGAAGCUACCAACGAAAACUUCAGAUUGGUCUACGACGUCAAGGGUAGAUUCGCUGUCCACCGUAUCACUG

ACGAAGAAGCUUCCUACAAGUUGGGUAAGGUCAAGAAGGUCCAAUUGGGUAAGAAGGGUGUUCCAUACGUUGUCACUGAC

GAUGGUAGAACYAUCAGAUACCCAG

SEQ ID NO: 116; >*C. glabrata*138
CATCACCTTGGAAGCTACCAACGAAAACTTCAGATTGGTCTACGACGTCAAGGGTAGATTCGCTGTCCACCGTATCACTG

ACGAAGAAGCTTCCTACAAGTTGGGTAAGGTCAAGAAGGTCCAATTGGGTAAGAAGGGTGTTCCATACGTTGTCACTGAC

GATGGTAGAACYATCAGATACCCAG

SEQ ID NO: 117; >*C. glabrata*138
CAUCACCUUGGAAGCUACCAACGAAAACUUCAGAUUGGUCUACGACGUCAAGGGUAGAUUCGCUGUCCACCGUAUCACUG

ACGAAGAAGCUUCCUACAAGUUGGGUAAGGUCAAGAAGGUCCAAUUGGGUAAGAAGGGUGUUCCAUACGUUGUCACUGAC

GAUGGUAGAACYAUCAGAUACCCAG

SEQ ID NO: 118; >*C. glabrata*3605
TATCACCTTGGAAGCTACCAACGAAAACTTCAGATTGGTCTACGACGTCAAGGGTAGATTCGCTGTCCACCGTATCACTG

ACGAAGAAGCTTCCTACAAGTTGGGTAAGGTCAAGAAGGTCCAATTGGGTAAGAAGGGTGTTCCATACGTTGTCACTGAC

GATGGTAGAACYATCAGATACCCAG

-continued

SEQ ID NO: 119; >*C. glabrata*3605
UAUCACCUUGGAAGCUACCAACGAAAACUUCAGAUUGGUCUACGACGUCAAGGGUAGAUUCGCUGUCCACCGUAUCACUG

ACGAAGAAGCUUCCUACAAGUUGGGUAAGGUCAAGAAGGUCCAAUUGGGUAAGAAGGGUGUUCCAUACGUUGUCACUGAC

GAUGGUAGAACYAUCAGAUACCCAG

SEQ ID NO: 120; >*C. glabrata*3897
TATCACCTTGGAAGCTACCAACGAAAACTTCAGATTGGTCTACGACGTCAAGGGTAGATTCGCTGTCCACCGTATCACTG

ACGAAGAAGCTTCCTACAAGTTGGGTAAGGTCAAGAAGGTCCAATTGGGTAAGAAGGGTGTTCCATACGTTGTCACTGAC

GATGGTAGAACYATCAGATACCCAG

SEQ ID NO: 121; >*C. glabrata*3897
UAUCACCUUGGAAGCUACCAACGAAAACUUCAGAUUGGUCUACGACGUCAAGGGUAGAUUCGCUGUCCACCGUAUCACUG

ACGAAGAAGCUUCCUACAAGUUGGGUAAGGUCAAGAAGGUCCAAUUGGGUAAGAAGGGUGUUCCAUACGUUGUCACUGAC

GAUGGUAGAACYAUCAGAUACCCAG

SEQ ID NO: 122; >*C. glabrata*8018
TATCACCTTGGAAGCTACCAACGAAAACTTCAGATTGGTCTACGACGTCAAGGGTAGATTCGCTGTCCACCGTATCACTG

ACGAAGAAGCTTCCTACAAGTTGGGTAAGGTCAAGAAGGTCCAATTGGGTAAGAAGGGTGTTCCATACGTTGTCACTGAC

GATGGTAGAACYATCAGATACCCAG

SEQ ID NO: 123; >*C. glabrata*8018
UAUCACCUUGGAAGCUACCAACGAAAACUUCAGAUUGGUCUACGACGUCAAGGGUAGAUUCGCUGUCCACCGUAUCACUG

ACGAAGAAGCUUCCUACAAGUUGGGUAAGGUCAAGAAGGUCCAAUUGGGUAAGAAGGGUGUUCCAUACGUUGUCACUGAC

GAUGGUAGAACYAUCAGAUACCCAG

SEQ ID NO: 124; >*C. glabrata*3863
TATCACCTTGGAAGCTACCAACGAAAACTTCAGATTGGTCTACGACGTCAAGGGTAGATTCGCTGTCCACCGTATCACTG

ACGAAGAAGCTTCCTACAAGTTGGGTAAGGTCAAGAAGGTCCAATTGGGTAAGAAGGGTGTTCCATACGTTGTCACTGAC

GATGGTAGAACYATCAGATACCCAG

SEQ ID NO: 125; >*C. glabrata*3863
UAUCACCUUGGAAGCUACCAACGAAAACUUCAGAUUGGUCUACGACGUCAAGGGUAGAUUCGCUGUCCACCGUAUCACUG

ACGAAGAAGCUUCCUACAAGUUGGGUAAGGUCAAGAAGGUCCAAUUGGGUAAGAAGGGUGUUCCAUACGUUGUCACUGAC

GAUGGUAGAACYAUCAGAUACCCAG

SEQ ID NO: 126; >*C. parapsilosis*3902
CATTACTTTGGAAGCCACYAATGAAAACTTTAGATTGATTTACGATGTCAAAGGTAGATTTGCTGTCCACAGAATCTCAG

CTGAAGAAGCCACTTACAAATTGGGTAAAGTCAAGAGAGTCCAATTGGGTAAGAAGGGAATCCCATACGTTGTCACCCAC

GATGGTAGAACYATCAGATACCCAG

SEQ ID NO: 127; >*C. parapsilosis*3902
CAUUACUUUGGAAGCCACYAAUGAAAACUUUAGAUUGAUUUACGAUGUCAAAGGUAGAUUUGCUGUCCACAGAAUCUCAG

CUGAAGAAGCCACUUACAAAUUGGGUAAAGUCAAGAGAGUCCAAUUGGGUAAGAAGGGAAUCCCAUACGUUGUCACCCAC

GAUGGUAGAACYAUCAGAUACCCAG

SEQ ID NO: 128; >*C. parapsilosis*604
CATTACTTTGGAAGCCACYAATGAAAACTTTAGATTGATTTACGATGTCAAAGGTAGATTTGCTGTCCACAGAATCTCAG

CTGAAGAAGCCACTTACAAATTGGGTAAAGTCAAGAGAGTCCAATTGGGTAAGAAGGGAATCCCATACGTTGTCACCCAC

GATGGTAGAACYATCAGATACCCAG

SEQ ID NO: 129; >*C. parapsilosis*604
CAUUACUUUGGAAGCCACYAAUGAAAACUUUAGAUUGAUUUACGAUGUCAAAGGUAGAUUUGCUGUCCACAGAAUCUCAG

CUGAAGAAGCCACUUACAAAUUGGGUAAAGUCAAGAGAGUCCAAUUGGGUAAGAAGGGAAUCCCAUACGUUGUCACCCAC

GAUGGUAGAACYAUCAGAUACCCAG

-continued

SEQ ID NO: 130; >*C. parapsilosis*2194
CATTACTTTGGAAGCCACYAATGAAAACTTTAGATTGATTTACGATGTCAAAGGTAGATTTGCTGTCCACAGAATCTCAG

CTGAAGAAGCCACTTACAAATTGGGTAAAGTCAAGAGAGTCCAATTGGGTAAGAAGGGAATCCCATACGTTGTCACCCAC

GATGGTAGAACYATCAGATACCCAG

SEQ ID NO: 131; >*C. parapsilosis*2194
CAUUACUUUGGAAGCCACYAAUGAAAACUUUAGAUUGAUUUACGAUGUCAAAGGUAGAUUUGCUGUCCACAGAAUCUCAG

CUGAAGAAGCCACUUACAAAUUGGGUAAAGUCAAGAGAGUCCAAUUGGGUAAGAAGGGAAUCCCAUACGUUGUCACCCAC

GAUGGUAGAACYAUCAGAUACCCAG

SEQ ID NO: 132; >*C. parapsilosis*2196
CATTACTTTGGAAGCCACYAATGAAAACTTTAGATTGATTTACGATGTCAAAGGTAGATTTGCTGTCCACAGAATCTCAG

CTGAAGAAGCCACTTACAAATTGGGTAAAGTCAAGAGAGTCCAATTGGGTAAGAAGGGAATCCCATACGTTGTCACCCAC

GATGGTAGAACYATCAGATACCCAG

SEQ ID NO: 133; >*C. parapsilosis*2196
CAUUACUUUGGAAGCCACYAAUGAAAACUUUAGAUUGAUUUACGAUGUCAAAGGUAGAUUUGCUGUCCACAGAAUCUCAG

CUGAAGAAGCCACUUACAAAUUGGGUAAAGUCAAGAGAGUCCAAUUGGGUAAGAAGGGAAUCCCAUACGUUGUCACCCAC

GAUGGUAGAACYAUCAGAUACCCAG

SEQ ID NO: 134; >*C. parapsilosis*1001
CATTACTTTGGAAGCCACYAATGAAAACTTTAGATTGATTTACGATGTCAAAGGTAGATTTGCTGTCCACAGAATCTCAG

CTGAAGAAGCCACTTACAAATTGGGTAAAGTCAAGAGAGTCCAATTGGGTAAGAAGGGAATCCCATACGTTGTCACCCAC

GATGGTAGAACYATCAGATACCCAG

SEQ ID NO: 135; >*C. parapsilosis*1001
CAUUACUUUGGAAGCCACYAAUGAAAACUUUAGAUUGAUUUACGAUGUCAAAGGUAGAUUUGCUGUCCACAGAAUCUCAG

CUGAAGAAGCCACUUACAAAUUGGGUAAAGUCAAGAGAGUCCAAUUGGGUAAGAAGGGAAUCCCAUACGUUGUCACCCAC

GAUGGUAGAACYAUCAGAUACCCAG

SEQ ID NO: 136; >*C. parapsilosis*1716
CATTACTTTGGAAGCCACYAATGAAAACTTTAGATTGATTTACGATGTCAAAGGTAGATTTGCTGTCCACAGAATCTCAG

CTGAAGAAGCCACTTACAAATTGGGTAAAGTCAAGAGAGTCCAATTGGGTAAGAAGGGAATCCCATACGTTGTCACCCAC

GATGGTAGAACYATCAGATACCCAG

SEQ ID NO: 137; >*C. parapsilosis*1716
CAUUACUUUGGAAGCCACYAAUGAAAACUUUAGAUUGAUUUACGAUGUCAAAGGUAGAUUUGCUGUCCACAGAAUCUCAG

CUGAAGAAGCCACUUACAAAUUGGGUAAAGUCAAGAGAGUCCAAUUGGGUAAGAAGGGAAUCCCAUACGUUGUCACCCAC

GAUGGUAGAACYAUCAGAUACCCAG

SEQ ID NO: 138; >*C. parapsilosis*9557
CATTACTTTGGAAGCCACYAATGAAAACTTTAGATTGATTTACGATGTCAAAGGTAGATTTGCTGTCCACAGAATCTCAG

CTGAAGAAGCCACTTACAAATTGGGTAAAGTCAAGAGAGTCCAATTGGGTAAGAAGGGAATCCCATACGTTGTCACCCAC

GATGGTAGAACYATCAGATACCCAG

SEQ ID NO: 139; >*C. parapsilosis*9557
CAUUACUUUGGAAGCCACYAAUGAAAACUUUAGAUUGAUUUACGAUGUCAAAGGUAGAUUUGCUGUCCACAGAAUCUCAG

CUGAAGAAGCCACUUACAAAUUGGGUAAAGUCAAGAGAGUCCAAUUGGGUAAGAAGGGAAUCCCAUACGUUGUCACCCAC

GAUGGUAGAACYAUCAGAUACCCAG

SEQ ID NO: 140; >*C. krusei*5579
CATCACTTTAGATGCAACCAACGAACACTTCAGATTAATCTATGACATCAAGGGTAGATTCGCAATCCACAGAATCACCC

CAGAAGAAGCTGCATACAAGTTATGTAAGGTCAAGAAGGTCCAATTAGGTAAGAAGGGTATTCCTTATGTTGTTACCCAC

GATGGTAGAACYATCAGATACCCAG

-continued

SEQ ID NO: 141; >*C. krusei*5579
CAUCACUUUAGAUGCAACCAACGAACACUUCAGAUUAAUCUAUGACAUCAAGGGUAGAUUCGCAAUCCACAGAAUCACCC

CAGAAGAAGCUGCAUACAAGUUAUGUAAGGUCAAGAAGGUCCAAUUAGGUAAGAAGGGUAUUCCUUAUGUUGUUACCCAC

GAUGGUAGAACYAUCAGAUACCCAG

SEQ ID NO: 142; >*C. krusei*9560
CATCACTTTAGATGCAACCAACGAACACTTCAGATTAATCTATGACATCAAGGGTAGATTCGCAATCCACAGAATCACCC

CAGAAGAAGCTGCATACAAGTTATGTAAGGTCAAGAAGGTCCAATTAGGTAAGAAGGGTATTCCTTATGTTGTTACCCAC

GATGGTAGAACYATCAGATACCCAG

SEQ ID NO: 143; >*C. krusei*9560
CAUCACUUUAGAUGCAACCAACGAACACUUCAGAUUAAUCUAUGACAUCAAGGGUAGAUUCGCAAUCCACAGAAUCACCC

CAGAAGAAGCUGCAUACAAGUUAUGUAAGGUCAAGAAGGUCCAAUUAGGUAAGAAGGGUAUUCCUUAUGUUGUUACCCAC

GAUGGUAGAACYAUCAGAUACCCAG

SEQ ID NO: 144; >*C. krusei*6055
CATCACTTTAGATGCAACCAACGAACACTTCAGATTAATCTATGACATCAAGGGTAGATTCGCAATCCACAGAATCACCC

CAGAAGAAGCTGCATACAAGTTATGTAAGGTCAAGAAGGTCCAATTAGGTAAGAAGGGTATTCCTTATGTTGTTACCCAC

GATGGTAGAACYATCAGATACCCAG

SEQ ID NO: 145; >*C. krusei*6055
CAUCACUUUAGAUGCAACCAACGAACACUUCAGAUUAAUCUAUGACAUCAAGGGUAGAUUCGCAAUCCACAGAAUCACCC

CAGAAGAAGCUGCAUACAAGUUAUGUAAGGUCAAGAAGGUCCAAUUAGGUAAGAAGGGUAUUCCUUAUGUUGUUACCCAC

GAUGGUAGAACYAUCAGAUACCCAG

SEQ ID NO: 146; >*C. krusei*17518
CATCACTTTAGATGCAACCAACGAACACTTCAGATTAATCTATGACATCAAGGGTAGATTCGCAATCCACAGAATCACCC

CAGAAGAAGCTGCATACAAGTTATGTAAGGTCAAGAAGGTCCAATTAGGTAAGAAGGGTATTCCTTATGTTGTTACCCAC

GATGGTAGAACYATCAGATACCCAG

SEQ ID NO: 147; >*C. krusei*17518
CAUCACUUUAGAUGCAACCAACGAACACUUCAGAUUAAUCUAUGACAUCAAGGGUAGAUUCGCAAUCCACAGAAUCACCC

CAGAAGAAGCUGCAUACAAGUUAUGUAAGGUCAAGAAGGUCCAAUUAGGUAAGAAGGGUAUUCCUUAUGUUGUUACCCAC

GAUGGUAGAACYAUCAGAUACCCAG

SEQ ID NO: 148; >*C. krusei*573
CATCACTTTAGATGCAACCAACGAACACTTCAGATTAATCTATGACATCAAGGGTAGATTCGCAATCCACAGAATCACCC

CAGAAGAAGCTGCATACAAGTTATGTAAGGTCAAGAAGGTCCAATTAGGTAAGAAGGGTATTCCTTATGTTGTTACCCAC

GATGGTAGAACYATCAGATACCCAG

SEQ ID NO: 149; >*C. krusei*573
CAUCACUUUAGAUGCAACCAACGAACACUUCAGAUUAAUCUAUGACAUCAAGGGUAGAUUCGCAAUCCACAGAAUCACCC

CAGAAGAAGCUGCAUACAAGUUAUGUAAGGUCAAGAAGGUCCAAUUAGGUAAGAAGGGUAUUCCUUAUGUUGUUACCCAC

GAUGGUAGAACYAUCAGAUACCCAG

SEQ ID NO: 150; >*C. krusei*3165
CATCACTTTAGATGCAACCAACGAACACTTCAGATTAATCTATGACATCAAGGGTAGATTCGCAATCCACAGAATCACCC

CAGAAGAAGCTGCATACAAGTTATGTAAGGTCAAGAAGGTCCAATTAGGTAAGAAGGGTATTCCTTATGTTGTTACCCAC

GATGGTAGAACYATCAGATACCCAG

SEQ ID NO: 151; >*C. krusei*3165
CAUCACUUUAGAUGCAACCAACGAACACUUCAGAUUAAUCUAUGACAUCAAGGGUAGAUUCGCAAUCCACAGAAUCACCC

CAGAAGAAGCUGCAUACAAGUUAUGUAAGGUCAAGAAGGUCCAAUUAGGUAAGAAGGGUAUUCCUUAUGUUGUUACCCAC

GAUGGUAGAACYAUCAGAUACCCAG

-continued

SEQ ID NO: 152; >*C. krusei*3922
CATCACTTTAGATGCAACCAACGAACACTTCAGATTAATCTATGACATCAAGGGTAGATTCGCAATCCACAGAATCACCC

CAGAAGAAGCTGCATACAAGTTATGTAAGGTCAAGAAGGTCCAATTAGGTAAGAAGGGTATTCCTTATGTTGTTACCCAC

GATGGTAGAACYATCAGATACCCAG

SEQ ID NO: 153; >*C. krusei*3922
CAUCACUUUAGAUGCAACCAACGAACACUUCAGAUUAAUCUAUGACAUCAAGGGUAGAUUCGCAAUCCACAGAAUCACCC

CAGAAGAAGCUGCAUACAAGUUAUGUAAGGUCAAGAAGGUCCAAUUAGGUAAGAAGGGUAUUCCUUAUGUUGUUACCCAC

GAUGGUAGAACYAUCAGAUACCCAG

SEQ ID NO: 154; >*C. krusei*3847
CATCACTTTAGATGCAACCAACGAACACTTCAGATTAATCTATGACATCAAGGGTAGATTCGCAATCCACAGAATCACCC

CAGAAGAAGCTGCATACAAGTTATGTAAGGTCAAGAAGGTCCAATTAGGTAAGAAGGGTATTCCTTATGTTGTTACCCAC

GATGGTAGAACYATCAGATACCCAG

SEQ ID NO: 155; >*C. krusei*3847
CAUCACUUUAGAUGCAACCAACGAACACUUCAGAUUAAUCUAUGACAUCAAGGGUAGAUUCGCAAUCCACAGAAUCACCC

CAGAAGAAGCUGCAUACAAGUUAUGUAAGGUCAAGAAGGUCCAAUUAGGUAAGAAGGGUAUUCCUUAUGUUGUUACCCAC

GAUGGUAGAACYAUCAGAUACCCAG

SEQ ID NO: 156; >*C. tropicalis*3895
CATTACCTTGGAAGCTACCAACGAACACTTCAGATTGATTTACGATGTTAAAGGTAAATTCGCTGTTCACAGAATTTCTG

CTGAAGAAGCTTCTTACAAATTAGGTAAAGTCAAGAAGGTTCAATTAGGTAAAAAAGGTGTTCCATACGTTGTCACCCAC

GATGGTAGAACYATCAGATACCCAG

SEQ ID NO: 157; >*C. tropicalis*3895
CAUUACCUUGGAAGCUACCAACGAACACUUCAGAUUGAUUUACGAUGUUAAAGGUAAAUUCGCUGUUCACAGAAUUUCUG

CUGAAGAAGCUUCUUACAAAUUAGGUAAAGUCAAGAAGGUUCAAUUAGGUAAAAAAGGUGUUCCAUACGUUGUCACCCAC

GAUGGUAGAACYAUCAGAUACCCAG

SEQ ID NO: 158; >*C. tropicalis*94
CATTACCTTGGAAGCTACCAACGAACACTTCAGATTGATTTACGATGTTAAAGGTAAATTCGCTGTTCACAGAATTTCTG

CTGAAGAAGCTTCTTACAAATTAGGTAAAGTCAAGAAGGTTCAATTAGGTAAAAAAGGTGTTCCATACGTTGTCACCCAC

GATGGTAGAACYATCAGATACCCAG

SEQ ID NO: 159; >*C. tropicalis*94
CAUUACCUUGGAAGCUACCAACGAACACUUCAGAUUGAUUUACGAUGUUAAAGGUAAAUUCGCUGUUCACAGAAUUUCUG

CUGAAGAAGCUUCUUACAAAUUAGGUAAAGUCAAGAAGGUUCAAUUAGGUAAAAAAGGUGUUCCAUACGUUGUCACCCAC

GAUGGUAGAACYAUCAGAUACCCAG

SEQ ID NO: 160; >*C. tropicalis*4225
CATTACCTTGGAAGCTACCAACGAACACTTCAGATTGATTTACGATGTTAAAGGTAAATTCGCTGTTCACAGAATTTCTG

CTGAAGAAGCTTCTTACAAATTAGGTAAAGTCAAGAAGGTTCAATTAGGTAAAAAAGGTGTTCCATACGTTGTCACCCAC

GATGGTAGAACYATCAGATACCCAG

SEQ ID NO: 161; >*C. tropicalis*4225
CAUUACCUUGGAAGCUACCAACGAACACUUGAGAUUGAUUUACGAUGUUAAAGGUAAAUUCGCUGUUCACAGAAUUUCUG

CUGAAGAAGCUUCUUACAAAUUAGGUAAAGUCAAGAAGGUUCAAUUAGGUAAAAAAGGUGUUCCAUACGUUGUCACCCAC

GAUGGUAGAACYAUCAGAUACCCAG

SEQ ID NO: 162; >*C. tropicalis*5557
CATTACCTTGGAAGCTACCAACGAACACTTCAGATTGATTTACGATGTTAAAGGTAAATTCGCTGTTCACAGAATTTCTG

CTGAAGAAGCTTCTTACAAATTAGGTAAAGTCAAGAAGGTTCAATTAGGTAAAAAAGGTGTTCCATACGTTGTCACCCAC

GATGGTAGAACYATCAGATACCCAG

-continued

SEQ ID NO: 163; >*C. tropicalis*5557
CAUUACCUUGGAAGCUACCAACGAACACUUCAGAUUGAUUUACGAUGUUAAAGGUAAAUUCGCUGUUCACAGAAUUUCUG

CUGAAGAAGCUUCUUACAAAUUAGGUAAAGUCAAGAAGGUUCAAUUAGGUAAAAAAGGUGUUCCAUACGUUGUCACCCAC

GAUGGUAGAACYAUCAGAUACCCAG

SEQ ID NO: 164; >*C. tropicalis*15902
CATTACCTTGGAAGCTACCAACGAACACTTCAGATTGATTTACGATGTTAAAGGTAAATTCGCTGTTCACAGAATTTCTG

CTGAAGAAGCTTCTTACAAATTAGGTAAAGTCAAGAAGGTTCAATTAGGTAAAAAAGGTGTTCCATACGTTGTCACCCAC

GATGGTAGAACYATCAGATACCCAG

SEQ ID NO: 165; >*C. tropicalis*15902
CAUUACCUUGGAAGCUACCAACGAACACUUCAGAUUGAUUUACGAUGUUAAAGGUAAAUUCGCUGUUCACAGAAUUUCUG

CUGAAGAAGCUUCUUACAAAUUAGGUAAAGUCAAGAAGGUUCAAUUAGGUAAAAAAGGUGUUCCAUACGUUGUCACCCAC

GAUGGUAGAACYAUCAGAUACCCAG

SEQ ID NO: 166; >*C. tropicalis*4139
CATTACCTTGGAAGCTACCAACGAACACTTCAGATTGATTTACGATGTTAAAGGTAAATTCGCTGTTCACAGAATTTCTG

CTGAAGAAGCTTCTTACAAATTAGGTAAAGTCAAGAAGGTTCAATTAGGTAAAAAAGGTGTTCCATACGTTGTCACCCAC

GATGGTAGAACYATCAGATACCCAG

SEQ ID NO: 167; >*C. tropicalis*4139
CAUUACCUUGGAAGCUACCAACGAACACUUCAGAUUGAUUUACGAUGUUAAAGGUAAAUUCGCUGUUCACAGAAUUUCUG

CUGAAGAAGCUUCUUACAAAUUAGGUAAAGUCAAGAAGGUUCAAUUAGGUAAAAAAGGUGUUCCAUACGUUGUCACCCAC

GAUGGUAGAACYAUCAGAUACCCAG

SEQ ID NO: 168; >*C. tropicalis*3873
CATTACCTTGGAAGCTACCAACGAACACTTCAGATTGATTTACGATGTTAAAGGTAAATTCGCTGTTCACAGAATTTCTG

CTGAAGAAGCTTCTTACAAATTAGGTAAAGTCAAGAAGGTTCAATTAGGTAAAAAAGGTGTTCCATACGTTGTCACCCAC

GATGGTAGAACYATCAGATACCCAG

SEQ ID NO: 169; >*C. tropicalis*3873
CAUUACCUUGGAAGCUACCAACGAACACUUCAGAUUGAUUUACGAUGUUAAAGGUAAAUUCGCUGUUCACAGAAUUUCUG

CUGAAGAAGCUUCUUACAAAUUAGGUAAAGUCAAGAAGGUUCAAUUAGGUAAAAAAGGUGUUCCAUACGUUGUCACCCAC

GAUGGUAGAACYAUCAGAUACCCAG

SEQ ID NO: 170; >*C. tropicalis*3870
CATTACCTTGGAAGCTACCAACGAACACTTCAGATTGATTTACGATGTTAAAGGTAAATTCGCTGTTCACAGAATTTCTG

CTGAAGAAGCTTCTTACAAATTAGGTAAAGTCAAGAAGGTTCAATTAGGTAAAAAAGGTGTTCCATACGTTGTCACCCAC

GATGGTAGAACYATCAGATACCCAG

SEQ ID NO: 171; >*C. tropicalis*3870
CAUUACCUUGGAAGCUACCAACGAACACUUCAGAUUGAUUUACGAUGUUAAAGGUAAAUUCGCUGUUCACAGAAUUUCUG

CUGAAGAAGCUUCUUACAAAUUAGGUAAAGUCAAGAAGGUUCAAUUAGGUAAAAAAGGUGUUCCAUACGUUGUCACCCAC

GAUGGUAGAACYAUCAGAUACCCAG

SEQ ID NO: 172; >*C. tropicalis*8157
CATTACCTTGGAAGCTACCAACGAACACTTCAGATTGATTTACGATGTTAAAGGTAAATTCGCTGTTCACAGAATTTCTG

CTGAAGAAGCTTCTTACAAATTAGGTAAAGTCAAGAAGGTTCAATTAGGTAAAAAAGGTGTTCCATACGTTGTCACCCAC

GATGGTAGAACYATCAGATACCCAG

SEQ ID NO: 173; >*C. tropicalis*8157
CAUUACCUUGGAAGCUACCAACGAACACUUCAGAUUGAUUUACGAUGUUAAAGGUAAAUUCGCUGUUCACAGAAUUUCUG

CUGAAGAAGCUUCUUACAAAUUAGGUAAAGUCAAGAAGGUUCAAUUAGGUAAAAAAGGUGUUCCAUACGUUGUCACCCAC

GAUGGUAGAACYAUCAGAUACCCAG

-continued

SEQ ID NO: 174; >*C. tropicalis*2311
CATCACCTTGGAAGCTACCAACGAACACTTCAGATTGATTTACGATGTTAAAGGTAAATTCGCTGTTCACAGAATTTCTG

CTGAAGAAGCTTCTTACAAATTAGGTAAAGTCAAGAAGGTTCAATTAGGTAAAAAAGGTGTTCCATACGTTGTCACCCAC

GATGGTAGAACYATCAGATACCCAG

SEQ ID NO: 175; >*C. tropicalis*2311
CAUCACCUUGGAAGCUACCAACGAACACUUCAGAUUGAUUUACGAUGUUAAAGGUAAAUUCGCUGUUCACAGAAUUUCUG

CUGAAGAAGCUUCUUACAAAUUAGGUAAAGUCAAGAAGGUUCAAUUAGGUAAAAAAGGUGUUCCAUACGUUGUCACCCAC

GAUGGUAGAACYAUCAGAUACCCAG

SEQ ID NO: 176; *Saccharomyces cerevisiae*
*Saccharomyces cerevisiae* probe 1
GATTGGTCTACGATGTCA SEQ ID NO 177; *Saccharomyces cerevisiae*
*Saccharomyces cerevisiae* probe 2
TGACATCGTAGACCAATC SEQ ID NO: 178; *Eremothecium gossypii*
*Eremothecium gossypii* probe 1
GATTGGTATACGATGTCA SEQ ID NO: 179; *Eremothecium gossypii*
*Eremothecium gossypii* probe 2
TGACATCGTATACCAATC SEQ ID NO 180; *Kluyveromyces lactis*
*Kluyveromyces lactis* probe 1
GATTGGTCTACGATGTTA SEQ ID NO: 181; *Kluyveromyces lactis*
*Kluyveromyces lactis* probe 2
TAACATCGTAGACCAATC SEQ ID NO 182; *C. dubliniensis* and *Candida glabrata*
*C. dubliniensis* and *Candida glabrata* probe 1
GATTGGTCTACGACGTCA SEQ ID NO 183; *C. dubliniensis* and *Candida glabrata*
*C. dubliniensis* and *Candida glabrata* probe 2
TGACGTCGTAGACCAATC SEQ ID NO 184; *Debaryomyces hansenii*
*Debaryomyces hansenii* probe 1
GATTGATCTATGACGTCA SEQ ID NO: 185; *Debaryomyces hansenii*
*Debaryomyces hansenii* probe 2
TGACGTCATAGATCAATC SEQ ID NO 186; *C. tropicalis*
*C. tropicalis* probe 1
GATTGATTTACGATGTTA SEQ ID NO 187; *C. tropicalis*
*C. tropicalis* probe 2
TAACATCGTAAATCAATC SEQ ID NO 188; *C. parapsilosis*
*C. parapsilosis* probe 1
GATTGATTTACGATGTCA SEQ ID NO 189; *C. parapsilosis* probe 2
*C. parapsilosis*
TGACATCGTAAATCAATC SEQ ID NO 190; *Saccharomyces cerevisiae*
ATGGCTAGAG GACCAAAGAA GCATCTAAAA AGATTAGCAG CTCCACACCA CTGGTTATTG 60

GACAAGTTGT CCGGTTGTTA CGCCCCAAGA CCATCTGCTG GTCCACACAA ATTGCGTGAA 120

TCCTTGCCAT TGATTGTCTT TCTAAGAAAC AGATTAAAGT ATGCTTTGAA CGGCCGTGAA 180

GTCAAGGCTA TCTTGATGCA ACGTCACGTT AAAGTGGACG GTAAGGTTAG AACCGACACT 240

ACCTACCC*AG CTGGTTTCAT* *GGATGT*CATC ACTCTAGATG CCACCAATGA AAACTTCAGA 300

-continued

TTGGTCTACG ATGTCAAGGG TAGATTCGCT GTCCACCGTA TCACCGATGA AGAAGCTTCT 360

TACAAGTTGG GTAAGGTCAA GAAGGTTCAA TTAGGTAAGA AGGTGTTCC ATACGTTGTT 420

ACCCACGATG GT*AGAACTAT CAGATACCCA GA*CCCAAACA TCAAGGTCAA TGACACTGTT 480

AAGATCGACT TGGCCTCTGG TAAGATTACT GATTTCATCA AGTTCGATGC CGGTAAGTTG 540

GTTTACGTTA CTGGTGGTCG TAACTTGGGT CGTATCGGTA CTATCGTTCA CAAGGAAAGA 600

CACGATGGTG GTTTCGATTT AGTTCACATC AAGGACTCCT TGGACAACAC TTTCGTCACT 660

AGATTGAACA ATGTCTTCGT CATCGGTGAA CAAGGTAAGC CTTACATTTC TTTGCCAGGT 720

AAGGGTAAGG GTATCAAGTT GTCTATTGCT GAAGAACGTG ACAGAAGAAG AGCTCAACAA 780

TTATAA--- 786

SEQ ID NO 191; RNA; *Saccharomyces cerevisiae*
AUGGCUAGAG GACCAAAGAA GCAUCUAAAA AGAUUAGCAG CUCCACACCA CUGGUUAUUG 60

GACAAGUUGU CCGGUUGUUA CGCCCCAAGA CCAUCUGCUG GUCCACACAA AUUGCGUGAA 120

UCCUUGCCAU UGAUUGUCUU UCUAAGAAAC AGAUUAAAGU AUGCUUUGAA CGGCCGUGAA 180

GUCAAGGCUA UCUUGAUGCA ACGUCACGUU AAAGUGGACG GUAAGGUUAG AACCGACACU 240

ACCUACCC*AG CUGGUUUCAU GGAUGU*CAUC ACUCUAGAUG CCACCAAUGA AAACUUCAGA 300

UUGGUCUACG AUGUCAAGGG UAGAUUCGCU GUCCACCGUA UCACCGAUGA AGAAGCUUCU 360

UACAAGUUGG GUAAGGUCAA GAAGGUUCAA UUAGGUAAGA AGGGUGUUCC AUACGUUGUU 420

ACCCACGAUG GU*AGAACUAU CAGAUACCCA GA*CCCAAACA UCAAGGUCAA UGACACUGUU 480

AAGAUCGACU UGGCCUCUGG UAAGAUUACU GAUUUCAUCA AGUUCGAUGC CGGUAAGUUG 540

GUUUACGUUA CUGGUGGUCG UAACUUGGGU CGUAUCGGUA CUAUCGUUCA CAAGGAAAGA 600

CACGAUGGUG GUUUCGAUUU AGUUCACAUC AAGGACUCCU UGGACAACAC UUUCGUCACU 660

AGAUUGAACA AUGUCUUCGU CAUCGGUGAA CAAGGUAAGC CUUACAUUUC UUUGCCAGGU 720

AAGGGUAAGG GUAUCAAGUU GUCUAUUGCU GAAGAACGUG ACAGAAGAAG AGCUCAACAA 780

UUAUAA--- 786

SEQ ID NO 192; *Candida glabrata*
ATGGCTAGAG GACCAAAGAA GCATCTAAAG AGATTAGCAG CTCCACACCA CTGGTTGTTG 60

GACAAGTTGT CCGGCTGTTA CGCCCCAAGA CCATCCGCTG GTCCACACAA GTTGCGTGAA 120

TCCCTACCAT TGATCGTTTT CTTGAGAAAC AGATTAAAGT ACGCTTTGAA CGGTCGTGAA 180

GTTAAGGCTA TCATGATGCA ACGTCATGTT AAGGTTGACG GTAAGGTCAG AACTGACGCT 240

ACCTACCC*G CTGGTTTCAT GGATGT*TATC ACCTTGGAAG CTACCAACGA AAACTTCAGA 300

TTGGTCTACG ACGTCAAGGG TAGATTCGCT GTCCACCGTA TCACTGACGA AGAAGCTTCC 360

TACAAGTTGG GTAAGGTCAA GAAGGTCCAA TTGGGTAAGA AGGGTGTTCC ATACGTTGTC 420

ACTGACGATG GT*AGAACTAT CAGATACCCA GA*CCCAAACA TCAAGGTCAA TGACACCGTC 480

AAGGTCGACT TGGCTTCCGG TAAGATCACT GACTACATCA AGTTCGACAT TGGTAAGTTG 540

GTCTACATCA CCGGTGGTCG TAACTTGGGT CGTATCGGTA CCATCGTTCA CAAGGAAAGA 600

CACGATGGTG GTTTCGACTT GGTTCACGTC AAGGACTCCT TGGACAACAC TTTCGTCACC 660

AGATTGAACA ACGTTTTCGT TATCGGTGAA CAAGGTAAGC CATACATCTC CTTGCCAAAG 720

GGTAAGGGTA TCAAGTTGAC CATTGCTGAA GAACGTGACA GAAGAAGAGC TCAACAAGGT 780

TTATAA--- 786

SEQ ID NO 193; RNA; *Candida glabrata*
AUGGCUAGAG GACCAAAGAA GCAUCUAAAG AGAUUAGCAG CUCCACACCA CUGGUUGUUG 60

GACAAGUUGU CCGGCUGUUA CGCCCCAAGA CCAUCCGCUG GUCCACACAA GUUGCGUGAA 120

-continued

UCCCUACCAU UGAUCGUUUU CUUGAGAAAC AGAUUAAAGU ACGCUUUGAA CGGUCGUGAA 180

GUUAAGGCUA UCAUGAUGCA ACGUCAUGUU AAGGUUGACG GUAAGGUCAG AACUGACGCU 240

ACCUACCC*AG CAGGUUUCAU GGAUGU*UAUC ACCUUGGAAG CUACCAACGA AAACUUCAGA 300

UUGGUCUACG ACGUCAAGGG UAGAUUCGCU GUCCACCGUA UCACUGACGA AGAAGCUUCC 360

UACAAGUUGG GUAAGGUCAA GAAGGUCCAA UUGGGUAAGA AGGGUGUUCC AUACGUUGUC 420

ACUGACGAUG GU*AGAACUAU CAGAUACCCA GA*CCCAAACA UCAAGGUCAA UGACACCGUC 480

AAGGUCGACU UGGCUUCCGG UAAGAUCACU GACUACAUCA AGUUCGACAU UGGUAAGUUG 540

GUCUACAUCA CCGGUGGUCG UAACUUGGGU CGUAUCGGUA CCAUCGUUCA CAAGGAAAGA 600

CACGAUGGUG GUUUCGACUU GGUUCACGUC AAGGACUCCU UGGACAACAC UUUCGUCACC 660

AGAUUGAACA ACGUUUUCGU UAUCGGUGAA CAAGGUAAGC CAUACAUCUC CUUGCCAAAG 720

GGUAAGGGUA UCAAGUUGAC CAUUGCUGAA GAACGUGACA GAAGAAGAGC UCAACAAGGU 780

UUAUAA--- 786

SEQ ID NO 194; *Eremothecium gossypii*
ATGGCTAGAG GACCAAAGAA GCACCTGAAG AGATTGGCAG CTCCACACCA CTGGTTGTTG 60

GACAAGCTAT CCGGCTGTTA CGCTCCAAGA CCATCCGCTG GTCCACACAA GTTGCGCGAG 120

TCTTTGCCAT TGATCGTCTT CTTGAGAAAC AGATTAAAGT ATGCTTTGAA CGGTCGCGAG 180

GTCAAGGCCA TCCTAATGCA GCGTCATGTT AAGGTTGACG GTAAGGTCAG AACTGACACT 240

ACCTACCC*AG CTGGTTTCAT GGATGT*CATC ACTCTAGAGG CTACCAACGA GAACTTCAGA 300

TTGGTATACG ATGTCAAGGG CAGATTTGCT GTCCACCGTA TCACCGATGA GGAGGCTACT 360

TACAAGTTGG GTAAGGTTAA GCGCGTTCAG CTAGGTAAGA AGGGTGTCCC ATACGTGGTC 420

ACTCACGACG GC*AGAACCAT CAGATACCCA GA*CCCAAACA TCAAGGTTAA CGACACCGTC 480

AAGGTTGACC TTGCTACTGG TAAGATTACC GACTTCATCA AGTTCGACAC TGGTAAGTTG 540

GTGTACGTCA CCGGTGGCCG TAACTTGGGC CGTATTGGTG TCATCACCCA CAGAGAGAGA 600

CACGAGGGTG GCTTTGACTT GGTTCACATC AAGGACTCCT TGGAGAACAC TTTCGTCACC 660

AGATTGAACA ACGTTTTCGT CATCGGTGAG CAAGGTAGAC CATGGATCTC CTTGCCAAGG 720

GGTAAGGGTA TTAAGTTGTC CATTGCTGAG GAGCGTGACC GTAGAAGAGC TCAACAAGGT 780

TTGTAA--- 786

SEQ ID NO 195; RNA; *Eremothecium gossypii*
AUGGCUAGAG GACCAAAGAA GCACCUGAAG AGAUUGGCAG CUCCACACCA CUGGUUGUUG 60

GACAAGCUAU CCGGCUGUUA CGCUCCAAGA CCAUCCGCUG GUCCACACAA GUUGCGCGAG 120

UCUUUGCCAU UGAUCGUCUU CUUGAGAAAC AGAUUAAAGU AUGCUUUGAA CGGUCGCGAG 180

GUCAAGGCCA UCCUAAUGCA GCGUCAUGUU AAGGUUGACG GUAAGGUCAG AACUGACACU 240

ACCUACCC*AG CUGGUUUCAU GGAUGU*CAUC ACUCUAGAGG CUACCAACGA GAACUUCAGA 300

UUGGUAUACG AUGUCAAGGG CAGAUUUGCU GUCCACCGUA UCACCGAUGA GGAGGCUACU 360

UACAAGUUGG GUAAGGUUAA GCGCGUUCAG CUAGGUAAGA AGGGUGUCCC AUACGUGGUC 420

ACUCACGACG GC*AGAACCAU CAGAUACCCA GA*CCCAAACA UCAAGGUUAA CGACACCGUC 480

AAGGUUGACC UUGCUACUGG UAAGAUUACC GACUUCAUCA AGUUCGACAC UGGUAAGUUG 540

GUGUACGUCA CCGGUGGCCG UAACUUGGGC CGUAUUGGUG UCAUCACCCA CAGAGAGAGA 600

CACGAGGGUG GCUUUGACUU GGUUCACAUC AAGGACUCCU UGGAGAACAC UUUCGUCACC 660

-continued

AGAUUGAACA ACGUUUUCGU CAUCGGUGAG CAAGGUAGAC CAUGGAUCUC CUUGCCAAGG 720

GGUAAGGGUA UUAAGUUGUC CAUUGCUGAG GAGCGUGACC GUAGAAGAGC UCAACAAGGU 780

UUGUAA--- 786

SEQ ID NO 196; *Kluyveromyces lactis*
ATGGCTAGAG GACCAAAGAA GCATCTAAAG AGATTAGCAG CTCCACATCA TTGGATGTTG 60

GACAAGTTGT CCGGTTGTTA CGCACCAAGA CCATCTGCTG GTCCACACAA GTTGCGTGAA 120

TCCTTGCCAT TGATCGTTTT CTTGAGAAAC AGATTAAAGT ATGCTTTGAA CGGTCGTGAA 180

GTCAAGGCCA TCTTGATGCA ACGTCATGTC AAGGTTGACG GTAAGGTCAG AACCGACACT 240

ACTTTCCC*AG CTGGTTTCAT GGATG*TATC ACCTTGGAAG CTACCAACGA AAACTTCAGA 300

TTGGTCTACG ATGTTAAGGG TAGATTCGCT GTCCACCGTA TCACTGATGA AGAAGCTTCC 360

TACAAGTTGG CTAAGGTCAA GAAGGTTCAA CTAGGTAAGA AGGGTATTCC ATACGTCGTT 420

ACCCACGACG GT*AGAACCAT CAGATACCCA GA*CCCAAACA TCAAGGTTAA CGACACCGTT 480

AAGGTTGATT TGGCTACTGG TACTATCACC GATTTCATCA AATTCGACAC TGGTAAGTTG 540

GTTTATGTTA CCGGTGGTCG TAACTTGGGT AGAGTTGGTA CCATCGTCCA CAGAGAAAGA 600

CACGAAGGTG GTTTCGATTT GGTTCACATC AAGGATTCTT TGGAAAACAC TTTCGTCACC 660

AGATTGAACA ACGTTTTCGT CATCGGTGAA CCAGGTAGAC CATGGATCTC CTTGCCAAAG 717

GGTAAGGGTA TCAAGTTGAC CATCTCTGAA GAACGTGACC GTAGAAGAGC TCAACATGGT 777

TTGTAA--- 786

SEQ ID NO 197; RNA; *Kluyveromyces lactis*
AUGGCUAGAG GACCAAAGAA GCAUCUAAAG AGAUUAGCAG CUCCACAUCA UUGGAUGUUG 60

GACAAGUUGU CCGGUUGUUA CGCACCAAGA CCAUCUGCUG GUCCACACAA GUUGCGUGAA 120

UCCUUGCCAU UGAUCGUUUU CUUGAGAAAC AGAUUAAAGU AUGCUUUGAA CGGUCGUGAA 180

GUCAAGGCCA UCUUGAUGCA ACGUCAUGUC AAGGUUGACG GUAAGGUCAG AACCGACACU 240

ACUUUCCC*AG CUGGUUUCAU GGAUGU*UAUC ACCUUGGAAG CUACCAACGA AAACUUCAGA 300

UUGGUCUACG AUGUUAAGGG UAGAUUCGCU GUCCACCGUA UCACUGAUGA AGAAGCUUCC 360

UACAAGUUGG CUAAGGUCAA GAAGGUUCAA CUAGGUAAGA AGGGUAUUCC AUACGUCGUU 420

ACCCACGACG GU*AGAACCAU CAGAUACCCA GA*CCCAAACA UCAAGGUUAA CGACACCGUU 480

AAGGUUGAUU UGGCUACUGG UACUAUCACC GAUUUCAUCA AAUUCGACAC UGGUAAGUUG 540

GUUUAUGUUA CCGGUGGUCG UAACUUGGGU AGAGUUGGUA CCAUCGUCCA CAGAGAAAGA 600

CACGAAGGUG GUUUCGAUUU GGUUCACAUC AAGGAUUCUU UGGAAAACAC UUUCGUCACC 660

AGAUUGAACA ACGUUUUCGU CAUCGGUGAA CCAGGUAGAC CAUGGAUCUC CUUGCCAAAG 717

GGUAAGGGUA UCAAGUUGAC CAUCUCUGAA GAACGUGACC GUAGAAGAGC UCAACAUGGU 777

UUGUAA--- 786

SEQ ID NO 198; *Candida albicans*
ATGGGTAGAG GTCCAAAGAA ACACTTGAAA AGATTAGCAG CTCCATCTCA CTGGATGTTG 60

GNCAAATTGT CCGGTACTTA TGCTCCAAGA CCATCTGCTG GTCCACACAN ATTGAGAGAA 120

TCATTACCAT TGGNTGTCTT TTTAAGAAAC AGATTGNAGT ATGCTTTGTG CGGTAGAGAA 180

GTCAAAGCCA TCATGATGCA ACAACACGTT CAAGTTGTCG GTAAAGTCAG AACTGATACC 240

ACCTACCC*AG CTGGTTCAT GGATGT*CATC ACCTTGGAAG CTACCAACGA ACATTTCAGA 300

TTAGCCTACG ATGTTAAAGG TAAATTCGCC GTTCACAGAA TTTCTGCTGA AGAAGCTGTC 360

TACAAATTGG GTAAAGTCAA GAAAGTCCAA TTAGGTAAGA AAGGTGTTCC ATACGTTGTT 420

ACCCACGACG GT*AGAACTAT CAGATACCCA GA*TCCATTGA TCAGAGCTAA CGATACCGTT 480

-continued

AAAATCGATT TGGCTACCGG TAAGATCGRT AGTTTCATCA AATTCGACAC TGGTAGATTA 540

GTTATGGTTA CTGGTGGTAG AAATTTGGGT AGAGTTGGTG TTATTGTCCA CAGAGAAAAA 600

CTCGAAGGAG GTTTCGATTT GGTCCACATC AAAGATGCTT TGGAAAACAC TTTCGTTACC 660

AGATTGTCTA ACGTTTTTGT TATTGGTACT GAAGCCGGTA AACCATGGGT CTCATTACCA 720

AAGGGTAAAG GTATCAAATT GTCTATTTCT GAAGAAAGAG ACAGAAGAAN AGCTCAACAA 780

GGTTTGTAA--- 789

SEQ ID NO 199; RNA; *Candida albicans*
AUGGGUAGAG GUCCAAAGAA ACACUUGAAA AGAUUAGCAG CUCCAUCUCA CUGGAUGUUG 60

GNCAAAUUGU CCGGUACUUA UGCUCCAAGA CCAUCUGCUG GUCCACACAN AUUGAGAGAA 120

UCAUUACCAU UGGNUGUCUU UUUAAGAAAC AGAUUGNAGU AUGCUUUGUG CGGUAGAGAA 180

GUCAAAGCCA UCAUGAUGCA ACAACACGUU CAAGUUGUCG GUAAAGUCAG AACUGAUACC 240

ACCUACCC*AG CUGGUUUCAU GGAUGU*CAUC ACCUUGGAAG CUACCAACGA ACAUUUCAGA 300

UUAGCCUACG AUGUUAAAGG UAAAUUCGCC GUUCACAGAA UUUCUGCUGA AGAAGCUGUC 360

UACAAAUUGG GUAAAGUCAA GAAAGUCCAA UUAGGUAAGA AAGGUGUUCC AUACGUUGUU 420

ACCCACGACG GU*AGAACUAU CAGAUACCCA GA*UCCAUUGA UCAGAGCUAA CGAUACCGUU 480

AAAAUCGAUU UGGCUACCGG UAAGAUCGRU AGUUUCAUCA AAUUCGACAC UGGUAGAUUA 540

GUUAUGGUUA CUGGUGGUAG AAAUUUGGGU AGAGUUGGUG UUAUUGUCCA CAGAGAAAAA 600

CUCGAAGGAG GUUUCGAUUU GGUCCACAUC AAAGAUGCUU UGGAAAACAC UUUCGUUACC 660

AGAUUGUCUA ACGUUUUUGU UAUUGGUACU GAAGCCGGUA AACCAUGGGU CUCAUUACCA 720

AAGGGUAAAG GUAUCAAAUU GUCUAUUUCU GAAGAAAGAG ACAGAAGAAN AGCUCAACAA 780

GGUUUGUAA--- 789

SEQ ID NO 200; *Debaryomyces hansenii*
ATGGGTAGAG GTCCAAAGAA GCACTTGAAG AGATTAGCAG CACCATCCCA CTGGATGTTG 60

GACAAATTGT CCGGTACTTA CGCACCAAGA CCATCTGCTG GTCCTCACAA ATTGAGAGAA 120

TCTTTACCAT TGGTTATCTT CTTAAGAAAC AGACTTAAGT ATGCCTTAAA CGGTAGAGAA 180

GTCAAGGCCA TCTTGATGCA AGAACACGTC AAGGTTGATG GTAAAGTTAG AACCGATGCT 240

ACTTTCCC*AG CTGGTTTCAT GGATGT*CATC ACTTTAGAAG CTACCAACGA ACACTTCAGA 300

TTAATCTATG ATGTCAAGGG TAGATTCACT GTCCACAGAA TCACTGCTGA AGAAGCTTCT 360

TACAAGTTAG CTAAGGTCAA GAAGGTCCAA TTAGGTAAGA GAGGTATTCC ATACGTTGTC 420

ACCCACGACG GT*AGAACTAT CAGATACCCA GA*TCCATTGA TCAGAGCCAA CGATTCCGTT 480

AAGGTTGACT TAGCTACCGG TAAGATCACT GACTTTATCA GCTTTGACAC TGGTAGATTA 540

GTCATGGTTA CTGGTGGTCG TAACATGGGT AGAGTTGGTG TTATCACCCA CAGAGAAAAG 600

CACGAGGGTG GTTTCGATTT AGTCCACATC AAGGATTCTT TGGAAAACAC TTTCGTTACC 660

AGATTAACTA ACGTCTTCAT CGTCGGTACT GAAGCTGGTA AGCCACACAT TTCTTTACCA 720

AAGGGTAAGG GTATTAAGTT ATCCATCTCT GAAGAACGTG ACAGAAGAAG AAACCAACAA 780

CTTATCAACT AA 792

SEQ ID NO 201; RNA; *Debaryomyces hansenii*
AUGGGUAGAG GUCCAAAGAA GCACUUGAAG AGAUUAGCAG CACCAUCCCA CUGGAUGUUG 60

GACAAAUUGU CCGGUACUUA CGCACCAAGA CCAUCUGCUG GUCCUCACAA AUUGAGAGAA 120

UCUUUACCAU UGGUUAUCUU CUUAAGAAAC AGACUUAAGU AUGCCUUAAA CGGUAGAGAA 180

GUCAAGGCCA UCUUGAUGCA AGAACACGUC AAGGUUGAUG GUAAAGUUAG AACCGAUGCU 240

ACUUUCCC*AG CUGGUUUCAU GGAUGU*CAUC ACUUUAGAAG CUACCAACGA ACACUUCAGA 300

-continued

UUAAUCUAUG AUGUCAAGGG UAGAUUCACU GUCCACAGAA UCACUGCUGA AGAAGCUUCU 360

UACAAGUUAG CUAAGGUCAA GAAGGUCCAA UUAGGUAAGA GAGGUAUUCC AUACGUUGUC 420

ACCCACGACG GU*AGAACUAU* *CUGAUACCCA GA*UCCAUUGA UCAGAGCCAA CGAUUCCGUU 480

AAGGUUGACU UAGCUACCGG UAAGAUCACU GACUUUAUCA GCUUUGACAC UGGUAGAUUA 540

GUCAUGGUUA CUGGUGGUCG UAACAUGGGU AGAGUUGGUG UUAUCACCCA CAGAGAAAAG 600

CACGAGGGUG GUUUCGAUUU AGUCCACAUC AAGGAUUCUU UGGAAAACAC UUUCGUUACC 660

AGAUUAACUA ACGUCUUCAU CGUCGGUACU GAAGCUGGUA AGCCACACAU UUCUUUACCA 720

AAGGGUAAGG GUAUUAAGUU AUCCAUCUCU GAAGAACGUG ACAGAAGAAG AAACCAACAA 780

CUUAUCAACU AA 792

SEQ ID NO 202; U37009.1 *Candida albicans* SGY-243
GAATTCGTTGCTTGAGCAAGAGGAAAAGCTTACTAAATTGATAAAGCAGGCAAATAGAAATAGTACTTGG

TTCAAATGGAATAAATAGTTTGTGTGTTGATTTCGCGAAAAAGAAATGTAAAGTAATACTGATTAGGGCT

ATAGCCCTAACTGGTTTCTCGCACTCTTTTCACTACCAATTACTAAAAAAAAAAAAATTTGGTGAAAAAAA

AAAATTATCTACCACTCCCTATACCATCATCATCAACAATAAACCCACAATGGGTAGAGGTCCAAAGAAA

CACTTGAAAAGATTAGCAGCTCCATCTCACTGGATGTTGGNCAAATTGTCCGGTACTTATGCTCCAAGAC

CATCTGCTGGTCCACACANATTGAGAGAATCATTACCATTGGNTGTCTTTTTAAGAAACAGATTGNAGTA

TGCTTTGTGCGGTAGAGAAGTCAAAGCCATCATGATGCAACAACACGTTCAAGTTGTCGGTAAAGTCAGA

ACTGATACCACCTACCCAGCTGGTTTCATGGATGTCATCACCTTGGAAGCTACCAACGAACATTTCAGAT

TAGCCTACGATGTTAAAGGTAAATTCGCCGTTCACAGAATTTCTGCTGAAGAAGCTGTCTACAAATTGGG

TAAAGTCAAGAAAGTCCAATTAGGTAAGAAAGGTGTTCCATACGTTGTTACCCACGACGGTAGAACTATC

AGATACCCAGATCCATTGATCAGAGCTAACGATACCGTTAAAATCGATTTGGCTACCGGTAAGATCGRTA

GTTTCATCAAATTCGACACTGGTAGATTAGTTATGGTTACTGGTGGTAGAAATTTGGGTAGAGTTGGTGT

TATTGTCCACAGAGAAAAACTCGAAGGAGGTTTCGATTTGGTCCACATCAAAGATGCTTTGGAAAACACT

TTCGTTACCAGATTGTCTAACGTTTTTGTTATTGGTACTGAAGCCGGTAAACCATGGGTCTCATTACCAA

AGGGTAAAGGTATCAAATTGTCTATTTCTGAAGAAAGAGACAGAAGAANAGCTCAACAAGGTTTGTAAGT

TTTATTCGCACTACAAAAAAAAAAATRTTTTRTGAAAATGAAAAAAACCAACGTAAATAATGTACATTAA

TTGCTAACCTTCAATAAGTTGTT

SEQ ID NO 203; RNA; *Candida albicans* SGY-243
GAAUUCGUUGCUUGAGCAAGAGGAAAAGCUUACUAAAUUGAUAAAGCAGGCAAAUAGAAAUAGUACUUGG

UUCAAAUGGAAUAAAUAGUUUGUGUGUUGAUUUCGCGAAAAAGAAAUGUAAAGUAAUACUGAUUAGGGCU

AUAGCCCUAACUGGUUUCUCGCACUCUUUUCACUACCAAUUACUAAAAAAAAAAAAAUUUGGUGAAAAAAA

AAAAUUAUCUACCACUCCCUAUACCAUCAUCAUCAACAAUAAACCCACAAUGGGUAGAGGUCCAAAGAAA

CACUUGAAAAGAUUAGCAGCUCCAUCUCACUGGAUGUUGGNCAAAUUGUCCGGUACUUAUGCUCCAAGAC

CAUCUGCUGGUCCACACANAUUGAGAGAAUCAUUACCAUUGGNUGUCUUUUUAAGAAACAGAUUGNAGUA

UGCUUUGUGCGGUAGAGAAGUCAAAGCCAUCAUGAUGCAACAACACGUUCAAGUUGUCGGUAAAGUCAGA

ACUGAUACCACCUACCCAGCUGGUUUCAUGGAUGUCAUCACCUUGGAAGCUACCAACGAACAUUUCAGAU

UAGCCUACGAUGUUAAAGGUAAAUUCGCCGUUCACAGAAUUUCUGCUGAAGAAGCUGUCUACAAAUUGGG

UAAAGUCAAGAAAGUCCAAUUAGGUAAGAAAGGUGUUCCAUACGUUGUUACCCACGACGGUAGAACUAUC

AGAUACCCAGAUCCAUUGAUCAGAGCUAACGAUACCGUUAAAAUCGAUUUGGCUACCGGUAAGAUCGRUA

GUUUCAUCAAAUUCGACACUGGUAGAUUAGUUAUGGUUACUGGUGGUAGAAAUUUGGGUAGAGUUGGUGU

UAUUGUCCACAGAGAAAAACUCGAAGGAGGUUUCGAUUUGGUCCACAUCAAAGAUGCUUUGGAAAACACU

-continued

UUCGUUACCAGAUUGUCUAACGUUUUUGUUAUUGGUACUGAAGCCGGUAAACCAUGGGUCUCAUUACCAA

AGGGUAAAGGUAUCAAAUUGUCUAUUUCUGAAGAAAGAGACAGAAGAANAGCUCAACAAGGUUUGUAAGU

UUUAUUCGCACUACAAAAAAAAAAAURUUUURUGAAAAUGAAAAAAACCAACGUAAAUAAUGUACAUUAA

UUGCUAACCUUCAAUAAGUUGUU

SEQ ID NO 204; XM_446360.1 *Candida glabrata* CBS138, partial mRNA
ATGGCTAGAGGACCAAAGAAGCATCTAAAGAGATTAGCAGCTCCACACCACTGGTTGTTGGACAAGTTGT

CCGGCTGTTACGCCCCAAGACCATCCGCTGGTCCACACAAGTTGCGTGAATCCCTACCATTGATCGTTTT

CTTGAGAAACAGATTAAAGTACGCTTTGAACGGTCGTGAAGTTAAGGCTATCATGATGCAACGTCATGTT

AAGGTTGACGGTAAGGTCAGAACTGACGCTACCTACCCAGCTGGTTTCATGGATGTTATCACCTTGGAAG

CTACCAACGAAAACTTCAGATTGGTCTACGACGTCAAGGGTAGATTCGCTGTCCACCGTATCACTGACGA

AGAAGCTTCCTACAAGTTGGGTAAGGTCAAGAAGGTCCAATTGGGTAAGAAGGGTGTTCCATACGTTGTC

ACTGACGATGGTAGAACTATCAGATACCCAGACCCAAACATCAAGGTCAATGACACCGTCAAGGTCGACT

TGGCTTCCGGTAAGATCACTGACTACATCAAGTTCGACATTGGTAAGTTGGTCTACATCACCGGTGGTCG

TAACTTGGGTCGTATCGGTACCATCGTTCACAAGGAAAGACACGATGGTGGTTTCGACTTGGTTCACGTC

AAGGACTCCTTGGACAACACTTTCGTCACCAGATTGAACAACGTTTTCGTTATCGGTGAACAAGGTAAGC

CATACATCTCCTTGCCAAAGGGTAAGGGTATCAAGTTGACCATTGCTGAAGAACGTGACAGAAGAAGAGC

TCAACAAGGTTTATAA

SEQ ID NO 205; RNA *Candida glabrata* CBS138, partial mRNA
AUGGCUAGAGGACCAAAGAAGCAUCUAAAGAGAUUAGCAGCUCCACACCACUGGUUGUUGGACAAGUUGU

CCGGCUGUUACGCCCCAAGACCAUCCGCUGGUCCACACAAGUUGCGUGAAUCCCUACCAUUGAUCGUUUU

CUUGAGAAACAGAUUAAAGUACGCUUUGAACGGUCGUGAAGUUAAGGCUAUCAUGAUGCAACGUCAUGUU

AAGGUUGACGGUAAGGUCAGAACUGACGCUACCUACCCAGCUGGUUUCAUGGAUGUUAUCACCUUGGAAG

CUACCAACGAAAACUUCAGAUUGGUCUACGACGUCAAGGGUAGAUUCGCUGUCCACCGUAUCACUGACGA

AGAAGCUUCCUACAAGUUGGGUAAGGUCAAGAAGGUCCAAUUGGGUAAGAAGGGUGUUCCAUACGUUGUC

ACUGACGAUGGUAGAACUAUCAGAUACCCAGACCCAAACAUCAAGGUCAAUGACACCGUCAAGGUCGACU

UGGCUUCCGGUAAGAUCACUGACUACAUCAAGUUCGACAUUGGUAAGUUGGUCUACAUCACCGGUGGUCG

UAACUUGGGUCGUAUCGGUACCAUCGUUCACAAGGAAAGACACGAUGGUGGUUUCGACUUGGUUCACGUC

AAGGACUCCUUGGACAACACUUUCGUCACCAGAUUGAACAACGUUUUCGUUAUCGGUGAACAAGGUAAGC

CAUACAUCUCCUUGCCAAAGGGUAAGGGUAUCAAGUUGACCAUUGCUGAAGAACGUGACAGAAGAAGAGC

UCAACAAGGUUUAUAA

SEQ ID NO 206; M64293. *S. cerevisiae* ribosomal protein S7 gene, exons 1 and 2
GATCTAATCCTTCTCCTGGCCTACCGTCTGTGCAACCATTAGTCATGATTACGTGTGTTGCGCCTTATCT

TGTCATTATGGCAGCATACTTTTCGTAGTCCTTTCCTGCGCACGTTGTCCATTTTCGTAACCACGTAAAA

AGTCCTAATGGAGAGCTGGGTACTGCATTTTTTTCGATGTTTTCAATATTCAGTTCAGCAGGAAATAAACA

AATAAACAAACATTAAAATATCTGGTTTTTTTTCCCAGAGACGCGTGGAAGCACCCATGCATCACTATTT

ATTTTTAAACAGCCGTACATTCTGTAATTTTGCTTCCTTTTTCTTCCTGCGTTCTTTTTTTCTTGAACTG

TCGTTTTCCGTTATTTTTTTCGGTGACATCAGTTGAAAGTAGCAGCGGCCTAGGCGACGGTAGCTCTTTG

TAGTCGTGGTAAGGGGGAGTAGCAATTCACTTAGTACGTGGTCTTGGAGTTAGGCTGGCTCGGACTGGCC

CTGGCAAGTCCTGTTCTGTGTGGTAGTATTGAAATTTCAGAGATTGTCGGCAATACTAGTATATTAAAAA

TTATACTATAATTTAATCTAGTGTTGAAATACTTTCTTATATAGCGATTTTTCTGCCCAAAACAAACCAA

AGAATCAATACGCAAAGATGGCTAGAGGACCGTATGTTTGACTATAGACTTTGATTATAATTACGCAAGG

ATGAGAAGAATGATAGACAAGAAACAAGTGGAGTCTTAACCAAACGAATAGGAACAACAATGAACCAGTT

-continued

TATGTCCATTTAATTTTAGATCATCCTGGGATTGTACAAATATTTTACGAGTAATGATTTACTAACGAGC

ACAATGAAAAAAATAAAATGTCTGTATCTTCATTATACATTCATTTTTGCCCTTTTTTCTCATTTTTTTC

CGTACAGAAAGAAGCATCTAAAAAGATTAGCAGCTCCACACCACTGGTTATTGGACAAGTTGTCCGGTTG

TTACGCCCCAAGACCATCTGCTGGTCCACACAAATTGCGTGAATCCTTGCCATTGATTGTCTTTCTAAGA

AACAGATTAAAGTATGCTTTGAACGGCCGTGAAGTCAAGGCTATCTTGATGCAACGTCACGTTAAAGTGG

ACGGTAAGGTTAGAACCGACACTACCTACCCAGCTGGTTTCATGGATGTCATCACTCTAGATGCCACCAA

TGAAAACTTCAGATTGGTCTACGATGTCAAGGGTAGATTCGCTGTCCACCGTATCACCGATGAAGAAGCT

TCTTACAAGTTGGGTAAGGTCAAGAAGGTTCAATTAGGTAAGAAGGGTGTTCCATACGTTGTTACCCACG

ATGGTAGAACTATCAGATACCCAGACCCAAACATCAAGGTCAATGACACTGTTAAGATCGACTTGGCCTC

TGGTAAGATTACTGATTTCATCAAGTTCGATGCCGGTAAGTTGGTTTACGTTACTGGTGGTCGTAACTTG

GGTCGTATCGGTACTATCGTTCACAAGGAAAGACACGATGGTGGTTTCGATTTAGTTCACATCAAGGACT

CCTTGGACAACACTTTCGTCACTAGATTGAACAATGTCTTCGTCATCGGTGAACAAGGTAAGCCTTACAT

TTCTTTGCCAAAGGGTAAGGGTATCAAGTTGTCTATTGCTGAAGAACGTGACAGAAGAAGAGCTCAACAA

GGTTTATAAATTTCATAACAACTTAATTATTTTCTTCTTTTGTATATCTCCATTAATGTTTATTAGAAAT

TGAATTTTAAAATAATACATCGTATCTTCCTTTTTCGACTGGCAGTAATATAACGTATAATATATATATT

AGGTGTGTGTATATATATCCGTATTGTAATATTGATAGTAAAAATACGCTAACCCTGAAATAGAAGGCGT

ATGATAAGACGTACTGACACTACGCACTACCACAATATATGCGTTGTGTGTGTGTGTGTGTGTGTGTGTG

TGTGTGATTGTATTGGAATATATATACTTACTAAAATTAAGCTTATATGGTTCGCATATTGACTATTTAT

AAGGATATTCAACTTGTATGTCCTTTCTTAACCAAATTTTCTTCTTTCTCTTGGTGGTAACATGTTCCAC

AAACTTCTCAGTACAATGATCCACTTTGAATTTCTTTATGAAAACAGGGTCCCATAATTCAGAACCGACG

CCGAGATC

SEQ ID NO 207; RNA *S. cerevisiae* ribosomal protein S7 gene, exons 1 and 2
GAUCUAAUCCUUCUCCUGGCCUACCGUCUGUGCAACCAUUAGUCAUGAUUACGUGUGUUGCGCCUUAUCU

UGUCAUUAUGGCAGCAUACUUUUCGUAGUCCUUUCCUGCGCACGUUGUCCAUUUUCGUAACCACGUAAAA

AGUCCUAAUGGAGAGCUGGGUACUGCAUUUUUUCGAUGUUUUCAAUAUUCAGUUCAGCAGGAAAUAAACA

AAUAAACAAACAUUAAAAUAUCUGGUUUUUUUUCCCAGAGACGCGUGGAAGCACCCAUGCAUCACUAUUU

AUUUUUAAACAGCCGUACAUUCUGUAAUUUUGCUUCCUUUUUCUUCCUGCGUUCUUUUUUUCUUGAACUG

UCGUUUUCCGUUAUUUUUUUCGGUGACAUCAGUUGAAAGUAGCAGCGGCCUAGGCGACGGUAGCUCUUUG

UAGUCGUGGUAAGGGGGAGUAGCAAUUCACUUAGUACGUGGUCUUGGAGUUAGGCUGGCUCGGACUGGCC

CUGGCAAGUCCUGUUCUGUGUGGUAGUAUUGAAAUUUCAGAGAUUGUCGGCAAUACUAGUAUAUUAAAAA

UUAUACUAUAAUUUAAUCUAGUGUUGAAAUACUUUCUUAUAUAGCGAUUUUUCUGCCCAAAACAAACCAA

AGAAUCAAUACGCAAAGAUGGCUAGAGGACCGUAUGUUUGACUAUAGACUUUGAUUAUAAUUACGCAAGG

AUGAGAAGAAUGAUAGACAAGAAACAAGUGGAGUCUUAACCAAACGAAUAGGAACAACAAUGAACCAGUU

UAUGUCCAUUUAAUUUUAGAUCAUCCUGGGAUUGUACAAAUAUUUUACGAGUAAUGAUUUACUAACGAGC

ACAAUGAAAAAAAUAAAAUGUCUGUAUCUUCAUUAUACAUUCAUUUUUGCCCUUUUUUCUCAUUUUUUUC

CGUACAGAAAGAAGCAUCUAAAAAGAUUAGCAGCUCCACACCACUGGUUAUUGGACAAGUUGUCCGGUUG

UUACGCCCCAAGACCAUCUGCUGGUCCACACAAAUUGCGUGAAUCCUUGCCAUUGAUUGUCUUUCUAAGA

AACAGAUUAAAGUAUGCUUUGAACGGCCGUGAAGUCAAGGCUAUCUUGAUGCAACGUCACGUUAAAGUGG

ACGGUAAGGUUAGAACCGACACUACCUACCCAGCUGGUUUCAUGGAUGUCAUCACUCUAGAUGCCACCAA

UGAAAACUUCAGAUUGGUCUACGAUGUCAAGGGUAGAUUCGCUGUCCACCGUAUCACCGAUGAAGAAGCU

UCUUACAAGUUGGGUAAGGUCAAGAAGGUUCAAUUAGGUAAGAAGGGUGUUCCAUACGUUGUUACCCACG

-continued

AUGGUAGAACUAUCAGAUACCCAGACCCAAACAUCAAGGUCAAUGACACUGUUAAGAUCGACUUGGCCUC

UGGUAAGAUUACUGAUUUCAUCAAGUUCGAUGCCGGUAAGUUGGUUUACGUUACUGGUGGUCGUAACUUG

GGUCGUAUCGGUACUAUCGUUCACAAGGAAAGACACGAUGGUGGUUUCGAUUUAGUUCACAUCAAGGACU

CCUUGGACAACACUUUCGUCACUAGAUUGAACAAUGUCUUCGUCAUCGGUGAACAAGGUAAGCCUUACAU

UUCUUUGCCAAAGGGUAAGGGUAUCAAGUUGUCUAUUGCUGAAGAACGUGACAGAAGAAGAGCUCAACAA

GGUUUAUAAAUUUCAUAACAACUUAAUUAUUUUCUUCUUUUGUAUAUCUCCAUUAAUGUUUAUUAGAAAU

UGAAUUUUAAAAUAAUACAUCGUAUCUUCCUUUUUCGACUGGCAGUAAUAUAACGUAUAAUAUAUAUAUU

AGGUGUGUGUAUAUAUAUCCGUAUUGUAAUAUUGAUAGUAAAAAUACGCUAACCCUGAAAUAGAAGGCGU

AUGAUAAGACGUACUGACACUACGCACUACCACAAUAUAUGCGUUGUGUGUGUGUGUGUGUGUGUGUGUG

UGUGUGAUUGUAUUGGAAUAUAUAUACUUACUAAAAUUAAGCUUAUAUGGUUCGCAUAUUGACUAUUUAU

AAGGAUAUUCAACUUGUAUGUCCUUUCUUAACCAAAUUUUCUUCUUUCUCUUGGUGGUAACAUGUUCCAC

AAACUUCUCAGUACAAUGAUCCACUUUGAAUUUCUUUAUGAAAACAGGGUCCCAUAAUUCAGAACCGACG

CCGAGAUC

SEQ ID NO 208; M64294. A *S. cerevisiae* ribosomal protein S7 gene, exons 1 and 2
GTAAGATTTAGAATAGTTTCTTTTCATATAACGTCGACTAAGTATAACAATAGATACACCACTATTGAGG

AAAGATGGCTAGAGGACCGTATGTTGATTTCCACCTAAAAAAATGAAGAGTTGGCAAAACAAGATAATAG

TTTTCTTTGAAGATGGGTACCCTCTCATGATTGGTACAAGTGATTTGCACCAAAGTGACGATGCGGACTA

AAGAAAGAATATAAGAAGTTGTGTTTATCTATCGGAAGATAGAATTCTGATGAGAAAACTTTATCCTTGT

TAAGAACAGATAAGCATTGCGGGATATTTTTACTAACAAGAGTACGTTTAATAATGTTAATACGATTTTT

CATATAGAAAGAAGCATCTAAAGAGATTAGCAGCTCCACACCATTGGTTATTGGACAAGTTGTCCGGTTG

TTACGCCCCAAGACCATCTGCTGGTCCACACAAATTGCGTGAATCCTTGCCATTGATTGTCTTTCTAAGA

AACAGATTAAAGTATGCTTTGAACGGCCGTGAAGTCAAGGCTATCTTGATGCAACGTCACGTCAAAGTTG

ACGGTAAGGTTAGAACTGACACCACCTACCCAGCTGGTTTCATGGACGTCATCACTCTAGATGCCACCAA

TGAAAACTTCAGATTGGTCTACGATGTCAAGGGTAGATTCGCTGTCCACCGTATCACCGATGAAGAAGCC

TCTTACAAATTGGGTAAGGTCAAGAAGGTTCAATTAGGTAAGAAGGGTGTTCCATACGTTGTTACCCACG

ATGGTAGAACTATCAGATACCCAGACCCAAACATCAAGGTCAATGACACTGTTAAGATTGATTTGGCCTC

TGGTAAGATTACTGATTTCATCAAGTTCGATGCCGGTAAGTTGGTTTACGTTACTGGTGGTCGTAACTTG

GGTCGTATCGGTACTATCGTTCACAAGGAAAGACACGATGGTGGTTTCGATTTGGTTCACATCAAGGACT

CCTTGGACAACACTTTCGTCACTAGATTGAACAATGTCTTCGTCATTGGTGAACAAGGTAAGCCTTACAT

TTCTTTGCCAAAGGGTAAGGGTATCAAGTTGTCTATTGCTGAAGAACGTGACAGAAGAAGAGCTCAACAA

GGTTTGTAAACATTTTAAATATTGTTATCTGCCCTCTCTTCGTCTTTTG

SEQ ID NO 209; RNA A *S. cerevisiae* ribosomal protein S7 gene, exons 1 and 2
GUAAGAUUUAGAAUAGUUUCUUUUCAUAUAACGUCGACUAAGUAUAACAAUAGAUACACCACUAUUGAGG

AAAGAUGGCUAGAGGACCGUAUGUUGAUUUCCACCUAAAAAAAUGAAGAGUUGGCAAAACAAGAUAAUAG

UUUUCUUUGAAGAUGGGUACCCUCUCAUGAUUGGUACAAGUGAUUUGCACCAAAGUGACGAUGCGGACUA

AAGAAAGAAUAUAAGAAGUUGUGUUUAUCUAUCGGAAGAUAGAAUUCUGAUGAGAAAACUUUAUCCUUGU

UAAGAACAGAUAAGCAUUGCGGGAUAUUUUUACUAACAAGAGUACGUUUAAUAAUGUUAAUACGAUUUUU

CAUAUAGAAAGAAGCAUCUAAAGAGAUUAGCAGCUCCACACCAUUGGUUAUUGGACAAGUUGUCCGGUUG

UUACGCCCCAAGACCAUCUGCUGGUCCACACAAAUUGCGUGAAUCCUUGCCAUUGAUUGUCUUUCUAAGA

AACAGAUUAAAGUAUGCUUUGAACGGCCGUGAAGUCAAGGCUAUCUUGAUGCAACGUCACGUCAAAGUUG

ACGGUAAGGUUAGAACUGACACCACCUACCCAGCUGGUUUCAUGGACGUCAUCACUCUAGAUGCCACCAA

UGAAAACUUCAGAUUGGUCUACGAUGUCAAGGGUAGAUUCGCUGUCCACCGUAUCACCGAUGAAGAAGCC

-continued

UCUUACAAAUUGGGUAAGGUCAAGAAGGUUCAAUUAGGUAAGAAGGGUGUUCCAUACGUUGUUACCCACG

AUGGUAGAACUAUCAGAUACCCAGACCCAAACAUCAAGGUCAAUGACACUGUUAAGAUUGAUUUGGCCUC

UGGUAAGAUUACUGAUUUCAUCAAGUUCGAUGCCGGUAAGUUGGUUUACGUUACUGGUGGUCGUAACUUG

GGUCGUAUCGGUACUAUCGUUCACAAGGAAAGACACGAUGGUGGUUUCGAUUUGGUUCACAUCAAGGACU

CCUUGGACAACACUUUCGUCACUAGAUUGAACAAUGUCUUCGUCAUUGGUGAACAAGGUAAGCCUUACAU

UUCUUUGCCAAAGGGUAAGGGUAUCAAGUUGUCUAUUGCUGAAGAACGUGACAGAAGAAGAGCUCAACAA

GGUUUGUAAACAUUUUAAAUAUUGUUAUCUGCCCUCUCUUCGUCUUUUG

SEQ ID NO 210
XM_451697.1 *Kluyveromyces lactis* NRRL Y-1140, KLLA0B03652g predicted mRNA
ATGGCTAGAGGACCAAAGAAGCATCTAAAGAGATTAGCAGCTCCACATCATTGGATGTTGGACAAGTTGT

CCGGTTGTTACGCACCAAGACCATCTGCTGGTCCACACAAGTTGCGTGAATCCTTGCCATTGATCGTTTT

CTTGAGAAACAGATTAAAGTATGCTTTGAACGGTCGTGAAGTCAAGGCCATCTTGATGCAACGTCATGTC

AAGGTTGACGGTAAGGTCAGAACCGACACTACTTTCCCAGCTGGTTTCATGGATGTTATCACCTTGGAAG

CTACCAACGAAAACTTCAGATTGGTCTACGATGTTAAGGGTAGATTCGCTGTCCACCGTATCACTGATGA

AGAAGCTTCCTACAAGTTGGCTAAGGTCAAGAAGGTTCAACTAGGTAAGAAGGGTATTCCATACGTCGTT

ACCCACGACGGTAGAACCATCAGATACCCAGACCCAAACATCAAGGTTAACGACACCGTTAAGGTTGATT

TGGCTACTGGTACTATCACCGATTTCATCAAATTCGACACTGGTAAGTTGGTTTATGTTACCGGTGGTCG

TAACTTGGGTAGAGTTGGTACCATCGTCCACAGAGAAAGACACGAAGGTGGTTTCGATTTGGTTCACATC

AAGGATTCTTTGGAAAACACTTTCGTCACCAGATTGAACAACGTTTTCGTCATCGGTGAACCAGGTAGAC

CATGGATCTCCTTGCCAAAGGGTAAGGGTATCAAGTTGACCATCTCTGAAGAACGTGACCGTAGAAGAGC

TCAACATGGTTTGTAA

SEQ ID NO 211
RNA *Kluyveromyces lactis* NRRL Y-1140, KLLA0B03652g predicted mRNA
AUGGCUAGAGGACCAAAGAAGCAUCUAAAGAGAUUAGCAGCUCCACAUCAUUGGAUGUUGGACAAGUUGU

CCGGUUGUUACGCACCAAGACCAUCUGCUGGUCCACACAAGUUGCGUGAAUCCUUGCCAUUGAUCGUUUU

CUUGAGAAACAGAUUAAAGUAUGCUUUGAACGGUCGUGAAGUCAAGGCCAUCUUGAUGCAACGUCAUGUC

AAGGUUGACGGUAAGGUCAGAACCGACACUACUUUCCCAGCUGGUUUCAUGGAUGUUAUCACCUUGGAAG

CUACCAACGAAAACUUCAGAUUGGUCUACGAUGUUAAGGGUAGAUUCGCUGUCCACCGUAUCACUGAUGA

AGAAGCUUCCUACAAGUUGGCUAAGGUCAAGAAGGUUCAACUAGGUAAGAAGGGUAUUCCAUACGUCGUU

ACCCACGACGGUAGAACCAUCAGAUACCCAGACCCAAACAUCAAGGUUAACGACACCGUUAAGGUUGAUU

UGGCUACUGGUACUAUCACCGAUUUCAUCAAAUUCGACACUGGUAAGUUGGUUUAUGUUACCGGUGGUCG

UAACUUGGGUAGAGUUGGUACCAUCGUCCACAGAGAAAGACACGAAGGUGGUUUCGAUUUGGUUCACAUC

AAGGAUUCUUUGGAAAACACUUUCGUCACCAGAUUGAACAACGUUUUCGUCAUCGGUGAACCAGGUAGAC

CAUGGAUCUCCUUGCCAAAGGGUAAGGGUAUCAAGUUGACCAUCUCUGAAGAACGUGACCGUAGAAGAGC

UCAACAUGGUUUGUAA

SEQ ID NO 212; NM_209058.1| *Eremothecium gossypii* ADL391Cp (ADL391C), mRNA
ATGGCTAGAGGACCAAAGAAGCACCTGAAGAGATTGGCAGCTCCACACCACTGGTTGTTGGACAAGCTAT

CCGGCTGTTACGCTCCAAGACCATCCGCTGGTCCACACAAGTTGCGCGAGTCTTTGCCATTGATCGTCTT

CTTGAGAAACAGATTAAAGTATGCTTTGAACGGTCGCGAGGTCAAGGCCATCCTAATGCAGCGTCATGTT

AAGGTTGACGGTAAGGTCAGAACTGACACTACCTACCCAGCTGGTTTCATGGATGTCATCACTCTAGAGG

CTACCAACGAGAACTTCAGATTGGTATACGATGTCAAGGGCAGATTTGCTGTCCACCGTATCACCGATGA

GGAGGCTACTTACAAGTTGGGTAAGGTTAAGCGCGTTCAGCTAGGTAAGAAGGGTGTCCCATACGTGGTC

ACTCACGACGGCAGAACCATCAGATACCCAGACCCAAACATCAAGGTTAACGACACCGTCAAGGTTGACC

-continued

TTGCTACTGGTAAGATTACCGACTTCATCAAGTTCGACACTGGTAAGTTGGTGTACGTCACCGGTGGCCG

TAACTTGGGCCGTATTGGTGTCATCACCCACAGAGAGAGACACGAGGGTGGCTTTGACTTGGTTCACATC

AAGGACTCCTTGGAGAACACTTTCGTCACCAGATTGAACAACGTTTTCGTCATCGGTGAGCAAGGTAGAC

CATGGATCTCCTTGCCAAGGGGTAAGGGTATTAAGTTGTCCATTGCTGAGGAGCGTGACCGTAGAAGAGC

TCAACAAGGTTTGTAA

SEQ ID NO 213; RNA *Eremothecium gossypii* ADL391Cp (ADL391C), mRNA
AUGGCUAGAGGACCAAAGAAGCACCUGAAGAGAUUGGCAGCUCCACACCACUGGUUGUUGGACAAGCUAU

CCGGCUGUUACGCUCCAAGACCAUCCGCUGGUCCACACAAGUUGCGCGAGUCUUUGCCAUUGAUCGUCUU

CUUGAGAAACAGAUUAAAGUAUGCUUUGAACGGUCGCGAGGUCAAGGCCAUCCUAAUGCAGCGUCAUGUU

AAGGUUGACGGUAAGGUCAGAACUGACACUACCUACCCAGCUGGUUUCAUGGAUGUCAUCACUCUAGAGG

CUACCAACGAGAACUUCAGAUUGGUAUACGAUGUCAAGGGCAGAUUUGCUGUCCACCGUAUCACCGAUGA

GGAGGCUACUUACAAGUUGGGUAAGGUUAAGCGCGUUCAGCUAGGUAAGAAGGGUGUCCCAUACGUGGUC

ACUCACGACGGCAGAACCAUCAGAUACCCAGACCCAAACAUCAAGGUUAACGACACCGUCAAGGUUGACC

UUGCUACUGGUAAGAUUACCGACUUCAUCAAGUUCGACACUGGUAAGUUGGUGUACGUCACCGGUGGCCG

UAACUUGGGCCGUAUUGGUGUCAUCACCCACAGAGAGAGACACGAGGGUGGCUUUGACUUGGUUCACAUC

AAGGACUCCUUGGAGAACACUUUCGUCACCAGAUUGAACAACGUUUUCGUCAUCGGUGAGCAAGGUAGAC

CAUGGAUCUCCUUGCCAAGGGGUAAGGGUAUUAAGUUGUCCAUUGCUGAGGAGCGUGACCGUAGAAGAGC

UCAACAAGGUUUGUAA

SEQ ID NO 214; XM_460509.1 *Debaryomyces hansenii* CBS767 hypothetical protein (DEHA0F03674g) partial mRNA
ATGGGTAGAGGTCCAAAGAAGCACTTGAAGAGATTAGCAGCACCATCCCACTGGATGTTGGACAAATTGT

CCGGTACTTACGCACCAAGACCATCTGCTGGTCCTCACAAATTGAGAGAATCTTTACCATTGGTTATCTT

CTTAAGAAACAGACTTAAGTATGCCTTAAACGGTAGAGAAGTCAAGGCCATCTTGATGCAAGAACACGTC

AAGGTTGATGGTAAAGTTAGAACCGATGCTACTTTCCCAGCTGGTTTCATGGATGTCATCACTTTAGAAG

CTACCAACGAACACTTCAGATTAATCTATGATGTCAAGGGTAGATTCACTGTCCACAGAATCACTGCTGA

AGAAGCTTCTTACAAGTTAGCTAAGGTCAAGAAGGTCCAATTAGGTAAGAGAGGTATTCCATACGTTGTC

ACCCACGACGGTAGAACTATCAGATACCCAGATCCATTGATCAGAGCCAACGATTCCGTTAAGGTTGACT

TAGCTACCGGTAAGATCACTGACTTTATCAGCTTTGACACTGGTAGATTAGTCATGGTTACTGGTGGTCG

TAACATGGGTAGAGTTGGTGTTATCACCCACAGAGAAAAGCACGAGGGTGGTTTCGATTTAGTCCACATC

AAGGATTCTTTGGAAAACACTTTCGTTACCAGATTAACTAACGTCTTCATCGTCGGTACTGAAGCTGGTA

AGCCACACATTTCTTTACCAAAGGGTAAGGGTATTAAGTTATCCATCTCTGAAGAACGTGACAGAAGAAG

AAACCAACAACTTATCAACTAA

SEQ ID NO 215; RNA *Debaryomyces hansenii* CBS767 hypothetical protein (DEHA0F03674g) partial mRNA
AUGGGUAGAGGUCCAAAGAAGCACUUGAAGAGAUUAGCAGCACCAUCCCACUGGAUGUUGGACAAAUUGU

CCGGUACUUACGCACCAAGACCAUCUGCUGGUCCUCACAAAUUGAGAGAAUCUUUACCAUUGGUUAUCUU

CUUAAGAAACAGACUUAAGUAUGCCUUAAACGGUAGAGAAGUCAAGGCCAUCUUGAUGCAAGAACACGUC

AAGGUUGAUGGUAAAGUUAGAACCGAUGCUACUUUCCCAGCUGGUUUCAUGGAUGUCAUCACUUUAGAAG

CUACCAACGAACACUUCAGAUUAAUCUAUGAUGUCAAGGGUAGAUUCACUGUCCACAGAAUCACUGCUGA

AGAAGCUUCUUACAAGUUAGCUAAGGUCAAGAAGGUCCAAUUAGGUAAGAGAGGUAUUCCAUACGUUGUC

ACCCACGACGGUAGAACUAUCAGAUACCCAGAUCCAUUGAUCAGAGCCAACGAUUCCGUUAAGGUUGACU

UAGCUACCGGUAAGAUCACUGACUUUAUCAGCUUUGACACUGGUAGAUUAGUCAUGGUUACUGGUGGUCG

UAACAUGGGUAGAGUUGGUGUUAUCACCCACAGAGAAAAGCACGAGGGUGGUUUCGAUUUAGUCCACAUC

-continued

AAGGAUUCUUUGGAAAACACUUUCGUUACCAGAUUAACUAACGUCUUCAUCGUCGGUACUGAAGCUGGUA

AGCCACACAUUUCUUUACCAAAGGGUAAGGGUAUUAAGUUAUCCAUCUCUGAAGAACGUGACAGAAGAAG

AAACCAACAACUUAUCAACUAA

SEQ ID NO 216; XM_657428.1 *Aspergillus nidulans* FGSC A4 40S ribosomal protein S7 (AN4916.2), mRNA

ATGGCTGCCATCAACAAGATCGCCCACAACTCGCCGTCGAGGCAGAACCCTTCCGAGCTGGAGACCGCGA

TCGCGGGTGCTCTCTTCGACTTGGAGAGCAACACACAGGACCTGAAGGCTACTCTCCGGCCTCTGCAGTT

CGTGTCTGCTCGTGAGGTCGAGGTCGGCCACGGCAAGAAGGCTGTCATCATCTTCGTCCCCGTCCCTCTC

CTCCAGGCCTTCCACAAGATCCAGCAGCGCCTTACCCGTGAACTCGAGAAGAAGTTCTCGGACCGCCACG

TCCTCTTCGTCGCTCAGCGCCGCATCCTCCCCAAGCCCAAGCGCTCCGTCAACTCCCGCACCAACCAGAA

GCAGAAGCGCCCCCGTTCCCGTACCCTTACTGCCGTTCACGACGCCATCCTCGACGACCTCGTCTACCCC

GTTGAGATTGTCGGCAAGCGCATCCGCACCAAGGAGGACGGCTCCAAGACCCTCAAGGTCATCCTCGACG

AGAAGGAGCGTGGTGGTGTTGACCACCGCCTCGACGCCTACGGCGAGGTCTACCGTCGTCTGACGGGTCG

TGCTGTCGTTTTCGAGTTCCCCCAGGGTGGTGCTTCTGAGTTTTAA

SEQ ID NO 217; RNA *Aspergillus nidulans* FGSC A4 40S ribosomal protein S7 (AN4916.2), mRNA

AUGGCUGCCAUCAACAAGAUCGCCCACAACUCGCCGUCGAGGCAGAACCCUUCCGAGCUGGAGACCGCGA

UCGCGGGUGCUCUCUUCGACUUGGAGAGCAACACACAGGACCUGAAGGCUACUCUCCGGCCUCUGCAGUU

CGUGUCUGCUCGUGAGGUCGAGGUCGGCCACGGCAAGAAGGCUGUCAUCAUCUUCGUCCCCGUCCCUCUC

CUCCAGGCCUUCCACAAGAUCCAGCAGCGCCUUACCCGUGAACUCGAGAAGAAGUUCUCGGACCGCCACG

UCCUCUUCGUCGCUCAGCGCCGCAUCCUCCCCAAGCCCAAGCGCUCCGUCAACUCCCGCACCAACCAGAA

GCAGAAGCGCCCCCGUUCCCGUACCCUUACUGCCGUUCACGACGCCAUCCUCGACGACCUCGUCUACCCC

GUUGAGAUUGUCGGCAAGCGCAUCCGCACCAAGGAGGACGGCUCCAAGACCCUCAAGGUCAUCCUCGACG

AGAAGGAGCGUGGUGGUGUUGACCACCGCCUCGACGCCUACGGCGAGGUCUACCGUCGUCUGACGGGUCG

UGCUGUCGUUUUCGAGUUCCCCCAGGGUGGUGCUUCUGAGUUUUAA

SEQ ID NO 218; >XM_749453.1 *Aspergillus fumigatus* Af293 ribosomal protein S7e (Afu3g10730) partial mRNA

ATGGCTGCTATCAACAAGATCGCCCACAACTCGCCATCGAGGCAGAACCCCTCCGAGCTGGAGACTGCGA

TCGCCGGCGCTCTCTACGACTTGGAGAGCAATACACAGGACCTGAAGGCCACCCTTCGGCCCCTGCAGTT

TGTCTCTGCCCGTGAGGTTGAGGTCGGCCACGGCAAGAAGGCCGTTATCATCTTCGTCCCCGTCCCTCTC

CTCCAGGGCTTCCACAAGATCCAGCAGCGCCTGACCCGTGAGCTCGAGAAGAAGTTCTCCGACCGCCACG

TCCTCTTTGTTGCTCAGCGCCGCATCCTGCCCCGCCCTAAGCGCTCTGTCAACTCCCGCACCAACCAGAA

GCAGAAGCGTCCTCGCTCTCGCACCCTGACCGCTGTCCACGACGCCATCCTCAACGACCTCGTTTACCCC

GTCGAGATCGTCGGCAAGCGTATCCGCACCAAGGAGGACGGCAGCAAGACTCTCAAGGTCATCCTGGACG

AGAAGGAGCGTGGTGGTGTTGACCACAGACTCGATGCCTACGGCGAGGTTTACCGCCGACTAACCGGCCG

CTCTGTTGTCTTCGAGTTCCCCCAGAGCGGTGCCGCCGAGTACTAG

SEQ ID NO 219; RNA *Aspergillus fumigatus* Af293 ribosomal protein S7e (Afu3g10730) partial mRNA

AUGGCUGCUAUCAACAAGAUCGCCCACAACUCGCCAUCGAGGCAGAACCCCUCCGAGCUGGAGACUGCGA

UCGCCGGCGCUCUCUACGACUUGGAGAGCAAUACACAGGACCUGAAGGCCACCCUUCGGCCCCUGCAGUU

UGUCUCUGCCCGUGAGGUUGAGGUCGGCCACGGCAAGAAGGCCGUUAUCAUCUUCGUCCCCGUCCCUCUC

CUCCAGGGCUUCCACAAGAUCCAGCAGCGCCUGACCCGUGAGCUCGAGAAGAAGUUCUCCGACCGCCACG

UCCUCUUUGUUGCUCAGCGCCGCAUCCUGCCCCGCCCUAAGCGCUCUGUCAACUCCCGCACCAACCAGAA

GCAGAAGCGUCCUCGCUCUCGCACCCUGACCGCUGUCCACGACGCCAUCCUCAACGACCUCGUUUACCCC

-continued

GUCGAGAUCGUCGGCAAGCGUAUCCGCACCAAGGAGGACGGCAGCAAGACUCUCAAGGUCAUCCUGGACG

AGAAGGAGCGUGGUGGUGUUGACCACAGACUCGAUGCCUACGGCGAGGUUUACCGCCGACUAACCGGCCG

CUCUGUUGUCUUCGAGUUCCCCCAGAGCGGUGCCGCCGAGUACUAG

SEQ ID NO 220: >XM_001213780.1 *Aspergillus terreus* NIH2624 40S ribosomal protein S7 (ATEG_04602) mRNA, complete cds
ATGGCTGCTATCAACAAGATCGCCCACAACTCGCCGTCTCGGCAGAACCCCTCCGAGCTGGAGACCGCGA

TCGCCGGTGCTCTGTTCGACCTCGAGAGCAACACCACCGACCTGAAGGCCACCCTCCGCCCCCTTCAGTT

CGTGTCTGCTCGTGAGGTTGAGGTCGGCCACGGCAAGAAGGCCGTCATCATCTTCGTCCCTGTCCCTCTC

CTCCAGGGCTTCCACAAGATCCAGCAGCGTCTGACCCGTGAGCTCGAGAAGAAGTTCTCCGACCGCCACG

TCCTCTTCGTTGCTCAGCGCCGCATCCTGCCCCGCCCCAAGCGCTCTGTCAACTCCCGCACCAACCAGAA

GCAGAAGCGTCCCCGTTCCCGCACTCTGACGGCCGTCCACGACGCCATCCTCACCGACCTCGTCTACCCC

GTCGAGATCGTCGGCAAGCGCATCCGCACCAAGGAGGACGGCTCCAAGACCCTCAAGGTCATCCTCGACG

AGAAGGAGCGCGGCGGTGTCGACCACCGCCTCGATGCCTACGGCGAGGTCTACCGTCGTCTCACCGGCCG

TGCCGTCGTCTTCGAGTTCCCCCAGAGCGGTGCTGCTGACTACTAA

SEQ ID NO 221; RNA *Aspergillus terreus* NIH2624 40S ribosomal protein S7 (AUEG_04602) mRNA, complete cds
AUGGCUGCUAUCAACAAGAUCGCCCACAACUCGCCGUCUCGGCAGAACCCCUCCGAGCUGGAGACCGCGA

UCGCCGGUGCUCUGUUCGACCUCGAGAGCAACACCACCGACCUGAAGGCCACCCUCCGCCCCCUUCAGUU

CGUGUCUGCUCGUGAGGUUGAGGUCGGCCACGGCAAGAAGGCCGUCAUCAUCUUCGUCCCUGUCCCUCUC

CUCCAGGGCUUCCACAAGAUCCAGCAGCGUCUGACCCGUGAGCUCGAGAAGAAGUUCUCCGACCGCCACG

UCCUCUUCGUUGCUCAGCGCCGCAUCCUGCCCCGCCCCAAGCGCUCUGUCAACUCCCGCACCAACCAGAA

GCAGAAGCGUCCCCGUUCCCGCACUCUGACGGCCGUCCACGACGCCAUCCUCACCGACCUCGUCUACCCC

GUCGAGAUCGUCGGCAAGCGCAUCCGCACCAAGGAGGACGGCUCCAAGACCCUCAAGGUCAUCCUCGACG

AGAAGGAGCGCGGCGGUGUCGACCACCGCCUCGAUGCCUACGGCGAGGUCUACCGUCGUCUCACCGGCCG

UGCCGUCGUCUUCGAGUUCCCCCAGAGCGGUGCUGCUGACUACUAA

SEQ NO 222: *C. albicans* 1899
CATCACYTTGGAAGCTACCAACGAACATTTCAGATTAGTCTACGATGTTAAAGGTAAATTYGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAGA

SEQ NO 223: *C. albicans* 1899
CAUCACYUUGGAAGCUACCAACGAACAUUUCAGAUUAGUCUACGAUGUUAAAGGUAAAUUYGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAGA

SEQ NO 224 *C. albicans* 2738
CATCACYTTGGAAGCTACCAACGAACATTTCAGATTAGTCTACGATGTTAAAGGTAAATTYGCTGTTCACAGAATYTCTG

STGAAGAAGCTGCCTAYAAATTGGGTAAAGTCAAGAAAGTYCAATTAGGTAAGAAAGGTGTTCCATACGTTGTTACCCAC

GACGGTAGAACYATCAGATACCCAGA

SEQ NO 225 *C. albicans* 2738
CAUCACYUUGGAAGCUACCAACGAACAUUUCAGAUUAGUCUACGAUGUUAAAGGUAAAUUYGCUGUUCACAGAAUYUCUG

SUGAAGAAGCUGCCUAYAAAUUGGGUAAAGUCAAGAAAGUYCAAUUAGGUAAGAAAGGUGUUCCAUACGUUGUUACCCAC

GACGGUAGAACYAUCAGAUACCCAGA

SEQ NO 226 *C. albicans* 1912
CATCACYTTGGAAGCTACCAACGAACATTTCAGATTAGTCTACGATGTTAAAGGTAAATTCGCTGTTCACAGAATTTCTG

CTGAAGAAGCTGCCTACAAATTGGGTAAAGTCAAGAAAGTCCAATTAGGTAAGAAAGGTGTTCCATACGTTGTTACCCAC

GACGGTAGAACYATCAGATACCCAGA

-continued

SEQ NO 227 *C. albicans* 1912
CAUCACYUUGGAAGCUACCAACGAACAUUUCAGAUUAGUCUACGAUGUUAAAGGUAAAUUCGCUGUUCACAGAAUUUCUG

CUGAAGAAGCUGCCUACAAAUUGGGUAAAGUCAAGAAAGUCCAAUUAGGUAAGAAAGGUGUUCCAUACGUUGUUACCCAC

GACGGUAGAACYAUCAGAUACCCAGA

SEQ NO 228 *C. parapsilosis* 6318
YATTACTTTGGAAGCCACYAATGAAAACTTTAGATTGATTTACGATGTCAAAGGTAGATTTGCTGTCCACAGAATCTCAG

CTGAAGAAGCCACTTACAAATTGGGTAAAGTCAAGAGAGTCCAATTGGGTAAGAAGGGAATCCCATACGTTGTCACCCAC

GATGGTAGAACYATCAGATACCCAGA

SEQ NO 229 *C. parapsilosis* 6318
YAUUACUUUGGAAGCCACYAAUGAAAACUUUAGAUUGAUUUACGAUGUCAAAGGUAGAUUUGCUGUCCACAGAAUCUCAG

CUGAAGAAGCCACUUACAAAUUGGGUAAAGUCAAGAGAGUCCAAUUGGGUAAGAAGGGAAUCCCAUACGUUGUCACCCAC

GAUGGUAGAACYAUCAGAUACCCAGA

SEQ NO 230 *C. parapsilosis* 6395
CATCACTTTGGAAGCTACYAAYGAACATTTTMGATTGATCTACGATGTYAAAGGTAGATTYGCTGTYCAYAGAATCTCTG

CTGAAGAAGCCACYTACAAATTGGGTAAAGTTAAGAAAGTCCAATTAGGTAAAAAGGGAATYCCATACGTTGTCACCCAC

GATGGTAGAACYATCAGATACCCAG

SEQ NO 231: *C. parapsilosis* 6395
CAUCACUUUGGAAGCUACYAAYGAACAUUUUMGAUUGAUCUACGAUGUYAAAGGUAGAUUYGCUGUYCAYAGAAUCUCUG

CUGAAGAAGCCACYUACAAAUUGGGUAAAGUUAAGAAAGUCCAAUUAGGUAAAAAGGGAAUYCCAUACGUUGUCACCCAC

GAUGGUAGAACYAUCAGAUACCCAG

SEQ NO 232: *C. parapsilosis* 96141
CATTACTTTGGAAGCCACCAACGAACACTTTAGATTGATTTACGATGTTAARGGTAGATTYGCTGTCCACAGAATYTCTG

CTGARGAAGCCACCTACAAATTGGGTAAAGTTAAGAAAGTCCAATTAGGTAAAAAGGGAATCCCATACGTTGTCACCCAC

GATGGYAGAACYATCAGATACCCAG

SEQ NO 233: *C. parapsilosis* 96141
CAUUACUUUGGAAGCCACCAACGAACACUUUAGAUUGAUUUACGAUGUUAARGGUAGAUUYGCUGUCCACAGAAUYUCUG

CUGARGAAGCCACCUACAAAUUGGGUAAAGUUAAGAAAGUCCAAUUAGGUAAAAAGGGAAUCCCAUACGUUGUCACCCAC

GAUGGYAGAACYAUCAGAUACCCAG

SEQ 234: *C. parapsilosis* 96137
CATTACTTTGGAAGCCACCAATGAAAACTTTAGATTGATTTACGATGTCAAAGGTAGATTTGCTGTCCACAGAATCTCAG

CTGAAGAAGCCACTTACAAATTGGGTAAAGTCAAGAGAGTCCAATTGGGTAAGAAGGGAATCCCATACGTTGTCACCCAC

GATGGTAGAACCATCAGATACCCAG

SEQ 235: *C. parapsilosis* 96137
CAUUACUUUGGAAGCCACCAAUGAAAACUUUAGAUUGAUUUACGAUGUCAAAGGUAGAUUUGCUGUCCACAGAAUCUCAG

CUGAAGAAGCCACUUACAAAUUGGGUAAAGUCAAGAGAGUCCAAUUGGGUAAGAAGGGAAUCCCAUACGUUGUCACCCAC

GAUGGUAGAACCAUCAGAUACCCAG

SEQ 236: *C. parapsilosis* 96143rep
CATCACTTTGGAAGCTACYAAYGAACATTTYAGATTGATCTACGATGTYAAAGGTAGATTYGCTGTYCAYAGAATCTCTG

CTGAAGAAGCCACYTACAAATTGGGTAAAGTTAAGAAAGTCCAATTAGGTAAAAAGGGAATYCCATACGTTGTCACCCAY

GATGGTAGAACYATCAGATACCCAG

SEQ 237: *C. parapsilosis* 96143rep
CAUCACUUUGGAAGCUACYAAYGAACAUUUYAGAUUGAUCUACGAUGUYAAAGGUAGAUUYGCUGUYCAYAGAAUCUCUG

CUGAAGAAGCCACYUACAAAUUGGGUAAAGUUAAGAAAGUCCAAUUAGGUAAAAAGGGAAUYCCAUACGUUGUCACCCAY

GAUGGUAGAACYAUCAGAUACCCAG

-continued

SEQ 238: *C. parapsilosis* 109
YAYTACTTTGGAAGCCACYAATGAAAACTTTAGATTGATTTACGATGTCAAAGGTAGATTTGCTGTCCACAGAATCTCAG

CTGAAGAAGCCACTTACAAATTGGGTAAAGTCAAGAGAGTCCAATTGGGTAAGAAGGGAATCCCATACGTTGTCACCCAC

GATGGTAGAACTATCAGATACCCAGA

SEQ 239: *C. parapsilosis* 109
YAYUACUUUGGAAGCCACYAAUGAAAACUUUAGAUUGAUUUACGAUGUCAAAGGUAGAUUUGCUGUCCACAGAAUCUCAG

CUGAAGAAGCCACUUACAAAUUGGGUAAAGUCAAGAGAGUCCAAUUGGGUAAGAAGGGAAUCCCAUACGUUGUCACCCAC

GAUGGUAGAACUAUCAGAUACCCAGA

SEQ 240: *C. parapsilosis* 2195
YATTACYTTGGAAGCYACYAAYGAAAACTTYAGATTGRTYTACGAYGTCAARGGTAGATTYGCTGTCCACMGWATMTCWG

MYGAAGAAGCYWCYTACAARTTGGGTAARGTCAAGARRGTCCAATTGGGTAAGAAGGGWRTYCCATACGTTGTCACYSAC

GATGGTAGAACYATCAGATACCCAGA

SEQ 241: *C. parapsilosis* 2195
YAUUACYUUGGAAGCYACYAAYGAAAACUUYAGAUUGRUYUACGAYGUCAARGGUAGAUUYGCUGUCCACMGWAUMUCWG

MYGAAGAAGCYWCYUACAARUUGGGUAARGUCAAGARRGUCCAAUUGGGUAAGAAGGGWRUYCCAUACGUUGUCACYSAC

GAUGGUAGAACYAUCAGAUACCCAGA

SEQ 242: *C. parapsilosis* 2315
CATCACTTTGGAAGCTACYAAYGAACATTTYAGATTGATCTACGATGTYAAAGGTAGATTYGCTGTCCACAGAATCTCTG

CTGAAGAAGCCACYTACAAATTGGGTAAAGTTAAGAAAGTCCAATTAGGTAAAAAGGGAATYCCATACGTTGTCACCCAY

GATGGTAGAACYATCAGATACCCAGA

SEQ 243: *C. parapsilosis* 2315
CAUCACUUUGGAAGCUACYAAYGAACAUUUYAGAUUGAUCUACGAUGUYAAAGGUAGAUUYGCUGUCCACAGAAUCUCUG

CUGAAGAAGCCACYUACAAAUUGGGUAAAGUUAAGAAAGUCCAAUUAGGUAAAAAGGGAAUYCCAUACGUUGUCACCCAY

GAUGGUAGAACYAUCAGAUACCCAGA

SEQ 244: *C. krusei* 6199
CATCACTTTAGAWGCAACCAACGAACACTTCAGATTAATCTATGACATCAAGGGTAGATTCGCAATCCACAGAATCACCC

CAGAAGAAGCTGCATACAAGTTATGTAAGGTCAAGAAGGTCCAATTAGGTAAGAAGGGTATTCCTTATGTTGTTACCCAC

GATGGTAGAACYATCAGATACCCAG

SEQ 245: *C. krusei* 6199
CAUCACUUUAGAWGCAACCAACGAACACUUCAGAUUAAUCUAUGACAUCAAGGGUAGAUUCGCAAUCCACAGAAUCACCC

CAGAAGAAGCUGCAUACAAGUUAUGUAAGGUCAAGAAGGUCCAAUUAGGUAAGAAGGGUAUUCCUUAUGUUGUUACCCAC

GAUGGUAGAACYAUCAGAUACCCAG

SEQ 246: *C. tropicalis* 8072
CATTACCTTGGAAGCTACCAACGAACACTTCAGATTGATTTACGATGTTAAAGGTAAATTCGCTGTTCACAGAATTTCTG

CTGAAGAAGCTTCTTACAAATTAGGTAAAGTCAAGAAGGTTCAATTAGGTAAAAAAGGTGTTCCATACGTTGTCACCCAC

GATGGTAGAACYATCAGATACCCAGA

SEQ 247: *C. tropicalis* 8072
CAUUACCUUGGAAGCUACCAACGAACACUUCAGAUUGAUUUACGAUGUUAAAGGUAAAUUCGCUGUUCACAGAAUUUCUG

CUGAAGAAGCUUCUUACAAAUUAGGUAAAGUCAAGAAGGUUCAAUUAGGUAAAAAAGGUGUUCCAUACGUUGUCACCCAC

GAUGGUAGAACYAUCAGAUACCCAGA

SEQ 248: *C. tropicalis* 2316
CATCACTTTRGAWGCWACCAACGAACAYTTCAGATTAATCTACGAYGTCAAGGGTAAATTCGCTGTCCACAGAATCACYG

CTGAAGAAGCTGCCTMCAAATTGGTTAARGTMAAGAAAGTCCAATTAGGTAAGARAGGTGTTCCWTACGTTGTTACCCAC

GAYGGTAGAACYATCAGATACCCAGA

-continued

SEQ 249: *C. tropicalis* 2316
CAUCACUUURGAWGCWACCAACGAACAYUUCAGAUUAAUCUACGAYGUCAAGGGUAAAUUCGCUGUCCACAGAAUCACYG

CUGAAGAAGCUGCCUMCAAAUUGGUUAARGUMAAGAAAGUCCAAUUAGGUAAGARAGGUGUUCCWUACGUUGUUACCCAC

GAYGGUAGAACYAUCAGAUACCCAGA

SEQ 250: *C. dubliniensis* 16971
CATYACYTTRGAAGCTACYAAYGAACATTTCAGATTAGTWTACGATGTTAAAGGTAAATTYGCYGTTCAYAGAATCTCTG

CTGAAGAAGCTKCCTACAAATTGGGTAAAGTYAARAAAGTCCAATTRGGTAARAAAGGTGTTCCATAYGTTGTTACCCAC

GACGGTAGAACYATCAGATACCCAG

SEQ 251: *C. dubliniensis* 16971
CAUYACYUURGAAGCUACYAAYGAACAUUUCAGAUUAGUWUACGAUGUUAAAGGUAAAUUYGCYGUUCAYGAAUCUCUG

CUGAAGAAGCUKCCUACAAAUUGGGUAAAGUYAARAAAGUCCAAUURGGUAARAAAGGUGUUCCAUAYGUUGUUACCCAC

GACGGUAGAACYAUCAGAUACCCAG

SEQ 252: *C. dublininesis* 16721
CATYACYTTRGAAGCTACYAAYGAACATTTCAGATTAGTWTACGATGTTAAAGGTAAATTYGCYGTTCAYAGAATCTCTG

CTGAAGAAGCTKCCTACAAATTGGGTAAAGTYAAGAAAGTCCAATTRGGTAARAAAGGTGTTCCATACGTTGTTACCCAC

GACGGTAGAACYATCAGATACCCAG

SEQ 253: *C. dublininesis* 16721
CAUYACYUURGAAGCUACYAAYGAACAUUUCAGAUUAGUWUACGAUGUUAAAGGUAAAUUYGCYGUUCAYAGAAUCUCUG

CUGAAGAAGCUKCCUACAAAUUGGGUAAAGUYAAGAAAGUCCAAUURGGUAARAAAGGUGUUCCAUACGUUGUUACCCAC

GACGGUAGAACYAUCAGAUACCCAG

SEQ 254: *C. dubliniensis* 16197
CATYACYTTRGAAGCTACYAAYGAACATTTCAGATTAGTWTACGATGTTAAAGGTAAATTYRCYGTTCAYAGAATCTCTG

CTGAAGAAGCTKCCTACAAATTGGGTAAAGTYAARAAAGTCCAATTRGGTAARAAAGGTGTTCCATACGTTGTTACCCAC

GACGGTAGAACYATCAGATACCCAGA

SEQ 255: *C.dubliniensis* 16197
CAUYACYUURGAAGCUACYAAYGAACAUUUCAGAUUAGUWUACGAUGUUAAAGGUAAAUUYRCYGUUCAYAGAAUCUCUG

CUGAAGAAGCUKCCUACAAAUUGGGUAAAGUYAARAAAGUCCAAUURGGUAARAAAGGUGUUCCAUACGUUGUUACCCAC

GACGGUAGAACYAUCAGAUACCCAGA

SEQ 256: *C. norvegenesis* 2145
TATCACTTTAGAAGCAACCAACGAAAACTTCAGATTAATCTACGACATCAAGGGTAGATTCGCAATTCACAGAATCACTC

CTGAAGAAGCAGCATACAAGTTATGTAAGATCAAGAAGGTCCAATTAGGTAAGAAGGGTATTCCATAYGTTGTTACACAC

GACGGTAGAACYATCAGATACCCAGA

SEQ 257: *C. norvegenesis* 2145
UAUCACUUUAGAAGCAACCAACGAAAACUUCAGAUUAAUCUACGACAUCAAGGGUAGAUUCGCAAUUCACAGAAUCACUC

CUGAAGAAGCAGCAUACAAGUUAUGUAAGAUCAAGAAGGUCCAAUUAGGUAAGAAGGGUAUUCCAUAYGUUGUUACACAC

GACGGUAGAACYAUCAGAUACCCAGA

SEQ 258: *C. guilliermondii* 23
CATCACCTTGGAGGCCACCAACGAGCACTTYAGATTGGTGTACGACGTCAAGGGTAGATTTGCTGTCCACAGAATCACCG

CTGAGGAGGCTTCCTACAAGTTGGGTAAGGTCAAGAAGGTTCAATTGGGYAAGAGAGGTATTCCATACGTTGTGACCCAC

GACGGTAGAACTATCAGATACCCAGA

SEQ 259: *C. guilliermondii* 23
CAUCACCUUGGAGGCCACCAACGAGCACUUYAGAUUGGUGUACGACGUCAAGGGUAGAUUUGCUGUCCACAGAAUCACCG

CUGAGGAGGCUUCCUACAAGUUGGGUAAGGUCAAGAAGGUUCAAUUGGGYAAGAGAGGUAUUCCAUACGUUGUGACCCAC

GACGGUAGAACUAUCAGAUACCCAGA

-continued

SEQ 260: *C. guilliermondii* 8167
ATCACCTTGGAGGCTACCAACGAGCACTTCAGATTGGTGTACGATGTCAAGGGTAGATTTGCTGTCCACAGAATCACCGC

TGAAGAGGCTTCCTACAAGTTGGGTAAGGTCAAGAAGGTTCAATTGGGTAAGAGAGGTATTCCATACGTTGTTACCCACG

ACGGTAGAACCATCAGATACCCAG

SEQ 261: *C. guilliermondii* 8167
AUCACCUUGGAGGCUACCAACGAGCACUUCAGAUUGGUGUACGAUGUCAAGGGUAGAUUUGCUGUCCACAGAAUCACCGC

UGAAGAGGCUUCCUACAAGUUGGGUAAGGUCAAGAAGGUUCAAUUGGGUAAGAGAGGUAUUCCAUACGUUGUUACCCACG

ACGGUAGAACCAUCAGAUACCCAG

SEQ 262: *C. lusitaniae* 64
CACCTTGGARGCCACCAACGAAAACTTCAGATTGGTGTACGACATCAAGGGTAGATTCACTGTCCACAGAATCACCGCTG

ARGAAGGTTCCTACAAGTTGGGTAAGGTCAAGAAGATYGCTTTGGGCAAGAAGGCTATCCCATACGTGGTTACCCACGAY

GGTAGAACTATCAGATACCCAG

SEQ 263: *C. lusitaniae* 64
CACCUUGGARGCCACCAACGAAAACUUCAGAUUGGUGUACGACAUCAAGGGUAGAUUCACUGUCCACAGAAUCACCGCUG

ARGAAGGUUCCUACAAGUUGGGUAAGGUCAAGAAGAUYGCUUUGGGCAAGAAGGCUAUCCCAUACGUGGUUACCCACGAY

GGUAGAACUAUCAGAUACCCAG

SEQ 264: *C. lipolytica* 112
CAGATTGGTGTACGACGTCAAGGGTAGATTCGCCGTGCACAGAATCACCGCCGAGGAGTCCACCTACAAGTTGGCCAAGA

TCAAGAAGGTCCAGTTGGGCAAGAAGAGTATCCCCTACGCCGTCACCCACGACGGTAGAACTATCAGATACCCAGA

SEQ 265: *C. lipolytica* 112
CAGAUUGGUGUACGACGUCAAGGGUAGAUUCGCCGUGCACAGAAUCACCGCCGAGGAGUCCACCUACAAGUUGGCCAAGA

UCAAGAAGGUCCAGUUGGGCAAGAAGAGUAUCCCCUACGCCGUCACCCACGACGGUAGAACUAUCAGAUACCCAGA

SEQ 266: *C. lipolytica* 31
CATCACCTTGGRRGCCACCAACGAAAACTTCAGATTGGTGTACGACATCAAGGGTAGATTCACTGTCCACAGAATCACCG

CTGAGGAAGGTTCCTACAAGTTGGGTAAGGTCAAGAAGATYGCTTTGGGCAAGAAGGCTATCCCATACGTGGTTACCCAC

GAYGGTAGAACTATCAGATACCCAGA

SEQ 267: *C. lipolytica* 31
CAUCACCUUGGRRGCCACCAACGAAAACUUCAGAUUGGUGUACGACAUCAAGGGUAGAUUCACUGUCCACAGAAUCACCG

CUGAGGAAGGUUCCUACAAGUUGGGUAAGGUCAAGAAGAUYGCUUUGGGCAAGAAGGCUAUCCCAUACGUGGUUACCCAC

GAYGGUAGAACUAUCAGAUACCCAGA

SEQ 268: *C. lipolytica* 113
TTCAGATTGGTGTACGACGTCAAGGGTAGATTCGCCGTGCACAGAATCACCGCCGAGGAGTCCACCTACAAGTTGGCCAA

GATCAAGAAGGTCCAGTTGGGCAAGAAGAGTATCCCCTACGCCGTCACCCACGACGGTAGAACTATCAGATACCCAGA

SEQ 269: *C. lipolytica* 113
UUCAGAUUGGUGUACGACGUCAAGGGUAGAUUCGCCGUGCACAGAAUCACCGCCGAGGAGUCCACCUACAAGUUGGCCAA

GAUCAAGAAGGUCCAGUUGGGCAAGAAGAGUAUCCCCUACGCCGUCACCCACGACGGUAGAACUAUCAGAUACCCAGA

SEQ 270: *C. rugosa* 85
CTTGAGCTACCAACGAAAACTTCASMTTGATCTACGACGTCAAGGGTAGATTTGCCGTCCACAGAATCACCGCTGAAGAA

GCTTCGTACAAGTTGGSYAAGGTYAAGTCCGTCCAATTGGGYAAGMGMSKKATYCCTTACGCYGTTACYCACGAYGGTAG

AACTATCAGATACCCAGA

SEQ 271: *C. rugosa* 85
CUUGAGCUACCAACGAAAACUUCASMUUGAUCUACGACGUCAAGGGUAGAUUUGCCGUCCACAGAAUCACCGCUGAAGAA

GCUUCGUACAAGUUGGSYAAGGUYAAGUCCGUCCAAUUGGGYAAGMGMSKKAUYCCUUACGCYGUUACYCACGAYGGUAG

AACUAUCAGAUACCCAGA

SEQ 272: *C. rugosa* 613
CCTTGGAAGCTACCAACGAAAACTTCAGATTGATCTACGACGTCAAGGGTAGATTTGCCGTCCACAGAATCACCGCTGAA

GAAGCTTCGTACAAGTTGGSYAAGGTYAAGTCCGTCCAATTGGGYAAGMGMSKKATTCCTTACGCYGTTACYCACGAYGG

TAGAACYATCAGATACCCAGA

SEQ 273: *C. rugosa* 613
CCUUGGAAGCUACCAACGAAAACUUCAGAUUGAUCUACGACGUCAAGGGUAGAUUUGCCGUCCACAGAAUCACCGCUGAA

GAAGCUUCGUACAAGUUGGSYAAGGUYAAGUCCGUCCAAUUGGGYAAGMGMSKKAUUCCUUACGCYGUUACYCACGAYGG

UAGAACYAUCAGAUACCCAGA

SEQ 274: *C. rugosa* 41
CATCTCGCTTGAAGCCACCAACGAAAACTTCAGATTGATCTACGACGTCAAGGGTAGATTTGCCGTCCACAGAATCACCG

CYGAAGWGGCYTCGTACAAGTTGGSYAAGGTYAAGTCCGTCCAATTGGGYAAGMGMSKKATYCCTTACGCYGTYACYCAC

GACGGTAGAACTAYCAGATACCCAG

SEQ 275: *C. rugosa* 41
CAUCUCGCUUGAAGCCACCAACGAAAACUUCAGAUUGAUCUACGACGUCAAGGGUAGAUUUGCCGUCCACAGAAUCACCG

CYGAAGWGGCYUCGUACAAGUUGGSYAAGGUYAAGUCCGUCCAAUUGGGYAAGMGMSKKAUYCCUUACGCYGUYACYCAC

GACGGUAGAACUAYCAGAUACCCAG

SEQ 276: *C. rugosa* 44
TCGCTTGAGCCACCAACGAAAACTTCAGATTGATCTACGACGTCAAGGGTAGATTTGCCGTCCACAGAATCACCGCTGAA

GAGGCYTCGTACAAGTTGGSYAAGGTYAAGTCCGTCCAATTGGGYAAGMGMSKKATYCCTTACGCYGTYACYCACGACGG

TAGAACTATCAGATACCCAG

SEQ 277: *C. rugosa* 44
UCGCUUGAGCCACCAACGAAAACUUCAGAUUGAUCUACGACGUCAAGGGUAGAUUUGCCGUCCACAGAAUCACCGCUGAA

GAGGCYUCGUACAAGUUGGSYAAGGUYAAGUCCGUCCAAUUGGGYAAGMGMSKKAUYCCUUACGCYGUYACYCACGACGG

UAGAACUAUCAGAUACCCAG

SEQ 278: *C. rugosa* 46
TCGCTTGAGCCACCAACGAAAACTTCAGATTGATCTACGACGTCAAGGGTAGATTTGCCGTCCACAGAATCACCGCTGAA

GAGGCYTCGTACAAGTTGGSYAAGGTYAAGTCCGTCCAATTGGGYAAGMGMSKKATYCCTTACGCYGTYACYCACGACGG

TAGAACTATCAGATACCCAG

SEQ 279: *C. rugosa* 46
UCGCUUGAGCCACCAACGAAAACUUCAGAUUGAUCUACGACGUCAAGGGUAGAUUUGCCGUCCACAGAAUCACCGCUGAA

GAGGCYUCGUACAAGUUGGSYAAGGUYAAGUCCGUCCAAUUGGGYAAGMGMSKKAUYCCUUACGCYGUYACYCACGACGG

UAGAACUAUCAGAUACCCAG

SEQ 280: *C. famata* 1
CATCACTTTAGAAGCYACCAACGAACACTTCAGATTAATCTAYGAYGTCAAGGGTAGATTCACTGTYCACAGAATCACCG

CYGAAGAAGCTTCTTACAAGTTAGCTAAGGTYAAGAAGGTYCAATTAGGTAAGAGWGGTATTCCATACGTTGTYACCCAC

GATGGTAGAACTATCAGATACCCAG

SEQ 281: *C. famata* 1
CAUCACUUUAGAAGCYACCAACGAACACUUCAGAUUAAUCUAYGAYGUCAAGGGUAGAUUCACUGUYCACAGAAUCACCG

CYGAAGAAGCUUCUUACAAGUUAGCUAAGGUYAAGAAGGUYCAAUUAGGUAAGAGWGGUAUUCCAUACGUUGUYACCCAC

GAUGGUAGAACUAUCAGAUACCCAG

SEQ 282: *C. famata* 2
CATCACYTTAGAAGCYACCAACGAACACTTCAGATTRATCTATGAYGTCAAGGGTAGATTCACTGTCCACAGAATCACYG

CTGAAGAAGCTTCTTACAAGTTAGCYAAGGTCAAGAAGGTCCAATTAGGTAAGAGAGGTATTCCATACGYTGTYACWCAC

GAYGGTAGAACTATCAGATACCCAG

-continued

SEQ 283: *C. famata* 2
CAUCACYUUAGAAGCYACCAACGAACACUUCAGAUURAUCUAUGAYGUCAAGGGUAGAUUCACUGUCCACAGAAUCACYG

CUGAAGAAGCUUCUUACAAGUUAGCYAAGGUCAAGAAGGUCCAAUUAGGUAAGAGAGGUAUUCCAUACGYUGUYACWCAC

GAYGGUAGAACUAUCAGAUACCCAG

SEQ 284: *C. famata* 3
CATCACTTTAGAAGCYACCAACGAACACTTCAGATTAATCTAYGAYGTCAAGGGTAGATTCACTGTYCACAGAATCACCG

CYGAAGAAGCTTCTTACAAGTTAGCTAAGGTYAAGAAGGTYCAATTAGGTAAGAGRGGTATTCCATACGTTGTYACCCAC

GATGGTAGAACTATCAGATACCCAG

SEQ 285: *C. famata* 3
CAUCACUUUAGAAGCYACCAACGAACACUUCAGAUUAAUCUAYGAYGUCAAGGGUAGAUUCACUGUYCACAGAAUCACCG

CYGAAGAAGCUUCUUACAAGUUAGCUAAGGUYAAGAAGGUYCAAUUAGGUAAGAGRGGUAUUCCAUACGUUGUYACCCAC

GAUGGUAGAACUAUCAGAUACCCAG

SEQ 286: *C. famata* 4
CATCACYTTAGAAGCYACCAACGAACACTTCAGATTRATCTATGAYGTCAAGGGTAGATTCACTGTCCACAGAATCACYG

CTGAAGAAGCTTCTTACAAGTTAGCYAAGGTCAAGAAGGTCCAATTAGGTAAGAGAGGTATTCCATAYGYTGTYACWCAC

GAYGGTAGAACTATCAGATACCCAG

SEQ 287: *C. famata* 4
CAUCACYUUAGAAGCYACCAACGAACACUUCAGAUURAUCUAUGAYGUCAAGGGUAGAUUCACUGUCCACAGAAUCACYG

CUGAAGAAGCUUCUUACAAGUUAGCYAAGGUCAAGAAGGUCCAAUUAGGUAAGAGAGGUAUUCCAUAYGYUGUYACWCAC

GAYGGUAGAACUAUCAGAUACCCAG

SEQ 288: *C. famata* 5
CATCACTTTAGAAGCYACCAACGAACACTTCAGATTRATCTATGAYGTCAAGGGTAGATTCACTGTCCACAGAATCACYG

CTGAAGAAGCTTCTTACAAGTTAGCYAAGGTCAAGAAGGTCCAATTAGGTAAGAGAGGTATTCCATACGTTGTYACMCAC

GAYGGTAGAACTATCAG

SEQ 289: *C. famata* 5
CAUCACUUUAGAAGCYACCAACGAACACUUCAGAUURAUCUAUGAYGUCAAGGGUAGAUUCACUGUCCACAGAAUCACYG

CUGAAGAAGCUUCUUACAAGUUAGCYAAGGUCAAGAAGGUCCAAUUAGGUAAGAGAGGUAUUCCAUACGUUGUYACMCAC

GAYGGUAGAACUAUCAG

SEQ 290: *C. haemuloni* 52
CACCTTGGAGGCCACCAACGAGAACTTCAGATTGGTGTACGATGTCAAGGGTAGATTCACTGTCCACAGAATCACCGCTG

AGGAGGCTTCCTACAAGCTCGGTAAGGTCARGAAGATCGCTTTGGGTAAGAGAGGTGTTCCATACGTTGTCACCCACGAC

GGTAGAACTATCAGATACCCAG

SEQ 291: *C. haemuloni* 52
CACCUUGGAGGCCACCAACGAGAACUUCAGAUUGGUGUACGAUGUCAAGGGUAGAUUCACUGUCCACAGAAUCACCGCUG

AGGAGGCUUCCUACAAGCUCGGUAAGGUCARGAAGAUCGCUUUGGGUAAGAGAGGUGUUCCAUACGUUGUCACCCACGAC

GGUAGAACUAUCAGAUACCCAG

SEQ 292: *C. haemulonii* 53
CACCTTGGAGGCCACCAACGAGAACTTCAGATTGGTGTACGAYGTCAAGGGTAGATTCACTGTCCACAGAATCACCGCTG

AGGAGGCTTCTTACAAGCTCGGTAAGGTCAGAAAGATCGCYTTGGGTAAGAGAGGTATYCCATACGTTGTCACCCACGAC

GGTAGAACTATCAGATACCCAG

SEQ 293: *C. haemulonii* 53
CACCUUGGAGGCCACCAACGAGAACUUCAGAUUGGUGUACGAYGUCAAGGGUAGAUUCACUGUCCACAGAAUCACCGCUG

AGGAGGCUUCUUACAAGCUCGGUAAGGUCAGAAAGAUCGCYUUGGGUAAGAGAGGUAUYCCAUACGUUGUCACCCACGAC

GGUAGAACUAUCAGAUACCCAG

-continued

SEQ 294: *C. pulcherrima* 36
GATCACTTTGGAGGCYACCAACGAGAACTTYAGATTGATCTAYGACGTVAAGGGTAGATTYACTGTGCACAGAATCACSR

CCGAGGAGGSCTCKTACAAGTTGGGYAAGGTCAGAAAGATCGCCTTGGGYAAGAGAGGYGTKCCTTACGCYGTSACCCAC

GACGGTAGAACTATCAGATACCCAG

SEQ 295: *C. pulcherrima* 36
GAUCACUUUGGAGGCYACCAACGAGAACUUYAGAUUGAUCUAYGACGUVAAGGGUAGAUUYACUGUGCACAGAAUCACSR

CCGAGGAGGSCUCKUACAAGUUGGGYAAGGUCAGAAAGAUCGCCUUGGGYAAGAGAGGYGUKCCUUACGCYGUSACCCAC

GACGGUAGAACUAUCAGAUACCCAG

SEQ 296: *C. pulcherrima* 37
GATCACTTTGGAGGCYACCAACGAGAACTTCAGATTGATCTAYGACGTMAAGGGTAGATTYACTGTGCACAGAATCACCG

CCGAGGAGGSCTCKTACAAGTTGGGYAAGGTCAGAAAGATYGCCTTGGGYAAGAGAGGYGTKCCTTACGCYGTVACYCAC

GACGGTAGAACTATCAGATACCCAG

SEQ 297: *C. pulcherrima* 37
GAUCACUUUGGAGGCYACCAACGAGAACUUCAGAUUGAUCUAYGACGUMAAGGGUAGAUUYACUGUGCACAGAAUCACCG

CCGAGGAGGSCUCKUACAAGUUGGGYAAGGUCAGAAAGAUYGCCUUGGGYAAGAGAGGYGUKCCUUACGCYGUVACYCAC

GACGGUAGAACUAUCAGAUACCCAG

SEQ 298: *C. pulcherrima* 38
GATCACTTTGGAGGCYACCAACGAGAACTTYAGATTGATCTAYGACGTVAAGGGTAGATTYACTGTGCACAGAATCACCG

CCGAGGAGGSCTCKTACAAGTTGGGYAAGGTCAGAAAGATCGCCTTGGGYAAGAGAGGYGTKCCTTACGCYGTSACYCAC

GACGGTAGAACTATCAGATACCCAG

SEQ 299: *C. pulcherrima* 38
GAUCACUUUGGAGGCYACCAACGAGAACUUYAGAUUGAUCUAYGACGUVAAGGGUAGAUUYACUGUGCACAGAAUCACCG

CCGAGGAGGSCUCKUACAAGUUGGGYAAGGUCAGAAAGAUCGCCUUGGGYAAGAGAGGYGUKCCUUACGCYGUSACYCAC

GACGGUAGAACUAUCAGAUACCCAG

SEQ 300: *C. pulcherrima* 39
GATCACTTTGGAGGCCACCAACRAGAACTTCAGATTGATCTAYGACGTMAAGGGTAGATTCACYGTGCACAGAATCACCG

CCGAGGAGGCCTCKTACAAGTTGGGYAAGGTCAGAAAGATCGCCTTGGGYAAGAGAGGYGTKCCTTACGCYGTMACYCAC

GACGGTAGAACTATCAGATACCCAG

SEQ 301: *C. pulcherrima* 39
GAUCACUUUGGAGGCCACCAACRAGAACUUCAGAUUGAUCUAYGACGUMAAGGGUAGAUUCACYGUGCACAGAAUCACCG

CCGAGGAGGCCUCKUACAAGUUGGGYAAGGUCAGAAAGAUCGCCUUGGGYAAGAGAGGYGUKCCUUACGCYGUMACYCAC

GACGGUAGAACUAUCAGAUACCCAG

SEQ 302: *C. pulcherrima* 40
GATCACTTTGGAGGCCACCAACGAGAACTTYAGATTGATCTAYGACGTSAAGGGTAGATTYACTGTGCACAGAATCACCG

CCGAGGAGGSCTCKTACAAGTTGGGYAAGGTCAGAAAGATYGCCTTGGGYAAGAGWGGYGTKCCTTACGCYGTSACYCAC

GACGGTAGAACTATCAGATACCCAG

SEQ 303: *C. pulcherrima* 40
GAUCACUUUGGAGGCCACCAACGAGAACUUYAGAUUGAUCUAYGACGUSAAGGGUAGAUUYACUGUGCACAGAAUCACCG

CCGAGGAGGSCUCKUACAAGUUGGGYAAGGUCAGAAAGAUYGCCUUGGGYAAGAGWGGYGUKCCUUACGCYGUSACYCAC

GACGGUAGAACUAUCAGAUACCCAG

SEQ 304: *C. utilis* 50
CTTGGAGGCCACCAACGAGAACTTCAGATTGGTCTACGATGTCAAGGGTAGATTTGCTGTCCACAGAATCACCGATGATG

AAGCTTCTTACAAGCTTGCTAAGGTCAAGAAGGTTCAATTGGGTAAGAGAGGTATCCCATACGTTGTTACCCACGACGGT

AGAACTATCAGATACCCAG

-continued

SEQ 305: *C. utilis* 50
CUUGGAGGCCACCAACGAGAACUUCAGAUUGGUCUACGAUGUCAAGGGUAGAUUUGCUGUCCACAGAAUCACCGAUGAUG

AAGCUUCUUACAAGCUUGCUAAGGUCAAGAAGGUUCAAUUGGGUAAGAGAGGUAUCCCAUACGUUGUUACCCACGACGGU

AGAACUAUCAGAUACCCAG

SEQ 306: *C. utilis* 51
CTTGGAGGCCACCAACGAGAACTTCAGATTGGTCTACGATGTCAAGGGTAGATTTGCTGTCCACAGAATCACCGATGATG

AAGCTTCTTACAAGCTTGCTAAGGTCAAGAAGGTTCARTTGGGTAAGAGAGGTATCCCATACGTTGTTACCCACGACGGT

AGAACTATCAGATACCCAG

SEQ 307: *C. utilis* 51
CUUGGAGGCCACCAACGAGAACUUCAGAUUGGUCUACGAUGUCAAGGGUAGAUUUGCUGUCCACAGAAUCACCGAUGAUG

AAGCUUCUUACAAGCUUGCUAAGGUCAAGAAGGUUCARUUGGGUAAGAGAGGUAUCCCAUACGUUGUUACCCACGACGGU

AGAACUAUCAGAUACCCAG

SEQ 308: *C. kefyr* 59
CACCTTGGACRCTACCAAMGAAAACTTCAGATTGGTCTACGACGTTAAGGGTAGATTCGCTGTCCACCGTATCACCGACG

AAGAAGCTTCTTACAAATTGGGTAAGGTCAGAAAGGTCCAACTAGGTAAGAAGGGTATTCCATACGTTGTTACCCACGAC

GGTAGAACTATCAGATACCCAG

SEQ 309: *C. kefyr* 59
CACCUUGGACRCUACCAAMGAAAACUUCAGAUUGGUCUACGACGUUAAGGGUAGAUUCGCUGUCCACCGUAUCACCGACG

AAGAAGCUUCUUACAAAUUGGGUAAGGUCAGAAAGGUCCAACUAGGUAAGAAGGGUAUUCCAUACGUUGUUACCCACGAC

GGUAGAACUAUCAGAUACCCAG

SEQ 310: *C. kefyr* 3898
TGTCACCTTGGACGCTACCAACGAAAACTTCAGATTGGTCTACGACGTTAAGGGTAGATTCGCTGTCCACCGTATCACCG

ACGAAGAAGCTTCTTACAAATTGGGTAAGGTCAGAAAGGTCCAACTAGGTAAGAAGGGTATTCCATACGTTGTTACCCAC

GACGGTAGAACYATCAGATACCCAG

SEQ 311: *C. kefyr* 3898
UGUCACCUUGGACGCUACCAACGAAAACUUCAGAUUGGUCUACGACGUUAAGGGUAGAUUCGCUGUCCACCGUAUCACCG

ACGAAGAAGCUUCUUACAAAUUGGGUAAGGUCAGAAAGGUCCAACUAGGUAAGAAGGGUAUUCCAUACGUUGUUACCCAC

GACGGUAGAACYAUCAGAUACCCAG

SEQ 312: *C. viswanathii* 92
CATCACCTTGGAAGCCACCAACGAACACTTCAGATTGGTCTACGACGTCAAGGGTAGATTTGCTGTCCACAGAATCTCCG

CTGAAGAAGCYTCCTACAAGTTGGGCAAGGTCAAGAAGGTTGCYTTGGGTAAGAAGGGTGTTCCTTACGTTGTCACCCAC

GACGGTAGAACTATCAGATACCCAGA

SEQ 313: *C. viswanathii* 92
CAUCACCUUGGAAGCCACCAACGAACACUUCAGAUUGGUCUACGACGUCAAGGGUAGAUUUGCUGUCCACAGAAUCUCCG

CUGAAGAAGCYUCCUACAAGUUGGGCAAGGUCAAGAAGGUUGCYUUGGGUAAGAAGGGUGUUCCUUACGUUGUCACCCAC

GACGGUAGAACUAUCAGAUACCCAGA

SEQ 314: *C. viswanathii* 93
YAYTACTTTGGAAGCCACYAATGAAAACTTTAGATTGATTTACGATGTCAAAGGTAGATTTGCTGTCCACAGAATCTCAG

CTGAAGAAGCCACTTACAAATTGGGTAAAGTCAAGAGAGTCCAATTGGGTAAGAAGGGAATCCCATACGTTGTCACCCAC

GATGGTAGAACTATCAGATACCCAGA

SEQ 315: *C. viswanathii* 93
YAYUACUUUGGAAGCCACYAAUGAAAACUUUAGAUUGAUUUACGAUGUCAAAGGUAGAUUUGCUGUCCACAGAAUCUCAG

CUGAAGAAGCCACUUACAAAUUGGGUAAAGUCAAGAGAGUCCAAUUGGGUAAGAAGGGAAUCCCAUACGUUGUCACCCAC

GAUGGUAGAACUAUCAGAUACCCAGA

-continued

SEQ 316: *C. zeylanoides* 74
TCTTGAGGCTACCAACGAGCACTTCAGATTGGTGTACGACGTCAAGGGTAGATTCGCCGTGCACAGAATCACCGCCGAGG

AGTCCACCTACAAGTTGGCCAAGATCAAGAAGGTCCAGTTGGGCAAGAAGAGTATCCCCTACGCCGTCACCCACGACGGT

AGAACTATCAGATACCCAGA

SEQ 317: *C. zeylanoides* 74
UCUUGAGGCUACCAACGAGCACUUCAGAUUGGUGUACGACGUCAAGGGUAGAUUCGCCGUGCACAGAAUCACCGCCGAGG

AGUCCACCUACAAGUUGGCCAAGAUCAAGAAGGUCCAGUUGGGCAAGAAGAGUAUCCCCUACGCCGUCACCCACGACGGU

AGAACUAUCAGAUACCCAGA

SEQ 318: *C. zeylanoides* 67
TCTCTCTTGAGCCACCAAYGAGCACTTCAGATTGGTGTAYGACGTMAAGGGTAGATTYGCYGTGCACAGAATCACCGCKG

AGGAGTCSAMYTACAAGTTGGCCAARATCAAGAAGGTKCASTTRGGCAAGAARAGCATCCCYTACGCYGTCACCCAYGAY

GGYAGAACTATCAGATACCCAG

SEQ 319: *C. zeylanoides* 67
UCUCUCUUGAGCCACCAAYGAGCACUUCAGAUUGGUGUAYGACGUMAAGGGUAGAUUYGCYGUGCACAGAAUCACCGCKG

AGGAGUCSAMYUACAAGUUGGCCAARAUCAAGAAGGUKCASUURGGCAAGAARAGCAUCCCYUACGCYGUCACCCAYGAY

GGYAGAACUAUCAGAUACCCAG

SEQ 320: *C. zeylanoides* 69
TCTCTCTTGAGCCACCAAYGAGCACTTCAGATTGGTGTAYGACGTMAAGGGTAGATTYGCYGTGCACAGAATCACCGCSG

AGGAGTCSAMYTACAAGTTGGCCAARATCAAGAAGGTKCASTTRGGCAAGAARAGCATCCCYTACGCYGTCACCCAYGAY

GGYAGAACTATCAGATACCCAG

SEQ 321: *C. zeylanoides* 69
UCUCUCUUGAGCCACCAAYGAGCACUUCAGAUUGGUGUAYGACGUMAAGGGUAGAUUYGCYGUGCACAGAAUCACCGCSG

AGGAGUCSAMYUACAAGUUGGCCAARAUCAAGAAGGUKCASUURGGCAAGAARAGCAUCCCYUACGCYGUCACCCAYGAY

GGYAGAACUAUCAGAUACCCAG

SEQ 322: *C. zeylanoides* 68
TCTCTCTTGAGCCWCCAACGAGCACTTCAGATTGGTGTACGACGTCAAGGGTAGATTCGCCGTGCACAGAATCACCGCCG

AGGAGTCCACCTACAAGTTGGCCAAGATCAAGAAGGTCCAGTTGGGCAAGAAGAGTATCCCCTACGCCGTCACCCACGAC

GGTAGAACTATCAGATACCCAG

SEQ 323: *C. zeylanoides* 68
UCUCUCUUGAGCCWCCAACGAGCACUUCAGAUUGGUGUACGACGUCAAGGGUAGAUUCGCCGUGCACAGAAUCACCGCCG

AGGAGUCCACCUACAAGUUGGCCAAGAUCAAGAAGGUCCAGUUGGGCAAGAAGAGUAUCCCCUACGCCGUCACCCACGAC

GGUAGAACUAUCAGAUACCCAG

SEQ 324: *C. zeylanoides* 70
CTACCAACRAACACTTCAGATTGATTTACGATGTTAAAGGTAAATTCGCTGTTCACAGAATTTCTGCTGAAGAAGCTTCT

TACAAATTAGGTAAAGTCAAGAAGGTTCAATTAGGTAAAAAAGGTGTTCCATACGTTGTCACCCACGATGGTAGAACTAT

CAGATACCCAG

SEQ 325: *C. zeylanoides* 70
CUACCAACRAACACUUCAGAUUGAUUUACGAUGUUAAAGGUAAAUUCGCUGUUCACAGAAUUUCUGCUGAAGAAGCUUCU

UACAAAUUAGGUAAAGUCAAGAAGGUUCAAUUAGGUAAAAAAGGUGUUCCAUACGUUGUCACCCACGAUGGUAGAACUAU

CAGAUACCCAG

SEQ 326: *A. fumigatus*2204
GTCGCTCAGCGCCGCATCCTGCCCCGCCCCAAGCGCTCTGTCAACTCCCGCACCAACCAGAAGCAGAAGCGTCCTCGCTC

TCGCACCCTGACCGCTGTCCACGACGCCATCCTCAACGACCTCGTTTACCCCGTCGAGATCGTCGGCAAGCGTATCCGCA

CCAAGGAGGACGGCAGCAAGACTCTCAAGGTCGTTCTGGACGAGAAGGAGCGTGGTGGTGTTGACCACAGACTCGATGCC

TACGGCGAGGTTTACCGCCGACTAACCGGCCGCTCTGTTGTTTTCGAGTTCCCCCAGAG

-continued

SEQ 327: *A. fumigatus*2204
GUCGCUCAGCGCCGCAUCCUGCCCCGCCCCAAGCGCUCUGUCAACUCCCGCACCAACCAGAAGCAGAAGCGUCCUCGCUC

UCGCACCCUGACCGCUGUCCACGACGCCAUCCUCAACGACCUCGUUUACCCCGUCGAGAUCGUCGGCAAGCGUAUCCGCA

CCAAGGAGGACGGCAGCAAGACUCUCAAGGUCGUUCUGGACGAGAAGGAGCGUGGUGGUGUUGACCACAGACUCGAUGCC

UACGGCGAGGUUUACCGCCGACUAACCGGCCGCUCUGUUGUUUUCGAGUUCCCCCAGAG

SEQ 328: *A. fumigatus*5062
CGTCGCTCAGCGCCGCATCCTGCCCCGCCCCAAGCGCTCTGTCAACTCCCGCACCAACCAGAAGCAGAAGCGTCCTCGCT

CTCGCACCCTGACCGCTGTCCACGACGCCATCCTCACCGACCTCGTTTACCCCGTCGAGATCGTCGGCAAGCGTATCCGC

ACCAAGGAGGACGGCAGCAAGACTCTCAAGGTCATCCTGGACGAGAAGGAGCGTGGTGGTGTTGACCACAGACTCGATGC

CTACGGCGAGGTTTACCGCCGACTAACCGGCCGCTCTGTTGTCTTCGAGTTCCCCCAGAG

SEQ 329: *A. fumigatus*5062
CGUCGCUCAGCGCCGCAUCCUGCCCCGCCCCAAGCGCUCUGUCAACUCCCGCACCAACCAGAAGCAGAAGCGUCCUCGCU

CUCGCACCCUGACCGCUGUCCACGACGCCAUCCUCACCGACCUCGUUUACCCCGUCGAGAUCGUCGGCAAGCGUAUCCGC

ACCAAGGAGGACGGCAGCAAGACUCUCAAGGUCAUCCUGGACGAGAAGGAGCGUGGUGGUGUUGACCACAGACUCGAUGC

CUACGGCGAGGUUUACCGCCGACUAACCGGCCGCUCUGUUGUCUUCGAGUUCCCCCAGAG

SEQ 330: *A. fumigatus*133.61
TGTTGCTCAGCGCCGCATCCTGCCCCGCCCTAAGCGCTCTGTCAACTCCCGCACCAACCAGAAGCAGAAGCGTCCTCGCT

CTCGCACCCTGACCGCTGTCCACGACGCCATCCTCAACGACCTCGTTTACCCCGTCGAGATCGTCGGCAAGCGTATCCGC

ACCAAGGAGGACGGCAGCAAGACTCTCAAGGTCATCCTGGACGAGAAGGAGCGTGGTGGTGTTGACCACAGACTCGATGC

CTACGGCGAGGTTTACCGCCGACTAACCGGCCGCTCTGTTGTCTTCGAGTTCCCCCAGAG

SEQ 331: *A. fumigatus*133.61
UGUUGCUCAGCGCCGCAUCCUGCCCCGCCCUAAGCGCUCUGUCAACUCCCGCACCAACCAGAAGCAGAAGCGUCCUCGCU

CUCGCACCCUGACCGCUGUCCACGACGCCAUCCUCAACGACCUCGUUUACCCCGUCGAGAUCGUCGGCAAGCGUAUCCGC

ACCAAGGAGGACGGCAGCAAGACUCUCAAGGUCAUCCUGGACGAGAAGGAGCGUGGUGGUGUUGACCACAGACUCGAUGC

CUACGGCGAGGUUUACCGCCGACUAACCGGCCGCUCUGUUGUCUUCGAGUUCCCCCAGAG

SEQ 332: *A. fumigatus*419.64
TGTTGCTCAGCGCCGCATCCTGCCCCGCCCTAAGCGCTCTGTCAACTCCCGCACCAACCAGAAGCAGAAGCGTCCTCGCT

CTCGCACCCTGACCGCTGTCCACGACGCCATCCTCAACGACCTCGTTTACCCCGTCGAGATCGTCGGCAAGCGTATCCGC

ACCAAGGAGGACGGCAGCAAGACTCTCAAGGTCATCCTGGACGAGAAGGAGCGTGGTGGTGTTGACCACAGACTCGATGC

CTACGGCGAGGTTTACCGCCGACTAACCGGCCGCTCTGTTATCTTCGAGTTCCCCCAGAG

SEQ 333: *A. fumigatus*419.64
UGUUGCUCAGCGCCGCAUCCUGCCCCGCCCUAAGCGCUCUGUCAACUCCCGCACCAACCAGAAGCAGAAGCGUCCUCGCU

CUCGCACCCUGACCGCUGUCCACGACGCCAUCCUCAACGACCUCGUUUACCCCGUCGAGAUCGUCGGCAAGCGUAUCCGC

ACCAAGGAGGACGGCAGCAAGACUCUCAAGGUCAUCCUGGACGAGAAGGAGCGUGGUGGUGUUGACCACAGACUCGAUGC

CUACGGCGAGGUUUACCGCCGACUAACCGGCCGCUCUGUUAUCUUCGAGUUCCCCCAGAG

SEQ 334: *A. terreus*2729
CGTTGCTCAGCGCCGCATCCTGCCCCGCCCCAAGCGCTCTGTCAACTCCCGCACCAACCAGAAGCAGAAGCGTCCCCGTT

CCCGCACTCTGACGGCCGTCCACGACGCCATCCTCACCGACCTCGTCTACCCCGTCGAGATCGTCGGCAAGCGCATCCGC

ACCAAGGAGGACGGCTCCAAGACCCTCAAGGTCATCCTCGACGAGAAGGAGCGCGGCGGTGTCGACCACCGCCTCGATGC

CTACGGCGAGGTCTACCGTCGTCTCACCGGCCGTGCCGTCGTCTTCGAGTTCCCCCAGAG

SEQ 335: *A. terreus*2729
CGUUGCUCAGCGCCGCAUCCUGCCCCGCCCCAAGCGCUCUGUCAACUCCCGCACCAACCAGAAGCAGAAGCGUCCCCGUU

CCCGCACUCUGACGGCCGUCCACGACGCCAUCCUCACCGACCUCGUCUACCCCGUCGAGAUCGUCGGCAAGCGCAUCCGC

ACCAAGGAGGACGGCUCCAAGACCCUCAAGGUCAUCCUCGACGAGAAGGAGCGCGGCGGUGUCGACCACCGCCUCGAUGC

CUACGGCGAGGUCUACCGUCGUCUCACCGGCCGUGCCGUCGUCUUCGAGUUCCCCCAGAG

-continued

SEQ 336: *A. flavus*108.30
CGTCGCTCAGCGCCGCATCCTGCCCAAGCCCAAGCGCTCTGTCAACTCCCGCACCAACCAGAAGCAGAAGCGTCCCCGTT

CCCGCACTCTGACTGCTGTCCACGACGCCATCCTCGGCGACCTGGTCTACCCCGTTGAGATCGTCGGCAAGCGCATCCGC

ACCAAGGAGGATGGCAGCAAGACCCTCAAGGTCATCCTGGATGAGAAGGAGCGTGGTGGTGTTGACCACCGTCTCGATGC

CTACGGCGAGGTCTACCGCCGTTTGACCGGCCGCAACGTCGTCTTCGAGTTCCCCCAGAG

SEQ 337: *A. flavus*108.30
CGUCGCUCAGCGCCGCAUCCUGCCCAAGCCCAAGCGCUCUGUCAACUCCCGCACCAACCAGAAGCAGAAGCGUCCCCGUU

CCCGCACUCUGACUGCUGUCCACGACGCCAUCCUCGGCGACCUGGUCUACCCCGUUGAGAUCGUCGGCAAGCGCAUCCGC

ACCAAGGAGGAUGGCAGCAAGACCCUCAAGGUCAUCCUGGAUGAGAAGGAGCGUGGUGGUGUUGACCACCGUCUCGAUGC

CUACGGCGAGGUCUACCGCCGUUUGACCGGCCGCAACGUCGUCUUCGAGUUCCCCCAGAG

SEQ 338: *A. flavus*117.62
CGTCGCTCAGCGCCGCATCCTGCCCAAGCCCAAGCGCTCTGTCAACTCCCGCACCAACCAGAAGCAGAAGCGTCCCCGTT

CCCGCACTCTGACTGCTGTCCACGACGCCATCCTCGGCGACCTGGTCTACCCCGTTGAGATCGTCGGCAAGCGCATCCGC

ACCAAGGAGGACGGCAGCAAGACCCTCAAGGTCATCCTGGATGAGAAGGAGCGTGGTGGTGTTGACCACCGTCTCGATGC

CTACGGCGAGGTCTACCGCCGTTTGACCGGCCGCAACGTCGTCTTCGAGTTCCCCCAGAG

SEQ 339: *A. flavus*117.62
CGUCGCUCAGCGCCGCAUCCUGCCCAAGCCCAAGCGCUCUGUCAACUCCCGCACCAACCAGAAGCAGAAGCGUCCCCGUU

CCCGCACUCUGACUGCUGUCCACGACGCCAUCCUCGGCGACCUGGUCUACCCCGUUGAGAUCGUCGGCAAGCGCAUCCGC

ACCAAGGAGGACGGCAGCAAGACCCUCAAGGUCAUCCUGGAUGAGAAGGAGCGUGGUGGUGUUGACCACCGUCUCGAUGC

CUACGGCGAGGUCUACCGCCGUUUGACCGGCCGCAACGUCGUCUUCGAGUUCCCCCAGAG

SEQ 340: *A. nidulans*5231
CGTCGCTCAGCGCCGCATCCTCCCCAAGCCCAAGCGCTCCGTCAACTCCCGCACCAACCAGAAGCAGAAGCGCCCCCGTT

CCCGTACCCTCACTGCTGTTCACGATGCCATCCTTGACGACCTCGTCTACCCCGTTGAGATTGTCGGCAAGCGCATCCGC

ACCAAGGAGGACGGCTCCAAGACTCTCAAGGTTATCCTCGACGAGAAGGAGCGTGGTGTTGACCACCACCGCCTCGACGC

CTACGGCGAGGTCTACCGTCGTCTGACGGGTCGTGCTGTCGTTTTCGAGTTCCCCCAGAG

SEQ 341: *A. nidulans*5231
CGUCGCUCAGCGCCGCAUCCUUCCCAAGCCCAAGCGCUCCGUCAACUCCCGCACCAACCAGAAGCAGAAGCGCCCCCGUU

CCCGUACCCUCACUGCUGUUCACGAUGCCAUCCUUGACGACCUCGUCUACCCCGUUGAGAUUGUCGGCAAGCGCAUCCGC

ACCAAGGAGGACGGCUCCAAGACUCUCAAGGUUAUCCUCGACGAGAAGGAGCGUGGUGGUGUUGACCACCGCCUCGACGC

CUACGGCGAGGUCUACCGUCGUCUGACGGGUCGUGCUGUCGUUUUCGAGUUCCCCCAGAG

SEQ 342: *A. nidulans*4190
CGTCGCTCAGCGCCGCATCCTCCCCAAGCCCAAGCGCTCCGTCAACTCCCGCACCAACCAGAAGCAGAAGCGCCCCCGTT

CCCGTACCCTTACTGCCGTTCACGACGCCATCCTCGACGACCTCGTCTACCCCGTTGAGATTGTCGGCAAGCGCATCCGC

ACCAAGGAGGACGGCTCCAAGACCCTCAAGGTCATCCTCGACGAGAAGGAGCGTGGTGGTGTTGACCACCGCCTCGACGC

CTACGGCGAGGTCTACCGTCGTCTGACGGGTCGTGCTGTCGTTTTCGAGTTCCCCCAGAG

SEQ 343: *A. nidulans*4190
CGUCGCUCAGCGCCGCAUCCUCCCCAAGCCCAAGCGCUCCGUCAACUCCCGCACCAACCAGAAGCAGAAGCGCCCCCGUU

CCCGUACCCUUACUGCCGUUCACGACGCCAUCCUCGACGACCUCGUCUACCCCGUUGAGAUUGUCGGCAAGCGCAUCCGC

ACCAAGGAGGACGGCUCCAAGACCCUCAAGGUCAUCCUCGACGAGAAGGAGCGUGGUGGUGUUGACCACCGCCUCGACGC

CUACGGCGAGGUCUACCGUCGUCUGACGGGUCGUGCUGUCGUUUUCGAGUUCCCCCAGAG

SEQ 344: *A. nidulans*100.2
CGTCGCTCAGCGCCGCATCCTCCCCAAGCCCAAGCGCTCCGTCAACTCCCGCACCAACCAGAAGCAGAAGCGCCCCCGTT

CCCGTACCCTTACTGCCGTTCACGACGCCATCCTCGACGACCTCGTCTACCCCGTTGAGATTGTCGGCAAGCGCATCCGC

ACCAAGGAGGACGGCTCCAAGACCCTCAAGGTCATCCTCGACGAGAAGGAGCGTGGTGGTGTTGACCACCGCCTCGACGC

CTACGGCGAGGTCTACCGTCGTCTGACGGGTCGTGCTGTCGTTTTCGAGTTCCCCCAGAG

-continued

SEQ 345: *A. nidulans*100.2
CGUCGCUCAGCGCCGCAUCCUCCCCAAGCCCAAGCGCUCCGUCAACUCCCGCACCAACCAGAAGCAGAAGCGCCCCCGUU

CCCGUACCCUUACUGCCGUUCACGACGCCAUCCUCGACGACCUCGUCUACCCCGUUGAGAUUGUCGGCAAGCGCAUCCGC

ACCAAGGAGGACGGCUCCAAGACCCUCAAGGUCAUCCUCGACGAGAAGGAGCGUGGUGGUGUUGACCACCGCCUCGACGC

CUACGGCGAGGUCUACCGUCGUCUGACGGGUCGUGCUGUCGUUUUCGAGUUCCCCCAGAG

SEQ 346: *A. versicolor* 323
CGTCGCTCAGCGCCGCATCCTTCCCAAGCCCAAGCGCTCCGTCAACTCTCGCACCAACCAGAAGCAGAAGCGCCCTCGTT

CTCGCACCCTGACGGCTGTCCACGACTCCATCCTTGACGACCTCGTCTACCCCGTTGAGATCGTCGGCAAGCGTACCCGC

ACCAAGGAGGACGGCAGCAAGACGCTCAAGGTCATCCTCGACGAGAAGGAGCGCGGCGGCGTTGACCACCGCCTCGACGC

CTACGGCGAGGTCTACCGTCGTTTGACCGGTCGTGCTGTTGTTTTCGAGTTCCCCCAGAG

SEQ 347: *A. versicolor*1323
CGUCGCUCAGCGCCGCAUCCUUCCCAAGCCCAAGCGCUCCGUCAACUCUCGCACCAACCAGAAGCAGAAGCGCCCUCGUU

CUCGCACCCUGACGGCUGUCCACGACUCCAUCCUUGACGACCUCGUCUACCCCGUUGAGAUCGUCGGCAAGCGUACCCGC

ACCAAGGAGGACGGCAGCAAGACGCUCAAGGUCAUCCUCGACGAGAAGGAGCGCGGCGGCGUUGACCACCGCCUCGACGC

CUACGGCGAGGUCUACCGUCGUUUGACCGGUCGUGCUGUUGUUUUCGAGUUCCCCCAGAG

SEQ 348: *A. versicolor*2196
CGTCGCTCAGCGCCGCATCCTTCCTAAGCCCAAGCGCTCCGTCAACTCCCGCACCAACCAGAAGCAGAAGCGCCCTCGTT

CTCGCACTCTGACGGCTGTCCACGACTCCATCCTTGACGACCTCGTCTACCCCGTTGAGATCGTCGGCAAGCGTACCCGC

ACCAAGGAGGACGGCAGCAAGACGCTCAAGGTCATCCTCGACGAGAAGGAGCGCGGCGGCGTTGACCACCGCCTCGACGC

CTACGGCGAGGTCTACCGTCGTTTGACCGGTCGTGCTGTTGTTTTCGAGTTCCCCCAGAG

SEQ 349: *A. versicolor*2196
CGUCGCUCAGCGCCGCAUCCUUCCUAAGCCCAAGCGCUCCGUCAACUCCCGCACCAACCAGAAGCAGAAGCGCCCUCGUU

CUCGCACUCUGACGGCUGUCCACGACUCCAUCCUUGACGACCUCGUCUACCCCGUUGAGAUCGUCGGCAAGCGUACCCGC

ACCAAGGAGGACGGCAGCAAGACGCUCAAGGUCAUCCUCGACGAGAAGGAGCGCGGCGGCGUUGACCACCGCCUCGACGC

CUACGGCGAGGUCUACCGUCGUUUGACCGGUCGUGCUGUUGUUUUCGAGUUCCCCCAGAG

SEQ 350: *A. versicolor*5058
CGTCGCTCAGCGCCGCATCCTTCCTAAGCCTAAGCGCTCCGTCAACTCCCGCACCAACCAGAAGCAGAAGCGCCCCCGTT

CCCGCACCCTGACGGCCGTCCACGATGCTATCCTTGACGACCTCGTCTACCCCGTTGAGATCGTCGGCAAGCGTACCCGC

ACCAAGGAGGACGGCAGCAAGACGCTCAAGATCATCCTCGACGAGAAGGAGCGCGGCGGCGTTGACCACCGCCTTGACGC

CTACGGCGAGGTCTACCGTCGTTTGACTGGTCGTGCTGTTGTTTTCGAGTTCCCCCAGAG

SEQ 351: *A. versicolor*5058
CGUCGCUCAGCGCCGCAUCCUUCCUAAGCCUAAGCGCUCCGUCAACUCCCGCACCAACCAGAAGCAGAAGCGCCCCCGUU

CCCGCACCCUGACGGCCGUCCACGAUGCUAUCCUUGACGACCUCGUCUACCCCGUUGAGAUCGUCGGCAAGCGUACCCGC

ACCAAGGAGGACGGCAGCAAGACGCUCAAGAUCAUCCUCGACGAGAAGGAGCGCGGCGGCGUUGACCACCGCCUUGACGC

CUACGGCGAGGUCUACCGUCGUUUGACUGGUCGUGCUGUUGUUUUCGAGUUCCCCCAGAG

SEQ 352: *A. versicolor*6898
CGTCGCTCAGCGCCGCATCCTTCCTAAGCCCAAGCGCTCCGTCAACTCCCGCACCAACCAGAAGCAGAAGCGCCCCCGTT

CCCGCACCCTGACGGCCGTCCACGATGCCATCCTTGACGACCTCGTCTACCCCGTTGAGATCGTCGGCAAGCGTACCCGC

ACCAAGGAGGACGGCAGCAAGACGCTCAAGATCATCCTCGACGAGAAGGAGCGCGGCGGCGTTGACCACCGCCTTGACGC

CTACGGCGAGGTCTACCGTCGTTTGACTGGTCGTGCTGTTGTTTTCGAGTTCCCCCAGAG

SEQ 353: *A. versicolor*6898
CGUCGCUCAGCGCCGCAUCCUUCCUAAGCCCAAGCGCUCCGUCAACUCCCGCACCAACCAGAAGCAGAAGCGCCCCCGUU

CCCGCACCCUGACGGCCGUCCACGAUGCCAUCCUUGACGACCUCGUCUACCCCGUUGAGAUCGUCGGCAAGCGUACCCGC

ACCAAGGAGGACGGCAGCAAGACGCUCAAGAUCAUCCUCGACGAGAAGGAGCGCGGCGGCGUUGACCACCGCCUUGACGC

CUACGGCGAGGUCUACCGUCGUUUGACUGGUCGUGCUGUUGUUUUCGAGUUCCCCCAGAG

-continued

SEQ 354: *A. versicolor*111.32
CGTTGCTCAGCGCCGCATCCTTCCTAAGCCTAAGCGCTCCGTCAACTCCCGCACCAACCAGAAGCAGAAGCGCCCCCGTT

CCCGCACCCTGACGGCCGTCCACGATGCTATCCTTGACGACCTCGTCTACCCCGTTGAGATCGTCGGCAAGCGTACCCGC

ACCAAGGAGGACGGCAGCAAGACGCTCAAGATCATCCTCGACGAGAAGGAGCGCGGCGGCGTTGACCACCGCCTTGACGC

CTACGGCGAGGTCTACCGTCGTTTGACTGGTCGTGCTGTTGTTTTCGAGTTCCCCCAGAG

SEQ 355: *A. versicolor*111.32
CGUUGCUCAGCGCCGCAUCCUUCCUAAGCCUAAGCGCUCCGUCAACUCCCGCACCAACCAGAAGCAGAAGCGCCCCCGUU

CCCGCACCCUGACGGCCGUCCACGAUGCUAUCCUUGACGACCUCGUCUACCCCGUUGAGAUCGUCGGCAAGCGUACCCGC

ACCAAGGAGGACGGCAGCAAGACGCUCAAGAUCAUCCUCGACGAGAAGGAGCGCGGCGGCGUUGACCACCGCCUUGACGC

CUACGGCGAGGUCUACCGUCGUUUGACUGGUCGUGCUGUUGUUUUCGAGUUCCCCCAGAG

SEQ 356: *A. clavatus*7944
CGTCGCTCAGCGCCGCATCCTGCCCCGCCCCAAGCGCTCTGTCAACTCCCGCACCAACCAGAAGCAGAAGCGTCCTCGCT

CCCGCACCCTGACTGCCGTTCACGACGCCATCCTCACCGACCTCGTCTACCCCGTCGAGATCGTCGGCAAGCGCACCCGC

ACCAAGGAGGACGGCTCCAAGACCCTCAAGGTCGTCCTTGACGAGAAGGAGCGTGGCGGTGTTGACCACAGACTCGATGC

CTACGGCGAGGTCTACCGCCGTTTAACCGGCCGCTCCGTTGTCTTCGAGTTCCCCCAGAG

SEQ 357: *A. clavatus*7944
CGUCGCUCAGCGCCGCAUCCUGCCCCGCCCCAAGCGCUCUGUCAACUCCCGCACCAACCAGAAGCAGAAGCGUCCUCGCU

CCCGCACCCUGACUGCCGUUCACGACGCCAUCCUCACCGACCUCGUCUACCCCGUCGAGAUCGUCGGCAAGCGCACCCGC

ACCAAGGAGGACGGCUCCAAGACCCUCAAGGUCGUCCUUGACGAGAAGGAGCGUGGCGGUGUUGACCACAGACUCGAUGC

CUACGGCGAGGUCUACCGCCGUUUAACCGGCCGCUCCGUUGUCUUCGAGUUCCCCCAGAG

SEQ 358: *A. clavatus*2391
CGTCGCTCAGCGCCGCATCCTGCCCCGCCCCAAGCGCTCCGTCAACTCCCGCTCCAACCAGAAGCAGAAGCGCCCTCGCT

CCCGCACTCTGACCGCTGTTCACGACGCCATCCTCACTGATCTCGTCTTCCCCGTCGAGATCGTCGGCAAGCGCACCCGC

ACCAAGGAGGACGGCTCCAAGACCCTCAAGGTCATCCTTGACGAGAAGGAGCGTGGTGGTGTTGACCACAGACTCGATGC

CTACGGCGAGGTCTACCGCCGCTTAACCGGCCGCTCCGTTGTCTTCGAGTTCCCCCAGAG

SEQ 359: *A. clavatus*2391

CGUCGCUCAGCGCCGCAUCCUGCCCCGCCCCAAGCGCUCCGUCAACUCCCGCUCCAACCAGAAGCAGAAGCGCCCUCGCU

CCCGCACUCUGACCGCUGUUCACGACGCCAUCCUCACUGAUCUCGUCUUCCCCGUCGAGAUCGUCGGCAAGCGCACCCGC

ACCAAGGAGGACGGCUCCAAGACCCUCAAGGUCAUCCUUGACGAGAAGGAGCGUGGUGGUGUUGACCACAGACUCGAUGC

CUACGGCGAGGUCUACCGCCGCUUAACCGGCCGCUCCGUUGUCUUCGAGUUCCCCCAGAG

SEQ 360: *A. candidus*9695
CGTCGCTCAGCGCCGCATCCTGTCGCGCCCCAAGCGCTCCGTCAACTCGCGCACCAACCAGAAGCAGAAGCGCCCCCGCT

CGCGCACTCTGACCGCCGTGCACGACAACATCCTGACCGACCTGGTCTACCCCGTCGAGATCGTCGGCAAGCGCATCCGC

ACCAAGGAGGACGGCAGCAAGACCCTCAAGGTTATCCTGGACGAGAAGGAGCGCGGCGGCGTTGACCACCGCCTGGACGC

CTACGGCGAGGTCTACCGCCGACTGACGGGCCGCAACGTTGTCTTCGAGTTCCCCCAGAG

SEQ 361: *A. candidus*9695
CGUCGCUCAGCGCCGCAUCCUGUCGCGCCCCAAGCGCUCCGUCAACUCGCGCACCAACCAGAAGCAGAAGCGCCCCCGCU

CGCGCACUCUGACCGCCGUGCACGACAACAUCCUGACCGACCUGGUCUACCCCGUCGAGAUCGUCGGCAAGCGCAUCCGC

ACCAAGGAGGACGGCAGCAAGACCCUCAAGGUUAUCCUGGACGAGAAGGAGCGCGGCGGCGUUGACCACCGCCUGGACGC

CUACGGCGAGGUCUACCGCCGACUGACGGGCCGCAACGUUGUCUUCGAGUUCCCCCAGAG

SEQ 362: *A. candidus*567.65
CGTCGCTCAGCGCCGCATCCTGTCGCGCCCCAAGCGCTCCGTCAACTCGCGCACCAACCAGAAGCAGAAGCGCCCCCGCT

CGCGCACTCTGACCGCCGTGCACGACAACATCCTGACCGACCTTGTCTACCCCGTCGAGATCGTCGGCAAGCGCGTCCGC

-continued

ACCAAGGAGGACGGCAGCAAGACCCTCAAGGTTATCCTGGACGAGAAGGAGCGTGGCGGCGTTGACCACCGTCTGGACGC

CTACGGCGAGGTCTACCGCCGACTGACGGGCCGCAACGTTGTCTTCGAGTTCCCCCAGAG

SEQ 363: *A. candidus*567.65
CGUCGCUCAGCGCCGCAUCCUGUCGCGCCCCAAGCGCUCCGUCAACUCGCGCACCAACCAGAAGCAGAAGCGCCCCCGCU

CGCGCACUCUGACCGCCGUGCACGACAACAUCCUGACCGACCUUGUCUACCCCGUCGAGAUCGUCGGCAAGCGCGUCCGC

ACCAAGGAGGACGGCAGCAAGACCCUCAAGGUUAUCCUGGACGAGAAGGAGCGUGGCGGCGUUGACCACCGUCUGGACGC

CUACGGCGAGGUCUACCGCCGACUGACGGGCCGCAACGUUGUCUUCGAGUUCCCCCAGAG

SEQ 364: *A. candidus*225.80
CGTCGCTCAGCGCCGCATCCTGTCGCGCCCCAAGCGCTCCGTCAACTCGCGCACCAACCAGAAGCAGAAGCGCCCCCGCT

CGCGCACTCTGACCGCCGTGCACGACAACATCCTGACCGACCTCGTCTACCCCGTCGAGATCGTCGGCAAGCGCGTCCGC

ACCAAGGAGGACGGCAGCAAGACCCTCAAGGTTATCCTGGACGAGAAGGAGCGCGGCGGCGTTGACCACCGCCTGGACGC

CTACGGCGAGGTCTACCGCCGACTCACCGGCCGCAACGTTGTCTTCGAGTTCCCCCAGAG

SEQ 365: *A. candidus*225.80
CGUCGCUCAGCGCCGCAUCCUGUCGCGCCCCAAGCGCUCCGUCAACUCGCGCACCAACCAGAAGCAGAAGCGCCCCCGCU

CGCGCACUCUGACCGCCGUGCACGACAACAUCCUGACCGACCUCGUCUACCCCGUCGAGAUCGUCGGCAAGCGCGUCCGC

ACCAAGGAGGACGGCAGCAAGACCCUCAAGGUUAUCCUGGACGAGAAGGAGCGCGGCGGCGUUGACCACCGCCUGGACGC

CUACGGCGAGGUCUACCGCCGACUCACCGGCCGCAACGUUGUCUUCGAGUUCCCCCAGAG

SEQ 366: *A. glaucus*2425
CGTCGCTCAGCGCCGCATCCTCTCCCGCCCCAAGCGCTCCGTCAACTCGCGCACCAACCAGACCCAGAAGCGTCCCCGTT

CGCGTACTCTGACCGCTGTCCACGACTCCATCCTCACCGACCTCGTCTACCCCGTCGAGATCGTTGGCAAGCGCATCCGC

ACCAAGGAGGACGGCAGCAAGACCATCAAGGTTGTTCTCGACGAGAAGGAGCGCGGTGGTGTTGACCACAGACTTGATGC

CTACGGCGAGGTCTACCGCAGACTGACCGGCCGTGCCGTTGTCTTCGAGTTCCCCCAGAG

SEQ 367: *A. glaucus*2425
CGUCGCUCAGCGCCGCAUCCUCUCCCGCCCCAAGCGCUCCGUCAACUCGCGCACCAACCAGACCCAGAAGCGUCCCCGUU

CGCGUACUCUGACCGCUGUCCACGACUCCAUCCUCACCGACCUCGUCUACCCCGUCGAGAUCGUUGGCAAGCGCAUCCGC

ACCAAGGAGGACGGCAGCAAGACCAUCAAGGUUGUUCUCGACGAGAAGGAGCGCGGUGGUGUUGACCACAGACUUGAUGC

CUACGGCGAGGUCUACCGCAGACUGACCGGCCGUGCCGUUGUCUUCGAGUUCCCCCAGAG

SEQ 368: *A. glaucus*MA542
CATCGCTCAGCGCCGCATCCTCTCCCGCCCCAAGCGCTCCGTCAACTCGCGCACCAACCAGACCCAGAAGCGTCCCCGTT

CCCGCACTCTGACCGCTGTCCACGACTCCATCCTCACTGACCTCGTCTACCCCGTCGAGATCGTTGGCAAGCGCATCCGC

ACCAAGGAGGACGGCAGCAAGACCATCAAGGTTGTTCTCGACGAGAAGGAGCGCGGTGGTGTTGACCACAGACTCGATGC

CTACGGCGAGGTCTACCGCAGACTGACCGGCCGTGCCGTTGTCTTCGAGTTCCCCCAGAG

SEQ 369: *A. glaucus*MA542
CAUCGCUCAGCGCCGCAUCCUCUCCCGCCCCAAGCGCUCCGUCAACUCGCGCACCAACCAGACCCAGAAGCGUCCCCGUU

CCCGCACUCUGACCGCUGUCCACGACUCCAUCCUCACUGACCUCGUCUACCCCGUCGAGAUCGUUGGCAAGCGCAUCCGC

ACCAAGGAGGACGGCAGCAAGACCAUCAAGGUUGUUCUCGACGAGAAGGAGCGCGGUGGUGUUGACCACAGACUCGAUGC

CUACGGCGAGGUCUACCGCAGACUGACCGGCCGUGCCGUUGUCUUCGAGUUCCCCCAGAG

SEQ 370: *A. glaucus*MA5279
CATCGCTCAGCGCCGCATCCTCTCCCGCCCCAAGCGCTCCGTCAACTCGCGCACCAACCAGACCCAGAAGCGTCCCCGTT

CCCGCACTCTGACTGCTGTCCACGACTCCATCCTCACCGACCTCGTCTACCCCGTCGAGATCGTTGGCAAGCGTATCCGC

ACCAAGGAGGACGGCAGCAAGACCATCAAGGTTGTTCTCGACGAGAAGGAGCGCGGTGGTGTTGACCACAGACTCGATGC

CTACGGCGAGGTCTACCGCAGACTGACCGGCCGTGCCGTTGTCTTCGAGTTCCCCCAGAG

SEQ 371: *A. glaucus*MA5279
CAUCGCUCAGCGCCGCAUCCUCUCCCGCCCCAAGCGCUCCGUCAACUCGCGCACCAACCAGACCCAGAAGCGUCCCCGUU

CCCGCACUCUGACUGCUGUCCACGACUCCAUCCUCACCGACCUCGUCUACCCCGUCGAGAUCGUUGGCAAGCGUAUCCGC

-continued

ACCAAGGAGGACGGCAGCAAGACCAUCAAGGUUGUUCUCGACGAGAAGGAGCGCGGUGGUGUUGACCACAGACUCGAUGC

CUACGGCGAGGUCUACCGCAGACUGACCGGCCGUGCCGUUGUCUUCGAGUUCCCCCAGAG

SEQ 372: *A. glaucus*117314
CGCTCAGCGCCGCATCCTCTCCCGCCCCAAGCGCTCCGTCAACTCGCGCACCAACCAGACCCAGAAGCGTCCCCGTTCCC

GCACTCTGACCGCTGTCCACGACTCCATCCTCACCGACCTCGTCTACCCCGTCGAGATCGTTGGCAAGCGCATCCGCACC

AAGGAGGACGGCAGCAAGACCATCAAGGTTGTTCTTGACGAGAAGGAGCGCGGTGGTGTTGACCACAGACTCGATGCCTA

CGGCGAGGTCTACCGCAGACTGACCGGCCGTGCCGTTGTCTTCGAGTTCCCCCAGAG

SEQ 373: *A. glaucus*117314
CGCUCAGCGCCGCAUCCUCUCCCGCCCCAAGCGCUCCGUCAACUCGCGCACCAACCAGACCCAGAAGCGUCCCCGUUCCC

GCACUCUGACCGCUGUCCACGACUCCAUCCUCACCGACCUCGUCUACCCCGUCGAGAUCGUUGGCAAGCGCAUCCGCACC

AAGGAGGACGGCAGCAAGACCAUCAAGGUUGUUCUUGACGAGAAGGAGCGCGGUGGUGUUGACCACAGACUCGAUGCCUA

CGGCGAGGUCUACCGCAGACUGACCGGCCGUGCCGUUGUCUUCGAGUUCCCCCAGAG

SEQ 374: *A. glaucus*297.71
CGCTCAGCGCCGCATCCTCTCCCGCCCCAAGCGCTCCGTCAACTCGCGCACCAACCAGACCCAGAAGCGTCCCCGTTCCC

GCACTCTGACTGCTGTCCACGASTCCATCCTCACCGACCTCGTCTACCCCGTCGAGATCGTTGGCAAGCGTATCCGCACC

AAGGAGGACGGCAGCAAGACCATCAAGGTTGTTCTCGACGAGAAGGAGCGCGGTGGTGTTGACCACAGACTCGATGCCTA

CGGCGAGGTCTACCGCAGACTGACCGGCCGTGCCGTTGTCTTCGAGTTCCCCCAGAG

SEQ 375: *A. glaucus*297.71
CGCUCAGCGCCGCAUCCUCUCCCGCCCCAAGCGCUCCGUCAACUCGCGCACCAACCAGACCCAGAAGCGUCCCCGUUCCC

GCACUCUGACUGCUGUCCACGASUCCAUCCUCACCGACCUCGUCUACCCCGUCGAGAUCGUUGGCAAGCGUAUCCGCACC

AAGGAGGACGGCAGCAAGACCAUCAAGGUUGUUCUCGACGAGAAGGAGCGCGGUGGUGUUGACCACAGACUCGAUGCCUA

CGGCGAGGUCUACCGCAGACUGACCGGCCGUGCCGUUGUCUUCGAGUUCCCCCAGAG

SEQ 376: *A. niger*124.49
CGTTGCTCAGCGCCGCATCCTGCCCCGCCCCAAGCGCTCCGCCAGCTCTCGTTCCAACCAGAAGCAGAAGCGTCCCCGTT

CCCGCACTCTGACTGCTGTCCACGACGCCATCCTCACCGACCTCGTCTACCCCGTCGAGATCGTCGGCAAGCGTACCCGC

ACCAAGGAGGACGGCTCCAAGACCCTCAAGGTCATCCTGGACGAGAAGGAGCGTGGTGGTGTTGACCACCGCCTTGATGC

CTACGGCGAGGTCTACCGTCGGTTGACTGGCCGTGCTGTTGTCTTTGAATTCCCCCAGGG

SEQ 377: *A. niger*124.49
CGUUGCUCAGCGCCGCAUCCUGCCCCGCCCCAAGCGCUCCGCCAGCUCUCGUUCCAACCAGAAGCAGAAGCGUCCCCGUU

CCCGCACUCUGACUGCUGUCCACGACGCCAUCCUCACCGACCUCGUCUACCCCGUCGAGAUCGUCGGCAAGCGUACCCGC

ACCAAGGAGGACGGCUCCAAGACCCUCAAGGUCAUCCUGGACGAGAAGGAGCGUGGUGGUGUUGACCACCGCCUUGAUGC

CUACGGCGAGGUCUACCGUCGGUUGACUGGCCGUGCUGUUGUCUUUGAAUUCCCCCAGGG

SEQ 378: Alb1
5' attgtctacgatgttaaaggtaaattc 3'

SEQ 379: Alb1
5' gaatttacctttaacatcgtagacaat 3'

SEQ 380: Alb2
5' agaatttctgctgaagaagctgcct 3'

SEQ 381: Alb2
5' aggcagcttcttcagcagaaattct 3'

SEQ 382: Alb3a
5' tcagattagtctacgatgttaaaggtaaa3'

SEQ 383: Alb3a
5' tttacctttaacatcgtagactaatctga 3'

SEQ 384: Alb3
5' tcagattagtctacgatgttaaaggtaaattc 3'

-continued

SEQ 385: Alb3
5' gaatttacctttaacatcgtagactaatctga 3'

SEQ 386: kru2
5' agctgcatacaagttatgtaaggtc 3'

SEQ 387: kru2
5' gaccttacataacttgtatgcagct 3'

SEQ 388: Kru1
5' tcaccccagaagaagctgcat 3'

SEQ 389: Kru1
5' atgcagcttcttctggggtga 3'

SEQ 390: Parap1
5' aaagtagatttgcttgccac 3'

SEQ 391: Parap1
5' gtggcaagcaaatctacttt 3'

SEQ 392: Parap2
5' aagggaatcccatacgttgtca 3'

SEQ 393: Parap2
5' tgacaacgtatgggattccctt 3'

SEQ 394: Trop1
5' taccaacgaacacttcagattgattta 3'

SEQ 395: Trop1
5' taaatcaatctgaagtgttcgttggta 3'

SEQ 396: Trop2
5' ttctgctgaagaagcttcttacaa 3'

SEQ 397: Trop2
5' ttgtaagaagcttcttcagcagaa 3'

SEQ 398: Trop3
5' acagaatttctgctgaagaagcttcttacaa 3'

SEQ 399: Trop3
5' ttgtaagaagcttcttcagcagaaattctgt 3'

SEQ 400: Trop4
5' cgaacacttcagattgatttacgatgttaaa 3'

SEQ 401: Trop4
5' tttaacatcgtaaatcaatctgaagtgttcg 3'

SEQ 402: Trop6
5' tttaacatcgtaaatcaatctgaagtgttcg3'

SEQ 403: Trop6
5' cgaacacttcagattgatttacgatgttaaa 3'

SEQ 404: Trop9
5' ttacctttaacatcgtaaatcaatctgaagtgttcgttggt 3'

SEQ 405: Trop9
5' accaacgaacacttcagattgatttacgatgttaaaggtaa 3'

SEQ 406: Glab1
5' tatcactgacgaagaagcttc 3'

SEQ 407: Glab1
5' gaagcttcttcgtcagtgata 3'

SEQ 408: Glab2
5' ttgggtaaggtcaagaaggtccaatt 3'

SEQ 409: Glab2
5' aattggaccttcttgaccttacccaa 3'

SEQ 410: Glab3
5' tatcactgacgaagaagcttcctacaa 3'

SEQ 411: Glab3
5' ttgtaggaagcttcttcgtcagtgata 3'

-continued

SEQ 412: Glab 5
5' atacgttgtcactgacgatggt 3'

SEQ 413: Glab 5
5' accatcgtcagtgacaacgtat 3'

SEQ 414: MycoSEQ AF1F
5' GACCGCCACGTCCTCTT 3'

SEQ 415: MycoSEQ AF1R
5' CTCTGGGGGAACTCGAA 3'

SEQ 416: MycoSEQ NIG1R
5' CCCTGGGGGAATTCAAA 3'

SEQ 417: MycoSEQ NIG1F
5' GACCGCCACGTTCTCTT 3'

SEQ 418: AF6 FOW
5' AGCAAGACTCTCAAGGTC 3'

SEQ 419: ASP2
5' AGGTTTACCGCCGACTAACC 3'

SEQ 420: ASP2
5' GGTTAGTCGGCGGTAAACCT 3'

SEQ 421: AFUM1
5' CGCTGTCCACGACGCCATCCTCA 3'

SEQ 422: AFUM1
5' TGAGGATGGCGTCGTGGACAGCG 3'

SEQ 423: AFUM2
5' CCGACTAACCGGCCGCTCTG 3'

SEQ 424: AFUM2
5' CAGAGCGGCCGGTTAGTCGG 3'

SEQ 425: ACAN1
5' CGTGCACGACAACATCCTGACCGA 3'

SEQ 426: ACAN1
5' TCGGTCAGGATGTTGTCGTGCACG 3'

SEQ 427: ACAN2
5' CGGCGGCGTTGACCACCGCCTGGAC 3'

SEQ 428: ACAN2
5' GTCCAGGCGGTGGTCAACGCCGCCG 3'

SEQ 429: ATERR1
5' CGGCGGTGTCGACCACCGCCTC 3'

SEQ 430: ATERR1
5' GAGGCGGTGGTCGACACCGCCG 3'

SEQ 431: ATERR2
5' CGTCTCACCGGCCGTGCCGTCGTC 3'

SEQ 432: ATERR2
5' GACGACGGCACGGCCGGTGAGACG 3'

SEQ 433: AVER1
5' CTTGACGACCTCGTCTACCCCGTTG 3'

SEQ 434: AVER1
5' CAACGGGGTAGACGAGGTCGTCAAG 3'

SEQ 435: AVER2
5' CTACCGTCGTTTGACCGGTCGTGCTGTTG 3'

SEQ 436: AVER2
5' CAACAGCACGACCGGTCAAACGACGGTAG 3'

SEQ 437: ANID1
5' GTACCCTCACTGCTGTTCACGATGC 3'

SEQ 438: ANID1
5' GCATCGTGAACAGCAGTGAGGGTAC 3'

-continued

SEQ 439: ANID2
5' GTCGTCTGACGGGTCGTGCTGTC 3'

SEQ 440: ANID2
5' GACAGCACGACCCGTCAGACGAC 3'

SEQ 441: AFLAV1
5' GCCGTTTGACCGGCCGCAACGTCGTC 3'

SEQ 442: AFLAV1
5' GACGACGTTGCGGCCGGTCAAACGGC 3'

SEQ 443: ACLAV1
5' CGAGATCGTCGGCAAGCGCAC 3'

SEQ 444: ACLAV1
5' GTGCGCTTGCCGACGATCTCG 3'

SEQ 445: ACLAV2
CGGCCGCTCCGTTGTCTTCGAG 3'

SEQ 446: ACLAV2
5' CTCGAAGACAACGGAGCGGCCG 3'

SEQ 447: ACLAV3
5' CGCCGTTTAACCGGCCGCTCCGTTGTC 3'

SEQ 448: ACLAV3
5' GACAACGGAGCGGCCGGTTAAACGGCG 3'

SEQ 449: *S. cerevisiae* 33
CATCACTCTAGATGCCACCAATGAAAACTTCAGATTGGTCTACGATGTCAAGGGTAGATTCGCTGTCCACCGTATCACCG

ATGAAGAAGCYTCTTACAARTTGGGTAAGGTCAAGAAGGTYCAATTAGGTAAGAAGGGTGTTCCATACGTTGTTACCCAC

GATGGTAGAACTATCAGATACCCAG

SEQ 450: *S. cerevisiae* 33
CAUCACUCUAGAUGCCACCAAUGAAAACUUCAGAUUGGUCUACGAUGUCAAGGGUAGAUUCGCUGUCCACCGUAUCACCG

AUGAAGAAGCYUCUUACAARUUGGGUAAGGUCAAGAAGGUYCAAUUAGGUAAGAAGGGUGUUCCAUACGUUGUUACCCAC

GAUGGUAGAACUAUCAGAUACCCAG

SEQ 451: *C. neoformans*114
GGTGTACGATGTCAAGGGTAGATTCACYSTSCACAGAATCACCGCYGAGGAGKCTWCCTACAAGYTSGSYAAGRTCARGA

AGRTCSMKTTGGGYAAGAGRRGTRTYCCMTACGYYGTCASCCACGACGGTAGAACTATCAGATACCCAGA

SEQ 452: *C. neoformans*114
GGUGUACGAUGUCAAGGGUAGAUUCACYSUSCACAGAAUCACCGCYGAGGAGKCUWCCUACAAGYUSGSYAAGRUCARGA

AGRUCSMKUUGGGYAAGAGRRGURUYCCMUACGYYGUCASCCACGACGGUAGAACUAUCAGAUACCCAGA

SEQ 453: *A. fischeri*_131700
CGTCGCTCAGCGCCGCATCCTGCCCCGCCCCAAGCGCTCCGTCAACTCCCGCACCAACCAGAAGCAGAAGCGTCCTCGCT

CTCGCACCCTGACCGCCGTCCACGACGCCATCCTCAACGACCTCGTTTACCCCGTCGAGATCGTCGGCAAGCGTACCCGC

ACCAAGGAAGACGGCAGCAAGACTCTCAAGGTCATCCTCGACGAGAAGGAGCGTGGCGGTGTTGACCACAGACTCGATGC

CTACGGCGAGGTCTACCGCCGACTGACCGGCCGCTCTGTTGTCTTCGAGTTCCCCCAGAG

SEQ 454: *A. fischeri*_131700
CGUCGCUCAGCGCCGCAUCCUGCCCCGCCCCAAGCGCUCCGUCAACUCCCGCACCAACCAGAAGCAGAAGCGUCCUCGCU

CUCGCACCCUGACCGCCGUCCACGACGCCAUCCUCAACGACCUCGUUUACCCCGUCGAGAUCGUCGGCAAGCGUACCCGC

ACCAAGGAAGACGGCAGCAAGACUCUCAAGGUCAUCCUCGACGAGAAGGAGCGUGGCGGUGUUGACCACAGACUCGAUGC

CUACGGCGAGGUCUACCGCCGACUGACCGGCCGCUCUGUUGUCUUCGAGUUCCCCCAGAG

SEQ 455: *A. fischeri*_211390
CGTCGCTCAGCGCCGCATCCTGCCCCGCCCCAAGCGCTCTGTCAACTCCCGCACCAACCAGAAGCAGAAGCGTCCTCGCT

CTCGCACCCTGACCGCTGTCCACGATGCCATCCTCAACGACCTCGTTTACCCCGTCGAGATCGTCGGCAAGCGTATCCGC

ACCAAGGAGGACGGCAGCAAGACTCTCAAGGTCATCCTGGACGAGAAGGAGCGTGGTGGTGTTGACCACAGACTCGATGC

CTACGGCGAGGTTTACCGCCGACTAACTGGCCGCTCTGTTGTCTTCGAGTTCCCCCAGAG

-continued

SEQ 456: *A. fischeri*_211390
CGUCGCUCAGCGCCGCAUCCUGCCCCGCCCCAAGCGCUCUGUCAACUCCCGCACCAACCAGAAGCAGAAGCGUCCUCGCU

CUCGCACCCUGACCGCUGUCCACGAUGCCAUCCUCAACGACCUCGUUUACCCCGUCGAGAUCGUCGGCAAGCGUAUCCGC

ACCAAGGAGGACGGCAGCAAGACUCUCAAGGUCAUCCUGGACGAGAAGGAGCGUGGUGGUGUUGACCACAGACUCGAUGC

CUACGGCGAGGUUUACCGCCGACUAACUGGCCGCUCUGUUGUCUUCGAGUUCCCCCAGAG

SEQ 457: *A. fischeri*_214525
CGTCGCTCAGCGCCGCATCCTGCCCCGCCCCAAGCGCTCTGTCAACTCCCGCACCAACCAGAAGCAGAAGCGTCCTCGCT

CTCGCACCCTGACCGCTGTCCACGATGCCATCCTCAACGACCTCGTTTACCCCGTCGAGATCGTCGGCAAGCGTATCCGC

ACCAAGGAGGACGGCAGCAAGACTCTCAAGGTCATCCTGGACGAGAAGGAGCGTGGTGGTGTTGACCACAGACTCGATGC

CTACGGCGAGGTTTACCGCCGACTAACTGGCCGCTCTGTTGTCTTCGAGTTCCCCCAGAG

SEQ 458: *A. fischeri*_214525
CGUCGCUCAGCGCCGCAUCCUGCCCCGCCCCAAGCGCUCUGUCAACUCCCGCACCAACCAGAAGCAGAAGCGUCCUCGCU

CUCGCACCCUGACCGCUGUCCACGAUGCCAUCCUCAACGACCUCGUUUACCCCGUCGAGAUCGUCGGCAAGCGUAUCCGC

ACCAAGGAGGACGGCAGCAAGACUCUCAAGGUCAUCCUGGACGAGAAGGAGCGUGGUGGUGUUGACCACAGACUCGAUGC

CUACGGCGAGGUUUACCGCCGACUAACUGGCCGCUCUGUUGUCUUCGAGUUCCCCCAGAG

SEQ 459: *N. fischeri*_1085
CGCTCAGCGCCGCATCCTGCCCCGCCCCAAGCGCTCCGTCAACTCCCGCACCAACCAGAAGCAGAAGCGCCCTCGCTCCC

GCACCCTGACCGCTGTCCACGACGCCATCCTCAACGACCTCGTTTACCCCGTCGAGATCGTCGGCAAGCGTATCCGCACC

AAGGAGGACGGCAGCAAGACTCTCAAGGTCATCCTGGACGAGAAGGAGCGTGGCGGTGTTGACCACAGACTCGATGCCTA

CGGCGAGGTTTACCGCCGACTAACCGGCCGCTCTGTTGTCTTCGAGTTCCCCCAGAG

SEQ 460: *N. fischeri*_1085
CGCUCAGCGCCGCAUCCUGCCCCGCCCCAAGCGCUCCGUCAACUCCCGCACCAACCAGAAGCAGAAGCGCCCUCGCUCCC

GCACCCUGACCGCUGUCCACGACGCCAUCCUCAACGACCUCGUUUACCCCGUCGAGAUCGUCGGCAAGCGUAUCCGCACC

AAGGAGGACGGCAGCAAGACUCUCAAGGUCAUCCUGGACGAGAAGGAGCGUGGCGGUGUUGACCACAGACUCGAUGCCUA

CGGCGAGGUUUACCGCCGACUAACCGGCCGCUCUGUUGUCUUCGAGUUCCCCCAGAG

SEQ 461: *N. fischeri*_14726
TGCTCAGCGCCGCATCCTGCCCCGCCCCAAGCGCTCTGTCAACTCCCGCACCAACCAGAAGCAGAAGCGCCCTCGCTCTC

GCACCCTGACCGCTGTCCACGACGCCATCCTCACCGACCTCGTTTACCCCGTCGAGATCGTCGGCAAGCGTATCCGCACC

AAGGAGGACGGCAGCAAGACTCTCAAGGTCATCCTGGACGAGAAGGAGCGTGGCGGTGTTGACCACAGACTCGATGCCTA

CGGCGAGGTCTACCGCCGACTAACCGGCCGCTCTGTTGTCTTCGAGTTCCCCCAGAG

SEQ 462: *N. fischeri*_14726
UGCUCAGCGCCGCAUCCUGCCCCGCCCCAAGCGCUCUGUCAACUCCCGCACCAACCAGAAGCAGAAGCGCCCUCGCUCUC

GCACCCUGACCGCUGUCCACGACGCCAUCCUCACCGACCUCGUUUACCCCGUCGAGAUCGUCGGCAAGCGUAUCCGCACC

AAGGAGGACGGCAGCAAGACUCUCAAGGUCAUCCUGGACGAGAAGGAGCGUGGCGGUGUUGACCACAGACUCGAUGCCUA

CGGCGAGGUCUACCGCCGACUAACCGGCCGCUCUGUUGUCUUCGAGUUCCCCCAGAG

SEQ 463: *N. fischeri*_19426
TGCTCAGCGCCGCATCCTGCCACGCCCCAAGCGCTCTGTCAACTCCCGCACCAACCAGAAGCAGAAGCGCCCTCGCTCTC

GCACCCTGACCGCCGTCCACGACGCCATCCTCGACGACCTCGTTTACCCCGTCGAGATCGTCGGCAAGCGTATCCGCACC

AAGGAGGACGGCAGCAAGACTCTCAAGGTCATCCTGGACGAGAAGGAGCGTGGCGGTGTTGACCACAGACTCGATGCCTA

CGGCGAGGTCTACCGCCGACTAACCGGCCGTGCTGTTGTCTTCGAGTTCCCCCAGAG

SEQ 464: *N. fischeri*_19426
UGCUCAGCGCCGCAUCCUGCCACGCCCCAAGCGCUCUGUCAACUCCCGCACCAACCAGAAGCAGAAGCGCCCUCGCUCUC

GCACCCUGACCGCCGUCCACGACGCCAUCCUCGACGACCUCGUUUACCCCGUCGAGAUCGUCGGCAAGCGUAUCCGCACC

AAGGAGGACGGCAGCAAGACUCUCAAGGUCAUCCUGGACGAGAAGGAGCGUGGCGGUGUUGACCACAGACUCGAUGCCUA

CGGCGAGGUCUACCGCCGACUAACCGGCCGUGCUGUUGUCUUCGAGUUCCCCCAGAG

-continued

SEQ 465: *N. fischeri*_20179
TGCTCAGCGCCGCATCCTGCCACGCCCCAAGCGCTCTGTCAACTCCCGCACCAACCAGAAGCAGAAGCGCCCTCGCTCTC

GCACCCTGACCGCCGTCCACGACGCCATCCTCGACGACCTCGTTTACCCCGTCGAGATCGTCGGCAAGCGTATCCGCACC

AAGGAGGACGGCAGCAAGACTCTCAAGGTCATCCTGGACGAGAAGGAGCGTGGCGGTGTTGACCACAGACTCGATGCCTA

CGGCGAGGTCTACCGCCGACTAACCGGCCGTGCTGTTGTCTTCGAGTTCCCCCAGAG

SEQ 466: *N. fischeri*_20179
UGCUCAGCGCCGCAUCCUGCCACGCCCCAAGCGCUCUGUCAACUCCCGCACCAACCAGAAGCAGAAGCGCCCUCGCUCUC

GCACCCUGACCGCCGUCCACGACGCCAUCCUCGACGACCUCGUUUACCCCGUCGAGAUCGUCGGCAAGCGUAUCCGCACC

AAGGAGGACGGCAGCAAGACUCUCAAGGUCAUCCUGGACGAGAAGGAGCGUGGCGGUGUUGACCACAGACUCGAUGCCUA

CGGCGAGGUCUACCGCCGACUAACCGGCCGUGCUGUUGUCUUCGAGUUCCCCCAGAG

REFERENCES

"*Stakeholder Insight: Invasive fungal infections*", Datamonitor, January 2004

"*Stakeholder Insight: Sepsis, Under reaction to an overreaction*", Datamonitor March 2006

Atkins S. D. and Clark I. M. (2004) Fungal Molecular Diagnostics: A Mini Review. *J. Appl. Genet.* 45, 3-15.

Delbrück, S., Sonneborn, A., Gerads, M., Grablowitz, A. H. And Ernst, J. F. (1997). Characterization and regulation of genes encoding ribosomal proteins L39 and S7 of human pathogen *Candida albicans*. Yeast. 13, 1199-1210.

Synetos, D., Dabeva, M. D. and Warner, J. R. (1992). The yeast ribosomal protein S7 and its genes. *J. Biol. Chem.* 267, 3008-3013.

The invention claimed is:

1. A method of detecting and/or discriminating a yeast or fungal species, subspecies or strain in a test sample, the method comprising the steps of:

(i) mixing the test sample with at least one primer and at least one probe for in vitro nucleic acid amplification, wherein the primer has a sequence homologous to or complementary to a portion of the RPS7 gene or its corresponding mRNA, wherein the portion of the RPS7 gene is a portion of exon 3 of the *Aspergillus* RPS7 gene, or a portion of base pair position 508 to base pair position 711 of the *C. albicans* RPS7 gene, wherein the probe is labeled with a detectable moiety, and wherein the probe is selected from the group consisting of SEQ ID NO: 1 through to SEQ ID NO: 49, SEQ ID NO: 176 through to SEQ ID NO: 189, and SEQ ID NO: 378 through to SEQ ID NO: 448;

(ii) conducting the in vitro nucleic acid amplification; and (iii) analyzing the amplification product(s).

2. A method of detecting a target organism in a test sample comprising the steps of:

(i) Mixing the test sample with at least one oligonucleotide probe capable of binding to at least a portion of the RPS7 gene or its corresponding mRNA, wherein the portion of the RPS7 gene is a portion of exon 3 of the *Aspergillus* RPS7 gene, or a portion of base pair position 508 to base pair position 711 of the *C. albicans* RPS7 gene:, wherein the probe is labeled with a detectable moiety;

(ii) hybridizing under high stringency conditions any nucleic acid that may be present in the test sample with the oligonucleotide probe; and (iii) determining whether a probe:target duplex is present, wherein detection of a probe:target duplex indicates the presence of the target organism.

3. The method as claimed in claim 2 wherein the probe is selected from the group consisting of SEQ ID NO: 1 through to SEQ ID NO: 49, SEQ ID NO: 176 through to SEQ ID NO: 189, and SEQ ID NO: 378 through to SEQ ID NO: 448.

4. The method of claim 1 or 2 for use in a diagnostic assay to measure yeast or fungal titres in a patient.

5. The method of claim 1 or 2 for use to assess the efficacy of a treatment regime designed to reduce yeast or fungal titre in a patient.

6. The method of claim 1 or 2 for use in a diagnostic assay to measure yeast or fungal contamination in a sample.

7. The method as claimed in claim 6, wherein the sample is a hospital sample, a food sample, an environmental sample, or an industrial sample.

8. The method of claim 1 or 2 for use in the identification or characterization of one or more disruptive agents that can be used to disrupt the RPS7 gene function.

9. The method as claimed in claim 8, wherein the disruptive agent is selected from the group consisting of antisense RNA, PNA, and siRNA.

10. The method of claim 1, wherein the primer is selected from the group consisting of: SEQ ID NO: 1 through SEQ ID NO: 466.

11. The method of claim 1 or 2, wherein the method is used in a diagnostic assay to measure yeast or fungal titres in a patient.

12. The method of claim 1 or 2, wherein the method is used to assess the efficacy of a treatment regime designed to reduce yeast or fungal titre in a patient.

13. The method of claim 1 or 2, wherein the method is used in a diagnostic assay to measure yeast or fungal contamination in a sample.

14. The method of claim 13, wherein the sample is a hospital sample, a food sample, an environmental sample, or an industrial sample.

15. The method of claim 1 or 2, wherein the method is used in the identification or characterization of one or more disruptive agents that can be used to disrupt the RPS7 gene function.

16. The method of claim 15, wherein the disruptive agent is selected from the group consisting of antisense RNA, PNA and siRNA.

17. The method of claim 1, wherein in step (i) the at least one primer comprises a forward and a reverse primer, both forward and reverse primers having a sequence substantially homologous to or substantially complementary to a portion of the RPS7 gene or its corresponding mRNA.

18. The method of claim 17, wherein the forward primer is selected from the group consisting of SEQ ID NO 8 through to SEQ ID NO 40, SEQ ID NO 414, SEQ ID NO 417, and SEQ ID NO 418, and wherein the reverse primer is selected from the group consisting of SEQ ID NO 3, SEQ ID NO 22 through to SEQ ID NO 49, SEQ ID NO 415 and SEQ ID NO 416.

19. The method of claim 1, wherein the in vitro nucleic acid amplification is selected from the group consisting of Polymerase Chain Reaction (PCR), Ligase Chain Reaction (LCR), Nucleic Acids Sequence Based Amplification (NASBA), Strand Displacement Amplification (SDA), Transcription Mediated Amplification (TMA), Branched DNA technology (bDNA), Rolling Circle Amplification Technology (RCAT), and the combination thereof.

20. A method of detecting and/or discriminating a yeast or fungal species, subspecies or strain in a test sample, the method comprising the steps of:

(i) mixing the test sample with at least one primer for in vitro nucleic acid amplification, wherein the primer has a sequence homologous to or complementary to a portion of the RPS7 gene or its corresponding mRNA, and wherein the primer is selected from the group consisting of: SEQ ID NOs: 2-5, SEQ ID NOs: 8-49, SEQ ID NOs: 414-418, and SEQ ID NO: 466;

(ii) conducting the in vitro nucleic acid amplification; and (iii) analyzing the amplification product(s).

21. The method of claim 20, wherein in step (i) the at least one primer comprises a forward and a reverse primer, both forward and reverse primers having a sequence homologous to or complementary to a portion of the RPS7 gene or its corresponding mRNA.

22. The method of claim 21, wherein the forward primer is selected from the group consisting of SEQ ID NO: 8 through to SEQ ID NO: 40, SEQ ID NO: 414, SEQ ID NO: 417, and SEQ ID NO: 418, and wherein the reverse primer is selected from the group consisting of SEQ ID NO: 3, SEQ ID NO: 22 through to SEQ ID NO: 49, SEQ ID NO: 415 and SEQ ID NO: 416.

23. The method of claim 20, wherein the in vitro nucleic acid amplification is selected from the group consisting of Polymerase Chain Reaction (PCR), Ligase Chain Reaction (LCR), Nucleic Acids Sequence Based Amplification (NASBA), Strand Displacement Amplification (SDA), Transcription Mediated Amplification (TMA), Branched DNA technology (bDNA), Rolling Circle Amplification Technology (RCAT), and the combination thereof.

24. The method of claim 20, wherein the portion of the RPS7 gene is a portion of exon 3 of the *Aspergillus* RPS7 gene, or is a portion of base pair position 508 to base pair position 711 of the *C. albicans* RPS7 gene.

25. A method of detecting a target organism in a test sample comprising the steps of:

(i) Mixing the test sample with at least one oligonucleotide probe capable of binding to at least a portion of the RPS7 gene or its corresponding mRNA, wherein the probe is selected from the group consisting of SEQ ID NO: 1 through to SEQ ID NO: 49, SEQ ID NO: 176 through to SEQ ID NO: 189, and SEQ ID NO: 378 through to SEQ ID NO: 448;

(ii) hybridizing under high stringency conditions any nucleic acid that may be present in the test sample with the oligonucleotide probe; and (iii) determining whether a probe:target duplex is present, wherein detection of a probe:target duplex indicates the presence of the target organism wherein the portion of the RPS7 gene is a portion of exon 3 of the *Aspergillus* RPS7 gene, or is a portion of base pair position 508 to base pair position 711 of the *C. albicans* RPS7 gene.

26. The method of claim 1 or 20, wherein the primer is selected from the group consisting of: SEQ ID NO: 3, SEQ ID NO: 10, SEQ ID NO: 40, SEQ ID NO: 415, SEQ ID NO: 418, and combinations thereof.

27. The method of claim 2 or 25, wherein the probe is selected from the group consisting of: SEQ ID NO: 384, SEQ ID NO: 386, SEQ ID NO: 392, SEQ ID NO: 400, SEQ ID NO: 402, SEQ ID NO: 403, SEQ ID NO: 410, SEQ ID NO: 412, SEQ ID NO: 419, and combinations thereof.

28. The method of claim 1 or 2, wherein the detectable moiety is a radioisotope, a fluorescent moiety, a chemiluminescent moiety, a nanoparticle moiety, an enzyme or a ligand.

* * * * *

SEQUENCE LISTING

<160> NUMBER OF SEQ ID NOS: 466

<210> SEQ ID NO 1
<211> LENGTH: 18
<212> TYPE: DNA
<213> ORGANISM: Artificial Sequence
<220> FEATURE:
<223> OTHER INFORMATION: Chemically Synthesized (CASP)

<400> SEQUENCE: 1
taacatcgta ggctaatc 18

<210> SEQ ID NO 2
<211> LENGTH: 19
<212> TYPE: DNA
<213> ORGANISM: Artificial Sequence
<220> FEATURE:
<223> OTHER INFORMATION: Chemically Synthesized (Can2R-n15)

<400> SEQUENCE: 2
tctgggtatc tgatgttct 19

<210> SEQ ID NO 3
<211> LENGTH: 20
<212> TYPE: DNA
<213> ORGANISM: Artificial Sequence
<220> FEATURE:
<223> OTHER INFORMATION: Chemically Synthesized (Can2R-d15)

<400> SEQUENCE: 3
tctgggtatc tgatrgttct 20

<210> SEQ ID NO 4
<211> LENGTH: 20
<212> TYPE: DNA
<213> ORGANISM: Artificial Sequence
<220> FEATURE:
<223> OTHER INFORMATION: Chemically Synthesized (Can2R-A15)

<400> SEQUENCE: 4
tctgggtatc tgatagttct 20

<210> SEQ ID NO 5
<211> LENGTH: 20
<212> TYPE: DNA
<213> ORGANISM: Artificial Sequence
<220> FEATURE:
<223> OTHER INFORMATION: Chemically Synthesized (Can2R-G15)

<400> SEQUENCE: 5
tctgggtatc tgatggttct 20

<210> SEQ ID NO 6
<211> LENGTH: 18
<212> TYPE: DNA
<213> ORGANISM: Artificial Sequence
<220> FEATURE:
<223> OTHER INFORMATION: Chemically Synthesized (C. albicans antisense probe)

<400> SEQUENCE: 6
taacatcgta ggctaatc 18

<210> SEQ ID NO 7
<211> LENGTH: 18
<212> TYPE: DNA
<213> ORGANISM: Artificial Sequence
<220> FEATURE:
<223> OTHER INFORMATION: Chemically Synthesized (C. albicans specific probe)

<400> SEQUENCE: 7
gattagccta cgatgtta 18

<210> SEQ ID NO 8
<211> LENGTH: 23
<212> TYPE: DNA
<213> ORGANISM: Artificial Sequence
<220> FEATURE:
<223> OTHER INFORMATION: Chemically Synthesized (RPS7 primer (i))
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 8
atggntagag gnccaaagaa nca 23

<210> SEQ ID NO 9
<211> LENGTH: 23
<212> TYPE: DNA
<213> ORGANISM: Artificial Sequence
<220> FEATURE:
<223> OTHER INFORMATION: Chemically Synthesized (RPS7)

<400> SEQUENCE: 9
atggstagag gwccaaagaa rca 23

<210> SEQ ID NO 10

<211> LENGTH: 23
<212> TYPE: DNA
<213> ORGANISM: Artificial Sequence
<220> FEATURE:
<223> OTHER INFORMATION: Chemically Synthesized (RPS7 primer (i))
<220> FEATURE:
<221> NAME/KEY: misc_feature
<222> LOCATION: (12)..(12)
<223> OTHER INFORMATION: n is a, c, g, or t

<400> SEQUENCE: 10
atggctagag gnccaaagaa gca 23

<210> SEQ ID NO 11
<211> LENGTH: 23
<212> TYPE: DNA
<213> ORGANISM: Artificial Sequence
<220> FEATURE:
<223> OTHER INFORMATION: Chemically Synthesized (RPS7 primer (i))
<220> FEATURE:
<221> NAME/KEY: misc_feature
<222> LOCATION: (12)..(12)
<223> OTHER INFORMATION: n is a, c, g, or t

<400> SEQUENCE: 11
atggctagag gnccaaagaa aca 23

<210> SEQ ID NO 12
<211> LENGTH: 23
<212> TYPE: DNA
<213> ORGANISM: Artificial Sequence
<220> FEATURE:
<223> OTHER INFORMATION: Chemically Synthesized (RPS7 primer (i))
<220> FEATURE:
<221> NAME/KEY: misc_feature
<222> LOCATION: (12)..(12)
<223> OTHER INFORMATION: n is a, c, g, or t

<400> SEQUENCE: 12
atgggtagag gnccaaagaa gca 23

<210> SEQ ID NO 13
<211> LENGTH: 23
<212> TYPE: DNA
<213> ORGANISM: Artificial Sequence
<220> FEATURE:
<223> OTHER INFORMATION: Chemically Synthesized (RPS7 primer (i))
<220> FEATURE:
<221> NAME/KEY: misc_feature
<222> LOCATION: (12)..(12)
<223> OTHER INFORMATION: n is a, c, g, or t

<400> SEQUENCE: 13
atgggtagag gnccaaagaa aca 23

<210> SEQ ID NO 14
<211> LENGTH: 23
<212> TYPE: DNA
<213> ORGANISM: Artificial Sequence
<220> FEATURE:
<223> OTHER INFORMATION: Chemically Synthesized (RPS7 primer (i))

<400> SEQUENCE: 14
atggctagag gaccaaagaa gca 23

<210> SEQ ID NO 15
<211> LENGTH: 23
<212> TYPE: DNA
<213> ORGANISM: Artificial Sequence

```
<220> FEATURE:
<223> OTHER INFORMATION: Chemically Synthesized (RPS7 primer (i))

<400> SEQUENCE: 15

atggctagag gaccaaagaa aca                                          23


<210> SEQ ID NO 16
<211> LENGTH: 23
<212> TYPE: DNA
<213> ORGANISM: Artificial Sequence
<220> FEATURE:
<223> OTHER INFORMATION: Chemically Synthesized (RPS7 primer (i))

<400> SEQUENCE: 16

atggctagag gtccaaagaa gca                                          23


<210> SEQ ID NO 17
<211> LENGTH: 23
<212> TYPE: DNA
<213> ORGANISM: Artificial Sequence
<220> FEATURE:
<223> OTHER INFORMATION: Chemically Synthesized (RPS7 primer (i))

<400> SEQUENCE: 17

atggctagag gtccaaagaa aca                                          23


<210> SEQ ID NO 18
<211> LENGTH: 23
<212> TYPE: DNA
<213> ORGANISM: Artificial Sequence
<220> FEATURE:
<223> OTHER INFORMATION: Chemically Synthesized (RPS7 primer (i))

<400> SEQUENCE: 18

atgggtagag gaccaaagaa gca                                          23


<210> SEQ ID NO 19
<211> LENGTH: 23
<212> TYPE: DNA
<213> ORGANISM: Artificial Sequence
<220> FEATURE:
<223> OTHER INFORMATION: Chemically Synthesized (RPS7 primer (i))

<400> SEQUENCE: 19

atgggtagag gaccaaagaa aca                                          23


<210> SEQ ID NO 20
<211> LENGTH: 23
<212> TYPE: DNA
<213> ORGANISM: Artificial Sequence
<220> FEATURE:
<223> OTHER INFORMATION: Chemically Synthesized (RPS7 primer (i))

<400> SEQUENCE: 20

atgggtagag gtccaaagaa gca                                          23


<210> SEQ ID NO 21
<211> LENGTH: 23
<212> TYPE: DNA
<213> ORGANISM: Artificial Sequence
<220> FEATURE:
<223> OTHER INFORMATION: Chemically Synthesized (RPS7 primer (i))

<400> SEQUENCE: 21

atgggtagag gtccaaagaa aca                                          23
```

```
<210> SEQ ID NO 22
<211> LENGTH: 28
<212> TYPE: DNA
<213> ORGANISM: Artificial Sequence
<220> FEATURE:
<223> OTHER INFORMATION: Chemically Synthesized (RPS7 primer (i))
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 22

gcnccaagac catcngctgg tccncaca                                    28


<210> SEQ ID NO 23
<211> LENGTH: 28
<212> TYPE: DNA
<213> ORGANISM: Artificial Sequence
<220> FEATURE:
<223> OTHER INFORMATION: Chemically Synthesized (RSP7 primer (ii))

<400> SEQUENCE: 23

gchccaagac catcygctgg tccwcaca                                    28


<210> SEQ ID NO 24
<211> LENGTH: 28
<212> TYPE: DNA
<213> ORGANISM: Artificial Sequence
<220> FEATURE:
<223> OTHER INFORMATION: Chemically Synthesized (RPS7 primer (ii))

<400> SEQUENCE: 24

gccccaagac catctgctgg tccacaca                                    28


<210> SEQ ID NO 25
<211> LENGTH: 28
<212> TYPE: DNA
<213> ORGANISM: Artificial Sequence
<220> FEATURE:
<223> OTHER INFORMATION: Chemically Synthesized (RPS7 primer (ii))

<400> SEQUENCE: 25

gctccaagac catctgctgg tccacaca                                    28


<210> SEQ ID NO 26
<211> LENGTH: 28
<212> TYPE: DNA
<213> ORGANISM: Artificial Sequence
<220> FEATURE:
<223> OTHER INFORMATION: Chemically Synthesized (RPS7 primer (ii))

<400> SEQUENCE: 26

gcaccaagac catctgctgg tccacaca                                    28


<210> SEQ ID NO 27
<211> LENGTH: 28
<212> TYPE: DNA
<213> ORGANISM: Artificial Sequence
<220> FEATURE:
<223> OTHER INFORMATION: Chemically Synthesized (RPS7 primer (ii))
```

-continued

<400> SEQUENCE: 27
gccccaagac catccgctgg tccacaca 28

<210> SEQ ID NO 28
<211> LENGTH: 28
<212> TYPE: DNA
<213> ORGANISM: Artificial Sequence
<220> FEATURE:
<223> OTHER INFORMATION: Chemically Synthesized (RPS7 primer (ii))

<400> SEQUENCE: 28
gctccaagac catccgctgg tccacaca 28

<210> SEQ ID NO 29
<211> LENGTH: 28
<212> TYPE: DNA
<213> ORGANISM: Artificial Sequence
<220> FEATURE:
<223> OTHER INFORMATION: Chemically Synthesized (RPS7 primer (ii))

<400> SEQUENCE: 29
gcaccaagac catccgctgg tccacaca 28

<210> SEQ ID NO 30
<211> LENGTH: 28
<212> TYPE: DNA
<213> ORGANISM: Artificial Sequence
<220> FEATURE:
<223> OTHER INFORMATION: Chemically Synthesized (RPS7 primer (ii))

<400> SEQUENCE: 30
gccccaagac catctgctgg tcctcaca 28

<210> SEQ ID NO 31
<211> LENGTH: 28
<212> TYPE: DNA
<213> ORGANISM: Artificial Sequence
<220> FEATURE:
<223> OTHER INFORMATION: Chemically Synthesized (RPS7 primer (ii))

<400> SEQUENCE: 31
gctccaagac catctgctgg tcctcaca 28

<210> SEQ ID NO 32
<211> LENGTH: 28
<212> TYPE: DNA
<213> ORGANISM: Artificial Sequence
<220> FEATURE:
<223> OTHER INFORMATION: Chemically Synthesized (RPS7 primer (ii))

<400> SEQUENCE: 32
gcaccaagac catctgctgg tcctcaca 28

<210> SEQ ID NO 33
<211> LENGTH: 28
<212> TYPE: DNA
<213> ORGANISM: Artificial Sequence
<220> FEATURE:
<223> OTHER INFORMATION: Chemically Synthesized (RPS7 primer (ii))

<400> SEQUENCE: 33
gccccaagac catccgctgg tcctcaca 28

<210> SEQ ID NO 34

<211> LENGTH: 28
<212> TYPE: DNA
<213> ORGANISM: Artificial Sequence
<220> FEATURE:
<223> OTHER INFORMATION: Chemically Synthesized (RPS7 primer (ii))

<400> SEQUENCE: 34
gctccaagac catccgctgg tcctcaca 28

<210> SEQ ID NO 35
<211> LENGTH: 28
<212> TYPE: DNA
<213> ORGANISM: Artificial Sequence
<220> FEATURE:
<223> OTHER INFORMATION: Chemically Synthesized (RPS7 primer (ii))

<400> SEQUENCE: 35
gcaccaagac catccgctgg tcctcaca 28

<210> SEQ ID NO 36
<211> LENGTH: 25
<212> TYPE: DNA
<213> ORGANISM: Artificial Sequence
<220> FEATURE:
<223> OTHER INFORMATION: Chemically Synthesized (RPS7 primer (ii))
<220> FEATURE:
<221> NAME/KEY: misc_feature
<222> LOCATION: (21)..(21)
<223> OTHER INFORMATION: n is a, c, g, or t

<400> SEQUENCE: 36
ccagctggtt tcatggatgt natca 25

<210> SEQ ID NO 37
<211> LENGTH: 26
<212> TYPE: DNA
<213> ORGANISM: Artificial Sequence
<220> FEATURE:
<223> OTHER INFORMATION: Chemically Synthesized (RPS7 primer (ii))

<400> SEQUENCE: 37
cccagctggt ttcatggatg tyatca 26

<210> SEQ ID NO 38
<211> LENGTH: 26
<212> TYPE: DNA
<213> ORGANISM: Artificial Sequence
<220> FEATURE:
<223> OTHER INFORMATION: Chemically Synthesized (RPS7 primer (iii))

<400> SEQUENCE: 38
cccagctggt ttcatggatg tcatca 26

<210> SEQ ID NO 39
<211> LENGTH: 26
<212> TYPE: DNA
<213> ORGANISM: Artificial Sequence
<220> FEATURE:
<223> OTHER INFORMATION: Chemically Synthesized (RPS7 primer (iii))

<400> SEQUENCE: 39
cccagctggt ttcatggatg ttatca 26

<210> SEQ ID NO 40
<211> LENGTH: 18
<212> TYPE: DNA
<213> ORGANISM: Artificial Sequence
<220> FEATURE:
<223> OTHER INFORMATION: Chemically Synthesized (Can1F genus specific primer)

<400> SEQUENCE: 40
agctggtttc atggatgt 18

<210> SEQ ID NO 41
<211> LENGTH: 24
<212> TYPE: DNA
<213> ORGANISM: Artificial Sequence
<220> FEATURE:
<223> OTHER INFORMATION: Chemically Synthesized (RPS7 primer (iv))
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 41
agaacnatca gatacccaga ncca 24

<210> SEQ ID NO 42
<211> LENGTH: 24
<212> TYPE: DNA
<213> ORGANISM: Artificial Sequence
<220> FEATURE:
<223> OTHER INFORMATION: Chemically Synthesized (RPS7 primer (iv))

<400> SEQUENCE: 42
agaacyatca gatacccaga ycca 24

<210> SEQ ID NO 43
<211> LENGTH: 24
<212> TYPE: DNA
<213> ORGANISM: Artificial Sequence
<220> FEATURE:
<223> OTHER INFORMATION: Chemically Synthesized (RPS7 primer (iv))

<400> SEQUENCE: 43
agaactatca gatacccaga ccca 24

<210> SEQ ID NO 44
<211> LENGTH: 24
<212> TYPE: DNA
<213> ORGANISM: Artificial Sequence
<220> FEATURE:
<223> OTHER INFORMATION: Chemically Synthesized (RPS7 primer (iv))

<400> SEQUENCE: 44
agaactatca gatacccaga tcca 24

<210> SEQ ID NO 45
<211> LENGTH: 24
<212> TYPE: DNA
<213> ORGANISM: Artificial Sequence
<220> FEATURE:
<223> OTHER INFORMATION: Chemically Synthesized (RPS7 primer (iv))

<400> SEQUENCE: 45
agaaccatca gatacccaga ccca 24

<210> SEQ ID NO 46
<211> LENGTH: 20

<212> TYPE: DNA
<213> ORGANISM: Artificial Sequence
<220> FEATURE:
<223> OTHER INFORMATION: Chemically Synthesized (RPS7 primer (iv))
<220> FEATURE:
<221> NAME/KEY: misc_feature
<222> LOCATION: (6)..(6)
<223> OTHER INFORMATION: n is a, c, g, or t

<400> SEQUENCE: 46
agaacnatca gatacccaga 20

<210> SEQ ID NO 47
<211> LENGTH: 20
<212> TYPE: DNA
<213> ORGANISM: Artificial Sequence
<220> FEATURE:
<223> OTHER INFORMATION: Chemically Synthesized (degen.3'-5'genus spec.primer)

<400> SEQUENCE: 47
agaacyatca gatacccaga 20

<210> SEQ ID NO 48
<211> LENGTH: 20
<212> TYPE: DNA
<213> ORGANISM: Artificial Sequence
<220> FEATURE:
<223> OTHER INFORMATION: Chemically Synthesized (RPS7 primer (iv))

<400> SEQUENCE: 48
agaaccatca gatacccaga 20

<210> SEQ ID NO 49
<211> LENGTH: 20
<212> TYPE: DNA
<213> ORGANISM: Artificial Sequence
<220> FEATURE:
<223> OTHER INFORMATION: Chemically Synthesized (RPS7 primer (iv))

<400> SEQUENCE: 49
agaactatca gatacccaga 20

<210> SEQ ID NO 50
<211> LENGTH: 197
<212> TYPE: DNA
<213> ORGANISM: Saccharomyces cerevisiae

<400> SEQUENCE: 50
agctggtttc atggatgtct agatgccacc aatgaaaact tcagattggt ctacgatgtc 60
aagggtagat tcgctgtcca ccgtatcacc gatgaagaag cttcttacaa gttgggtaag 120
gtcaagaagg ttcaattagg taagaagggt gttccatacg ttgttaccca cgatggtaga 180
actatcagat acccaga 197

<210> SEQ ID NO 51
<211> LENGTH: 197
<212> TYPE: RNA
<213> ORGANISM: Saccharomyces cerevisiae

<400> SEQUENCE: 51
agcugguuuc auggaugucu agaugccacc aaugaaaacu ucagauuggu cuacgauguc 60
aaggguagau ucgcugucca ccguaucacc gaugaagaag cuucuuacaa guuggguaag 120
gucaagaagg uucaauuagg uaagaagggu guuccauacg uuguuaccca cgaugguaga 180
acuaucagau acccaga 197

<210> SEQ ID NO 52
<211> LENGTH: 197
<212> TYPE: DNA
<213> ORGANISM: Candida glabrata

<400> SEQUENCE: 52
agctggtttc atggatgttt ggaagctacc aacgaaaact tcagattggt ctacgacgtc 60
aagggtagat tcgctgtcca ccgtatcact gacgaagaag cttcctacaa gttgggtaag 120
gtcaagaagg tccaattggg taagaagggt gttccatacg ttgtcactga cgatggtaga 180
actatcagat acccaga 197

<210> SEQ ID NO 53
<211> LENGTH: 197
<212> TYPE: RNA
<213> ORGANISM: Candida glabrata

<400> SEQUENCE: 53
agcugguuuc auggauguuu ggaagcuacc aacgaaaacu ucagauuggu cuacgacguc 60
aaggguagau ucgcugucca ccguaucacu gacgaagaag cuuccuacaa guuggguaag 120
gucaagaagg uccaauuggg uaagaagggu guuccauacg uugucacuga cgaugguaga 180
acuaucagau acccaga 197

<210> SEQ ID NO 54
<211> LENGTH: 197
<212> TYPE: DNA
<213> ORGANISM: Eremothecium gossypii

<400> SEQUENCE: 54
agctggtttc atggatgtct agaggctacc aacgagaact tcagattggt atacgatgtc 60
aagggcagat ttgctgtcca ccgtatcacc gatgaggagg ctacttacaa gttgggtaag 120
gttaagcgcg ttcagctagg taagaagggt gtcccatacg tggtcactca cgacggcaga 180
accatcagat acccaga 197

<210> SEQ ID NO 55
<211> LENGTH: 197
<212> TYPE: RNA
<213> ORGANISM: Eremothecium gossypii

<400> SEQUENCE: 55
agcugguuuc auggaugucu agaggcuacc aacgagaacu ucagauuggu auacgauguc 60
aagggcagau uugcugucca ccguaucacc gaugaggagg cuacuuacaa guuggguaag 120
guuaagcgcg uucagcuagg uaagaagggu gucccauacg uggucacuca cgacggcaga 180
accaucagau acccaga 197

<210> SEQ ID NO 56
<211> LENGTH: 197
<212> TYPE: DNA
<213> ORGANISM: Kluyveromyces lactis

<400> SEQUENCE: 56
agctggtttc atggatgttt ggaagctacc aacgaaaact tcagattggt ctacgatgtt 60
aagggtagat tcgctgtcca ccgtatcact gatgaagaag cttcctacaa gttggctaag 120

-continued gtcaagaagg ttcaactagg taagaagggt attccatacg tcgttaccca cgacggtaga 180
accatcagat acccaga 197

<210> SEQ ID NO 57
<211> LENGTH: 197
<212> TYPE: RNA
<213> ORGANISM: Kluyveromyces lactis

<400> SEQUENCE: 57
agcugguuuc auggauguuu ggaagcuacc aacgaaaacu ucagauuggu cuacgauguu 60
aaggguagau ucgcugucca ccguaucacu gaugaagaag cuuccuacaa guuggcuaag 120
gucaagaagg uucaacuagg uaagaagggu auuccauacg ucguuaccca cgacgguaga 180
accaucagau acccaga 197

<210> SEQ ID NO 58
<211> LENGTH: 197
<212> TYPE: DNA
<213> ORGANISM: Candida albicans

<400> SEQUENCE: 58
agctggtttc atggatgtct ggaagctacc aacgaacatt tcagattagc ctacgatgtt 60
aaaggtaaat tcgccgttca cagaatttct gctgaagaag ctgtctacaa attgggtaaa 120
gtcaagaaag tccaattagg taagaaaggt gttccatacg ttgttaccca cgacggtaga 180
actatcagat acccaga 197

<210> SEQ ID NO 59
<211> LENGTH: 197
<212> TYPE: RNA
<213> ORGANISM: Candida albicans

<400> SEQUENCE: 59
agcugguuuc auggaugucu ggaagcuacc aacgaacauu ucagauuagc cuacgauguu 60
aaagguaaau ucgccguuca cagaauuucu gcugaagaag cugucuacaa auuggguaaa 120
gucaagaaag uccaauuagg uaagaaaggu guuccauacg uuguuaccca cgacgguaga 180
acuaucagau acccaga 197

<210> SEQ ID NO 60
<211> LENGTH: 197
<212> TYPE: DNA
<213> ORGANISM: Debaryomyces hansenii

<400> SEQUENCE: 60
agctggtttc atggatgtct agaagctacc aacgaacact tcagattaat ctatgatgtc 60
aagggtagat tcactgtcca cagaatcact gctgaagaag cttcttacaa gttagctaag 120
gtcaagaagg tccaattagg taagagaggt attccatacg ttgtcaccca cgacggtaga 180
actatcagat acccaga 197

<210> SEQ ID NO 61
<211> LENGTH: 197
<212> TYPE: RNA
<213> ORGANISM: Debaryomyces hansenii

<400> SEQUENCE: 61
agcugguuuc auggaugucu agaagcuacc aacgaacacu ucagauuaau cuaugauguc 60
aaggguagau ucacugucca cagaaucacu gcugaagaag cuucuuacaa guuagcuaag 120
gucaagaagg uccaauuagg uaagagaggu auuccauacg uugucaccca cgacgguaga 180
acuaucagau acccaga 197

<210> SEQ ID NO 62
<211> LENGTH: 240
<212> TYPE: DNA
<213> ORGANISM: Candida albicans

<400> SEQUENCE: 62
acctacccag ctggtttcat ggatgtcatc accttggaag ctaccaacga acatttcaga 60
ttagcctacg atgttaaagg taaattcgcc gttcacagaa tttctgctga agaagctgtc 120
tacaaattgg gtaaagtcaa gaaagtccaa ttaggtaaga aaggtgttcc atacgttgtt 180
acccacgacg gtagaactat cagataccca gatccattga tcagagctaa cgataccgtt 240

<210> SEQ ID NO 63
<211> LENGTH: 240
<212> TYPE: RNA
<213> ORGANISM: Candida albicans

<400> SEQUENCE: 63
accuacccag cugguuucau ggaugucauc accuuggaag cuaccaacga acauuucaga 60
uuagccuacg auguuaaagg uaaauucgcc guucacagaa uuucugcuga agaagcuguc 120
uacaaauugg guaaagucaa gaaaguccaa uuagguaaga aagguguucc auacguuguu 180
acccacgacg guagaacuau cagauaccca gauccauuga ucagagcuaa cgauaccguu 240

<210> SEQ ID NO 64
<211> LENGTH: 240
<212> TYPE: DNA
<213> ORGANISM: Candida glabrata

<400> SEQUENCE: 64
acctacccag ctggtttcat ggatgttatc accttggaag ctaccaacga aaacttcaga 60
ttggtctacg acgtcaaggg tagattcgct gtccaccgta tcactgacga agaagcttcc 120
tacaagttgg gtaaggtcaa gaaggtccaa ttgggtaaga agggtgttcc atacgttgtc 180
actgacgatg gtagaactat cagataccca gacccaaaca tcaaggtcaa tgacaccgtc 240

<210> SEQ ID NO 65
<211> LENGTH: 240
<212> TYPE: RNA
<213> ORGANISM: Candida glabrata

<400> SEQUENCE: 65
accuacccag cugguuucau ggauguuauc accuuggaag cuaccaacga aaacuucaga 60
uuggucuacg acgucaaggg uagauucgcu guccaccgua ucacugacga agaagcuucc 120
uacaaguugg guaaggucaa gaagguccaa uuggguaaga aggguguucc auacguuguc 180
acugacgaug guagaacuau cagauaccca gacccaaaca ucaaggucaa ugacaccguc 240

<210> SEQ ID NO 66
<211> LENGTH: 177
<212> TYPE: DNA
<213> ORGANISM: Candida tropicalis

<400> SEQUENCE: 66
ggaagctacc aacgaacact tcagattgat ttacgatgtt aaaggtaaat tcgctgttca 60
cagaatttct gctgaagaag cttcttacaa attaggtaaa gtcaagaagg ttcaattagg 120
taaaaaaggt gttccatacg ttgtcaccca cgatggtaga accatcagat acccaga 177

<210> SEQ ID NO 67
<211> LENGTH: 177
<212> TYPE: RNA
<213> ORGANISM: Candida tropicalis

<400> SEQUENCE: 67
ggaagcuacc aacgaacacu ucagauugau uuacgauguu aaagguaaau ucgcuguuca 60
cagaauuucu gcugaagaag cuucuuacaa auuagguaaa gucaagaagg uucaauuagg 120
uaaaaaaggu guuccauacg uugucaccca cgaugguaga accaucagau acccaga 177

<210> SEQ ID NO 68
<211> LENGTH: 177
<212> TYPE: DNA
<213> ORGANISM: Candida parapsilosis

<400> SEQUENCE: 68
ggaagccacc aatgaaaact ttagattgat ttacgatgtc aaaggtagat ttgctgtcca 60
cagaatctca gctgaagaag ccacttacaa attgggtaaa gtcaagagag tccaattggg 120
taagaaggga atcccatacg ttgtcaccca cgatggtaga accatcagat acccaga 177

<210> SEQ ID NO 69
<211> LENGTH: 177
<212> TYPE: RNA
<213> ORGANISM: Candida parapsilosis

<400> SEQUENCE: 69
ggaagccacc aaugaaaacu uuagauugau uuacgauguc aaagguagau uugcugucca 60
cagaaucuca gcugaagaag ccacuuacaa auuggguaaa gucaagagag uccaauuggg 120
uaagaaggga aucccauacg uugucaccca cgaugguaga accaucagau acccaga 177

<210> SEQ ID NO 70
<211> LENGTH: 177
<212> TYPE: DNA
<213> ORGANISM: Candida dubliniensis

<400> SEQUENCE: 70
ggaagctacc aacgaaaact tcagattggt ctacgacgtc aagggtagat tcgctgtcca 60
ccgtatcact gacgaagaag cttcctacaa gttgggtaag gtcaagaagg tccaattggg 120
taagaagggt gttccatacg ttgtcactga cgatggtaga acyatcagat acccaga 177

<210> SEQ ID NO 71
<211> LENGTH: 177
<212> TYPE: RNA
<213> ORGANISM: Candida dubliniensis

<400> SEQUENCE: 71
ggaagcuacc aacgaaaacu ucagauuggu cuacgacguc aaggguagau ucgcugucca 60
ccguaucacu gacgaagaag cuuccuacaa guuggguaag gucaagaagg uccaauuggg 120
uaagaagggu guuccauacg uugucacuga cgaugguaga acyaucagau acccaga 177

<210> SEQ ID NO 72
<211> LENGTH: 185
<212> TYPE: DNA
<213> ORGANISM: Candida albicans

<400> SEQUENCE: 72
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 73
<211> LENGTH: 185
<212> TYPE: RNA
<213> ORGANISM: Candida albicans

<400> SEQUENCE: 73
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 74
<211> LENGTH: 185
<212> TYPE: DNA
<213> ORGANISM: Candida albicans

<400> SEQUENCE: 74
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 75
<211> LENGTH: 185
<212> TYPE: RNA
<213> ORGANISM: Candida albicans

<400> SEQUENCE: 75
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 76
<211> LENGTH: 185
<212> TYPE: DNA
<213> ORGANISM: Candida albicans

<400> SEQUENCE: 76
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 77
<211> LENGTH: 185
<212> TYPE: RNA

-continued

<213> ORGANISM: Candida albicans

<400> SEQUENCE: 77
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 78
<211> LENGTH: 185
<212> TYPE: DNA
<213> ORGANISM: Candida albicans

<400> SEQUENCE: 78
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 79
<211> LENGTH: 185
<212> TYPE: RNA
<213> ORGANISM: Candida albicans

<400> SEQUENCE: 79
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 80
<211> LENGTH: 185
<212> TYPE: DNA
<213> ORGANISM: Candida albicans

<400> SEQUENCE: 80
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 81
<211> LENGTH: 185
<212> TYPE: RNA
<213> ORGANISM: Candida albicans

<400> SEQUENCE: 81
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 82
<211> LENGTH: 185

<212> TYPE: DNA
<213> ORGANISM: Candida albicans

<400> SEQUENCE: 82
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 83
<211> LENGTH: 185
<212> TYPE: RNA
<213> ORGANISM: Candida albicans

<400> SEQUENCE: 83
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 84
<211> LENGTH: 185
<212> TYPE: DNA
<213> ORGANISM: Candida albicans

<400> SEQUENCE: 84
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 85
<211> LENGTH: 185
<212> TYPE: RNA
<213> ORGANISM: Candida albicans

<400> SEQUENCE: 85
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 86
<211> LENGTH: 185
<212> TYPE: DNA
<213> ORGANISM: Candida albicans

<400> SEQUENCE: 86
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 87

<211> LENGTH: 185
<212> TYPE: RNA
<213> ORGANISM: Candida albicans

<400> SEQUENCE: 87
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 88
<211> LENGTH: 185
<212> TYPE: DNA
<213> ORGANISM: Candida albicans

<400> SEQUENCE: 88
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 89
<211> LENGTH: 185
<212> TYPE: RNA
<213> ORGANISM: Candida albicans

<400> SEQUENCE: 89
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 90
<211> LENGTH: 185
<212> TYPE: DNA
<213> ORGANISM: Candida albicans

<400> SEQUENCE: 90
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 91
<211> LENGTH: 185
<212> TYPE: RNA
<213> ORGANISM: Candida albicans

<400> SEQUENCE: 91
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 92
<211> LENGTH: 185
<212> TYPE: DNA
<213> ORGANISM: Candida albicans

<400> SEQUENCE: 92
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 93
<211> LENGTH: 185
<212> TYPE: RNA
<213> ORGANISM: Candida albicans

<400> SEQUENCE: 93
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 94
<211> LENGTH: 185
<212> TYPE: DNA
<213> ORGANISM: Candida albicans

<400> SEQUENCE: 94
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 95
<211> LENGTH: 185
<212> TYPE: RNA
<213> ORGANISM: Candida albicans

<400> SEQUENCE: 95
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 96
<211> LENGTH: 185
<212> TYPE: DNA
<213> ORGANISM: Candida albicans

<400> SEQUENCE: 96
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

-continued

<210> SEQ ID NO 97
<211> LENGTH: 185
<212> TYPE: RNA
<213> ORGANISM: Candida albicans

<400> SEQUENCE: 97
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 98
<211> LENGTH: 185
<212> TYPE: DNA
<213> ORGANISM: Candida albicans

<400> SEQUENCE: 98
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 99
<211> LENGTH: 185
<212> TYPE: RNA
<213> ORGANISM: Candida albicans

<400> SEQUENCE: 99
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 100
<211> LENGTH: 185
<212> TYPE: DNA
<213> ORGANISM: Candida albicans

<400> SEQUENCE: 100
catcaccttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccag 185

<210> SEQ ID NO 101
<211> LENGTH: 185
<212> TYPE: RNA
<213> ORGANISM: Candida albicans

<400> SEQUENCE: 101
caucaccuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccag 185

<210> SEQ ID NO 102
<211> LENGTH: 185
<212> TYPE: DNA
<213> ORGANISM: Candida glabrata

<400> SEQUENCE: 102
catcaccttg gaagctacca acgaaaactt cagattggtc tacgacgtca agggtagatt 60
cgctgtccac cgtatcactg acgaagaagc ttcctacaag ttgggtaagg tcaagaaggt 120
ccaattgggt aagaagggtg ttccatacgt tgtcactgac gatggtagaa cyatcagata 180
cccag 185

<210> SEQ ID NO 103
<211> LENGTH: 185
<212> TYPE: RNA
<213> ORGANISM: Candida glabrata

<400> SEQUENCE: 103
caucaccuug gaagcuacca acgaaaacuu cagauugguc uacgacguca aggguagauu 60
cgcuguccac cguaucacug acgaagaagc uuccuacaag uuggguaagg ucaagaaggu 120
ccaauugggu aagaagggug uuccauacgu ugucacugac gaugguagaa cyaucagaua 180
cccag 185

<210> SEQ ID NO 104
<211> LENGTH: 185
<212> TYPE: DNA
<213> ORGANISM: Candida glabrata

<400> SEQUENCE: 104
catcaccttg gaagctacca acgaaaactt cagattggtc tacgacgtca agggtagatt 60
cgctgtccac cgtatcactg acgaagaagc ttcctacaag ttgggtaagg tcaagaaggt 120
ccaattgggt aagaagggtg ttccatacgt tgtcactgac gatggtagaa cyatcagata 180
cccag 185

<210> SEQ ID NO 105
<211> LENGTH: 185
<212> TYPE: RNA
<213> ORGANISM: Candida glabrata

<400> SEQUENCE: 105
caucaccuug gaagcuacca acgaaaacuu cagauugguc uacgacguca aggguagauu 60
cgcuguccac cguaucacug acgaagaagc uuccuacaag uuggguaagg ucaagaaggu 120
ccaauugggu aagaagggug uuccauacgu ugucacugac gaugguagaa cyaucagaua 180
cccag 185

<210> SEQ ID NO 106
<211> LENGTH: 185
<212> TYPE: DNA
<213> ORGANISM: Candida glabrata

<400> SEQUENCE: 106
catcaccttg gaagctacca acgaaaactt cagattggtc tacgacgtca agggtagatt 60
cgctgtccac cgtatcactg acgaagaagc ttcctacaag ttgggtaagg tcaagaaggt 120
ccaattgggt aagaagggtg ttccatacgt tgtcactgac gatggtagaa cyatcagata 180

-continued cccag 185

<210> SEQ ID NO 107
<211> LENGTH: 185
<212> TYPE: RNA
<213> ORGANISM: Candida glabrata

<400> SEQUENCE: 107
caucaccuug gaagcuacca acgaaaacuu cagauugguc uacgacguca aggguagauu 60
cgcuguccac cguaucacug acgaagaagc uuccuacaag uuggguaagg ucaagaaggu 120
ccaauugggu aagaagggug uuccauacgu ugucacugac gaugguagaa cyaucagaua 180
cccag 185

<210> SEQ ID NO 108
<211> LENGTH: 185
<212> TYPE: DNA
<213> ORGANISM: Candida glabrata

<400> SEQUENCE: 108
catcaccttg gaagctacca acgaaaactt cagattggtc tacgacgtca agggtagatt 60
cgctgtccac cgtatcactg acgaagaagc ttcctacaag ttgggtaagg tcaagaaggt 120
ccaattgggt aagaagggtg ttccatacgt tgtcactgac gatggtagaa cyatcagata 180
cccag 185

<210> SEQ ID NO 109
<211> LENGTH: 185
<212> TYPE: RNA
<213> ORGANISM: Candida glabrata

<400> SEQUENCE: 109
caucaccuug gaagcuacca acgaaaacuu cagauugguc uacgacguca aggguagauu 60
cgcuguccac cguaucacug acgaagaagc uuccuacaag uuggguaagg ucaagaaggu 120
ccaauugggu aagaagggug uuccauacgu ugucacugac gaugguagaa cyaucagaua 180
cccag 185

<210> SEQ ID NO 110
<211> LENGTH: 185
<212> TYPE: DNA
<213> ORGANISM: Candida glabrata

<400> SEQUENCE: 110
catcaccttg gaagctacca acgaaaactt cagattggtc tacgacgtca agggtagatt 60
cgctgtccac cgtatcactg acgaagaagc ttcctacaag ttgggtaagg tcaagaaggt 120
ccaattgggt aagaagggtg ttccatacgt tgtcactgac gatggtagaa cyatcagata 180
cccag 185

<210> SEQ ID NO 111
<211> LENGTH: 185
<212> TYPE: RNA
<213> ORGANISM: Candida glabrata

<400> SEQUENCE: 111
caucaccuug gaagcuacca acgaaaacuu cagauugguc uacgacguca aggguagauu 60
cgcuguccac cguaucacug acgaagaagc uuccuacaag uuggguaagg ucaagaaggu 120
ccaauugggu aagaagggug uuccauacgu ugucacugac gaugguagaa cyaucagaua 180

-continued cccag 185

<210> SEQ ID NO 112
<211> LENGTH: 185
<212> TYPE: DNA
<213> ORGANISM: Candida glabrata

<400> SEQUENCE: 112
catcaccttg gaagctacca acgaaaactt cagattggtc tacgacgtca agggtagatt 60
cgctgtccac cgtatcactg acgaagaagc ttcctacaag ttgggtaagg tcaagaaggt 120
ccaattgggt aagaagggtg ttccatacgt tgtcactgac gatggtagaa cyatcagata 180
cccag 185

<210> SEQ ID NO 113
<211> LENGTH: 185
<212> TYPE: RNA
<213> ORGANISM: Candida glabrata

<400> SEQUENCE: 113
caucaccuug gaagcuacca acgaaaacuu cagauugguc uacgacguca aggguagauu 60
cgcuguccac cguaucacug acgaagaagc uuccuacaag uuggguaagg ucaagaaggu 120
ccaauugggu aagaagggug uuccauacgu ugucacugac gaugguagaa cyaucagaua 180
cccag 185

<210> SEQ ID NO 114
<211> LENGTH: 185
<212> TYPE: DNA
<213> ORGANISM: Candida glabrata

<400> SEQUENCE: 114
catcaccttg gaagctacca acgaaaactt cagattggtc tacgacgtca agggtagatt 60
cgctgtccac cgtatcactg acgaagaagc ttcctacaag ttgggtaagg tcaagaaggt 120
ccaattgggt aagaagggtg ttccatacgt tgtcactgac gatggtagaa cyatcagata 180
cccag 185

<210> SEQ ID NO 115
<211> LENGTH: 185
<212> TYPE: RNA
<213> ORGANISM: Candida glabrata

<400> SEQUENCE: 115
caucaccuug gaagcuacca acgaaaacuu cagauugguc uacgacguca aggguagauu 60
cgcuguccac cguaucacug acgaagaagc uuccuacaag uuggguaagg ucaagaaggu 120
ccaauugggu aagaagggug uuccauacgu ugucacugac gaugguagaa cyaucagaua 180
cccag 185

<210> SEQ ID NO 116
<211> LENGTH: 185
<212> TYPE: DNA
<213> ORGANISM: Candida glabrata

<400> SEQUENCE: 116
catcaccttg gaagctacca acgaaaactt cagattggtc tacgacgtca agggtagatt 60
cgctgtccac cgtatcactg acgaagaagc ttcctacaag ttgggtaagg tcaagaaggt 120

-continued ccaattgggt aagaagggtg ttccatacgt tgtcactgac gatggtagaa cyatcagata 180
cccag 185

<210> SEQ ID NO 117
<211> LENGTH: 185
<212> TYPE: RNA
<213> ORGANISM: Candida glabrata

<400> SEQUENCE: 117
caucaccuug gaagcuacca acgaaaacuu cagauugguc uacgacguca aggguagauu 60
cgcuguccac cguaucacug acgaagaagc uuccuacaag uuggguaagg ucaagaaggu 120
ccaauugggu aagaagggug uuccauacgu ugucacugac gaugguagaa cyaucagaua 180
cccag 185

<210> SEQ ID NO 118
<211> LENGTH: 185
<212> TYPE: DNA
<213> ORGANISM: Candida glabrata

<400> SEQUENCE: 118
tatcaccttg gaagctacca acgaaaactt cagattggtc tacgacgtca agggtagatt 60
cgctgtccac cgtatcactg acgaagaagc ttcctacaag ttgggtaagg tcaagaaggt 120
ccaattgggt aagaagggtg ttccatacgt tgtcactgac gatggtagaa cyatcagata 180
cccag 185

<210> SEQ ID NO 119
<211> LENGTH: 185
<212> TYPE: RNA
<213> ORGANISM: Candida glabrata

<400> SEQUENCE: 119
uaucaccuug gaagcuacca acgaaaacuu cagauugguc uacgacguca aggguagauu 60
cgcuguccac cguaucacug acgaagaagc uuccuacaag uuggguaagg ucaagaaggu 120
ccaauugggu aagaagggug uuccauacgu ugucacugac gaugguagaa cyaucagaua 180
cccag 185

<210> SEQ ID NO 120
<211> LENGTH: 185
<212> TYPE: DNA
<213> ORGANISM: Candida glabrata

<400> SEQUENCE: 120
tatcaccttg gaagctacca acgaaaactt cagattggtc tacgacgtca agggtagatt 60
cgctgtccac cgtatcactg acgaagaagc ttcctacaag ttgggtaagg tcaagaaggt 120
ccaattgggt aagaagggtg ttccatacgt tgtcactgac gatggtagaa cyatcagata 180
cccag 185

<210> SEQ ID NO 121
<211> LENGTH: 185
<212> TYPE: RNA
<213> ORGANISM: Candida glabrata

<400> SEQUENCE: 121
uaucaccuug gaagcuacca acgaaaacuu cagauugguc uacgacguca aggguagauu 60
cgcuguccac cguaucacug acgaagaagc uuccuacaag uuggguaagg ucaagaaggu 120
ccaauugggu aagaagggug uuccauacgu ugucacugac gaugguagaa cyaucagaua 180
cccag 185

<210> SEQ ID NO 122
<211> LENGTH: 185
<212> TYPE: DNA
<213> ORGANISM: Candida glabrata

<400> SEQUENCE: 122
tatcaccttg gaagctacca acgaaaactt cagattggtc tacgacgtca agggtagatt 60
cgctgtccac cgtatcactg acgaagaagc ttcctacaag ttgggtaagg tcaagaaggt 120
ccaattgggt aagaagggtg ttccatacgt tgtcactgac gatggtagaa cyatcagata 180
cccag 185

<210> SEQ ID NO 123
<211> LENGTH: 185
<212> TYPE: RNA
<213> ORGANISM: Candida glabrata

<400> SEQUENCE: 123
uaucaccuug gaagcuacca acgaaaacuu cagauugguc uacgacguca aggguagauu 60
cgcuguccac cguaucacug acgaagaagc uuccuacaag uuggguaagg ucaagaaggu 120
ccaauugggu aagaagggug uuccauacgu ugucacugac gaugguagaa cyaucagaua 180
cccag 185

<210> SEQ ID NO 124
<211> LENGTH: 185
<212> TYPE: DNA
<213> ORGANISM: Candida glabrata

<400> SEQUENCE: 124
tatcaccttg gaagctacca acgaaaactt cagattggtc tacgacgtca agggtagatt 60
cgctgtccac cgtatcactg acgaagaagc ttcctacaag ttgggtaagg tcaagaaggt 120
ccaattgggt aagaagggtg ttccatacgt tgtcactgac gatggtagaa cyatcagata 180
cccag 185

<210> SEQ ID NO 125
<211> LENGTH: 185
<212> TYPE: RNA
<213> ORGANISM: Candida glabrata

<400> SEQUENCE: 125
uaucaccuug gaagcuacca acgaaaacuu cagauugguc uacgacguca aggguagauu 60
cgcuguccac cguaucacug acgaagaagc uuccuacaag uuggguaagg ucaagaaggu 120
ccaauugggu aagaagggug uuccauacgu ugucacugac gaugguagaa cyaucagaua 180
cccag 185

<210> SEQ ID NO 126
<211> LENGTH: 185
<212> TYPE: DNA
<213> ORGANISM: Candida parapsilosis

<400> SEQUENCE: 126
cattactttg gaagccacya atgaaaactt tagattgatt tacgatgtca aaggtagatt 60

-continued

```
tgctgtccac agaatctcag ctgaagaagc cacttacaaa ttgggtaaag tcaagagagt    120

ccaattgggt aagaagggaa tcccatacgt tgtcacccac gatggtagaa cyatcagata    180

cccag                                                                185


<210> SEQ ID NO 127
<211> LENGTH: 185
<212> TYPE: RNA
<213> ORGANISM: Candida parapsilosis

<400> SEQUENCE: 127

cauuacuuug gaagccacya augaaaacuu uagauugauu uacgauguca aagguagauu     60

ugcuguccac agaaucucag cugaagaagc cacuuacaaa uuggguaaag ucaagagagu    120

ccaauugggu aagaagggaa ucccauacgu ugucacccac gaugguagaa cyaucagaua    180

cccag                                                                185


<210> SEQ ID NO 128
<211> LENGTH: 185
<212> TYPE: DNA
<213> ORGANISM: Candida parapsilosis

<400> SEQUENCE: 128

cattactttg gaagccacya atgaaaactt tagattgatt tacgatgtca aaggtagatt     60

tgctgtccac agaatctcag ctgaagaagc cacttacaaa ttgggtaaag tcaagagagt    120

ccaattgggt aagaagggaa tcccatacgt tgtcacccac gatggtagaa cyatcagata    180

cccag                                                                185


<210> SEQ ID NO 129
<211> LENGTH: 185
<212> TYPE: RNA
<213> ORGANISM: Candida parapsilosis

<400> SEQUENCE: 129

cauuacuuug gaagccacya augaaaacuu uagauugauu uacgauguca aagguagauu     60

ugcuguccac agaaucucag cugaagaagc cacuuacaaa uuggguaaag ucaagagagu    120

ccaauugggu aagaagggaa ucccauacgu ugucacccac gaugguagaa cyaucagaua    180

cccag                                                                185


<210> SEQ ID NO 130
<211> LENGTH: 185
<212> TYPE: DNA
<213> ORGANISM: Candida parapsilosis

<400> SEQUENCE: 130

cattactttg gaagccacya atgaaaactt tagattgatt tacgatgtca aaggtagatt     60

tgctgtccac agaatctcag ctgaagaagc cacttacaaa ttgggtaaag tcaagagagt    120

ccaattgggt aagaagggaa tcccatacgt tgtcacccac gatggtagaa cyatcagata    180

cccag                                                                185


<210> SEQ ID NO 131
<211> LENGTH: 185
<212> TYPE: RNA
<213> ORGANISM: Candida parapsilosis

<400> SEQUENCE: 131

cauuacuuug gaagccacya augaaaacuu uagauugauu uacgauguca aagguagauu     60
```

ugcuguccac agaaucucag cugaagaagc cacuuacaaa uuggguaaag ucaagagagu 120
ccaauugggu aagaagggaa ucccauacgu ugucacccac gaugguagaa cyaucagaua 180
cccag 185

<210> SEQ ID NO 132
<211> LENGTH: 185
<212> TYPE: DNA
<213> ORGANISM: Candida parapsilosis

<400> SEQUENCE: 132
cattactttg gaagccacya atgaaaactt tagattgatt tacgatgtca aaggtagatt 60
tgctgtccac agaatctcag ctgaagaagc cacttacaaa ttgggtaaag tcaagagagt 120
ccaattgggt aagaagggaa tcccatacgt tgtcacccac gatggtagaa cyatcagata 180
cccag 185

<210> SEQ ID NO 133
<211> LENGTH: 185
<212> TYPE: RNA
<213> ORGANISM: Candida parapsilosis

<400> SEQUENCE: 133
cauuacuuug gaagccacya augaaaacuu uagauugauu uacgauguca aagguagauu 60
ugcuguccac agaaucucag cugaagaagc cacuuacaaa uuggguaaag ucaagagagu 120
ccaauugggu aagaagggaa ucccauacgu ugucacccac gaugguagaa cyaucagaua 180
cccag 185

<210> SEQ ID NO 134
<211> LENGTH: 185
<212> TYPE: DNA
<213> ORGANISM: Candida parapsilosis

<400> SEQUENCE: 134
cattactttg gaagccacya atgaaaactt tagattgatt tacgatgtca aaggtagatt 60
tgctgtccac agaatctcag ctgaagaagc cacttacaaa ttgggtaaag tcaagagagt 120
ccaattgggt aagaagggaa tcccatacgt tgtcacccac gatggtagaa cyatcagata 180
cccag 185

<210> SEQ ID NO 135
<211> LENGTH: 185
<212> TYPE: RNA
<213> ORGANISM: Candida parapsilosis

<400> SEQUENCE: 135
cauuacuuug gaagccacya augaaaacuu uagauugauu uacgauguca aagguagauu 60
ugcuguccac agaaucucag cugaagaagc cacuuacaaa uuggguaaag ucaagagagu 120
ccaauugggu aagaagggaa ucccauacgu ugucacccac gaugguagaa cyaucagaua 180
cccag 185

<210> SEQ ID NO 136
<211> LENGTH: 185
<212> TYPE: DNA
<213> ORGANISM: Candida parapsilosis

<400> SEQUENCE: 136
cattactttg gaagccacya atgaaaactt tagattgatt tacgatgtca aaggtagatt 60
tgctgtccac agaatctcag ctgaagaagc cacttacaaa ttgggtaaag tcaagagagt 120
ccaattgggt aagaagggaa tcccatacgt tgtcacccac gatggtagaa cyatcagata 180
cccag 185

<210> SEQ ID NO 137
<211> LENGTH: 185
<212> TYPE: RNA
<213> ORGANISM: Candida parapsilosis

<400> SEQUENCE: 137
cauuacuuug gaagccacya augaaaacuu uagauugauu uacgauguca aagguagauu 60
ugcuguccac agaaucucag cugaagaagc cacuuacaaa uuggguaaag ucaagagagu 120
ccaauugggu aagaagggaa ucccauacgu ugucacccac gaugguagaa cyaucagaua 180
cccag 185

<210> SEQ ID NO 138
<211> LENGTH: 185
<212> TYPE: DNA
<213> ORGANISM: Candida parapsilosis

<400> SEQUENCE: 138
cattactttg gaagccacya atgaaaactt tagattgatt tacgatgtca aaggtagatt 60
tgctgtccac agaatctcag ctgaagaagc cacttacaaa ttgggtaaag tcaagagagt 120
ccaattgggt aagaagggaa tcccatacgt tgtcacccac gatggtagaa cyatcagata 180
cccag 185

<210> SEQ ID NO 139
<211> LENGTH: 185
<212> TYPE: RNA
<213> ORGANISM: Candida parapsilosis

<400> SEQUENCE: 139
cauuacuuug gaagccacya augaaaacuu uagauugauu uacgauguca aagguagauu 60
ugcuguccac agaaucucag cugaagaagc cacuuacaaa uuggguaaag ucaagagagu 120
ccaauugggu aagaagggaa ucccauacgu ugucacccac gaugguagaa cyaucagaua 180
cccag 185

<210> SEQ ID NO 140
<211> LENGTH: 185
<212> TYPE: DNA
<213> ORGANISM: Candida Krusei

<400> SEQUENCE: 140
catcacttta gatgcaacca acgaacactt cagattaatc tatgacatca agggtagatt 60
cgcaatccac agaatcaccc cagaagaagc tgcatacaag ttatgtaagg tcaagaaggt 120
ccaattaggt aagaagggta ttccttatgt tgttacccac gatggtagaa cyatcagata 180
cccag 185

<210> SEQ ID NO 141
<211> LENGTH: 185
<212> TYPE: RNA
<213> ORGANISM: Candida Krusei

<400> SEQUENCE: 141
caucacuuua gaugcaacca acgaacacuu cagauuaauc uaugacauca aggguagauu 60
cgcaauccac agaaucaccc cagaagaagc ugcauacaag uuauguaagg ucaagaaggu 120
ccaauuaggu aagaagggua uuccuuaugu uguuacccac gaugguagaa cyaucagaua 180
cccag 185

<210> SEQ ID NO 142
<211> LENGTH: 185
<212> TYPE: DNA
<213> ORGANISM: Candida Krusei

<400> SEQUENCE: 142
catcacttta gatgcaacca acgaacactt cagattaatc tatgacatca agggtagatt 60
cgcaatccac agaatcaccc cagaagaagc tgcatacaag ttatgtaagg tcaagaaggt 120
ccaattaggt aagaagggta ttccttatgt tgttacccac gatggtagaa cyatcagata 180
cccag 185

<210> SEQ ID NO 143
<211> LENGTH: 185
<212> TYPE: RNA
<213> ORGANISM: Candida krusei

<400> SEQUENCE: 143
caucacuuua gaugcaacca acgaacacuu cagauuaauc uaugacauca aggguagauu 60
cgcaauccac agaaucaccc cagaagaagc ugcauacaag uuauguaagg ucaagaaggu 120
ccaauuaggu aagaagggua uuccuuaugu uguuacccac gaugguagaa cyaucagaua 180
cccag 185

<210> SEQ ID NO 144
<211> LENGTH: 185
<212> TYPE: DNA
<213> ORGANISM: Candida krusei

<400> SEQUENCE: 144
catcacttta gatgcaacca acgaacactt cagattaatc tatgacatca agggtagatt 60
cgcaatccac agaatcaccc cagaagaagc tgcatacaag ttatgtaagg tcaagaaggt 120
ccaattaggt aagaagggta ttccttatgt tgttacccac gatggtagaa cyatcagata 180
cccag 185

<210> SEQ ID NO 145
<211> LENGTH: 185
<212> TYPE: RNA
<213> ORGANISM: Candida krusei

<400> SEQUENCE: 145
caucacuuua gaugcaacca acgaacacuu cagauuaauc uaugacauca aggguagauu 60
cgcaauccac agaaucaccc cagaagaagc ugcauacaag uuauguaagg ucaagaaggu 120
ccaauuaggu aagaagggua uuccuuaugu uguuacccac gaugguagaa cyaucagaua 180
cccag 185

<210> SEQ ID NO 146
<211> LENGTH: 185
<212> TYPE: DNA
<213> ORGANISM: Candida krusei

<400> SEQUENCE: 146
catcacttta gatgcaacca acgaacactt cagattaatc tatgacatca agggtagatt 60
cgcaatccac agaatcaccc cagaagaagc tgcatacaag ttatgtaagg tcaagaaggt 120
ccaattaggt aagaagggta ttccttatgt tgttacccac gatggtagaa cyatcagata 180
cccag 185

<210> SEQ ID NO 147
<211> LENGTH: 185
<212> TYPE: RNA
<213> ORGANISM: Candida krusei

<400> SEQUENCE: 147
caucacuuua gaugcaacca acgaacacuu cagauuaauc uaugacauca aggguagauu 60
cgcaauccac agaaucaccc cagaagaagc ugcauacaag uuauguaagg ucaagaaggu 120
ccaauuaggu aagaagggua uuccuuaugu uguuacccac gaugguagaa cyaucagaua 180
cccag 185

<210> SEQ ID NO 148
<211> LENGTH: 185
<212> TYPE: DNA
<213> ORGANISM: Candida krusei

<400> SEQUENCE: 148
catcacttta gatgcaacca acgaacactt cagattaatc tatgacatca agggtagatt 60
cgcaatccac agaatcaccc cagaagaagc tgcatacaag ttatgtaagg tcaagaaggt 120
ccaattaggt aagaagggta ttccttatgt tgttacccac gatggtagaa cyatcagata 180
cccag 185

<210> SEQ ID NO 149
<211> LENGTH: 185
<212> TYPE: RNA
<213> ORGANISM: Candida krusei

<400> SEQUENCE: 149
caucacuuua gaugcaacca acgaacacuu cagauuaauc uaugacauca aggguagauu 60
cgcaauccac agaaucaccc cagaagaagc ugcauacaag uuauguaagg ucaagaaggu 120
ccaauuaggu aagaagggua uuccuuaugu uguuacccac gaugguagaa cyaucagaua 180
cccag 185

<210> SEQ ID NO 150
<211> LENGTH: 185
<212> TYPE: DNA
<213> ORGANISM: Candida krusei

<400> SEQUENCE: 150
catcacttta gatgcaacca acgaacactt cagattaatc tatgacatca agggtagatt 60
cgcaatccac agaatcaccc cagaagaagc tgcatacaag ttatgtaagg tcaagaaggt 120
ccaattaggt aagaagggta ttccttatgt tgttacccac gatggtagaa cyatcagata 180
cccag 185

<210> SEQ ID NO 151
<211> LENGTH: 185
<212> TYPE: RNA
<213> ORGANISM: Candida krusei

<400> SEQUENCE: 151
caucacuuua gaugcaacca acgaacacuu cagauuaauc uaugacauca aggguagauu 60
cgcaauccac agaaucaccc cagaagaagc ugcauacaag uuauguaagg ucaagaaggu 120
ccaauuaggu aagaagggua uuccuuaugu uguuacccac gaugguagaa cyaucagaua 180
cccag 185

<210> SEQ ID NO 152
<211> LENGTH: 185
<212> TYPE: DNA
<213> ORGANISM: Candida krusei

<400> SEQUENCE: 152
catcacttta gatgcaacca acgaacactt cagattaatc tatgacatca agggtagatt 60
cgcaatccac agaatcaccc cagaagaagc tgcatacaag ttatgtaagg tcaagaaggt 120
ccaattaggt aagaagggta ttccttatgt tgttacccac gatggtagaa cyatcagata 180
cccag 185

<210> SEQ ID NO 153
<211> LENGTH: 185
<212> TYPE: RNA
<213> ORGANISM: Candida krusei

<400> SEQUENCE: 153
caucacuuua gaugcaacca acgaacacuu cagauuaauc uaugacauca aggguagauu 60
cgcaauccac agaaucaccc cagaagaagc ugcauacaag uuauguaagg ucaagaaggu 120
ccaauuaggu aagaagggua uuccuuaugu uguuacccac gaugguagaa cyaucagaua 180
cccag 185

<210> SEQ ID NO 154
<211> LENGTH: 185
<212> TYPE: DNA
<213> ORGANISM: Candida krusei

<400> SEQUENCE: 154
catcacttta gatgcaacca acgaacactt cagattaatc tatgacatca agggtagatt 60
cgcaatccac agaatcaccc cagaagaagc tgcatacaag ttatgtaagg tcaagaaggt 120
ccaattaggt aagaagggta ttccttatgt tgttacccac gatggtagaa cyatcagata 180
cccag 185

<210> SEQ ID NO 155
<211> LENGTH: 185
<212> TYPE: RNA
<213> ORGANISM: Candida krusei

<400> SEQUENCE: 155
caucacuuua gaugcaacca acgaacacuu cagauuaauc uaugacauca aggguagauu 60
cgcaauccac agaaucaccc cagaagaagc ugcauacaag uuauguaagg ucaagaaggu 120
ccaauuaggu aagaagggua uuccuuaugu uguuacccac gaugguagaa cyaucagaua 180
cccag 185

<210> SEQ ID NO 156
<211> LENGTH: 185
<212> TYPE: DNA

<213> ORGANISM: Candida tropicalis

<400> SEQUENCE: 156
cattaccttg gaagctacca acgaacactt cagattgatt tacgatgtta aaggtaaatt 60
cgctgttcac agaatttctg ctgaagaagc ttcttacaaa ttaggtaaag tcaagaaggt 120
tcaattaggt aaaaaaggtg ttccatacgt tgtcacccac gatggtagaa cyatcagata 180
cccag 185

<210> SEQ ID NO 157
<211> LENGTH: 185
<212> TYPE: RNA
<213> ORGANISM: Candida tropicalis

<400> SEQUENCE: 157
cauuaccuug gaagcuacca acgaacacuu cagauugauu uacgauguua aagguaaauu 60
cgcuguucac agaauuucug cugaagaagc uucuuacaaa uuagguaaag ucaagaaggu 120
ucaauuaggu aaaaaaggug uuccauacgu ugucacccac gaugguagaa cyaucagaua 180
cccag 185

<210> SEQ ID NO 158
<211> LENGTH: 185
<212> TYPE: DNA
<213> ORGANISM: Candida tropicalis

<400> SEQUENCE: 158
cattaccttg gaagctacca acgaacactt cagattgatt tacgatgtta aaggtaaatt 60
cgctgttcac agaatttctg ctgaagaagc ttcttacaaa ttaggtaaag tcaagaaggt 120
tcaattaggt aaaaaaggtg ttccatacgt tgtcacccac gatggtagaa cyatcagata 180
cccag 185

<210> SEQ ID NO 159
<211> LENGTH: 185
<212> TYPE: RNA
<213> ORGANISM: Candida tropicalis

<400> SEQUENCE: 159
cauuaccuug gaagcuacca acgaacacuu cagauugauu uacgauguua aagguaaauu 60
cgcuguucac agaauuucug cugaagaagc uucuuacaaa uuagguaaag ucaagaaggu 120
ucaauuaggu aaaaaaggug uuccauacgu ugucacccac gaugguagaa cyaucagaua 180
cccag 185

<210> SEQ ID NO 160
<211> LENGTH: 185
<212> TYPE: DNA
<213> ORGANISM: Candida tropicalis

<400> SEQUENCE: 160
cattaccttg gaagctacca acgaacactt cagattgatt tacgatgtta aaggtaaatt 60
cgctgttcac agaatttctg ctgaagaagc ttcttacaaa ttaggtaaag tcaagaaggt 120
tcaattaggt aaaaaaggtg ttccatacgt tgtcacccac gatggtagaa cyatcagata 180
cccag 185

<210> SEQ ID NO 161
<211> LENGTH: 185

-continued

<212> TYPE: RNA
<213> ORGANISM: Candida tropicalis

<400> SEQUENCE: 161
cauuaccuug gaagcuacca acgaacacuu cagauugauu uacgauguua aagguaaauu 60
cgcuguucac agaauuucug cugaagaagc uucuuacaaa uuagguaaag ucaagaaggu 120
ucaauuaggu aaaaaaggug uuccauacgu ugucacccac gaugguagaa cyaucagaua 180
cccag 185

<210> SEQ ID NO 162
<211> LENGTH: 185
<212> TYPE: DNA
<213> ORGANISM: Candida tropicalis

<400> SEQUENCE: 162
cattaccttg gaagctacca acgaacactt cagattgatt tacgatgtta aaggtaaatt 60
cgctgttcac agaatttctg ctgaagaagc ttcttacaaa ttaggtaaag tcaagaaggt 120
tcaattaggt aaaaaaggtg ttccatacgt tgtcacccac gatggtagaa cyatcagata 180
cccag 185

<210> SEQ ID NO 163
<211> LENGTH: 185
<212> TYPE: RNA
<213> ORGANISM: Candida tropicalis

<400> SEQUENCE: 163
cauuaccuug gaagcuacca acgaacacuu cagauugauu uacgauguua aagguaaauu 60
cgcuguucac agaauuucug cugaagaagc uucuuacaaa uuagguaaag ucaagaaggu 120
ucaauuaggu aaaaaaggug uuccauacgu ugucacccac gaugguagaa cyaucagaua 180
cccag 185

<210> SEQ ID NO 164
<211> LENGTH: 185
<212> TYPE: DNA
<213> ORGANISM: Candida tropicalis

<400> SEQUENCE: 164
cattaccttg gaagctacca acgaacactt cagattgatt tacgatgtta aaggtaaatt 60
cgctgttcac agaatttctg ctgaagaagc ttcttacaaa ttaggtaaag tcaagaaggt 120
tcaattaggt aaaaaaggtg ttccatacgt tgtcacccac gatggtagaa cyatcagata 180
cccag 185

<210> SEQ ID NO 165
<211> LENGTH: 185
<212> TYPE: RNA
<213> ORGANISM: Candida tropicalis

<400> SEQUENCE: 165
cauuaccuug gaagcuacca acgaacacuu cagauugauu uacgauguua aagguaaauu 60
cgcuguucac agaauuucug cugaagaagc uucuuacaaa uuagguaaag ucaagaaggu 120
ucaauuaggu aaaaaaggug uuccauacgu ugucacccac gaugguagaa cyaucagaua 180
cccag 185

<210> SEQ ID NO 166

<211> LENGTH: 185
<212> TYPE: DNA
<213> ORGANISM: Candida tropicalis

<400> SEQUENCE: 166
cattaccttg gaagctacca acgaacactt cagattgatt tacgatgtta aaggtaaatt 60
cgctgttcac agaatttctg ctgaagaagc ttcttacaaa ttaggtaaag tcaagaaggt 120
tcaattaggt aaaaaaggtg ttccatacgt tgtcacccac gatggtagaa cyatcagata 180
cccag 185

<210> SEQ ID NO 167
<211> LENGTH: 185
<212> TYPE: RNA
<213> ORGANISM: Candida tropicalis

<400> SEQUENCE: 167
cauuaccuug gaagcuacca acgaacacuu cagauugauu uacgauguua aagguaaauu 60
cgcuguucac agaauuucug cugaagaagc uucuuacaaa uuagguaaag ucaagaaggu 120
ucaauuaggu aaaaaaggug uuccauacgu ugucacccac gaugguagaa cyaucagaua 180
cccag 185

<210> SEQ ID NO 168
<211> LENGTH: 185
<212> TYPE: DNA
<213> ORGANISM: Candida tropicalis

<400> SEQUENCE: 168
cattaccttg gaagctacca acgaacactt cagattgatt tacgatgtta aaggtaaatt 60
cgctgttcac agaatttctg ctgaagaagc ttcttacaaa ttaggtaaag tcaagaaggt 120
tcaattaggt aaaaaaggtg ttccatacgt tgtcacccac gatggtagaa cyatcagata 180
cccag 185

<210> SEQ ID NO 169
<211> LENGTH: 185
<212> TYPE: RNA
<213> ORGANISM: Candida tropicalis

<400> SEQUENCE: 169
cauuaccuug gaagcuacca acgaacacuu cagauugauu uacgauguua aagguaaauu 60
cgcuguucac agaauuucug cugaagaagc uucuuacaaa uuagguaaag ucaagaaggu 120
ucaauuaggu aaaaaaggug uuccauacgu ugucacccac gaugguagaa cyaucagaua 180
cccag 185

<210> SEQ ID NO 170
<211> LENGTH: 185
<212> TYPE: DNA
<213> ORGANISM: Candida tropicalis

<400> SEQUENCE: 170
cattaccttg gaagctacca acgaacactt cagattgatt tacgatgtta aaggtaaatt 60
cgctgttcac agaatttctg ctgaagaagc ttcttacaaa ttaggtaaag tcaagaaggt 120
tcaattaggt aaaaaaggtg ttccatacgt tgtcacccac gatggtagaa cyatcagata 180
cccag 185

<210> SEQ ID NO 171
<211> LENGTH: 185
<212> TYPE: RNA
<213> ORGANISM: Candida tropicalis

<400> SEQUENCE: 171
cauuaccuug gaagcuacca acgaacacuu cagauugauu uacgauguua aagguaaauu 60
cgcuguucac agaauuucug cugaagaagc uucuuacaaa uuagguaaag ucaagaaggu 120
ucaauuaggu aaaaaaggug uuccauacgu ugucacccac gaugguagaa cyaucagaua 180
cccag 185

<210> SEQ ID NO 172
<211> LENGTH: 185
<212> TYPE: DNA
<213> ORGANISM: Candida tropicalis

<400> SEQUENCE: 172
cattaccttg gaagctacca acgaacactt cagattgatt tacgatgtta aaggtaaatt 60
cgctgttcac agaatttctg ctgaagaagc ttcttacaaa ttaggtaaag tcaagaaggt 120
tcaattaggt aaaaaaggtg ttccatacgt tgtcacccac gatggtagaa cyatcagata 180
cccag 185

<210> SEQ ID NO 173
<211> LENGTH: 185
<212> TYPE: RNA
<213> ORGANISM: Candida tropicalis

<400> SEQUENCE: 173
cauuaccuug gaagcuacca acgaacacuu cagauugauu uacgauguua aagguaaauu 60
cgcuguucac agaauuucug cugaagaagc uucuuacaaa uuagguaaag ucaagaaggu 120
ucaauuaggu aaaaaaggug uuccauacgu ugucacccac gaugguagaa cyaucagaua 180
cccag 185

<210> SEQ ID NO 174
<211> LENGTH: 185
<212> TYPE: DNA
<213> ORGANISM: Candida tropicalis

<400> SEQUENCE: 174
catcaccttg gaagctacca acgaacactt cagattgatt tacgatgtta aaggtaaatt 60
cgctgttcac agaatttctg ctgaagaagc ttcttacaaa ttaggtaaag tcaagaaggt 120
tcaattaggt aaaaaaggtg ttccatacgt tgtcacccac gatggtagaa cyatcagata 180
cccag 185

<210> SEQ ID NO 175
<211> LENGTH: 185
<212> TYPE: RNA
<213> ORGANISM: Candida tropicalis

<400> SEQUENCE: 175
caucaccuug gaagcuacca acgaacacuu cagauugauu uacgauguua aagguaaauu 60
cgcuguucac agaauuucug cugaagaagc uucuuacaaa uuagguaaag ucaagaaggu 120
ucaauuaggu aaaaaaggug uuccauacgu ugucacccac gaugguagaa cyaucagaua 180
cccag 185

<210> SEQ ID NO 176
<211> LENGTH: 18
<212> TYPE: DNA
<213> ORGANISM: Artificial Sequence
<220> FEATURE:
<223> OTHER INFORMATION: Chemically Synthesized (Saccharomyces cerevisiae probe 1)

<400> SEQUENCE: 176
gattggtcta cgatgtca 18

<210> SEQ ID NO 177
<211> LENGTH: 18
<212> TYPE: DNA
<213> ORGANISM: Artificial Sequence
<220> FEATURE:
<223> OTHER INFORMATION: Chemically Synthesized (Saccharomyces cerevisiae probe 2)

<400> SEQUENCE: 177
tgacatcgta gaccaatc 18

<210> SEQ ID NO 178
<211> LENGTH: 18
<212> TYPE: DNA
<213> ORGANISM: Artificial Sequence
<220> FEATURE:
<223> OTHER INFORMATION: Chemically Synthesized (Eremothecium gossypii probe 1)

<400> SEQUENCE: 178
gattggtata cgatgtca 18

<210> SEQ ID NO 179
<211> LENGTH: 18
<212> TYPE: DNA
<213> ORGANISM: Artificial Sequence
<220> FEATURE:
<223> OTHER INFORMATION: Chemically Synthesized (Eremothecium gossypii probe 2)

<400> SEQUENCE: 179
tgacatcgta taccaatc 18

<210> SEQ ID NO 180
<211> LENGTH: 18
<212> TYPE: DNA
<213> ORGANISM: Artificial Sequence
<220> FEATURE:
<223> OTHER INFORMATION: Chemically Synthesized (Kluyveromyces lactis probe 1)

<400> SEQUENCE: 180
gattggtcta cgatgtta 18

<210> SEQ ID NO 181
<211> LENGTH: 18
<212> TYPE: DNA
<213> ORGANISM: Artificial Sequence
<220> FEATURE:
<223> OTHER INFORMATION: Chemically Synthesized (Kluyveromyces lactis probe 2)

<400> SEQUENCE: 181
taacatcgta gaccaatc 18

-continued

<210> SEQ ID NO 182
<211> LENGTH: 18
<212> TYPE: DNA
<213> ORGANISM: Artificial Sequence
<220> FEATURE:
<223> OTHER INFORMATION: Chemically Synthesized (Candida dubliniensis and Candida glabrata probe 1)

<400> SEQUENCE: 182
gattggtcta cgacgtca 18

<210> SEQ ID NO 183
<211> LENGTH: 18
<212> TYPE: DNA
<213> ORGANISM: Artificial Sequence
<220> FEATURE:
<223> OTHER INFORMATION: Chemically Synthesized (Candida dubliniensis and Candida glabrata probe 2)

<400> SEQUENCE: 183
tgacgtcgta gaccaatc 18

<210> SEQ ID NO 184
<211> LENGTH: 18
<212> TYPE: DNA
<213> ORGANISM: Artificial Sequence
<220> FEATURE:
<223> OTHER INFORMATION: Chemically Synthesized (Debaryomyces hansenii probe 1)

<400> SEQUENCE: 184
gattgatcta tgacgtca 18

<210> SEQ ID NO 185
<211> LENGTH: 18
<212> TYPE: DNA
<213> ORGANISM: Artificial Sequence
<220> FEATURE:
<223> OTHER INFORMATION: Chemically Synthesized (Debaryomyces hansenii probe 2)

<400> SEQUENCE: 185
tgacgtcata gatcaatc 18

<210> SEQ ID NO 186
<211> LENGTH: 18
<212> TYPE: DNA
<213> ORGANISM: Artificial Sequence
<220> FEATURE:
<223> OTHER INFORMATION: Chemically Synthesized (Candida tropicalis probe 1)

<400> SEQUENCE: 186
gattgattta cgatgtta 18

<210> SEQ ID NO 187
<211> LENGTH: 18
<212> TYPE: DNA
<213> ORGANISM: Artificial Sequence
<220> FEATURE:
<223> OTHER INFORMATION: Chemically Synthesized (Candida tropicalis probe 2)

<400> SEQUENCE: 187
taacatcgta aatcaatc 18

<210> SEQ ID NO 188

```
<211> LENGTH: 18
<212> TYPE: DNA
<213> ORGANISM: Artificial Sequence
<220> FEATURE:
<223> OTHER INFORMATION: Chemically Synthesized (Candida parapsilosis
      probe 1)

<400> SEQUENCE: 188

gattgattta cgatgtca                                                18


<210> SEQ ID NO 189
<211> LENGTH: 18
<212> TYPE: DNA
<213> ORGANISM: Artificial Sequence
<220> FEATURE:
<223> OTHER INFORMATION: Chemically Synthesized (Candida parapsilosis
      probe 2)

<400> SEQUENCE: 189

tgacatcgta aatcaatc                                                18


<210> SEQ ID NO 190
<211> LENGTH: 786
<212> TYPE: DNA
<213> ORGANISM: Saccharomyces cerevisiae

<400> SEQUENCE: 190

atggctagag gaccaaagaa gcatctaaaa agattagcag ctccacacca ctggttattg     60

gacaagttgt ccggttgtta cgccccaaga ccatctgctg gtccacacaa attgcgtgaa    120

tccttgccat tgattgtctt tctaagaaac agattaaagt atgctttgaa cggccgtgaa    180

gtcaaggcta tcttgatgca acgtcacgtt aaagtggacg gtaaggttag aaccgacact    240

acctacccag ctggtttcat ggatgtcatc actctagatg ccaccaatga aaacttcaga    300

ttggtctacg atgtcaaggg tagattcgct gtccaccgta tcaccgatga agaagcttct    360

tacaagttgg gtaaggtcaa gaaggttcaa ttaggtaaga agggtgttcc atacgttgtt    420

acccacgatg gtagaactat cagataccca gacccaaaca tcaaggtcaa tgacactgtt    480

aagatcgact tggcctctgg taagattact gatttcatca agttcgatgc cggtaagttg    540

gtttacgtta ctggtggtcg taacttgggt cgtatcggta ctatcgttca caaggaaaga    600

cacgatggtg gtttcgattt agttcacatc aaggactcct tggacaacac tttcgtcact    660

agattgaaca atgtcttcgt catcggtgaa caaggtaagc cttacatttc tttgccaggt    720

aagggtaagg gtatcaagtt gtctattgct gaagaacgtg acagaagaag agctcaacaa    780

ttataa                                                              786


<210> SEQ ID NO 191
<211> LENGTH: 786
<212> TYPE: RNA
<213> ORGANISM: Saccharomyces cerevisiae

<400> SEQUENCE: 191

auggcuagag gaccaaagaa gcaucuaaaa agauuagcag cuccacacca cugguuauug     60

gacaaguugu ccgguuguua cgccccaaga ccaucugcug guccacacaa auugcgugaa    120

uccuugccau ugauugucuu ucuaagaaac agauuaaagu augcuuugaa cggccgugaa    180

gucaaggcua ucuugaugca acgucacguu aaaguggacg guaagguuag aaccgacacu    240

accuacccag cugguuucau ggaugucauc acucuagaug ccaccaauga aaacuucaga    300

uuggucuacg augucaaggg uagauucgcu guccaccgua ucaccgauga agaagcuucu    360
```

```
uacaaguugg guaaggucaa gaagguucaa uuagguaaga agggguguucc auacguuguu    420

acccacgaug guagaacuau cagauaccca gacccaaaca ucaaggucaa ugacacuguu    480

aagaucgacu uggccucugg uaagauuacu gauuucauca aguucgaugc cgguaaguug    540

guuuacguua cuggugucg uaacuugggu cguaucggua cuaucguuca caaggaaaga    600

cacgauggug guuucgauuu aguucacauc aaggacuccu uggacaacac uuucgucacu    660

agauugaaca augucuucgu caucggugaa caagguaagc cuuacauuuc uuugccaggu    720

aagguaagg guaucaaguu gucuauugcu gaagaacgug acagaagaag agcucaacaa    780

uuauaa                                                               786
```

<210> SEQ ID NO 192
<211> LENGTH: 786
<212> TYPE: DNA
<213> ORGANISM: Candida glabrata

<400> SEQUENCE: 192

```
atggctagag gaccaaagaa gcatctaaag agattagcag ctccacacca ctggttgttg     60

gacaagttgt ccggctgtta cgccccaaga ccatccgctg gtccacacaa gttgcgtgaa    120

tccctaccat tgatcgtttt cttgagaaac agattaaagt acgctttgaa cggtcgtgaa    180

gttaaggcta tcatgatgca acgtcatgtt aaggttgacg gtaaggtcag aactgacgct    240

acctacccag ctggtttcat ggatgttatc accttggaag ctaccaacga aaacttcaga    300

ttggtctacg acgtcaaggg tagattcgct gtccaccgta tcactgacga agaagcttcc    360

tacaagttgg gtaaggtcaa gaaggtccaa ttgggtaaga agggtgttcc atacgttgtc    420

actgacgatg gtagaactat cagataccca gacccaaaca tcaaggtcaa tgacaccgtc    480

aaggtcgact tggcttccgg taagatcact gactacatca agttcgacat tggtaagttg    540

gtctacatca ccggtggtcg taacttgggt cgtatcggta ccatcgttca caaggaaaga    600

cacgatggtg gtttcgactt ggttcacgtc aaggactcct tggacaacac tttcgtcacc    660

agattgaaca acgttttcgt tatcggtgaa caaggtaagc catacatctc cttgccaaag    720

ggtaagggta tcaagttgac cattgctgaa gaacgtgaca gaagaagagc tcaacaaggt    780

ttataa                                                               786
```

<210> SEQ ID NO 193
<211> LENGTH: 786
<212> TYPE: RNA
<213> ORGANISM: Candida glabrata

<400> SEQUENCE: 193

```
auggcuagag gaccaaagaa gcaucuaaag agauuagcag cuccacacca cugguuguug     60

gacaaguugu ccggcuguua cgccccaaga ccauccgcug guccacacaa guugcgugaa    120

ucccuaccau ugaucguuuu cuugagaaac agauuaaagu acgcuuugaa cggucgugaa    180

guuaaggcua ucaugaugca acgucauguu aagguugacg guaaggucag aacugacgcu    240

accuacccag cugguuucau ggauguuauc accuuggaag cuaccaacga aaacuucaga    300

uuggucuacg acgucaaggg uagauucgcu guccaccgua ucacugacga agaagcuucc    360

uacaaguugg guaaggucaa gaagguccaa uuggguaaga aggguguucc auacguuguc    420

acugacgaug guagaacuau cagauaccca gacccaaaca ucaaggucaa ugacaccguc    480

aaggucgacu uggcuuccgg uaagaucacu gacuacauca aguucgacau ugguaaguug    540
```

-continued

```
gucuacauca ccgguggucg uaacuugggu cguaucggua ccaucguuca caaggaaaga    600

cacgauggug guuucgacuu gguucacguc aaggacuccu uggacaacac uuucgucacc    660

agauugaaca acguuuucgu uaucggugaa caagguaagc cauacaucuc cuugccaaag    720

gguaagggua ucaaguugac cauugcugaa gaacgugaca gaagaagagc ucaacaaggu    780

uuauaa                                                               786
```

<210> SEQ ID NO 194
<211> LENGTH: 786
<212> TYPE: DNA
<213> ORGANISM: Eremothecium gossypii

<400> SEQUENCE: 194

```
atggctagag gaccaaagaa gcacctgaag agattggcag ctccacacca ctggttgttg     60

gacaagctat ccggctgtta cgctccaaga ccatccgctg gtccacacaa gttgcgcgag    120

tctttgccat tgatcgtctt cttgagaaac agattaaagt atgctttgaa cggtcgcgag    180

gtcaaggcca tcctaatgca gcgtcatgtt aaggttgacg gtaaggtcag aactgacact    240

acctacccag ctggtttcat ggatgtcatc actctagagg ctaccaacga gaacttcaga    300

ttggtatacg atgtcaaggg cagatttgct gtccaccgta tcaccgatga ggaggctact    360

tacaagttgg gtaaggttaa gcgcgttcag ctaggtaaga agggtgtccc atacgtggtc    420

actcacgacg gcagaaccat cagataccca gacccaaaca tcaaggttaa cgacaccgtc    480

aaggttgacc ttgctactgg taagattacc gacttcatca agttcgacac tggtaagttg    540

gtgtacgtca ccggtggccg taacttgggc cgtattggtg tcatcaccca cagagagaga    600

cacgagggtg gctttgactt ggttcacatc aaggactcct tggagaacac tttcgtcacc    660

agattgaaca acgttttcgt catcggtgag caaggtagac catggatctc cttgccaagg    720

ggtaagggta ttaagttgtc cattgctgag gagcgtgacc gtagaagagc tcaacaaggt    780

ttgtaa                                                               786
```

<210> SEQ ID NO 195
<211> LENGTH: 786
<212> TYPE: RNA
<213> ORGANISM: Eremothecium gossypii

<400> SEQUENCE: 195

```
auggcuagag gaccaaagaa gcaccugaag agauuggcag cuccacacca cugguuguug     60

gacaagcuau ccggcuguua cgcuccaaga ccauccgcug guccacacaa guugcgcgag    120

ucuuugccau ugaucgucuu cuugagaaac agauuaaagu augcuuugaa cggucgcgag    180

gucaaggcca uccuaaugca gcgucauguu aagguugacg guaaggucag aacugacacu    240

accuacccag cugguuucau ggaugucauc acucuagagg cuaccaacga gaacuucaga    300

uugguauacg augucaaggg cagauuugcu guccaccgua ucaccgauga ggaggcuacu    360

uacaaguugg guaagguuaa gcgcguucag cuagguaaga aggguguccc auacgugguc    420

acucacgacg gcagaaccau cagauaccca gacccaaaca ucaagguuaa cgacaccguc    480

aagguugacc uugcuacugg uaagauuacc gacuucauca aguucgacac ugguaaguug    540

guguacguca ccgguggccg uaacuugggc cguauuggug ucaucaccca cagagagaga    600

cacgagggug gcuuugacuu gguucacauc aaggacuccu uggagaacac uuucgucacc    660

agauugaaca acguuuucgu caucggugag caagguagac cauggaucuc cuugccaagg    720

gguaagggua uuaaguuguc cauugcugag gagcgugacc guagaagagc ucaacaaggu    780
```

uuguaa 786

<210> SEQ ID NO 196
<211> LENGTH: 786
<212> TYPE: DNA
<213> ORGANISM: Kluyveromyces lactis

<400> SEQUENCE: 196
atggctagag gaccaaagaa gcatctaaag agattagcag ctccacatca ttggatgttg 60
gacaagttgt ccggttgtta cgcaccaaga ccatctgctg gtccacacaa gttgcgtgaa 120
tccttgccat tgatcgtttt cttgagaaac agattaaagt atgctttgaa cggtcgtgaa 180
gtcaaggcca tcttgatgca acgtcatgtc aaggttgacg gtaaggtcag aaccgacact 240
actttcccag ctggtttcat ggatgttatc accttggaag ctaccaacga aaacttcaga 300
ttggtctacg atgttaaggg tagattcgct gtccaccgta tcactgatga agaagcttcc 360
tacaagttgg ctaaggtcaa gaaggttcaa ctaggtaaga agggtattcc atacgtcgtt 420
acccacgacg gtagaaccat cagataccca gacccaaaca tcaaggttaa cgacaccgtt 480
aaggttgatt tggctactgg tactatcacc gatttcatca aattcgacac tggtaagttg 540
gtttatgtta ccggtggtcg taacttgggt agagttggta ccatcgtcca cagagaaaga 600
cacgaaggtg gtttcgattt ggttcacatc aaggattctt tggaaaacac tttcgtcacc 660
agattgaaca acgttttcgt catcggtgaa ccaggtagac catggatctc cttgccaaag 720
ggtaagggta tcaagttgac catctctgaa gaacgtgacc gtagaagagc tcaacatggt 780
ttgtaa 786

<210> SEQ ID NO 197
<211> LENGTH: 786
<212> TYPE: RNA
<213> ORGANISM: Kluyveromyces lactis

<400> SEQUENCE: 197
auggcuagag gaccaaagaa gcaucuaaag agauuagcag cuccacauca uuggauguug 60
gacaaguugu ccgguuguua cgcaccaaga ccaucugcug guccacacaa guugcgugaa 120
uccuugccau ugaucguuuu cuugagaaac agauuaaagu augcuuugaa cggucgugaa 180
gucaaggcca ucuugaugca acgucauguc aagguugacg guaaggucag aaccgacacu 240
acuuucccag cugguuucau ggauguuauc accuuggaag cuaccaacga aaacuucaga 300
uuggucuacg auguuaaggg uagauucgcu guccaccgua ucacugauga agaagcuucc 360
uacaaguugg cuaaggucaa gaagguucaa cuagguaaga aggguauucc auacgucguu 420
acccacgacg guagaaccau cagauaccca gacccaaaca ucaagguuaa cgacaccguu 480
aagguugauu uggcuacugg uacuaucacc gauuucauca aauucgacac ugguaaguug 540
guuuauguua ccgguggucg uaacuugggu agaguuggua ccaucgucca cagagaaaga 600
cacgaaggug guuucgauuu gguucacauc aaggauucuu uggaaaacac uuucgucacc 660
agauugaaca acguuuucgu caucggugaa ccagguagac cauggaucuc cuugccaaag 720
gguaagggua ucaaguugac caucucugaa gaacgugacc guagaagagc ucaacauggu 780
uuguaa 786

<210> SEQ ID NO 198
<211> LENGTH: 789
<212> TYPE: DNA

<213> ORGANISM: Candida albicans
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t

<400> SEQUENCE: 198

```
atgggtagag gtccaaagaa acacttgaaa agattagcag ctccatctca ctggatgttg     60

gncaaattgt ccggtactta tgctccaaga ccatctgctg gtccacacan attgagagaa    120

tcattaccat tggntgtctt tttaagaaac agattgnagt atgctttgtg cggtagagaa    180

gtcaaagcca tcatgatgca acaacacgtt caagttgtcg gtaaagtcag aactgatacc    240

acctacccag ctggtttcat ggatgtcatc accttggaag ctaccaacga acatttcaga    300

ttagcctacg atgttaaagg taaattcgcc gttcacagaa tttctgctga agaagctgtc    360

tacaaattgg gtaaagtcaa gaaagtccaa ttaggtaaga aaggtgttcc atacgttgtt    420

acccacgacg gtagaactat cagataccca gatccattga tcagagctaa cgataccgtt    480

aaaatcgatt tggctaccgg taagatcgrt agtttcatca aattcgacac tggtagatta    540

gttatggtta ctggtggtag aaatttgggt agagttggtg ttattgtcca cagagaaaaa    600

ctcgaaggag gtttcgattt ggtccacatc aaagatgctt tggaaaacac tttcgttacc    660

agattgtcta acgtttttgt tattggtact gaagccggta aaccatgggt ctcattacca    720

aagggtaaag gtatcaaatt gtctatttct gaagaaagag acagaagaan agctcaacaa    780

ggtttgtaa                                                            789
```

<210> SEQ ID NO 199
<211> LENGTH: 789
<212> TYPE: RNA
<213> ORGANISM: Candida albicans
<220> FEATURE:
<221> NAME/KEY: misc_feature
<222> LOCATION: (62)..(62)
<223> OTHER INFORMATION: n is a, c, g, or u
<220> FEATURE:
<221> NAME/KEY: misc_feature
<222> LOCATION: (110)..(110)
<223> OTHER INFORMATION: n is a, c, g, or u
<220> FEATURE:
<221> NAME/KEY: misc_feature
<222> LOCATION: (134)..(134)
<223> OTHER INFORMATION: n is a, c, g, or u
<220> FEATURE:
<221> NAME/KEY: misc_feature
<222> LOCATION: (157)..(157)
<223> OTHER INFORMATION: n is a, c, g, or u
<220> FEATURE:
<221> NAME/KEY: misc_feature
<222> LOCATION: (770)..(770)
<223> OTHER INFORMATION: n is a, c, g, or u

<400> SEQUENCE: 199 augggguagag guccaaagaa acacuugaaa agauuagcag cuccaucuca cuggauguug 60
gncaaauugu ccgguacuua ugcuccaaga ccaucugcug guccacacan auugagagaa 120
ucauuaccau uggnugucuu uuuaagaaac agauugnagu augcuuugug cgguagagaa 180
gucaaagcca ucaugaugca acaacacguu caaguugucg guaaagucag aacugauacc 240
accuacccag cugguuucau ggaugucauc accuuggaag cuaccaacga acauuucaga 300
uuagccuacg auguuaaagg uaaauucgcc guucacagaa uuucugcuga agaagcuguc 360
uacaaauugg guaaagucaa gaaaguccaa uuagguaaga aagguguucc auacguuguu 420
acccacgacg guagaacuau cagauaccca gauccauuga ucagagcuaa cgauaccguu 480
aaaaucgauu uggcuaccgg uaagaucgru aguuucauca aauucgacac ugguagauua 540
guuaugguua cuggugguag aaauuugggu agaguuggug uuauugucca cagagaaaaa 600
cucgaaggag guuucgauuu gguccacauc aaagaugcuu uggaaaacac uuucguuacc 660
agauugucua acguuuuugu uauugguacu gaagccggua aaccaugggu cucauuacca 720
aaggguaaag guaucaaauu gucuauuucu gaagaaagag acagaagaan agcucaacaa 780
gguuuguaa 789

<210> SEQ ID NO 200
<211> LENGTH: 792
<212> TYPE: DNA
<213> ORGANISM: Debaryomyces hansenii

<400> SEQUENCE: 200
atgggtagag gtccaaagaa gcacttgaag agattagcag caccatccca ctggatgttg 60
gacaaattgt ccggtactta cgcaccaaga ccatctgctg gtcctcacaa attgagagaa 120
tctttaccat tggttatctt cttaagaaac agacttaagt atgccttaaa cggtagagaa 180
gtcaaggcca tcttgatgca agaacacgtc aaggttgatg gtaaagttag aaccgatgct 240
actttcccag ctggtttcat ggatgtcatc actttagaag ctaccaacga acacttcaga 300
ttaatctatg atgtcaaggg tagattcact gtccacagaa tcactgctga agaagcttct 360
tacaagttag ctaaggtcaa gaaggtccaa ttaggtaaga gaggtattcc atacgttgtc 420
acccacgacg gtagaactat cagataccca gatccattga tcagagccaa cgattccgtt 480
aaggttgact tagctaccgg taagatcact gactttatca gctttgacac tggtagatta 540
gtcatggtta ctggtggtcg taacatgggt agagttggtg ttatcaccca cagagaaaag 600
cacgagggtg gtttcgattt agtccacatc aaggattctt tggaaaacac tttcgttacc 660
agattaacta acgtcttcat cgtcggtact gaagctggta agccacacat ttctttacca 720
aagggtaagg gtattaagtt atccatctct gaagaacgtg acagaagaag aaaccaacaa 780
cttatcaact aa 792

<210> SEQ ID NO 201
<211> LENGTH: 792
<212> TYPE: RNA
<213> ORGANISM: Debaryomyces hansenii

<400> SEQUENCE: 201
auggguagag guccaaagaa gcacuugaag agauuagcag caccauccca cuggauguug 60
gacaaauugu ccgguacuua cgcaccaaga ccaucugcug guccucacaa auugagagaa 120
ucuuuaccau ugguuaucuu cuuaagaaac agacuuaagu augccuuaaa cgguagagaa 180
gucaaggcca ucuugaugca agaacacguc aagguugaug guaaaguuag aaccgaugcu 240
acuuucccag cugguuucau ggaugucauc acuuuagaag cuaccaacga acacuucaga 300
uuaaucuaug augucaaggg uagauucacu guccacagaa ucacugcuga agaagcuucu 360
uacaaguuag cuaaggucaa gaagguccaa uuagguaaga gagguauucc auacguuguc 420
acccacgacg guagaacuau cagauaccca gauccauuga ucagagccaa cgauuccguu 480
aagguugacu uagcuaccgg uaagaucacu gacuuuauca gcuuugacac ugguagauua 540
gucaugguua cuggugucg uaacaugggu agaguuggug uuaucaccca cagagaaaag 600
cacgagggug guuucgauuu aguccacauc aaggauucuu uggaaaacac uuucguuacc 660
agauuaacua acgucuucau cgucgguacu gaagcuggua agccacacau uucuuuacca 720
aaggguaagg guauuaaguu auccaucucu gaagaacgug acagaagaag aaaccaacaa 780
cuuaucaacu aa 792

<210> SEQ ID NO 202
<211> LENGTH: 1143
<212> TYPE: DNA
<213> ORGANISM: Candida albicans
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (1029)..(1029)
<223> OTHER INFORMATION: n is a, c, g, or t

<400> SEQUENCE: 202
gaattcgttg cttgagcaag aggaaaagct tactaaattg ataaagcagg caaatagaaa 60
tagtacttgg ttcaaatgga ataaatagtt tgtgtgttga tttcgcgaaa aagaaatgta 120
aagtaatact gattagggct atagccctaa ctggtttctc gcactctttt cactaccaat 180
tactaaaaaa aaaaaatttg gtgaaaaaaa aaaattatct accactccct ataccatcat 240
catcaacaat aaacccacaa tgggtagagg tccaaagaaa cacttgaaaa gattagcagc 300
tccatctcac tggatgttgg ncaaattgtc cggtacttat gctccaagac catctgctgg 360
tccacacana ttgagagaat cattaccatt ggntgtcttt ttaagaaaca gattgnagta 420
tgctttgtgc ggtagagaag tcaaagccat catgatgcaa caacacgttc aagttgtcgg 480
taaagtcaga actgatacca cctacccagc tggtttcatg gatgtcatca ccttggaagc 540
taccaacgaa catttcagat tagcctacga tgttaaaggt aaattcgccg ttcacagaat 600
ttctgctgaa gaagctgtct acaaattggg taaagtcaag aaagtccaat taggtaagaa 660
aggtgttcca tacgttgtta cccacgacgg tagaactatc agatacccag atccattgat 720
cagagctaac gataccgtta aaatcgattt ggctaccggt aagatcgrta gtttcatcaa 780
attcgacact ggtagattag ttatggttac tggtggtaga aatttgggta gagttggtgt 840
tattgtccac agagaaaaac tcgaaggagg tttcgatttg gtccacatca aagatgcttt 900

```
ggaaaacact ttcgttacca gattgtctaa cgtttttgtt attggtactg aagccggtaa    960

accatgggtc tcattaccaa agggtaaagg tatcaaattg tctatttctg aagaaagaga   1020

cagaagaana gctcaacaag gtttgtaagt tttattcgca ctacaaaaaa aaaaatrttt   1080

trtgaaaatg aaaaaaacca acgtaaataa tgtacattaa ttgctaacct tcaataagtt   1140

gtt                                                                 1143
```

<210> SEQ ID NO 203
<211> LENGTH: 1143
<212> TYPE: RNA
<213> ORGANISM: Candida albicans
<220> FEATURE:
<221> NAME/KEY: misc_feature
<222> LOCATION: (321)..(321)
<223> OTHER INFORMATION: n is a, c, g, or u
<220> FEATURE:
<221> NAME/KEY: misc_feature
<222> LOCATION: (369)..(369)
<223> OTHER INFORMATION: n is a, c, g, or u
<220> FEATURE:
<221> NAME/KEY: misc_feature
<222> LOCATION: (393)..(393)
<223> OTHER INFORMATION: n is a, c, g, or u
<220> FEATURE:
<221> NAME/KEY: misc_feature
<222> LOCATION: (416)..(416)
<223> OTHER INFORMATION: n is a, c, g, or u
<220> FEATURE:
<221> NAME/KEY: misc_feature
<222> LOCATION: (1029)..(1029)
<223> OTHER INFORMATION: n is a, c, g, or u

<400> SEQUENCE: 203

```
gaauucguug cuugagcaag aggaaaagcu uacuaaauug auaaagcagg caaauagaaa     60

uaguacuugg uucaaaugga auaaaauagu ugugugguga uuucgcgaaa aagaaaugua    120

aaguaauacu gauuagggcu auagcccuaa cugguuucuc gcacucuuuu cacuaccaau    180

uacuaaaaaa aaaaaauuug gugaaaaaaa aaaauuaucu accacucccu auaccaucau    240

caucaacaau aaacccacaa ugguagagg uccaaagaaa cacuugaaaa gauuagcagc    300

uccaucucac uggauguugg ncaaauuguc cgguacuuau gcuccaagac caucugcugg    360

uccacacana uugagagaau cauuaccauu ggnugucuuu uuaagaaaca gauugnagua    420

ugcuuugugc gguagagaag ucaaagccau caugaugcaa caacacguuc aaguugucgg    480

uaaagucaga acugauacca ccuacccagc ugguuucaug gaugucauca ccuuggaagc    540

uaccaacgaa cauuucagau uagccuacga uguuaaaggu aaauucgccg uucacagaau    600

uucugcugaa gaagcugucu acaaauuggg uaaagucaag aaaguccaau uagguaagaa    660

aggguguucca uacguuguua cccacgacgg uagaacuauc agauacccag auccauugau    720

cagagcuaac gauaccguua aaaucgauuu ggcuaccggu aagaucgrua guuucaucaa    780

auucgacacu gguagauuag uuaugguuac uggugguaga aauuugggua gaguuggugu    840

uauuguccac agagaaaaac ucgaaggagg uuucgauuug guccacauca aagaugcuuu    900

ggaaaacacu uucguuacca gauugucuaa cguuuuuguu auugguacug aagccgguaa    960

accaugggu c ucauuaccaa aggguaaagg uaucaaauug ucuauuucug aagaaagaga   1020

cagaagaana gcucaacaag guuuguaagu uuuauucgca cuacaaaaaa aaaaauruuu   1080

urugaaaaug aaaaaaacca acguaaauaa uguacauuaa uugcuaaccu ucaauaaguu   1140

guu                                                                 1143
```

<210> SEQ ID NO 204
<211> LENGTH: 786
<212> TYPE: DNA
<213> ORGANISM: Candida albicans

<400> SEQUENCE: 204
atggctagag gaccaaagaa gcatctaaag agattagcag ctccacacca ctggttgttg 60
gacaagttgt ccggctgtta cgccccaaga ccatccgctg gtccacacaa gttgcgtgaa 120
tccctaccat tgatcgtttt cttgagaaac agattaaagt acgctttgaa cggtcgtgaa 180
gttaaggcta tcatgatgca acgtcatgtt aaggttgacg gtaaggtcag aactgacgct 240
acctacccag ctggtttcat ggatgttatc accttggaag ctaccaacga aaacttcaga 300
ttggtctacg acgtcaaggg tagattcgct gtccaccgta tcactgacga agaagcttcc 360
tacaagttgg gtaaggtcaa gaaggtccaa ttgggtaaga agggtgttcc atacgttgtc 420
actgacgatg gtagaactat cagataccca gacccaaaca tcaaggtcaa tgacaccgtc 480
aaggtcgact tggcttccgg taagatcact gactacatca agttcgacat tggtaagttg 540
gtctacatca ccggtggtcg taacttgggt cgtatcggta ccatcgttca caaggaaaga 600
cacgatggtg gtttcgactt ggttcacgtc aaggactcct tggacaacac tttcgtcacc 660
agattgaaca acgttttcgt tatcggtgaa caaggtaagc catacatctc cttgccaaag 720
ggtaagggta tcaagttgac cattgctgaa gaacgtgaca gaagaagagc tcaacaaggt 780
ttataa 786

<210> SEQ ID NO 205
<211> LENGTH: 786
<212> TYPE: RNA
<213> ORGANISM: Candida glabrata

<400> SEQUENCE: 205
auggcuagag gaccaaagaa gcaucuaaag agauuagcag cuccacacca cugguuguug 60
gacaaguugu ccggcuguua cgccccaaga ccauccgcug guccacacaa guugcgugaa 120
ucccuaccau ugaucguuuu cuugagaaac agauuaaagu acgcuuugaa cggucgugaa 180
guuaaggcua ucaugaugca acgucauguu aagguugacg guaaggucag aacugacgcu 240
accuacccag cugguuucau ggauguuauc accuuggaag cuaccaacga aaacuucaga 300
uuggucuacg acgucaaggg uagauucgcu guccaccgua ucacugacga agaagcuucc 360
uacaaguugg guaaggucaa gaagguccaa uuggguaaga aggguguucc auacguuguc 420
acugacgaug guagaacuau cagauaccca gacccaaaca ucaaggucaa ugacaccguc 480
aaggucgacu uggcuuccgg uaagaucacu gacuacauca aguucgacau ugguaaguug 540
gucuacauca ccgguggucg uaacuugggu cguaucggua ccaucguuca caaggaaaga 600
cacgauggug guuucgacuu gguucacguc aaggacuccu uggacaacac uuucgucacc 660
agauugaaca acguuuucgu uaucggugaa caagguaagc cauacaucuc cuugccaaag 720
gguaagggua ucaaguugac cauugcugaa gaacgugaca gaagaagagc ucaacaaggu 780
uuauaa 786

<210> SEQ ID NO 206
<211> LENGTH: 2178
<212> TYPE: DNA
<213> ORGANISM: Saccharomyces cerevisiae
<220> FEATURE:
<223> OTHER INFORMATION: ribosomal protein S7 gene, exons 1 and 2

-continued

<400> SEQUENCE: 206

```
gatctaatcc ttctcctggc ctaccgtctg tgcaaccatt agtcatgatt acgtgtgttg     60
cgccttatct tgtcattatg gcagcatact tttcgtagtc ctttcctgcg cacgttgtcc    120
attttcgtaa ccacgtaaaa agtcctaatg gagagctggg tactgcattt tttcgatgtt    180
ttcaatattc agttcagcag gaaataaaca aataaacaaa cattaaaata tctggttttt    240
tttcccagag acgcgtggaa gcacccatgc atcactattt atttttaaac agccgtacat    300
tctgtaattt tgcttccttt ttcttcctgc gttctttttt tcttgaactg tcgttttccg    360
ttattttttt cggtgacatc agttgaaagt agcagcggcc taggcgacgg tagctctttg    420
tagtcgtggt aagggggagt agcaattcac ttagtacgtg gtcttggagt taggctggct    480
cggactggcc ctggcaagtc ctgttctgtg tggtagtatt gaaatttcag agattgtcgg    540
caatactagt atattaaaaa ttatactata atttaatcta gtgttgaaat actttcttat    600
atagcgattt ttctgcccaa aacaaaccaa agaatcaata cgcaaagatg gctagaggac    660
cgtatgtttg actatagact ttgattataa ttacgcaagg atgagaagaa tgatagacaa    720
gaaacaagtg gagtcttaac caaacgaata ggaacaacaa tgaaccagtt tatgtccatt    780
taattttaga tcatcctggg attgtacaaa tattttacga gtaatgattt actaacgagc    840
acaatgaaaa aaataaaatg tctgtatctt cattatacat tcatttttgc ccttttttct    900
catttttttc cgtacagaaa gaagcatcta aaaagattag cagctccaca ccactggtta    960
ttggacaagt tgtccggttg ttacgcccca agaccatctg ctggtccaca caaattgcgt   1020
gaatccttgc cattgattgt ctttctaaga aacagattaa agtatgcttt gaacggccgt   1080
gaagtcaagg ctatcttgat gcaacgtcac gttaaagtgg acggtaaggt tagaaccgac   1140
actacctacc cagctggttt catggatgtc atcactctag atgccaccaa tgaaaacttc   1200
agattggtct acgatgtcaa gggtagattc gctgtccacc gtatcaccga tgaagaagct   1260
tcttacaagt tgggtaaggt caagaaggtt caattaggta agaagggtgt tccatacgtt   1320
gttacccacg atggtagaac tatcagatac ccagacccaa acatcaaggt caatgacact   1380
gttaagatcg acttggcctc tggtaagatt actgatttca tcaagttcga tgccggtaag   1440
ttggtttacg ttactggtgg tcgtaacttg ggtcgtatcg gtactatcgt tcacaaggaa   1500
agacacgatg gtggtttcga tttagttcac atcaaggact ccttggacaa cactttcgtc   1560
actagattga acaatgtctt cgtcatcggt gaacaaggta agccttacat ttctttgcca   1620
aagggtaagg gtatcaagtt gtctattgct gaagaacgtg acagaagaag agctcaacaa   1680
ggtttataaa tttcataaca acttaattat tttcttcttt tgtatatctc cattaatgtt   1740
tattagaaat tgaattttaa aataatacat cgtatcttcc tttttcgact ggcagtaata   1800
taacgtataa tatatatatt aggtgtgtgt atatatatcc gtattgtaat attgatagta   1860
aaaatacgct aaccctgaaa tagaaggcgt atgataagac gtactgacac tacgcactac   1920
cacaatatat gcgttgtgtg tgtgtgtgtg tgtgtgtgtg tgtgtgattg tattggaata   1980
tatatactta ctaaaattaa gcttatatgg ttcgcatatt gactatttat aaggatattc   2040
aacttgtatg tcctttctta accaaatttt cttctttctc ttggtggtaa catgttccac   2100
aaacttctca gtacaatgat ccactttgaa tttctttatg aaaacagggt cccataattc   2160
agaaccgacg ccgagatc                                                 2178
```

<210> SEQ ID NO 207

<211> LENGTH: 2178
<212> TYPE: RNA
<213> ORGANISM: Saccharomyces cerevisiae
<220> FEATURE:
<223> OTHER INFORMATION: protein S7 gene, exons 1 and 2

<400> SEQUENCE: 207

```
gaucuaaucc uucuccuggc cuaccgucug ugcaaccauu agucaugauu acguguguug     60
cgccuuaucu ugucauuaug gcagcauacu uuucguaguc cuuuccugcg cacguugucc    120
auuuucguaa ccacguaaaa aguccuaaug gagagcuggg uacugcauuu uuucgauguu    180
uucaauauuc aguucagcag gaaauaaaca aauaaacaaa cauuaaaaua ucugguuuuu    240
uuucccagag acgcguggaa gcacccaugc aucacuauuu auuuuuaaac agccguacau    300
ucuguaauuu ugcuuccuuu uucuuccugc guucuuuuuu ucuugaacug ucguuuuccg    360
uuauuuuuuu cggugacauc aguugaaagu agcagcggcc uaggcgacgg uagcucuuug    420
uagucguggu aagggggagu agcaauucac uuaguacgug gucuuggagu uaggcuggcu    480
cggacuggcc cuggcaaguc cuguucugug ugguaguauu gaaauuucag agauugucgg    540
caauacuagu auauuaaaaa uuauacuaua auuuaaucua guguugaaau acuuucuuau    600
auagcgauuu uucugcccaa aacaaaccaa agaaucaaua cgcaaagaug gcuagaggac    660
cguauguuug acuauagacu uugauuauaa uuacgcaagg augagaagaa ugauagacaa    720
gaaacaagug gagucuuaac caaacgaaua ggaacaacaa ugaaccaguu uauguccauu    780
uaauuuuaga ucauccuggg auuguacaaa uauuuuacga guaaugauuu acuaacgagc    840
acaaugaaaa aaauaaaaug ucuguaucuu cauuauacau ucauuuuugc ccuuuuuucu    900
cauuuuuuuc cguacagaaa gaagcaucua aaaagauuag cagcuccaca ccacugguua    960
uuggacaagu uguccgguug uuacgcccca agaccaucug cugguccaca caaauugcgu   1020
gaauccuugc cauugauugu cuuucuaaga aacagauuaa aguaugcuuu gaacggccgu   1080
gaagucaagg cuaucuugau gcaacgucac guuaaagugg acgguaaggu uagaaccgac   1140
acuaccuacc cagcugguuu cauggauguc aucacucuag augccaccaa ugaaaacuuc   1200
agauuggucu acgaugucaa ggguagauuc gcuguccacc guaucaccga ugaagaagcu   1260
ucuuacaagu uggguaaggu caagaagguu caauuaggua agaagggugu uccauacguu   1320
guuacccacg augguagaac uaucagauac ccagacccaa acaucaaggu caaugacacu   1380
guuaagaucg acuuggccuc ugguaagauu acugauuuca ucaaguucga ugccgguaag   1440
uugguuuacg uuacuggugg ucguaacuug ggucguaucg guacuaucgu ucacaaggaa   1500
agacacgaug gugguuucga uuuaguucac aucaaggacu ccuuggacaa cacuuucguc   1560
acuagauuga acaaugucuu cgucaucggu gaacaaggua agccuuacau uucuuugcca   1620
aaggguaagg guaucaaguu gucuauugcu gaagaacgug acagaagaag agcucaacaa   1680
gguuuauaaa uuucauaaca acuuaauuau uuucuucuuu uguauaucuc cauuaauguu   1740
uauuagaaau ugaauuuuaa aauaauacau cguaucuucc uuuuucgacu ggcaguaaua   1800
uaacguauaa uauauauauu aggugugugu auauauaucc guauuguaau auugauagua   1860
aaaauacgcu aacccugaaa uagaaggcgu augauaagac guacugacac uacgcacuac   1920
cacaauauau gcguugugug ugugugugug ugugugugug ugugugauug uauuggaaua   1980
uauauacuua cuaaaauuaa gcuuauaugg uucgcauauu gacuauuuau aaggauauuc   2040
aacuuguaug uccuuucuua accaaauuuu cuucuuucuc uuggugguaa cauguuccac   2100
aaacuucuca guacaaugau ccacuuugaa uuucuuuaug aaaacagggu cccauaauuc   2160
```

agaaccgacg ccgagauc 2178

<210> SEQ ID NO 208
<211> LENGTH: 1169
<212> TYPE: DNA
<213> ORGANISM: Saccharomyces cerevisiae
<220> FEATURE:
<223> OTHER INFORMATION: ribosomal protein S7 gene, exon 1 and 2.

<400> SEQUENCE: 208
gtaagattta gaatagtttc ttttcatata acgtcgacta agtataacaa tagatacacc 60
actattgagg aaagatggct agaggaccgt atgttgattt ccacctaaaa aaatgaagag 120
ttggcaaaac aagataatag ttttctttga agatgggtac cctctcatga ttggtacaag 180
tgatttgcac caaagtgacg atgcggacta aagaaagaat ataagaagtt gtgtttatct 240
atcggaagat agaattctga tgagaaaact ttatccttgt taagaacaga taagcattgc 300
gggatatttt tactaacaag agtacgttta ataatgttaa tacgattttt catatagaaa 360
gaagcatcta aagagattag cagctccaca ccattggtta ttggacaagt tgtccggttg 420
ttacgcccca agaccatctg ctggtccaca caaattgcgt gaatccttgc cattgattgt 480
ctttctaaga aacagattaa agtatgcttt gaacggccgt gaagtcaagg ctatcttgat 540
gcaacgtcac gtcaaagttg acggtaaggt tagaactgac accacctacc cagctggttt 600
catggacgtc atcactctag atgccaccaa tgaaaacttc agattggtct acgatgtcaa 660
gggtagattc gctgtccacc gtatcaccga tgaagaagcc tcttacaaat tgggtaaggt 720
caagaaggtt caattaggta agaagggtgt tccatacgtt gttacccacg atggtagaac 780
tatcagatac ccagacccaa acatcaaggt caatgacact gttaagattg atttggcctc 840
tggtaagatt actgatttca tcaagttcga tgccggtaag ttggtttacg ttactggtgg 900
tcgtaacttg ggtcgtatcg gtactatcgt tcacaaggaa agacacgatg gtggtttcga 960
tttggttcac atcaaggact ccttggacaa cactttcgtc actagattga acaatgtctt 1020
cgtcattggt gaacaaggta agccttacat ttctttgcca aagggtaagg gtatcaagtt 1080
gtctattgct gaagaacgtg acagaagaag agctcaacaa ggtttgtaaa cattttaaat 1140
attgttatct gccctctctt cgtcttttg 1169

<210> SEQ ID NO 209
<211> LENGTH: 1169
<212> TYPE: RNA
<213> ORGANISM: Saccharomyces cerevisiae
<220> FEATURE:
<223> OTHER INFORMATION: ribosomal protein S7 gene exons 1 and 2

<400> SEQUENCE: 209
guaagauuua gaauaguuuc uuuucauaua acgucgacua aguauaacaa uagauacacc 60
acuauugagg aaagauggcu agaggaccgu auguugauuu ccaccuaaaa aaaugaagag 120
uuggcaaaac aagauaauag uuuucuuuga agauggguac ccucucauga uugguacaag 180
ugauuugcac caaagugacg augcggacua aagaaagaau auaagaaguu guguuuaucu 240
aucggaagau agaauucuga ugagaaaacu uuauccuugu uaagaacaga uaagcauugc 300
gggauauuuu uacuaacaag aguacguuua auaauguuaa uacgauuuuu cauauagaaa 360
gaagcaucua aagagauuag cagcuccaca ccauugguua uuggacaagu uguccgguug 420
uuacgcccca agaccaucug cugguccaca caaauugcgu gaauccuugc cauugauugu 480

```
cuuucuaaga aacagauuaa aguaugcuuu gaacggccgu gaagucaagg cuaucuugau    540
gcaacgucac gucaaaguug acgguaaggu uagaacugac accaccuacc cagcugguuu    600
cauggacguc aucacucuag augccaccaa ugaaaacuuc agauuggucu acgaugucaa    660
ggguagauuc gcuguccacc guaucaccga ugaagaagcc ucuuacaaau uggguaaggu    720
caagaagguu caauuaggua agaagggugu uccauacguu guuacccacg augguagaac    780
uaucagauac ccagacccaa acaucaaggu caaugacacu guuaagauug auuuggccuc    840
ugguaagauu acugauuuca ucaaguucga ugccgguaag uugguuuacg uuacuggugg    900
ucguaacuug ggucguaucg guacuaucgu ucacaaggaa agacacgaug gugguuucga    960
uuugguucac aucaaggacu ccuuggacaa cacuuucguc acuagauuga acaaugucuu   1020
cgucauuggu gaacaaggua agccuuacau uucuuugcca aaggguaagg guaucaaguu   1080
gucuauugcu gaagaacgug acagaagaag agcucaacaa gguuuguaaa cauuuuaaau   1140
auuguuaucu gcccucucuu cgucuuuug                                     1169
```

<210> SEQ ID NO 210
<211> LENGTH: 786
<212> TYPE: DNA
<213> ORGANISM: Kluyveromyces lactis

<400> SEQUENCE: 210

```
atggctagag gaccaaagaa gcatctaaag agattagcag ctccacatca ttggatgttg     60
gacaagttgt ccggttgtta cgcaccaaga ccatctgctg gtccacacaa gttgcgtgaa    120
tccttgccat tgatcgtttt cttgagaaac agattaaagt atgctttgaa cggtcgtgaa    180
gtcaaggcca tcttgatgca acgtcatgtc aaggttgacg gtaaggtcag aaccgacact    240
actttcccag ctggtttcat ggatgttatc accttggaag ctaccaacga aaacttcaga    300
ttggtctacg atgttaaggg tagattcgct gtccaccgta tcactgatga agaagcttcc    360
tacaagttgg ctaaggtcaa gaaggttcaa ctaggtaaga agggtattcc atacgtcgtt    420
acccacgacg gtagaaccat cagataccca gacccaaaca tcaaggttaa cgacaccgtt    480
aaggttgatt tggctactgg tactatcacc gatttcatca aattcgacac tggtaagttg    540
gtttatgtta ccggtggtcg taacttgggt agagttggta ccatcgtcca cagagaaaga    600
cacgaaggtg gtttcgattt ggttcacatc aaggattctt tggaaaacac tttcgtcacc    660
agattgaaca acgttttcgt catcggtgaa ccaggtagac catggatctc cttgccaaag    720
ggtaagggta tcaagttgac catctctgaa gaacgtgacc gtagaagagc tcaacatggt    780
ttgtaa                                                               786
```

<210> SEQ ID NO 211
<211> LENGTH: 786
<212> TYPE: RNA
<213> ORGANISM: Kluyveromyces lactis

<400> SEQUENCE: 211

```
auggcuagag gaccaaagaa gcaucuaaag agauuagcag cuccacauca uuggauguug     60
gacaaguugu ccgguuguua cgcaccaaga ccaucugcug guccacacaa guugcgugaa    120
uccuugccau ugaucguuuu cuugagaaac agauuaaagu augcuuugaa cggucgugaa    180
gucaaggcca ucuugaugca acgucauguc aagguugacg guaaggucag aaccgacacu    240
acuuucccag cugguuucau ggauguuauc accuuggaag cuaccaacga aaacuucaga    300
uuggucuacg auguuaaggg uagauucgcu guccaccgua ucacugauga agaagcuucc    360
```

```
uacaaguugg cuaaggucaa gaagguucaa cuagguaaga aggguauucc auacgucguu    420

acccacgacg guagaaccau cagauaccca gacccaaaca ucaagguuaa cgacaccguu    480

aagguugauu uggcuacugg uacuaucacc gauuucauca aauucgacac ugguaaguug    540

guuuauguua ccggugqucg uaacuugggu agaguuggua ccaucgucca cagagaaaga    600

cacgaaggug guuucgauuu gguucacauc aaggauucuu uggaaaacac uuucgucacc    660

agauugaaca acguuuucgu caucggugaa ccagguagac cauggaucuc cuugccaaag    720

gguaagggua ucaaguugac caucucugaa gaacgugacc guagaagagc ucaacauggu    780

uuguaa                                                               786
```

```
<210> SEQ ID NO 212
<211> LENGTH: 786
<212> TYPE: DNA
<213> ORGANISM: Eremothecium gossypii

<400> SEQUENCE: 212

atggctagag gaccaaagaa gcacctgaag agattggcag ctccacacca ctggttgttg     60

gacaagctat ccggctgtta cgctccaaga ccatccgctg gtccacacaa gttgcgcgag    120

tctttgccat tgatcgtctt cttgagaaac agattaaagt atgctttgaa cggtcgcgag    180

gtcaaggcca tcctaatgca gcgtcatgtt aaggttgacg gtaaggtcag aactgacact    240

acctacccag ctggtttcat ggatgtcatc actctagagg ctaccaacga gaacttcaga    300

ttggtatacg atgtcaaggg cagatttgct gtccaccgta tcaccgatga ggaggctact    360

tacaagttgg gtaaggttaa gcgcgttcag ctaggtaaga agggtgtccc atacgtggtc    420

actcacgacg gcagaaccat cagataccca gacccaaaca tcaaggttaa cgacaccgtc    480

aaggttgacc ttgctactgg taagattacc gacttcatca agttcgacac tggtaagttg    540

gtgtacgtca ccggtggccg taacttgggc cgtattggtg tcatcaccca cagagagaga    600

cacgagggtg gctttgactt ggttcacatc aaggactcct tggagaacac tttcgtcacc    660

agattgaaca acgttttcgt catcggtgag caaggtagac catggatctc cttgccaagg    720

ggtaagggta ttaagttgtc cattgctgag gagcgtgacc gtagaagagc tcaacaaggt    780

ttgtaa                                                               786
```

```
<210> SEQ ID NO 213
<211> LENGTH: 786
<212> TYPE: RNA
<213> ORGANISM: Eremothecium gossypii

<400> SEQUENCE: 213

auggcuagag gaccaaagaa gcaccugaag agauuggcag cuccacacca cugguuguug     60

gacaagcuau ccggcuguua cgcuccaaga ccauccgcug guccacacaa guugcgcgag    120

ucuuugccau ugaucgucuu cuugagaaac agauuaaagu augcuuugaa cggucgcgag    180

gucaaggcca uccuaaugca gcgucauguu aagguugacg guaaggucag aacugacacu    240

accuacccag cugguuucau ggaugucauc acucuagagg cuaccaacga gaacuucaga    300

uugguauacg augucaaggg cagauuugcu guccaccgua ucaccgauga ggaggcuacu    360

uacaaguugg guaagguuaa gcgcguucag cuagguaaga agggaguccc auacgugguc    420

acucacgacg gcagaaccau cagauaccca gacccaaaca ucaagguuaa cgacaccguc    480

aagguugacc uugcuacugg uaagauuacc gacuucauca aguucgacac ugguaaguug    540
```

guguacguca ccgguggccg uaacuugggc cguauuggug ucaucaccca cagagagaga 600
cacgagggug gcuuugacuu gguucacauc aaggacuccu uggagaacac uuucgucacc 660
agauugaaca acguuuucgu caucggugag caagguagac cauggaucuc cuugccaagg 720
gguaagggua uuaaguuguc cauugcugag gagcgugacc guagaagagc ucaacaaggu 780
uuguaa 786

<210> SEQ ID NO 214
<211> LENGTH: 792
<212> TYPE: DNA
<213> ORGANISM: Debaryomyces hansenii

<400> SEQUENCE: 214
atgggtagag gtccaaagaa gcacttgaag agattagcag caccatccca ctggatgttg 60
gacaaattgt ccggtactta cgcaccaaga ccatctgctg gtcctcacaa attgagagaa 120
tctttaccat tggttatctt cttaagaaac agacttaagt atgccttaaa cggtagagaa 180
gtcaaggcca tcttgatgca agaacacgtc aaggttgatg gtaaagttag aaccgatgct 240
actttcccag ctggtttcat ggatgtcatc actttagaag ctaccaacga acacttcaga 300
ttaatctatg atgtcaaggg tagattcact gtccacagaa tcactgctga agaagcttct 360
tacaagttag ctaaggtcaa gaaggtccaa ttaggtaaga gaggtattcc atacgttgtc 420
acccacgacg gtagaactat cagataccca gatccattga tcagagccaa cgattccgtt 480
aaggttgact tagctaccgg taagatcact gactttatca gctttgacac tggtagatta 540
gtcatggtta ctggtggtcg taacatgggt agagttggtg ttatcaccca cagagaaaag 600
cacgagggtg gtttcgattt agtccacatc aaggattctt tggaaaacac tttcgttacc 660
agattaacta acgtcttcat cgtcggtact gaagctggta agccacacat ttctttacca 720
aagggtaagg gtattaagtt atccatctct gaagaacgtg acagaagaag aaaccaacaa 780
cttatcaact aa 792

<210> SEQ ID NO 215
<211> LENGTH: 792
<212> TYPE: RNA
<213> ORGANISM: Debaryomyces hansenii

<400> SEQUENCE: 215
auggguagag guccaaagaa gcacuugaag agauuagcag caccauccca cuggauguug 60
gacaaauugu ccgguacuua cgcaccaaga ccaucugcug guccucacaa auugagagaa 120
ucuuuaccau ugguuaucuu cuuaagaaac agacuuaagu augccuuaaa cgguagagaa 180
gucaaggcca ucuugaugca agaacacguc aagguugaug guaaaguuag aaccgaugcu 240
acuuucccag cugguuucau ggaugucauc acuuuagaag cuaccaacga acacuucaga 300
uuaaucuaug augucaaggg uagauucacu guccacagaa ucacugcuga agaagcuucu 360
uacaaguuag cuaaggucaa gaagguccaa uuagguaaga gagguauucc auacguuguc 420
acccacgacg guagaacuau cagauaccca gauccauuga ucagagccaa cgauuccguu 480
aagguugacu uagcuaccgg uaagaucacu gacuuuauca gcuuugacac ugguagauua 540
gucaugguua cugguggucg uaacaugggu agaguuggug uuaucaccca cagagaaaag 600
cacgagggug guuucgauuu aguccacauc aaggauucuu uggaaaacac uuucguuacc 660
agauuaacua acgucuucau cgucgguacu gaagcuggua agccacacau uucuuuacca 720
aaggguaagg guauuaaguu auccaucucu gaagaacgug acagaagaag aaaccaacaa 780
cuuaucaacu aa 792

<210> SEQ ID NO 216
<211> LENGTH: 606
<212> TYPE: DNA
<213> ORGANISM: Aspergillus nidulans

<400> SEQUENCE: 216
atggctgcca tcaacaagat cgcccacaac tcgccgtcga ggcagaaccc ttccgagctg 60
gagaccgcga tcgcgggtgc tctcttcgac ttggagagca acacacagga cctgaaggct 120
actctccggc ctctgcagtt cgtgtctgct cgtgaggtcg aggtcggcca cggcaagaag 180
gctgtcatca tcttcgtccc cgtccctctc ctccaggcct tccacaagat ccagcagcgc 240
cttacccgtg aactcgagaa gaagttctcg gaccgccacg tcctcttcgt cgctcagcgc 300
cgcatcctcc ccaagcccaa gcgctccgtc aactcccgca ccaaccagaa gcagaagcgc 360
ccccgttccc gtacccttac tgccgttcac gacgccatcc tcgacgacct cgtctacccc 420
gttgagattg tcggcaagcg catccgcacc aaggaggacg gctccaagac cctcaaggtc 480
atcctcgacg agaaggagcg tggtggtgtt gaccaccgcc tcgacgccta cggcgaggtc 540
taccgtcgtc tgacgggtcg tgctgtcgtt ttcgagttcc cccagggtgg tgcttctgag 600
ttttaa 606

<210> SEQ ID NO 217
<211> LENGTH: 606
<212> TYPE: RNA
<213> ORGANISM: Aspergillus nidulans

<400> SEQUENCE: 217
auggcugcca ucaacaagau cgcccacaac ucgccgucga ggcagaaccc uuccgagcug 60
gagaccgcga ucgcgggugc ucucuucgac uuggagagca acacacagga ccugaaggcu 120
acucuccggc cucugcaguu cgugucugcu cgugaggucg aggucggcca cggcaagaag 180
gcugucauca ucuucguccc cgucccucuc cuccaggccu uccacaagau ccagcagcgc 240
cuuacccgug aacucgagaa gaaguucucg gaccgccacg uccucuucgu cgcucagcgc 300
cgcauccucc ccaagcccaa gcgcuccguc aacucccgca ccaaccagaa gcagaagcgc 360
ccccguuccc guacccuuac ugccguucac gacgccaucc ucgacgaccu cgucuacccc 420
guugagauug ucggcaagcg cauccgcacc aaggaggacg gcuccaagac ccucaagguc 480
auccucgacg agaaggagcg ugguggugau gaccaccgcc ucgacgccua cggcgagguc 540
uaccgucguc ugacgggucg ugcugucguu uucgaguucc cccagggugg ugcuucugag 600
uuuuaa 606

<210> SEQ ID NO 218
<211> LENGTH: 606
<212> TYPE: DNA
<213> ORGANISM: Aspergillus fumigatus

<400> SEQUENCE: 218
atggctgcta tcaacaagat cgcccacaac tcgccatcga ggcagaaccc ctccgagctg 60
gagactgcga tcgccggcgc tctctacgac ttggagagca atacacagga cctgaaggcc 120
acccttcggc ccctgcagtt tgtctctgcc cgtgaggttg aggtcggcca cggcaagaag 180
gccgttatca tcttcgtccc cgtccctctc ctccagggct tccacaagat ccagcagcgc 240

```
ctgacccgtg agctcgagaa gaagttctcc gaccgccacg tcctctttgt tgctcagcgc    300

cgcatcctgc cccgccctaa gcgctctgtc aactcccgca ccaaccagaa gcagaagcgt    360

cctcgctctc gcaccctgac cgctgtccac gacgccatcc tcaacgacct cgtttacccc    420

gtcgagatcg tcggcaagcg tatccgcacc aaggaggacg gcagcaagac tctcaaggtc    480

atcctggacg agaaggagcg tggtggtgtt gaccacagac tcgatgccta cggcgaggtt    540

taccgccgac taaccggccg ctctgttgtc ttcgagttcc cccagagcgg tgccgccgag    600

tactag                                                               606
```

```
<210> SEQ ID NO 219
<211> LENGTH: 606
<212> TYPE: RNA
<213> ORGANISM: Aspergillus fumigatus

<400> SEQUENCE: 219

auggcugcua ucaacaagau cgcccacaac ucgccaucga ggcagaaccc cuccgagcug     60

gagacugcga ucgccggcgc ucucuacgac uuggagagca auacacagga ccugaaggcc    120

acccuucggc cccugcaguu ugucucugcc cgugagguug aggucggcca cggcaagaag    180

gccguuauca ucuucguccc cgucccucuc cuccagggcu uccacaagau ccagcagcgc    240

cugacccgug agcucgagaa gaaguucucc gaccgccacg uccucuuugu ugcucagcgc    300

cgcauccugc cccgcccuaa gcgcucuguc aacucccgca ccaaccagaa gcagaagcgu    360

ccucgcucuc gcacccugac cgcuguccac gacgccaucc ucaacgaccu cguuuacccc    420

gucgagaucg ucggcaagcg uauccgcacc aaggaggacg gcagcaagac ucucaagguc    480

auccuggacg agaaggagcg ugguggugu gaccacagac ucgaugccua cggcgagguu    540

uaccgccgac uaaccggccg cucuguuguc uucgaguucc cccagagcgg ugccgccgag    600

uacuag                                                               606
```

```
<210> SEQ ID NO 220
<211> LENGTH: 606
<212> TYPE: DNA
<213> ORGANISM: Aspergillus terreus

<400> SEQUENCE: 220

atggctgcta tcaacaagat cgcccacaac tcgccgtctc ggcagaaccc ctccgagctg     60

gagaccgcga tcgccggtgc tctgttcgac ctcgagagca acaccaccga cctgaaggcc    120

accctccgcc cccttcagtt cgtgtctgct cgtgaggttg aggtcggcca cggcaagaag    180

gccgtcatca tcttcgtccc tgtccctctc ctccagggct tccacaagat ccagcagcgt    240

ctgacccgtg agctcgagaa gaagttctcc gaccgccacg tcctcttcgt tgctcagcgc    300

cgcatcctgc cccgccccaa gcgctctgtc aactcccgca ccaaccagaa gcagaagcgt    360

ccccgttccc gcactctgac ggccgtccac gacgccatcc tcaccgacct cgtctacccc    420

gtcgagatcg tcggcaagcg catccgcacc aaggaggacg gctccaagac cctcaaggtc    480

atcctcgacg agaaggagcg cggcggtgtc gaccaccgcc tcgatgccta cggcgaggtc    540

taccgtcgtc tcaccggccg tgccgtcgtc ttcgagttcc cccagagcgg tgctgctgac    600

tactaa                                                               606
```

```
<210> SEQ ID NO 221
<211> LENGTH: 606
<212> TYPE: RNA
<213> ORGANISM: Aspergillus terreus
```

<400> SEQUENCE: 221
auggcugcua ucaacaagau cgcccacaac ucgccgucuc ggcagaaccc cuccgagcug 60
gagaccgcga ucgccggugc ucuguucgac cucgagagca acaccaccga ccugaaggcc 120
acccuccgcc cccuucaguu cgugucugcu cgugagguug aggucggcca cggcaagaag 180
gccgucauca ucuucguccc ugucccucuc cuccagggcu uccacaagau ccagcagcgu 240
cugacccgug agcucgagaa gaaguucucc gaccgccacg uccucuucgu ugcucagcgc 300
cgcauccugc cccgccccaa gcgcucuguc aacuccccgca ccaaccagaa gcagaagcgu 360
ccccguuccc gcacucugac ggccguccac gacgccaucc ucaccgaccu cgucuacccc 420
gucgagaucg ucggcaagcg cauccgcacc aaggaggacg gcuccaagac ccucaagguc 480
auccucgacg agaaggagcg cggcggugug gaccaccgcc ucgaugccua cggcgagguc 540
uaccgucguc ucaccggccg ugccgucguc uucgaguucc cccagagcgg ugcugcugac 600
uacuaa 606

<210> SEQ ID NO 222
<211> LENGTH: 186
<212> TYPE: DNA
<213> ORGANISM: Candida albicans

<400> SEQUENCE: 222
catcacyttg gaagctacca acgaacattt cagattagtc tacgatgtta aaggtaaatt 60
ygctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccaga 186

<210> SEQ ID NO 223
<211> LENGTH: 186
<212> TYPE: RNA
<213> ORGANISM: Candida albicans

<400> SEQUENCE: 223
caucacyuug gaagcuacca acgaacauuu cagauuaguc uacgauguua aagguaaauu 60
ygcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccaga 186

<210> SEQ ID NO 224
<211> LENGTH: 186
<212> TYPE: DNA
<213> ORGANISM: Candida albicans

<400> SEQUENCE: 224
catcacyttg gaagctacca acgaacattt cagattagtc tacgatgtta aaggtaaatt 60
ygctgttcac agaatytctg stgaagaagc tgcctayaaa ttgggtaaag tcaagaaagt 120
ycaattaggt aagaaaggtg ttccatacgt tgttacccac gacggtagaa cyatcagata 180
cccaga 186

<210> SEQ ID NO 225
<211> LENGTH: 186
<212> TYPE: RNA
<213> ORGANISM: Candida albicans

<400> SEQUENCE: 225
caucacyuug gaagcuacca acgaacauuu cagauuaguc uacgauguua aagguaaauu 60
ygcuguucac agaauyucug sugaagaagc ugccuayaaa uuggguaaag ucaagaaagu 120
ycaauuaggu aagaaaggug uuccauacgu uguuacccac gacgguagaa cyaucagaua 180
cccaga 186

<210> SEQ ID NO 226
<211> LENGTH: 186
<212> TYPE: DNA
<213> ORGANISM: Candida albicans

<400> SEQUENCE: 226
catcacyttg gaagctacca acgaacattt cagattagtc tacgatgtta aaggtaaatt 60
cgctgttcac agaatttctg ctgaagaagc tgcctacaaa ttgggtaaag tcaagaaagt 120
ccaattaggt aagaaaggtg ttccatacgt tgttacccac gacggtagaa cyatcagata 180
cccaga 186

<210> SEQ ID NO 227
<211> LENGTH: 186
<212> TYPE: RNA
<213> ORGANISM: Candida albicans

<400> SEQUENCE: 227
caucacyuug gaagcuacca acgaacauuu cagauuaguc uacgauguua aagguaaauu 60
cgcuguucac agaauuucug cugaagaagc ugccuacaaa uuggguaaag ucaagaaagu 120
ccaauuaggu aagaaaggug uuccauacgu uguuacccac gacgguagaa cyaucagaua 180
cccaga 186

<210> SEQ ID NO 228
<211> LENGTH: 186
<212> TYPE: DNA
<213> ORGANISM: Candida parapsilosis

<400> SEQUENCE: 228
yattactttg gaagccacya atgaaaactt tagattgatt tacgatgtca aaggtagatt 60
tgctgtccac agaatctcag ctgaagaagc cacttacaaa ttgggtaaag tcaagagagt 120
ccaattgggt aagaagggaa tcccatacgt tgtcacccac gatggtagaa cyatcagata 180
cccaga 186

<210> SEQ ID NO 229
<211> LENGTH: 186
<212> TYPE: RNA
<213> ORGANISM: Candida parapsilosis

<400> SEQUENCE: 229
yauuacuuug gaagccacya augaaaacuu uagauugauu uacgauguca aagguagauu 60
ugcuguccac agaaucucag cugaagaagc cacuuacaaa uuggguaaag ucaagagagu 120
ccaauugggu aagaagggaa ucccauacgu ugucacccac gaugguagaa cyaucagaua 180
cccaga 186

<210> SEQ ID NO 230
<211> LENGTH: 185
<212> TYPE: DNA
<213> ORGANISM: Candida parapsilosis

<400> SEQUENCE: 230
catcactttg gaagctacya aygaacattt tmgattgatc tacgatgtya aaggtagatt 60
ygctgtycay agaatctctg ctgaagaagc cacytacaaa ttgggtaaag ttaagaaagt 120
ccaattaggt aaaaagggaa tyccatacgt tgtcacccac gatggtagaa cyatcagata 180
cccag 185

<210> SEQ ID NO 231
<211> LENGTH: 185
<212> TYPE: RNA
<213> ORGANISM: Candida parapsilosis

<400> SEQUENCE: 231
caucacuuug gaagcuacya aygaacauuu umgauugauc uacgauguya aagguagauu 60
ygcuguycay agaaucucug cugaagaagc cacyuacaaa uuggguaaag uuaagaaagu 120
ccaauuaggu aaaaagggaa uyccauacgu ugucacccac gaugguagaa cyaucagaua 180
cccag 185

<210> SEQ ID NO 232
<211> LENGTH: 185
<212> TYPE: DNA
<213> ORGANISM: Candida parapsilosis

<400> SEQUENCE: 232
cattactttg gaagccacca acgaacactt tagattgatt tacgatgtta arggtagatt 60
ygctgtccac agaatytctg ctgargaagc cacctacaaa ttgggtaaag ttaagaaagt 120
ccaattaggt aaaaagggaa tcccatacgt tgtcacccac gatggyagaa cyatcagata 180
cccag 185

<210> SEQ ID NO 233
<211> LENGTH: 185
<212> TYPE: RNA
<213> ORGANISM: Candida parapsilosis

<400> SEQUENCE: 233
cauuacuuug gaagccacca acgaacacuu uagauugauu uacgauguua argguagauu 60
ygcuguccac agaauyucug cugargaagc caccuacaaa uuggguaaag uuaagaaagu 120
ccaauuaggu aaaaagggaa ucccauacgu ugucacccac gauggyagaa cyaucagaua 180
cccag 185

<210> SEQ ID NO 234
<211> LENGTH: 185
<212> TYPE: DNA
<213> ORGANISM: Candida parapsilosis

<400> SEQUENCE: 234
cattactttg gaagccacca atgaaaactt tagattgatt tacgatgtca aaggtagatt 60
tgctgtccac agaatctcag ctgaagaagc cacttacaaa ttgggtaaag tcaagagagt 120
ccaattgggt aagaagggaa tcccatacgt tgtcacccac gatggtagaa ccatcagata 180
cccag 185

<210> SEQ ID NO 235
<211> LENGTH: 185
<212> TYPE: RNA

<213> ORGANISM: Candida parapsilosis

<400> SEQUENCE: 235
cauuacuuug gaagccacca augaaaacuu uagauugauu uacgauguca aagguagauu 60
ugcuguccac agaaucucag cugaagaagc cacuuacaaa uuggguaaag ucaagagagu 120
ccaauugggu aagaagggaa ucccauacgu ugucacccac gaugguagaa ccaucagaua 180
cccag 185

<210> SEQ ID NO 236
<211> LENGTH: 185
<212> TYPE: DNA
<213> ORGANISM: Candida parapsilosis

<400> SEQUENCE: 236
catcactttg gaagctacya aygaacattt yagattgatc tacgatgtya aaggtagatt 60
ygctgtycay agaatctctg ctgaagaagc cacytacaaa ttgggtaaag ttaagaaagt 120
ccaattaggt aaaaagggaa tyccatacgt tgtcacccay gatggtagaa cyatcagata 180
cccag 185

<210> SEQ ID NO 237
<211> LENGTH: 185
<212> TYPE: RNA
<213> ORGANISM: Candida parapsilosis

<400> SEQUENCE: 237
caucacuuug gaagcuacya aygaacauuu yagauugauc uacgauguya aagguagauu 60
ygcuguycay agaaucucug cugaagaagc cacyuacaaa uuggguaaag uuaagaaagu 120
ccaauuaggu aaaaagggaa uyccauacgu ugucacccay gaugguagaa cyaucagaua 180
cccag 185

<210> SEQ ID NO 238
<211> LENGTH: 186
<212> TYPE: DNA
<213> ORGANISM: Candida parapsilosis

<400> SEQUENCE: 238
yaytactttg gaagccacya atgaaaactt tagattgatt tacgatgtca aaggtagatt 60
tgctgtccac agaatctcag ctgaagaagc cacttacaaa ttgggtaaag tcaagagagt 120
ccaattgggt aagaagggaa tcccatacgt tgtcacccac gatggtagaa ctatcagata 180
cccaga 186

<210> SEQ ID NO 239
<211> LENGTH: 186
<212> TYPE: RNA
<213> ORGANISM: Candida parapsilosis

<400> SEQUENCE: 239
yayuacuuug gaagccacya augaaaacuu uagauugauu uacgauguca aagguagauu 60
ugcuguccac agaaucucag cugaagaagc cacuuacaaa uuggguaaag ucaagagagu 120
ccaauugggu aagaagggaa ucccauacgu ugucacccac gaugguagaa cuaucagaua 180
cccaga 186

<210> SEQ ID NO 240
<211> LENGTH: 186

<212> TYPE: DNA
<213> ORGANISM: Candida parapsilosis

<400> SEQUENCE: 240
yattacyttg gaagcyacya aygaaaactt yagattgrty tacgaygtca arggtagatt 60
ygctgtccac mgwatmtcwg mygaagaagc ywcytacaar ttgggtaarg tcaagarrgt 120
ccaattgggt aagaagggwr tyccatacgt tgtcacysac gatggtagaa cyatcagata 180
cccaga 186

<210> SEQ ID NO 241
<211> LENGTH: 186
<212> TYPE: RNA
<213> ORGANISM: Candida parapsilosis

<400> SEQUENCE: 241
yauuacyuug gaagcyacya aygaaaacuu yagauugruy uacgayguca argguagauu 60
ygcuguccac mgwaumucwg mygaagaagc ywcyuacaar uuggguaarg ucaagarrgu 120
ccaauugggu aagaagggwr uyccauacgu ugucacysac gaugguagaa cyaucagaua 180
cccaga 186

<210> SEQ ID NO 242
<211> LENGTH: 186
<212> TYPE: DNA
<213> ORGANISM: Candida parapsilosis

<400> SEQUENCE: 242
catcactttg gaagctacya aygaacattt yagattgatc tacgatgtya aaggtagatt 60
ygctgtccac agaatctctg ctgaagaagc cacytacaaa ttgggtaaag ttaagaaagt 120
ccaattaggt aaaaagggaa tyccatacgt tgtcacccay gatggtagaa cyatcagata 180
cccaga 186

<210> SEQ ID NO 243
<211> LENGTH: 186
<212> TYPE: RNA
<213> ORGANISM: Candida parapsilosis

<400> SEQUENCE: 243
caucacuuug gaagcuacya aygaacauuu yagauugauc uacgauguya aagguagauu 60
ygcuguccac agaaucucug cugaagaagc cacyuacaaa uuggguaaag uuaagaaagu 120
ccaauuaggu aaaaagggaa uyccauacgu ugucacccay gaugguagaa cyaucagaua 180
cccaga 186

<210> SEQ ID NO 244
<211> LENGTH: 185
<212> TYPE: DNA
<213> ORGANISM: Candida krusei

<400> SEQUENCE: 244
catcacttta gawgcaacca acgaacactt cagattaatc tatgacatca agggtagatt 60
cgcaatccac agaatcaccc cagaagaagc tgcatacaag ttatgtaagg tcaagaaggt 120
ccaattaggt aagaagggta ttccttatgt tgttacccac gatggtagaa cyatcagata 180
cccag 185

<210> SEQ ID NO 245

-continued

<211> LENGTH: 185
<212> TYPE: RNA
<213> ORGANISM: Candida krusei

<400> SEQUENCE: 245
caucacuuua gawgcaacca acgaacacuu cagauuaauc uaugacauca aggguagauu 60
cgcaauccac agaaucaccc cagaagaagc ugcauacaag uuauguaagg ucaagaaggu 120
ccaauuaggu aagaagggua uuccuuaugu uguuacccac gaugguagaa cyaucagaua 180
cccag 185

<210> SEQ ID NO 246
<211> LENGTH: 186
<212> TYPE: DNA
<213> ORGANISM: Candida tropicalis

<400> SEQUENCE: 246
cattaccttg gaagctacca acgaacactt cagattgatt tacgatgtta aaggtaaatt 60
cgctgttcac agaatttctg ctgaagaagc ttcttacaaa ttaggtaaag tcaagaaggt 120
tcaattaggt aaaaaaggtg ttccatacgt tgtcacccac gatggtagaa cyatcagata 180
cccaga 186

<210> SEQ ID NO 247
<211> LENGTH: 186
<212> TYPE: RNA
<213> ORGANISM: Candida tropicalis

<400> SEQUENCE: 247
cauuaccuug gaagcuacca acgaacacuu cagauugauu uacgauguua aagguaaauu 60
cgcuguucac agaauuucug cugaagaagc uucuuacaaa uuagguaaag ucaagaaggu 120
ucaauuaggu aaaaaaggug uuccauacgu ugucacccac gaugguagaa cyaucagaua 180
cccaga 186

<210> SEQ ID NO 248
<211> LENGTH: 186
<212> TYPE: DNA
<213> ORGANISM: Candida tropicalis

<400> SEQUENCE: 248
catcactttr gawgcwacca acgaacaytt cagattaatc tacgaygtca agggtaaatt 60
cgctgtccac agaatcacyg ctgaagaagc tgcctmcaaa ttggttaarg tmaagaaagt 120
ccaattaggt aagaraggtg ttccwtacgt tgttacccac gayggtagaa cyatcagata 180
cccaga 186

<210> SEQ ID NO 249
<211> LENGTH: 186
<212> TYPE: RNA
<213> ORGANISM: Candida tropicalis

<400> SEQUENCE: 249
caucacuuur gawgcwacca acgaacayuu cagauuaauc uacgayguca aggguaaauu 60
cgcuguccac agaaucacyg cugaagaagc ugccumcaaa uugguuaarg umaagaaagu 120
ccaauuaggu aagaraggug uuccwuacgu uguuacccac gaygguagaa cyaucagaua 180
cccaga 186

<210> SEQ ID NO 250
<211> LENGTH: 185
<212> TYPE: DNA
<213> ORGANISM: Candida dubliniensis

<400> SEQUENCE: 250
catyacyttr gaagctacya aygaacattt cagattagtw tacgatgtta aaggtaaatt 60
ygcygttcay agaatctctg ctgaagaagc tkcctacaaa ttgggtaaag tyaaraaagt 120
ccaattrggt aaraaaggtg ttccataygt tgttacccac gacggtagaa cyatcagata 180
cccag 185

<210> SEQ ID NO 251
<211> LENGTH: 185
<212> TYPE: RNA
<213> ORGANISM: Candida dubliniensis

<400> SEQUENCE: 251
cauyacyuur gaagcuacya aygaacauuu cagauuaguw uacgauguua aagguaaauu 60
ygcyguucay agaaucucug cugaagaagc ukccuacaaa uuggguaaag uyaaraaagu 120
ccaauurggu aaraaaggug uuccauaygu uguuacccac gacgguagaa cyaucagaua 180
cccag 185

<210> SEQ ID NO 252
<211> LENGTH: 185
<212> TYPE: DNA
<213> ORGANISM: Candida dubliniensis

<400> SEQUENCE: 252
catyacyttr gaagctacya aygaacattt cagattagtw tacgatgtta aaggtaaatt 60
ygcygttcay agaatctctg ctgaagaagc tkcctacaaa ttgggtaaag tyaagaaagt 120
ccaattrggt aaraaaggtg ttccatacgt tgttacccac gacggtagaa cyatcagata 180
cccag 185

<210> SEQ ID NO 253
<211> LENGTH: 185
<212> TYPE: RNA
<213> ORGANISM: Candida dubliniensis

<400> SEQUENCE: 253
cauyacyuur gaagcuacya aygaacauuu cagauuaguw uacgauguua aagguaaauu 60
ygcyguucay agaaucucug cugaagaagc ukccuacaaa uuggguaaag uyaagaaagu 120
ccaauurggu aaraaaggug uuccauacgu uguuacccac gacgguagaa cyaucagaua 180
cccag 185

<210> SEQ ID NO 254
<211> LENGTH: 186
<212> TYPE: DNA
<213> ORGANISM: Candida dubliniensis

<400> SEQUENCE: 254
catyacyttr gaagctacya aygaacattt cagattagtw tacgatgtta aaggtaaatt 60
yrcygttcay agaatctctg ctgaagaagc tkcctacaaa ttgggtaaag tyaaraaagt 120
ccaattrggt aaraaaggtg ttccatacgt tgttacccac gacggtagaa cyatcagata 180
cccaga 186

<210> SEQ ID NO 255
<211> LENGTH: 186
<212> TYPE: RNA
<213> ORGANISM: Candida dubliniensis

<400> SEQUENCE: 255
cauyacyuur gaagcuacya aygaacauuu cagauuaguw uacgauguua aagguaaauu 60
yrcyguucay agaaucucug cugaagaagc ukccuacaaa uuggguaaag uyaaraaagu 120
ccaauurggu aaraaaggug uuccauacgu uguuacccac gacgguagaa cyaucagaua 180
cccaga 186

<210> SEQ ID NO 256
<211> LENGTH: 186
<212> TYPE: DNA
<213> ORGANISM: Candida norvegenesis

<400> SEQUENCE: 256
tatcacttta gaagcaacca acgaaaactt cagattaatc tacgacatca agggtagatt 60
cgcaattcac agaatcactc ctgaagaagc agcatacaag ttatgtaaga tcaagaaggt 120
ccaattaggt aagaagggta ttccataygt tgttacacac gacggtagaa cyatcagata 180
cccaga 186

<210> SEQ ID NO 257
<211> LENGTH: 186
<212> TYPE: RNA
<213> ORGANISM: Candida norvegenesis

<400> SEQUENCE: 257
uaucacuuua gaagcaacca acgaaaacuu cagauuaauc uacgacauca aggguagauu 60
cgcaauucac agaaucacuc cugaagaagc agcauacaag uuauguaaga ucaagaaggu 120
ccaauuaggu aagaagggua uuccauaygu uguuacacac gacgguagaa cyaucagaua 180
cccaga 186

<210> SEQ ID NO 258
<211> LENGTH: 186
<212> TYPE: DNA
<213> ORGANISM: Candida guilliermondii

<400> SEQUENCE: 258
catcaccttg gaggccacca acgagcactt yagattggtg tacgacgtca agggtagatt 60
tgctgtccac agaatcaccg ctgaggaggc ttcctacaag ttgggtaagg tcaagaaggt 120
tcaattgggy aagagaggta ttccatacgt tgtgacccac gacggtagaa ctatcagata 180
cccaga 186

<210> SEQ ID NO 259
<211> LENGTH: 186
<212> TYPE: RNA
<213> ORGANISM: Candida guilliermondii

<400> SEQUENCE: 259
caucaccuug gaggccacca acgagcacuu yagauuggug uacgacguca aggguagauu 60
ugcuguccac agaaucaccg cugaggaggc uuccuacaag uuggguaagg ucaagaaggu 120
ucaauugggy aagagaggua uuccauacgu ugugacccac gacgguagaa cuaucagaua 180
cccaga 186

<210> SEQ ID NO 260
<211> LENGTH: 184
<212> TYPE: DNA
<213> ORGANISM: Candida guilliermondii

<400> SEQUENCE: 260
atcaccttgg aggctaccaa cgagcacttc agattggtgt acgatgtcaa gggtagattt 60
gctgtccaca gaatcaccgc tgaagaggct tcctacaagt tgggtaaggt caagaaggtt 120
caattgggta agagaggtat tccatacgtt gttacccacg acggtagaac catcagatac 180
ccag 184

<210> SEQ ID NO 261
<211> LENGTH: 184
<212> TYPE: RNA
<213> ORGANISM: Candida guilliermondii

<400> SEQUENCE: 261
aucaccuugg aggcuaccaa cgagcacuuc agauuggugu acgaugucaa ggguagauuu 60
gcuguccaca gaaucaccgc ugaagaggcu uccuacaagu uggguaaggu caagaagguu 120
caauugggua agagagguau uccauacguu guuacccacg acgguagaac caucagauac 180
ccag 184

<210> SEQ ID NO 262
<211> LENGTH: 182
<212> TYPE: DNA
<213> ORGANISM: Candida lusitaniae

<400> SEQUENCE: 262
caccttggar gccaccaacg aaaacttcag attggtgtac gacatcaagg gtagattcac 60
tgtccacaga atcaccgctg argaaggttc ctacaagttg ggtaaggtca agaagatygc 120
tttgggcaag aaggctatcc catacgtggt tacccacgay ggtagaacta tcagataccc 180
ag 182

<210> SEQ ID NO 263
<211> LENGTH: 182
<212> TYPE: RNA
<213> ORGANISM: Candida lusitaniae

<400> SEQUENCE: 263
caccuuggar gccaccaacg aaaacuucag auugguguac gacaucaagg guagauucac 60
uguccacaga aucaccgcug argaagguuc cuacaaguug gguaagguca agaagauygc 120
uuugggcaag aaggcuaucc cauacguggu uacccacgay gguagaacua ucagauaccc 180
ag 182

<210> SEQ ID NO 264
<211> LENGTH: 156
<212> TYPE: DNA
<213> ORGANISM: Candida lipolytica

<400> SEQUENCE: 264
cagattggtg tacgacgtca agggtagatt cgccgtgcac agaatcaccg ccgaggagtc 60
cacctacaag ttggccaaga tcaagaaggt ccagttgggc aagaagagta tcccctacgc 120
cgtcacccac gacggtagaa ctatcagata cccaga 156

<210> SEQ ID NO 265
<211> LENGTH: 156
<212> TYPE: RNA
<213> ORGANISM: Candida lipolytica

<400> SEQUENCE: 265
cagauuggug uacgacguca aggguagauu cgccgugcac agaaucaccg ccgaggaguc 60
caccuacaag uuggccaaga ucaagaaggu ccaguugggc aagaagagua uccccuacgc 120
cgucacccac gacgguagaa cuaucagaua cccaga 156

<210> SEQ ID NO 266
<211> LENGTH: 186
<212> TYPE: DNA
<213> ORGANISM: Candida lipolytica

<400> SEQUENCE: 266
catcaccttg grrgccacca acgaaaactt cagattggtg tacgacatca agggtagatt 60
cactgtccac agaatcaccg ctgaggaagg ttcctacaag ttgggtaagg tcaagaagat 120
ygctttgggc aagaaggcta tcccatacgt ggttacccac gayggtagaa ctatcagata 180
cccaga 186

<210> SEQ ID NO 267
<211> LENGTH: 186
<212> TYPE: RNA
<213> ORGANISM: Candida lipolytica

<400> SEQUENCE: 267
caucaccuug grrgccacca acgaaaacuu cagauuggug uacgacauca aggguagauu 60
cacuguccac agaaucaccg cugaggaagg uuccuacaag uuggguaagg ucaagaagau 120
ygcuuugggc aagaaggcua ucccauacgu gguuacccac gaygguagaa cuaucagaua 180
cccaga 186

<210> SEQ ID NO 268
<211> LENGTH: 158
<212> TYPE: DNA
<213> ORGANISM: Candida lipolytica

<400> SEQUENCE: 268
ttcagattgg tgtacgacgt caagggtaga ttcgccgtgc acagaatcac cgccgaggag 60
tccacctaca agttggccaa gatcaagaag gtccagttgg gcaagaagag tatcccctac 120
gccgtcaccc acgacggtag aactatcaga tacccaga 158

<210> SEQ ID NO 269
<211> LENGTH: 158
<212> TYPE: RNA
<213> ORGANISM: Candida lipolytica

<400> SEQUENCE: 269
uucagauugg uguacgacgu caaggguaga uucgccgugc acagaaucac cgccgaggag 60
uccaccuaca aguuggccaa gaucaagaag guccaguugg gcaagaagag uauccccuac 120
gccgucaccc acgacgguag aacuaucaga uacccaga 158

<210> SEQ ID NO 270
<211> LENGTH: 178
<212> TYPE: DNA
<213> ORGANISM: Candida rugosa

<400> SEQUENCE: 270
cttgagctac caacgaaaac ttcasmttga tctacgacgt caagggtaga tttgccgtcc 60
acagaatcac cgctgaagaa gcttcgtaca agttggsyaa ggtyaagtcc gtccaattgg 120
gyaagmgmsk katyccttac gcygttacyc acgayggtag aactatcaga tacccaga 178

<210> SEQ ID NO 271
<211> LENGTH: 178
<212> TYPE: RNA
<213> ORGANISM: Candida rugosa

<400> SEQUENCE: 271
cuugagcuac caacgaaaac uucasmuuga ucuacgacgu caaggguaga uuugccgucc 60
acagaaucac cgcugaagaa gcuucguaca aguuggsyaa gguyaagucc guccaauugg 120
gyaagmgmsk kauyccuuac gcyguuacyc acgaygguag aacuaucaga uacccaga 178

<210> SEQ ID NO 272
<211> LENGTH: 181
<212> TYPE: DNA
<213> ORGANISM: Candida rugosa

<400> SEQUENCE: 272
ccttggaagc taccaacgaa aacttcagat tgatctacga cgtcaagggt agatttgccg 60
tccacagaat caccgctgaa gaagcttcgt acaagttggs yaaggtyaag tccgtccaat 120
tgggyaagmg mskkattcct tacgcygtta cycacgaygg tagaacyatc agatacccag 180
a 181

<210> SEQ ID NO 273
<211> LENGTH: 181
<212> TYPE: RNA
<213> ORGANISM: Candida rugosa

<400> SEQUENCE: 273
ccuuggaagc uaccaacgaa aacuucagau ugaucuacga cgucaagggu agauuugccg 60
uccacagaau caccgcugaa gaagcuucgu acaaguuggs yaagguyaag uccguccaau 120
ugggyaagmg mskkauuccu uacgcyguua cycacgaygg uagaacyauc agauacccag 180
a 181

<210> SEQ ID NO 274
<211> LENGTH: 185
<212> TYPE: DNA
<213> ORGANISM: Candida rugosa

<400> SEQUENCE: 274
catctcgctt gaagccacca acgaaaactt cagattgatc tacgacgtca agggtagatt 60
tgccgtccac agaatcaccg cygaagwggc ytcgtacaag ttggsyaagg tyaagtccgt 120
ccaattgggy aagmgmskka tyccttacgc ygtyacycac gacggtagaa ctaycagata 180
cccag 185

<210> SEQ ID NO 275
<211> LENGTH: 185
<212> TYPE: RNA
<213> ORGANISM: Candida rugosa

<400> SEQUENCE: 275

```
caucucgcuu gaagccacca acgaaaacuu cagauugauc uacgacguca aggguagauu     60

ugccguccac agaaucaccg cygaagwggc yucguacaag uuggsyaagg uyaaguccgu    120

ccaauugggy aagmgmskka uyccuuacgc yguyacycac gacgguagaa cuaycagaua    180

cccag                                                                185


<210> SEQ ID NO 276
<211> LENGTH: 180
<212> TYPE: DNA
<213> ORGANISM: Candida rugosa

<400> SEQUENCE: 276

tcgcttgagc caccaacgaa aacttcagat tgatctacga cgtcaagggt agatttgccg     60

tccacagaat caccgctgaa gaggcytcgt acaagttggs yaaggtyaag tccgtccaat    120

tgggyaagmg mskkatycct tacgcygtya cycacgacgg tagaactatc agatacccag    180


<210> SEQ ID NO 277
<211> LENGTH: 180
<212> TYPE: RNA
<213> ORGANISM: Candida rugosa

<400> SEQUENCE: 277

ucgcuugagc caccaacgaa aacuucagau ugaucuacga cgucaagggu agauuugccg     60

uccacagaau caccgcugaa gaggcyucgu acaaguuggs yaagguyaag uccguccaau    120

ugggyaagmg mskkauyccu uacgcyguya cycacgacgg uagaacuauc agauacccag    180


<210> SEQ ID NO 278
<211> LENGTH: 180
<212> TYPE: DNA
<213> ORGANISM: Candida rugosa

<400> SEQUENCE: 278

tcgcttgagc caccaacgaa aacttcagat tgatctacga cgtcaagggt agatttgccg     60

tccacagaat caccgctgaa gaggcytcgt acaagttggs yaaggtyaag tccgtccaat    120

tgggyaagmg mskkatycct tacgcygtya cycacgacgg tagaactatc agatacccag    180


<210> SEQ ID NO 279
<211> LENGTH: 180
<212> TYPE: RNA
<213> ORGANISM: Candida rugosa

<400> SEQUENCE: 279

ucgcuugagc caccaacgaa aacuucagau ugaucuacga cgucaagggu agauuugccg     60

uccacagaau caccgcugaa gaggcyucgu acaaguuggs yaagguyaag uccguccaau    120

ugggyaagmg mskkauyccu uacgcyguya cycacgacgg uagaacuauc agauacccag    180


<210> SEQ ID NO 280
<211> LENGTH: 185
<212> TYPE: DNA
<213> ORGANISM: Candida famata

<400> SEQUENCE: 280

catcacttta gaagcyacca acgaacactt cagattaatc taygaygtca agggtagatt     60

cactgtycac agaatcaccg cygaagaagc ttcttacaag ttagctaagg tyaagaaggt    120

ycaattaggt aagagwggta ttccatacgt tgtyacccac gatggtagaa ctatcagata    180

cccag                                                                185
```

<210> SEQ ID NO 281
<211> LENGTH: 185
<212> TYPE: RNA
<213> ORGANISM: Candida famata

<400> SEQUENCE: 281
caucacuuua gaagcyacca acgaacacuu cagauuaauc uaygayguca aggguagauu 60
cacuguycac agaaucaccg cygaagaagc uucuuacaag uuagcuaagg uyaagaaggu 120
ycaauuaggu aagagwggua uuccauacgu uguyacccac gaugguagaa cuaucagaua 180
cccag 185

<210> SEQ ID NO 282
<211> LENGTH: 185
<212> TYPE: DNA
<213> ORGANISM: Candida famata

<400> SEQUENCE: 282
catcacytta gaagcyacca acgaacactt cagattratc tatgaygtca agggtagatt 60
cactgtccac agaatcacyg ctgaagaagc ttcttacaag ttagcyaagg tcaagaaggt 120
ccaattaggt aagagaggta ttccatacgy tgtyacwcac gayggtagaa ctatcagata 180
cccag 185

<210> SEQ ID NO 283
<211> LENGTH: 185
<212> TYPE: RNA
<213> ORGANISM: Candida famata

<400> SEQUENCE: 283
caucacyuua gaagcyacca acgaacacuu cagauurauc uaugayguca aggguagauu 60
cacuguccac agaaucacyg cugaagaagc uucuuacaag uuagcyaagg ucaagaaggu 120
ccaauuaggu aagagaggua uuccauacgy uguyacwcac gaygguagaa cuaucagaua 180
cccag 185

<210> SEQ ID NO 284
<211> LENGTH: 185
<212> TYPE: DNA
<213> ORGANISM: Candida famata

<400> SEQUENCE: 284
catcacttta gaagcyacca acgaacactt cagattaatc taygaygtca agggtagatt 60
cactgtycac agaatcaccg cygaagaagc ttcttacaag ttagctaagg tyaagaaggt 120
ycaattaggt aagagrggta ttccatacgt tgtyacccac gatggtagaa ctatcagata 180
cccag 185

<210> SEQ ID NO 285
<211> LENGTH: 185
<212> TYPE: RNA
<213> ORGANISM: Candida famata

<400> SEQUENCE: 285
caucacuuua gaagcyacca acgaacacuu cagauuaauc uaygayguca aggguagauu 60
cacuguycac agaaucaccg cygaagaagc uucuuacaag uuagcuaagg uyaagaaggu 120
ycaauuaggu aagagrggua uuccauacgu uguyacccac gaugguagaa cuaucagaua 180
cccag 185

<210> SEQ ID NO 286
<211> LENGTH: 185
<212> TYPE: DNA
<213> ORGANISM: Candida famata

<400> SEQUENCE: 286
catcacytta gaagcyacca acgaacactt cagattratc tatgaygtca agggtagatt 60
cactgtccac agaatcacyg ctgaagaagc ttcttacaag ttagcyaagg tcaagaaggt 120
ccaattaggt aagagaggta ttccataygy tgtyacwcac gayggtagaa ctatcagata 180
cccag 185

<210> SEQ ID NO 287
<211> LENGTH: 185
<212> TYPE: RNA
<213> ORGANISM: Candida famata

<400> SEQUENCE: 287
caucacyuua gaagcyacca acgaacacuu cagauurauc uaugayguca aggguagauu 60
cacuguccac agaaucacyg cugaagaagc uucuuacaag uuagcyaagg ucaagaaggu 120
ccaauuaggu aagagaggua uuccauaygy uguyacwcac gaygguagaa cuaucagaua 180
cccag 185

<210> SEQ ID NO 288
<211> LENGTH: 177
<212> TYPE: DNA
<213> ORGANISM: Candida famata

<400> SEQUENCE: 288
catcacttta gaagcyacca acgaacactt cagattratc tatgaygtca agggtagatt 60
cactgtccac agaatcacyg ctgaagaagc ttcttacaag ttagcyaagg tcaagaaggt 120
ccaattaggt aagagaggta ttccatacgt tgtyacmcac gayggtagaa ctatcag 177

<210> SEQ ID NO 289
<211> LENGTH: 177
<212> TYPE: RNA
<213> ORGANISM: Candida famata

<400> SEQUENCE: 289
caucacuuua gaagcyacca acgaacacuu cagauurauc uaugayguca aggguagauu 60
cacuguccac agaaucacyg cugaagaagc uucuuacaag uuagcyaagg ucaagaaggu 120
ccaauuaggu aagagaggua uuccauacgu uguyacmcac gaygguagaa cuaucag 177

<210> SEQ ID NO 290
<211> LENGTH: 182
<212> TYPE: DNA
<213> ORGANISM: Candida haemulonii

<400> SEQUENCE: 290
caccttggag gccaccaacg agaacttcag attggtgtac gatgtcaagg gtagattcac 60
tgtccacaga atcaccgctg aggaggcttc ctacaagctc ggtaaggtca rgaagatcgc 120
tttgggtaag agaggtgttc catacgttgt cacccacgac ggtagaacta tcagataccc 180
ag 182

<210> SEQ ID NO 291
<211> LENGTH: 182
<212> TYPE: RNA
<213> ORGANISM: Candida haemulonii

<400> SEQUENCE: 291
caccuuggag gccaccaacg agaacuucag auuggugjuac gaugucaagg guagauucac 60
uguccacaga aucaccgcug aggaggcuuc cuacaagcuc gguaagguca rgaagaucgc 120
uuuggguaag agagguguuc cauacguugu cacccacgac gguagaacua ucagauaccc 180
ag 182

<210> SEQ ID NO 292
<211> LENGTH: 182
<212> TYPE: DNA
<213> ORGANISM: Candida haemulonii

<400> SEQUENCE: 292
caccttggag gccaccaacg agaacttcag attggtgtac gaygtcaagg gtagattcac 60
tgtccacaga atcaccgctg aggaggcttc ttacaagctc ggtaaggtca gaaagatcgc 120
yttgggtaag agaggtatyc catacgttgt cacccacgac ggtagaacta tcagataccc 180
ag 182

<210> SEQ ID NO 293
<211> LENGTH: 182
<212> TYPE: RNA
<213> ORGANISM: Candida haemulonii

<400> SEQUENCE: 293
caccuuggag gccaccaacg agaacuucag auuggugjuac gaygucaagg guagauucac 60
uguccacaga aucaccgcug aggaggcuuc uuacaagcuc gguaagguca gaaagaucgc 120
yuuggguaag agagguauyc cauacguugu cacccacgac gguagaacua ucagauaccc 180
ag 182

<210> SEQ ID NO 294
<211> LENGTH: 185
<212> TYPE: DNA
<213> ORGANISM: Candida pulcherrima

<400> SEQUENCE: 294
gatcactttg gaggcyacca acgagaactt yagattgatc taygacgtva agggtagatt 60
yactgtgcac agaatcacsr ccgaggaggs ctcktacaag ttgggyaagg tcagaaagat 120
cgccttgggy aagagaggyg tkccttacgc ygtsacccac gacggtagaa ctatcagata 180
cccag 185

<210> SEQ ID NO 295
<211> LENGTH: 185
<212> TYPE: RNA
<213> ORGANISM: Candida pulcherrima

<400> SEQUENCE: 295
gaucacuuug gaggcyacca acgagaacuu yagauugauc uaygacguva aggguagauu 60
yacugugcac agaaucacsr ccgaggaggs cuckuacaag uugggyaagg ucagaaagau 120
cgccuugggy aagagaggyg ukccuuacgc ygusacccac gacgguagaa cuaucagaua 180
cccag 185

<210> SEQ ID NO 296
<211> LENGTH: 185
<212> TYPE: DNA
<213> ORGANISM: Candida pulcherrima

<400> SEQUENCE: 296
gatcactttg gaggcyacca acgagaactt cagattgatc taygacgtma agggtagatt 60
yactgtgcac agaatcaccg ccgaggaggs ctcktacaag ttgggyaagg tcagaaagat 120
ygccttgggy aagagaggyg tkccttacgc ygtvacycac gacggtagaa ctatcagata 180
cccag 185

<210> SEQ ID NO 297
<211> LENGTH: 185
<212> TYPE: RNA
<213> ORGANISM: Candida pulcherrima

<400> SEQUENCE: 297
gaucacuuug gaggcyacca acgagaacuu cagauugauc uaygacguma aggguagauu 60
yacugugcac agaaucaccg ccgaggaggs cuckuacaag uugggyaagg ucagaaagau 120
ygccuugggy aagagaggyg ukccuuacgc yguvacycac gacgguagaa cuaucagaua 180
cccag 185

<210> SEQ ID NO 298
<211> LENGTH: 185
<212> TYPE: DNA
<213> ORGANISM: Candida pulcherrima

<400> SEQUENCE: 298
gatcactttg gaggcyacca acgagaactt yagattgatc taygacgtva agggtagatt 60
yactgtgcac agaatcaccg ccgaggaggs ctcktacaag ttgggyaagg tcagaaagat 120
cgccttgggy aagagaggyg tkccttacgc ygtsacycac gacggtagaa ctatcagata 180
cccag 185

<210> SEQ ID NO 299
<211> LENGTH: 185
<212> TYPE: RNA
<213> ORGANISM: Candida pulcherrima

<400> SEQUENCE: 299
gaucacuuug gaggcyacca acgagaacuu yagauugauc uaygacguva aggguagauu 60
yacugugcac agaaucaccg ccgaggaggs cuckuacaag uugggyaagg ucagaaagau 120
cgccuugggy aagagaggyg ukccuuacgc ygusacycac gacgguagaa cuaucagaua 180
cccag 185

<210> SEQ ID NO 300
<211> LENGTH: 185
<212> TYPE: DNA
<213> ORGANISM: Candida pulcherrima

<400> SEQUENCE: 300
gatcactttg gaggccacca acragaactt cagattgatc taygacgtma agggtagatt 60
cacygtgcac agaatcaccg ccgaggaggc ctcktacaag ttgggyaagg tcagaaagat 120
cgccttgggy aagagaggyg tkccttacgc ygtmacycac gacggtagaa ctatcagata 180
cccag 185

<210> SEQ ID NO 301
<211> LENGTH: 185
<212> TYPE: RNA
<213> ORGANISM: Candida pulcherrima

<400> SEQUENCE: 301
gaucacuuug gaggccacca acragaacuu cagauugauc uaygacguma aggguagauu 60
cacygugcac agaaucaccg ccgaggaggc cuckuacaag uugggyaagg ucagaaagau 120
cgccuugggy aagagaggyg ukccuuacgc ygumacycac gacgguagaa cuaucagaua 180
cccag 185

<210> SEQ ID NO 302
<211> LENGTH: 185
<212> TYPE: DNA
<213> ORGANISM: Candida pulcherrima

<400> SEQUENCE: 302
gatcactttg gaggccacca acgagaactt yagattgatc taygacgtsa agggtagatt 60
yactgtgcac agaatcaccg ccgaggaggs ctcktacaag ttgggyaagg tcagaaagat 120
ygccttgggy aagagwggyg tkccttacgc ygtsacycac gacggtagaa ctatcagata 180
cccag 185

<210> SEQ ID NO 303
<211> LENGTH: 185
<212> TYPE: RNA
<213> ORGANISM: Candida pulcherrima

<400> SEQUENCE: 303
gaucacuuug gaggccacca acgagaacuu yagauugauc uaygacgusa aggguagauu 60
yacugugcac agaaucaccg ccgaggaggs cuckuacaag uugggyaagg ucagaaagau 120
ygccuugggy aagagwggyg ukccuuacgc ygusacycac gacgguagaa cuaucagaua 180
cccag 185

<210> SEQ ID NO 304
<211> LENGTH: 179
<212> TYPE: DNA
<213> ORGANISM: Candida utilis

<400> SEQUENCE: 304
cttggaggcc accaacgaga acttcagatt ggtctacgat gtcaagggta gatttgctgt 60
ccacagaatc accgatgatg aagcttctta caagcttgct aaggtcaaga aggttcaatt 120
gggtaagaga ggtatcccat acgttgttac ccacgacggt agaactatca gatacccag 179

<210> SEQ ID NO 305
<211> LENGTH: 179
<212> TYPE: RNA
<213> ORGANISM: Candida utilis

<400> SEQUENCE: 305
cuuggaggcc accaacgaga acuucagauu ggucuacgau gucaagggua gauuugcugu 60
ccacagaauc accgaugaug aagcuucuua caagcuugcu aaggucaaga agguucaauu 120
ggguaagaga gguaucccau acguuguuac ccacgacggu agaacuauca gauacccag 179

<210> SEQ ID NO 306

<211> LENGTH: 179
<212> TYPE: DNA
<213> ORGANISM: Candida utilis

<400> SEQUENCE: 306
cttggaggcc accaacgaga acttcagatt ggtctacgat gtcaagggta gatttgctgt 60
ccacagaatc accgatgatg aagcttctta caagcttgct aaggtcaaga aggttcartt 120
gggtaagaga ggtatcccat acgttgttac ccacgacggt agaactatca gatacccag 179

<210> SEQ ID NO 307
<211> LENGTH: 179
<212> TYPE: RNA
<213> ORGANISM: Candida utilis

<400> SEQUENCE: 307
cuuggaggcc accaacgaga acuucagauu ggucuacgau gucaagggua gauuugcugu 60
ccacagaauc accgaugaug aagcuucuua caagcuugcu aaggucaaga agguucaruu 120
ggguaagaga gguaucccau acguuguuac ccacgacggu agaacuauca gauacccag 179

<210> SEQ ID NO 308
<211> LENGTH: 182
<212> TYPE: DNA
<213> ORGANISM: Candida kefyr

<400> SEQUENCE: 308
caccttggac rctaccaamg aaaacttcag attggtctac gacgttaagg gtagattcgc 60
tgtccaccgt atcaccgacg aagaagcttc ttacaaattg ggtaaggtca gaaaggtcca 120
actaggtaag aagggtattc catacgttgt tacccacgac ggtagaacta tcagataccc 180
ag 182

<210> SEQ ID NO 309
<211> LENGTH: 182
<212> TYPE: RNA
<213> ORGANISM: Candida kefyr

<400> SEQUENCE: 309
caccuuggac rcuaccaamg aaaacuucag auuggucuac gacguuaagg guagauucgc 60
uguccaccgu aucaccgacg aagaagcuuc uuacaaauug gguaagguca gaaaggucca 120
acuagguaag aaggguauuc cauacguugu uacccacgac gguagaacua ucagauaccc 180
ag 182

<210> SEQ ID NO 310
<211> LENGTH: 185
<212> TYPE: DNA
<213> ORGANISM: Candida kefyr

<400> SEQUENCE: 310
tgtcaccttg gacgctacca acgaaaactt cagattggtc tacgacgtta agggtagatt 60
cgctgtccac cgtatcaccg acgaagaagc ttcttacaaa ttgggtaagg tcagaaaggt 120
ccaactaggt aagaagggta ttccatacgt tgttacccac gacggtagaa cyatcagata 180
cccag 185

<210> SEQ ID NO 311
<211> LENGTH: 185
<212> TYPE: RNA
<213> ORGANISM: Candida kefyr

<400> SEQUENCE: 311
ugucaccuug gacgcuacca acgaaaacuu cagauugguc uacgacguua aggguagauu 60
cgcuguccac cguaucaccg acgaagaagc uucuuacaaa uuggguaagg ucagaaaggu 120
ccaacuaggu aagaagggua uuccauacgu uguuacccac gacgguagaa cyaucagaua 180
cccag 185

<210> SEQ ID NO 312
<211> LENGTH: 186
<212> TYPE: DNA
<213> ORGANISM: Candida viswanathii

<400> SEQUENCE: 312
catcaccttg gaagccacca acgaacactt cagattggtc tacgacgtca agggtagatt 60
tgctgtccac agaatctccg ctgaagaagc ytcctacaag ttgggcaagg tcaagaaggt 120
tgcyttgggt aagaagggtg ttccttacgt tgtcacccac gacggtagaa ctatcagata 180
cccaga 186

<210> SEQ ID NO 313
<211> LENGTH: 186
<212> TYPE: RNA
<213> ORGANISM: Candida viswanathii

<400> SEQUENCE: 313
caucaccuug gaagccacca acgaacacuu cagauugguc uacgacguca aggguagauu 60
ugcuguccac agaaucuccg cugaagaagc yuccuacaag uugggcaagg ucaagaaggu 120
ugcyuugggu aagaagggug uuccuuacgu ugucacccac gacgguagaa cuaucagaua 180
cccaga 186

<210> SEQ ID NO 314
<211> LENGTH: 186
<212> TYPE: DNA
<213> ORGANISM: Candida viswanathii

<400> SEQUENCE: 314
yaytactttg gaagccacya atgaaaactt tagattgatt tacgatgtca aaggtagatt 60
tgctgtccac agaatctcag ctgaagaagc cacttacaaa ttgggtaaag tcaagagagt 120
ccaattgggt aagaagggaa tcccatacgt tgtcacccac gatggtagaa ctatcagata 180
cccaga 186

<210> SEQ ID NO 315
<211> LENGTH: 186
<212> TYPE: RNA
<213> ORGANISM: Candida viswanathii

<400> SEQUENCE: 315
yayuacuuug gaagccacya augaaaacuu uagauugauu uacgauguca aagguagauu 60
ugcuguccac agaaucucag cugaagaagc cacuuacaaa uuggguaaag ucaagagagu 120
ccaauugggu aagaagggaa ucccauacgu ugucacccac gaugguagaa cuaucagaua 180
cccaga 186

<210> SEQ ID NO 316
<211> LENGTH: 180
<212> TYPE: DNA

<213> ORGANISM: Candida zeylanoides

<400> SEQUENCE: 316
tcttgaggct accaacgagc acttcagatt ggtgtacgac gtcaagggta gattcgccgt 60
gcacagaatc accgccgagg agtccaccta caagttggcc aagatcaaga aggtccagtt 120
gggcaagaag agtatcccct acgccgtcac ccacgacggt agaactatca gatacccaga 180

<210> SEQ ID NO 317
<211> LENGTH: 180
<212> TYPE: RNA
<213> ORGANISM: Candida zeylanoides

<400> SEQUENCE: 317
ucuugaggcu accaacgagc acuucagauu gguguacgac gucaagggua gauucgccgu 60
gcacagaauc accgccgagg aguccaccua caaguuggcc aagaucaaga agguccaguu 120
gggcaagaag aguaucccu acgccgucac ccacgacggu agaacuauca gauacccaga 180

<210> SEQ ID NO 318
<211> LENGTH: 182
<212> TYPE: DNA
<213> ORGANISM: Candida zeylanoides

<400> SEQUENCE: 318
tctctcttga gccaccaayg agcacttcag attggtgtay gacgtmaagg gtagattygc 60
ygtgcacaga atcaccgckg aggagtcsam ytacaagttg gccaaratca agaaggtkca 120
sttrggcaag aaragcatcc cytacgcygt cacccaygay ggyagaacta tcagataccc 180
ag 182

<210> SEQ ID NO 319
<211> LENGTH: 182
<212> TYPE: RNA
<213> ORGANISM: Candida zeylanoides

<400> SEQUENCE: 319
ucucucuuga gccaccaayg agcacuucag auugguguay gacgumaagg guagauuygc 60
ygugcacaga aucaccgckg aggagucsam yuacaaguug gccaarauca agaaggukca 120
suurggcaag aaragcaucc cyuacgcygu cacccaygay ggyagaacua ucagauaccc 180
ag 182

<210> SEQ ID NO 320
<211> LENGTH: 182
<212> TYPE: DNA
<213> ORGANISM: Candida zeylanoides

<400> SEQUENCE: 320
tctctcttga gccaccaayg agcacttcag attggtgtay gacgtmaagg gtagattygc 60
ygtgcacaga atcaccgcsg aggagtcsam ytacaagttg gccaaratca agaaggtkca 120
sttrggcaag aaragcatcc cytacgcygt cacccaygay ggyagaacta tcagataccc 180
ag 182

<210> SEQ ID NO 321
<211> LENGTH: 182
<212> TYPE: RNA
<213> ORGANISM: Candida zeylanoides

<400> SEQUENCE: 321
ucucucuuga gccaccaayg agcacuucag auugguguay gacgumaagg guagauuygc 60
ygugcacaga aucaccgcsg aggagucsam yuacaaguug gccaarauca agaaggukca 120
suurggcaag aaragcaucc cyuacgcygu cacccaygay ggyagaacua ucagauaccc 180
ag 182

<210> SEQ ID NO 322
<211> LENGTH: 182
<212> TYPE: DNA
<213> ORGANISM: Candida zeylanoides

<400> SEQUENCE: 322
tctctcttga gccwccaacg agcacttcag attggtgtac gacgtcaagg gtagattcgc 60
cgtgcacaga atcaccgccg aggagtccac ctacaagttg gccaagatca agaaggtcca 120
gttgggcaag aagagtatcc cctacgccgt cacccacgac ggtagaacta tcagataccc 180
ag 182

<210> SEQ ID NO 323
<211> LENGTH: 182
<212> TYPE: RNA
<213> ORGANISM: Candida zeylanoides

<400> SEQUENCE: 323
ucucucuuga gccwccaacg agcacuucag auugguguac gacgucaagg guagauucgc 60
cgugcacaga aucaccgccg aggaguccac cuacaaguug gccaagauca agaaggucca 120
guugggcaag aagaguaucc ccuacgccgu cacccacgac gguagaacua ucagauaccc 180
ag 182

<210> SEQ ID NO 324
<211> LENGTH: 171
<212> TYPE: DNA
<213> ORGANISM: Candida zeylanoides

<400> SEQUENCE: 324
ctaccaacra acacttcaga ttgatttacg atgttaaagg taaattcgct gttcacagaa 60
tttctgctga agaagcttct tacaaattag gtaaagtcaa gaaggttcaa ttaggtaaaa 120
aaggtgttcc atacgttgtc acccacgatg gtagaactat cagataccca g 171

<210> SEQ ID NO 325
<211> LENGTH: 171
<212> TYPE: RNA
<213> ORGANISM: Candida zeylanoides

<400> SEQUENCE: 325
cuaccaacra acacuucaga uugauuuacg auguuaaagg uaaauucgcu guucacagaa 60
uuucugcuga agaagcuucu uacaaauuag guaaagucaa gaagguucaa uuagguaaaa 120
aagguguucc auacguuguc acccacgaug guagaacuau cagauaccca g 171

<210> SEQ ID NO 326
<211> LENGTH: 299
<212> TYPE: DNA
<213> ORGANISM: Aspergillus fumigatus

<400> SEQUENCE: 326
gtcgctcagc gccgcatcct gccccgcccc aagcgctctg tcaactcccg caccaaccag 60

-continued

```
aagcagaagc gtcctcgctc tcgcaccctg accgctgtcc acgacgccat cctcaacgac    120

ctcgtttacc ccgtcgagat cgtcggcaag cgtatccgca ccaaggagga cggcagcaag    180

actctcaagg tcgttctgga cgagaaggag cgtggtggtg ttgaccacag actcgatgcc    240

tacggcgagg tttaccgccg actaaccggc cgctctgttg ttttcgagtt cccccagag     299
```

```
<210> SEQ ID NO 327
<211> LENGTH: 299
<212> TYPE: RNA
<213> ORGANISM: Aspergillus fumigatus

<400> SEQUENCE: 327

gucgcucagc gccgcauccu gccccgcccc aagcgcucug ucaacucccg caccaaccag     60

aagcagaagc guccucgcuc ucgcacccug accgcugucc acgacgccau ccucaacgac    120

cucguuuacc ccgucgagau cgucggcaag cguauccgca ccaaggagga cggcagcaag    180

acucucaagg ucguucugga cgagaaggag cguggugwug uugaccacag acucgaugcc    240

uacggcgagg uuuaccgccg acuaaccggc cgcucuguug uuuucgaguu cccccagag     299
```

```
<210> SEQ ID NO 328
<211> LENGTH: 300
<212> TYPE: DNA
<213> ORGANISM: Aspergillus fumigatus

<400> SEQUENCE: 328

cgtcgctcag cgccgcatcc tgccccgccc caagcgctct gtcaactccc gcaccaacca     60

gaagcagaag cgtcctcgct ctcgcaccct gaccgctgtc cacgacgcca tcctcaccga    120

cctcgtttac cccgtcgaga tcgtcggcaa gcgtatccgc accaaggagg acggcagcaa    180

gactctcaag gtcatcctgg acgagaagga gcgtggtggt gttgaccaca gactcgatgc    240

ctacggcgag gtttaccgcc gactaaccgg ccgctctgtt gtcttcgagt tcccccagag    300
```

```
<210> SEQ ID NO 329
<211> LENGTH: 300
<212> TYPE: RNA
<213> ORGANISM: Aspergillus fumigatus

<400> SEQUENCE: 329

cgucgcucag cgccgcaucc ugccccgccc caagcgcucu gucaacuccc gcaccaacca     60

gaagcagaag cguccucgcu cucgcacccu gaccgcuguc cacgacgcca uccucaccga    120

ccucguuuac cccgucgaga ucgucggcaa gcguauccgc accaaggagg acggcagcaa    180

gacucucaag gucauccugg acgagaagga gcgugguggu guugaccaca gacucgaugc    240

cuacggcgag guuuaccgcc gacuaaccgg ccgcucuguu gucuucgagu ucccccagag    300
```

```
<210> SEQ ID NO 330
<211> LENGTH: 300
<212> TYPE: DNA
<213> ORGANISM: Aspergillus fumigatus

<400> SEQUENCE: 330

tgttgctcag cgccgcatcc tgccccgccc taagcgctct gtcaactccc gcaccaacca     60

gaagcagaag cgtcctcgct ctcgcaccct gaccgctgtc cacgacgcca tcctcaacga    120

cctcgtttac cccgtcgaga tcgtcggcaa gcgtatccgc accaaggagg acggcagcaa    180

gactctcaag gtcatcctgg acgagaagga gcgtggtggt gttgaccaca gactcgatgc    240

ctacggcgag gtttaccgcc gactaaccgg ccgctctgtt gtcttcgagt tcccccagag    300
```

<210> SEQ ID NO 331
<211> LENGTH: 300
<212> TYPE: RNA
<213> ORGANISM: Aspergillus fumigatus

<400> SEQUENCE: 331
uguugcucag cgccgcaucc ugccccgccc uaagcgcucu gucaacuccc gcaccaacca 60
gaagcagaag cguccucgcu cucgcacccu gaccgcuguc cacgacgcca uccucaacga 120
ccucguuuac cccgucgaga ucgucggcaa gcguauccgc accaaggagg acggcagcaa 180
gacucucaag gucauccugg acgagaagga gcgugguggu guugaccaca gacucgaugc 240
cuacggcgag guuuaccgcc gacuaaccgg ccgcucuguu gucuucgagu ucccccagag 300

<210> SEQ ID NO 332
<211> LENGTH: 300
<212> TYPE: DNA
<213> ORGANISM: Aspergillus fumigatus

<400> SEQUENCE: 332
tgttgctcag cgccgcatcc tgccccgccc taagcgctct gtcaactccc gcaccaacca 60
gaagcagaag cgtcctcgct ctcgcaccct gaccgctgtc cacgacgcca tcctcaacga 120
cctcgtttac cccgtcgaga tcgtcggcaa gcgtatccgc accaaggagg acggcagcaa 180
gactctcaag gtcatcctgg acgagaagga gcgtggtggt gttgaccaca gactcgatgc 240
ctacggcgag gtttaccgcc gactaaccgg ccgctctgtt atcttcgagt tcccccagag 300

<210> SEQ ID NO 333
<211> LENGTH: 300
<212> TYPE: RNA
<213> ORGANISM: Aspergillus fumigatus

<400> SEQUENCE: 333
uguugcucag cgccgcaucc ugccccgccc uaagcgcucu gucaacuccc gcaccaacca 60
gaagcagaag cguccucgcu cucgcacccu gaccgcuguc cacgacgcca uccucaacga 120
ccucguuuac cccgucgaga ucgucggcaa gcguauccgc accaaggagg acggcagcaa 180
gacucucaag gucauccugg acgagaagga gcgugguggu guugaccaca gacucgaugc 240
cuacggcgag guuuaccgcc gacuaaccgg ccgcucuguu aucuucgagu ucccccagag 300

<210> SEQ ID NO 334
<211> LENGTH: 300
<212> TYPE: DNA
<213> ORGANISM: Aspergillus terreus

<400> SEQUENCE: 334
cgttgctcag cgccgcatcc tgccccgccc caagcgctct gtcaactccc gcaccaacca 60
gaagcagaag cgtccccgtt cccgcactct gacggccgtc cacgacgcca tcctcaccga 120
cctcgtctac cccgtcgaga tcgtcggcaa gcgcatccgc accaaggagg acggctccaa 180
gaccctcaag gtcatcctcg acgagaagga gcgcggcggt gtcgaccacc gcctcgatgc 240
ctacggcgag gtctaccgtc gtctcaccgg ccgtgccgtc gtcttcgagt tcccccagag 300

<210> SEQ ID NO 335
<211> LENGTH: 300
<212> TYPE: RNA
<213> ORGANISM: Aspergillus terreus

<400> SEQUENCE: 335
cguugcucag cgccgcaucc ugccccgccc caagcgcucu gucaacuccc gcaccaacca 60
gaagcagaag cguccccguu cccgcacucu gacggccguc cacgacgcca uccucaccga 120
ccucgucuac cccgucgaga ucgucggcaa gcgcauccgc accaaggagg acggcuccaa 180
gacccucaag gucauccucg acgagaagga gcgcggcggu gucgaccacc gccucgaugc 240
cuacggcgag gucuaccguc gucucaccgg ccgugccguc gucuucgagu ucccccagag 300

<210> SEQ ID NO 336
<211> LENGTH: 300
<212> TYPE: DNA
<213> ORGANISM: Aspergillus flavus

<400> SEQUENCE: 336
cgtcgctcag cgccgcatcc tgcccaagcc caagcgctct gtcaactccc gcaccaacca 60
gaagcagaag cgtccccgtt cccgcactct gactgctgtc cacgacgcca tcctcggcga 120
cctggtctac cccgttgaga tcgtcggcaa gcgcatccgc accaaggagg atggcagcaa 180
gaccctcaag gtcatcctgg atgagaagga gcgtggtggt gttgaccacc gtctcgatgc 240
ctacggcgag gtctaccgcc gtttgaccgg ccgcaacgtc gtcttcgagt tcccccagag 300

<210> SEQ ID NO 337
<211> LENGTH: 300
<212> TYPE: RNA
<213> ORGANISM: Aspergillus flavus

<400> SEQUENCE: 337
cgucgcucag cgccgcaucc ugcccaagcc caagcgcucu gucaacuccc gcaccaacca 60
gaagcagaag cguccccguu cccgcacucu gacugcuguc cacgacgcca uccucggcga 120
ccuggucuac cccguugaga ucgucggcaa gcgcauccgc accaaggagg auggcagcaa 180
gacccucaag gucauccugg augagaagga gcgugguggu guugaccacc gucucgaugc 240
cuacggcgag gucuaccgcc guuugaccgg ccgcaacguc gucuucgagu ucccccagag 300

<210> SEQ ID NO 338
<211> LENGTH: 300
<212> TYPE: DNA
<213> ORGANISM: Aspergillus flavus

<400> SEQUENCE: 338
cgtcgctcag cgccgcatcc tgcccaagcc caagcgctct gtcaactccc gcaccaacca 60
gaagcagaag cgtccccgtt cccgcactct gactgctgtc cacgacgcca tcctcggcga 120
cctggtctac cccgttgaga tcgtcggcaa gcgcatccgc accaaggagg acggcagcaa 180
gaccctcaag gtcatcctgg atgagaagga gcgtggtggt gttgaccacc gtctcgatgc 240
ctacggcgag gtctaccgcc gtttgaccgg ccgcaacgtc gtcttcgagt tcccccagag 300

<210> SEQ ID NO 339
<211> LENGTH: 300
<212> TYPE: RNA
<213> ORGANISM: Aspergillus flavus

<400> SEQUENCE: 339
cgucgcucag cgccgcaucc ugcccaagcc caagcgcucu gucaacuccc gcaccaacca 60
gaagcagaag cguccccguu cccgcacucu gacugcuguc cacgacgcca uccucggcga 120
ccuggucuac cccguugaga ucgucggcaa gcgcauccgc accaaggagg acggcagcaa 180
gacccucaag gucauccugg augagaagga gcgugguggu guugaccacc gucucgaugc 240
cuacggcgag gucuaccgcc guuugaccgg ccgcaacguc gucuucgagu ucccccagag 300

<210> SEQ ID NO 340
<211> LENGTH: 300
<212> TYPE: DNA
<213> ORGANISM: Aspergillus nidulans

<400> SEQUENCE: 340
cgtcgctcag cgccgcatcc ttcccaagcc caagcgctcc gtcaactccc gcaccaacca 60
gaagcagaag cgcccccgtt cccgtaccct cactgctgtt cacgatgcca tccttgacga 120
cctcgtctac cccgttgaga ttgtcggcaa gcgcatccgc accaaggagg acggctccaa 180
gactctcaag gttatcctcg acgagaagga gcgtggtggt gttgaccacc gcctcgacgc 240
ctacggcgag gtctaccgtc gtctgacggg tcgtgctgtc gttttcgagt tcccccagag 300

<210> SEQ ID NO 341
<211> LENGTH: 300
<212> TYPE: RNA
<213> ORGANISM: Aspergillus nidulans

<400> SEQUENCE: 341
cgucgcucag cgccgcaucc uucccaagcc caagcgcucc gucaacuccc gcaccaacca 60
gaagcagaag cgcccccguu cccguacccu cacugcuguu cacgaugcca uccuugacga 120
ccucgucuac cccguugaga uugucggcaa gcgcauccgc accaaggagg acggcuccaa 180
gacucucaag guuauccucg acgagaagga gcgugguggu guugaccacc gccucgacgc 240
cuacggcgag gucuaccguc gucugacggg ucgugcuguc guuuucgagu ucccccagag 300

<210> SEQ ID NO 342
<211> LENGTH: 300
<212> TYPE: DNA
<213> ORGANISM: Aspergillus nidulans

<400> SEQUENCE: 342
cgtcgctcag cgccgcatcc tccccaagcc caagcgctcc gtcaactccc gcaccaacca 60
gaagcagaag cgcccccgtt cccgtaccct tactgccgtt cacgacgcca tcctcgacga 120
cctcgtctac cccgttgaga ttgtcggcaa gcgcatccgc accaaggagg acggctccaa 180
gaccctcaag gtcatcctcg acgagaagga gcgtggtggt gttgaccacc gcctcgacgc 240
ctacggcgag gtctaccgtc gtctgacggg tcgtgctgtc gttttcgagt tcccccagag 300

<210> SEQ ID NO 343
<211> LENGTH: 300
<212> TYPE: RNA
<213> ORGANISM: Aspergillus nidulans

<400> SEQUENCE: 343
cgucgcucag cgccgcaucc uccccaagcc caagcgcucc gucaacuccc gcaccaacca 60
gaagcagaag cgcccccguu cccguacccu uacugccguu cacgacgcca uccucgacga 120
ccucgucuac cccguugaga uugucggcaa gcgcauccgc accaaggagg acggcuccaa 180
gacccucaag gucauccucg acgagaagga gcgugguggu guugaccacc gccucgacgc 240
cuacggcgag gucuaccguc gucugacggg ucgugcuguc guuuucgagu ucccccagag 300

<210> SEQ ID NO 344

<211> LENGTH: 300
<212> TYPE: DNA
<213> ORGANISM: Aspergillus nidulans

<400> SEQUENCE: 344
cgtcgctcag cgccgcatcc tccccaagcc caagcgctcc gtcaactccc gcaccaacca 60
gaagcagaag cgcccccgtt cccgtaccct tactgccgtt cacgacgcca tcctcgacga 120
cctcgtctac cccgttgaga ttgtcggcaa gcgcatccgc accaaggagg acggctccaa 180
gaccctcaag gtcatcctcg acgagaagga gcgtggtggt gttgaccacc gcctcgacgc 240
ctacggcgag gtctaccgtc gtctgacggg tcgtgctgtc gttttcgagt tcccccagag 300

<210> SEQ ID NO 345
<211> LENGTH: 300
<212> TYPE: RNA
<213> ORGANISM: Aspergillus nidulans

<400> SEQUENCE: 345
cgucgcucag cgccgcaucc uccccaagcc caagcgcucc gucaacuccc gcaccaacca 60
gaagcagaag cgcccccguu cccguacccu uacugccguu cacgacgcca uccucgacga 120
ccucgucuac cccguugaga uugucggcaa gcgcauccgc accaaggagg acggcuccaa 180
gacccucaag gucauccucg acgagaagga gcgugguggu guugaccacc gccucgacgc 240
cuacggcgag gucuaccguc gucugacggg ucgugcuguc guuuucgagu ucccccagag 300

<210> SEQ ID NO 346
<211> LENGTH: 300
<212> TYPE: DNA
<213> ORGANISM: Aspergillus versicolor

<400> SEQUENCE: 346
cgtcgctcag cgccgcatcc ttcccaagcc caagcgctcc gtcaactctc gcaccaacca 60
gaagcagaag cgccctcgtt ctcgcaccct gacggctgtc cacgactcca tccttgacga 120
cctcgtctac cccgttgaga tcgtcggcaa gcgtacccgc accaaggagg acggcagcaa 180
gacgctcaag gtcatcctcg acgagaagga gcgcggcggc gttgaccacc gcctcgacgc 240
ctacggcgag gtctaccgtc gtttgaccgg tcgtgctgtt gttttcgagt tcccccagag 300

<210> SEQ ID NO 347
<211> LENGTH: 300
<212> TYPE: RNA
<213> ORGANISM: Aspergillus versicolor

<400> SEQUENCE: 347
cgucgcucag cgccgcaucc uucccaagcc caagcgcucc gucaacucuc gcaccaacca 60
gaagcagaag cgcccucguu cucgcacccu gacggcuguc cacgacucca uccuugacga 120
ccucgucuac cccguugaga ucgucggcaa gcguacccgc accaaggagg acggcagcaa 180
gacgcucaag gucauccucg acgagaagga gcgcggcggc guugaccacc gccucgacgc 240
cuacggcgag gucuaccguc guuugaccgg ucgugcuguu guuuucgagu ucccccagag 300

<210> SEQ ID NO 348
<211> LENGTH: 300
<212> TYPE: DNA
<213> ORGANISM: Aspergillus versicolor

<400> SEQUENCE: 348
cgtcgctcag cgccgcatcc ttcctaagcc caagcgctcc gtcaactccc gcaccaacca 60
gaagcagaag cgccctcgtt ctcgcactct gacggctgtc cacgactcca tccttgacga 120
cctcgtctac cccgttgaga tcgtcggcaa gcgtacccgc accaaggagg acggcagcaa 180
gacgctcaag gtcatcctcg acgagaagga gcgcggcggc gttgaccacc gcctcgacgc 240
ctacggcgag gtctaccgtc gtttgaccgg tcgtgctgtt gttttcgagt tcccccagag 300

<210> SEQ ID NO 349
<211> LENGTH: 300
<212> TYPE: RNA
<213> ORGANISM: Aspergillus versicolor

<400> SEQUENCE: 349
cgucgcucag cgccgcaucc uuccuaagcc caagcgcucc gucaacuccc gcaccaacca 60
gaagcagaag cgcccucguu cucgcacucu gacggcuguc cacgacucca uccuugacga 120
ccucgucuac cccguugaga ucgucggcaa gcguacccgc accaaggagg acggcagcaa 180
gacgcucaag gucauccucg acgagaagga gcgcggcggc guugaccacc gccucgacgc 240
cuacggcgag gucuaccguc guuugaccgg ucgugcuguu guuuucgagu ucccccagag 300

<210> SEQ ID NO 350
<211> LENGTH: 300
<212> TYPE: DNA
<213> ORGANISM: Aspergillus versicolor

<400> SEQUENCE: 350
cgtcgctcag cgccgcatcc ttcctaagcc taagcgctcc gtcaactccc gcaccaacca 60
gaagcagaag cgcccccgtt cccgcaccct gacggccgtc cacgatgcta tccttgacga 120
cctcgtctac cccgttgaga tcgtcggcaa gcgtacccgc accaaggagg acggcagcaa 180
gacgctcaag atcatcctcg acgagaagga gcgcggcggc gttgaccacc gccttgacgc 240
ctacggcgag gtctaccgtc gtttgactgg tcgtgctgtt gttttcgagt tcccccagag 300

<210> SEQ ID NO 351
<211> LENGTH: 300
<212> TYPE: RNA
<213> ORGANISM: Aspergillus versicolor

<400> SEQUENCE: 351
cgucgcucag cgccgcaucc uuccuaagcc uaagcgcucc gucaacuccc gcaccaacca 60
gaagcagaag cgcccccguu cccgcacccu gacggccguc cacgaugcua uccuugacga 120
ccucgucuac cccguugaga ucgucggcaa gcguacccgc accaaggagg acggcagcaa 180
gacgcucaag aucauccucg acgagaagga gcgcggcggc guugaccacc gccuugacgc 240
cuacggcgag gucuaccguc guuugacugg ucgugcuguu guuuucgagu ucccccagag 300

<210> SEQ ID NO 352
<211> LENGTH: 300
<212> TYPE: DNA
<213> ORGANISM: Aspergillus versicolor

<400> SEQUENCE: 352
cgtcgctcag cgccgcatcc ttcctaagcc caagcgctcc gtcaactccc gcaccaacca 60
gaagcagaag cgcccccgtt cccgcaccct gacggccgtc cacgatgcca tccttgacga 120
cctcgtctac cccgttgaga tcgtcggcaa gcgtacccgc accaaggagg acggcagcaa 180
gacgctcaag atcatcctcg acgagaagga gcgcggcggc gttgaccacc gccttgacgc 240
ctacggcgag gtctaccgtc gtttgactgg tcgtgctgtt gttttcgagt tcccccagag 300

<210> SEQ ID NO 353
<211> LENGTH: 300
<212> TYPE: RNA
<213> ORGANISM: Aspergillus versicolor

<400> SEQUENCE: 353
cgucgcucag cgccgcaucc uuccuaagcc caagcgcucc gucaacuccc gcaccaacca 60
gaagcagaag cgcccccguu cccgcacccu gacggccguc cacgaugcca uccuugacga 120
ccucgucuac cccguugaga ucgucggcaa gcguacccgc accaaggagg acggcagcaa 180
gacgcucaag aucauccucg acgagaagga gcgcggcggc guugaccacc gccuugacgc 240
cuacggcgag gucuaccguc guuugacugg ucgugcuguu guuuucgagu ucccccagag 300

<210> SEQ ID NO 354
<211> LENGTH: 300
<212> TYPE: DNA
<213> ORGANISM: Aspergillus versicolor

<400> SEQUENCE: 354
cgttgctcag cgccgcatcc ttcctaagcc taagcgctcc gtcaactccc gcaccaacca 60
gaagcagaag cgcccccgtt cccgcaccct gacggccgtc cacgatgcta tccttgacga 120
cctcgtctac cccgttgaga tcgtcggcaa gcgtacccgc accaaggagg acggcagcaa 180
gacgctcaag atcatcctcg acgagaagga gcgcggcggc gttgaccacc gccttgacgc 240
ctacggcgag gtctaccgtc gtttgactgg tcgtgctgtt gttttcgagt tcccccagag 300

<210> SEQ ID NO 355
<211> LENGTH: 300
<212> TYPE: RNA
<213> ORGANISM: Aspergillus versicolor

<400> SEQUENCE: 355
cguugcucag cgccgcaucc uuccuaagcc uaagcgcucc gucaacuccc gcaccaacca 60
gaagcagaag cgcccccguu cccgcacccu gacggccguc cacgaugcua uccuugacga 120
ccucgucuac cccguugaga ucgucggcaa gcguacccgc accaaggagg acggcagcaa 180
gacgcucaag aucauccucg acgagaagga gcgcggcggc guugaccacc gccuugacgc 240
cuacggcgag gucuaccguc guuugacugg ucgugcuguu guuuucgagu ucccccagag 300

<210> SEQ ID NO 356
<211> LENGTH: 300
<212> TYPE: DNA
<213> ORGANISM: Aspergillus clavatus

<400> SEQUENCE: 356
cgtcgctcag cgccgcatcc tgccccgccc caagcgctct gtcaactccc gcaccaacca 60
gaagcagaag cgtcctcgct cccgcaccct gactgccgtt cacgacgcca tcctcaccga 120
cctcgtctac cccgtcgaga tcgtcggcaa gcgcacccgc accaaggagg acggctccaa 180
gaccctcaag gtcgtccttg acgagaagga gcgtggcggt gttgaccaca gactcgatgc 240
ctacggcgag gtctaccgcc gtttaaccgg ccgctccgtt gtcttcgagt tcccccagag 300

<210> SEQ ID NO 357
<211> LENGTH: 300
<212> TYPE: RNA
<213> ORGANISM: Aspergillus clavatus

<400> SEQUENCE: 357
cgucgcucag cgccgcaucc ugccccgccc caagcgcucu gucaacuccc gcaccaacca 60
gaagcagaag cguccucgcu cccgcacccu gacugccguu cacgacgcca uccucaccga 120
ccucgucuac cccgucgaga ucgucggcaa gcgcacccgc accaaggagg acggcuccaa 180
gacccucaag gucguccuug acgagaagga gcguggcggu guugaccaca gacucgaugc 240
cuacggcgag gucuaccgcc guuuaaccgg ccgcuccguu gucuucgagu ucccccagag 300

<210> SEQ ID NO 358
<211> LENGTH: 300
<212> TYPE: DNA
<213> ORGANISM: Aspergillus clavatus

<400> SEQUENCE: 358
cgtcgctcag cgccgcatcc tgccccgccc caagcgctcc gtcaactccc gctccaacca 60
gaagcagaag cgccctcgct cccgcactct gaccgctgtt cacgacgcca tcctcactga 120
tctcgtcttc cccgtcgaga tcgtcggcaa gcgcacccgc accaaggagg acggctccaa 180
gaccctcaag gtcatccttg acgagaagga gcgtggtggt gttgaccaca gactcgatgc 240
ctacggcgag gtctaccgcc gcttaaccgg ccgctccgtt gtcttcgagt tcccccagag 300

<210> SEQ ID NO 359
<211> LENGTH: 300
<212> TYPE: RNA
<213> ORGANISM: Aspergillus clavatus

<400> SEQUENCE: 359
cgucgcucag cgccgcaucc ugccccgccc caagcgcucc gucaacuccc gcuccaacca 60
gaagcagaag cgcccucgcu cccgcacucu gaccgcuguu cacgacgcca uccucacuga 120
ucucgucuuc cccgucgaga ucgucggcaa gcgcacccgc accaaggagg acggcuccaa 180
gacccucaag gucauccuug acgagaagga gcgugguggu guugaccaca gacucgaugc 240
cuacggcgag gucuaccgcc gcuuaaccgg ccgcuccguu gucuucgagu ucccccagag 300

<210> SEQ ID NO 360
<211> LENGTH: 300
<212> TYPE: DNA
<213> ORGANISM: Aspergillus candidus

<400> SEQUENCE: 360
cgtcgctcag cgccgcatcc tgtcgcgccc caagcgctcc gtcaactcgc gcaccaacca 60
gaagcagaag cgcccccgct cgcgcactct gaccgccgtg cacgacaaca tcctgaccga 120
cctggtctac cccgtcgaga tcgtcggcaa gcgcatccgc accaaggagg acggcagcaa 180
gaccctcaag gttatcctgg acgagaagga gcgcggcggc gttgaccacc gcctggacgc 240
ctacggcgag gtctaccgcc gactgacggg ccgcaacgtt gtcttcgagt tcccccagag 300

<210> SEQ ID NO 361
<211> LENGTH: 300
<212> TYPE: RNA
<213> ORGANISM: Aspergillus candidus

<400> SEQUENCE: 361
cgucgcucag cgccgcaucc ugucgcgccc caagcgcucc gucaacucgc gcaccaacca 60
gaagcagaag cgcccccgcu cgcgcacucu gaccgccgug cacgacaaca uccugaccga 120

```
ccuggucuac cccgucgaga ucgucggcaa gcgcauccgc accaaggagg acggcagcaa    180

gacccucaag guuauccugg acgagaagga gcgcggcggc guugaccacc gccuggacgc    240

cuacggcgag gucuaccgcc gacugacggg ccgcaacguu gucuucgagu ucccccagag    300


<210> SEQ ID NO 362
<211> LENGTH: 300
<212> TYPE: DNA
<213> ORGANISM: Aspergillus candidus

<400> SEQUENCE: 362

cgtcgctcag cgccgcatcc tgtcgcgccc caagcgctcc gtcaactcgc gcaccaacca     60

gaagcagaag cgcccccgct cgcgcactct gaccgccgtg cacgacaaca tcctgaccga    120

ccttgtctac cccgtcgaga tcgtcggcaa gcgcgtccgc accaaggagg acggcagcaa    180

gaccctcaag gttatcctgg acgagaagga gcgtggcggc gttgaccacc gtctggacgc    240

ctacggcgag gtctaccgcc gactgacggg ccgcaacgtt gtcttcgagt tcccccagag    300


<210> SEQ ID NO 363
<211> LENGTH: 300
<212> TYPE: RNA
<213> ORGANISM: Aspergillus candidus

<400> SEQUENCE: 363

cgucgcucag cgccgcaucc ugucgcgccc caagcgcucc gucaacucgc gcaccaacca     60

gaagcagaag cgcccccgcu cgcgcacucu gaccgccgug cacgacaaca uccugaccga    120

ccuugucuac cccgucgaga ucgucggcaa gcgcguccgc accaaggagg acggcagcaa    180

gacccucaag guuauccugg acgagaagga gcguggcggc guugaccacc gucuggacgc    240

cuacggcgag gucuaccgcc gacugacggg ccgcaacguu gucuucgagu ucccccagag    300


<210> SEQ ID NO 364
<211> LENGTH: 300
<212> TYPE: DNA
<213> ORGANISM: Aspergillus candidus

<400> SEQUENCE: 364

cgtcgctcag cgccgcatcc tgtcgcgccc caagcgctcc gtcaactcgc gcaccaacca     60

gaagcagaag cgcccccgct cgcgcactct gaccgccgtg cacgacaaca tcctgaccga    120

cctcgtctac cccgtcgaga tcgtcggcaa gcgcgtccgc accaaggagg acggcagcaa    180

gaccctcaag gttatcctgg acgagaagga gcgcggcggc gttgaccacc gcctggacgc    240

ctacggcgag gtctaccgcc gactcaccgg ccgcaacgtt gtcttcgagt tcccccagag    300


<210> SEQ ID NO 365
<211> LENGTH: 300
<212> TYPE: RNA
<213> ORGANISM: Aspergillus candidus

<400> SEQUENCE: 365

cgucgcucag cgccgcaucc ugucgcgccc caagcgcucc gucaacucgc gcaccaacca     60

gaagcagaag cgcccccgcu cgcgcacucu gaccgccgug cacgacaaca uccugaccga    120

ccucgucuac cccgucgaga ucgucggcaa gcgcguccgc accaaggagg acggcagcaa    180

gacccucaag guuauccugg acgagaagga gcgcggcggc guugaccacc gccuggacgc    240

cuacggcgag gucuaccgcc gacucaccgg ccgcaacguu gucuucgagu ucccccagag    300
```

<210> SEQ ID NO 366
<211> LENGTH: 300
<212> TYPE: DNA
<213> ORGANISM: Aspergillus glaucus

<400> SEQUENCE: 366
cgtcgctcag cgccgcatcc tctcccgccc caagcgctcc gtcaactcgc gcaccaacca 60
gacccagaag cgtccccgtt cgcgtactct gaccgctgtc cacgactcca tcctcaccga 120
cctcgtctac cccgtcgaga tcgttggcaa gcgcatccgc accaaggagg acggcagcaa 180
gaccatcaag gttgttctcg acgagaagga gcgcggtggt gttgaccaca gacttgatgc 240
ctacggcgag gtctaccgca gactgaccgg ccgtgccgtt gtcttcgagt tcccccagag 300

<210> SEQ ID NO 367
<211> LENGTH: 300
<212> TYPE: RNA
<213> ORGANISM: Aspergillus glaucus

<400> SEQUENCE: 367
cgucgcucag cgccgcaucc ucucccgccc caagcgcucc gucaacucgc gcaccaacca 60
gacccagaag cguccccguu cgcguacucu gaccgcuguc cacgacucca uccucaccga 120
ccucgucuac cccgucgaga ucguuggcaa gcgcauccgc accaaggagg acggcagcaa 180
gaccaucaag guuguucucg acgagaagga gcgcgguggu guugaccaca gacuugaugc 240
cuacggcgag gucuaccgca gacugaccgg ccgugccguu gucuucgagu ucccccagag 300

<210> SEQ ID NO 368
<211> LENGTH: 300
<212> TYPE: DNA
<213> ORGANISM: Aspergillus glaucus

<400> SEQUENCE: 368
catcgctcag cgccgcatcc tctcccgccc caagcgctcc gtcaactcgc gcaccaacca 60
gacccagaag cgtccccgtt cccgcactct gaccgctgtc cacgactcca tcctcactga 120
cctcgtctac cccgtcgaga tcgttggcaa gcgcatccgc accaaggagg acggcagcaa 180
gaccatcaag gttgttctcg acgagaagga gcgcggtggt gttgaccaca gactcgatgc 240
ctacggcgag gtctaccgca gactgaccgg ccgtgccgtt gtcttcgagt tcccccagag 300

<210> SEQ ID NO 369
<211> LENGTH: 300
<212> TYPE: RNA
<213> ORGANISM: Aspergillus glaucus

<400> SEQUENCE: 369
caucgcucag cgccgcaucc ucucccgccc caagcgcucc gucaacucgc gcaccaacca 60
gacccagaag cguccccguu cccgcacucu gaccgcuguc cacgacucca uccucacuga 120
ccucgucuac cccgucgaga ucguuggcaa gcgcauccgc accaaggagg acggcagcaa 180
gaccaucaag guuguucucg acgagaagga gcgcgguggu guugaccaca gacucgaugc 240
cuacggcgag gucuaccgca gacugaccgg ccgugccguu gucuucgagu ucccccagag 300

<210> SEQ ID NO 370
<211> LENGTH: 300
<212> TYPE: DNA
<213> ORGANISM: Aspergillus glaucus

<400> SEQUENCE: 370

-continued catcgctcag cgccgcatcc tctcccgccc caagcgctcc gtcaactcgc gcaccaacca 60
gacccagaag cgtccccgtt cccgcactct gactgctgtc cacgactcca tcctcaccga 120
cctcgtctac cccgtcgaga tcgttggcaa gcgtatccgc accaaggagg acggcagcaa 180
gaccatcaag gttgttctcg acgagaagga gcgcggtggt gttgaccaca gactcgatgc 240
ctacggcgag gtctaccgca gactgaccgg ccgtgccgtt gtcttcgagt tcccccagag 300

<210> SEQ ID NO 371
<211> LENGTH: 300
<212> TYPE: RNA
<213> ORGANISM: Aspergillus glaucus

<400> SEQUENCE: 371
caucgcucag cgccgcaucc ucucccgccc caagcgcucc gucaacucgc gcaccaacca 60
gacccagaag cguccccguu cccgcacucu gacugcuguc cacgacucca uccucaccga 120
ccucgucuac cccgucgaga ucguuggcaa gcguauccgc accaaggagg acggcagcaa 180
gaccaucaag guuguucucg acgagaagga gcgcggugu guugaccaca gacucgaugc 240
cuacggcgag gucuaccgca gacugaccgg ccgugccguu gucuucgagu ucccccagag 300

<210> SEQ ID NO 372
<211> LENGTH: 297
<212> TYPE: DNA
<213> ORGANISM: Aspergillus glaucus

<400> SEQUENCE: 372
cgctcagcgc cgcatcctct cccgccccaa gcgctccgtc aactcgcgca ccaaccagac 60
ccagaagcgt ccccgttccc gcactctgac cgctgtccac gactccatcc tcaccgacct 120
cgtctacccc gtcgagatcg ttggcaagcg catccgcacc aaggaggacg gcagcaagac 180
catcaaggtt gttcttgacg agaaggagcg cggtggtgtt gaccacagac tcgatgccta 240
cggcgaggtc taccgcagac tgaccggccg tgccgttgtc ttcgagttcc cccagag 297

<210> SEQ ID NO 373
<211> LENGTH: 297
<212> TYPE: RNA
<213> ORGANISM: Aspergillus glaucus

<400> SEQUENCE: 373
cgcucagcgc cgcauccucu cccgccccaa gcgcuccguc aacucgcgca ccaaccagac 60
ccagaagcgu ccccguuccc gcacucugac cgcuguccac gacuccaucc ucaccgaccu 120
cgucuacccc gucgagaucg uuggcaagcg cauccgcacc aaggaggacg gcagcaagac 180
caucaagguu guucuugacg agaaggagcg cgguggu guu gaccacagac ucgaugccua 240
cggcgagguc uaccgcagac ugaccggccg ugccguuguc uucgaguucc cccagag 297

<210> SEQ ID NO 374
<211> LENGTH: 297
<212> TYPE: DNA
<213> ORGANISM: Aspergillus glaucus

<400> SEQUENCE: 374
cgctcagcgc cgcatcctct cccgccccaa gcgctccgtc aactcgcgca ccaaccagac 60
ccagaagcgt ccccgttccc gcactctgac tgctgtccac gastccatcc tcaccgacct 120
cgtctacccc gtcgagatcg ttggcaagcg tatccgcacc aaggaggacg gcagcaagac 180
catcaaggtt gttctcgacg agaaggagcg cggtggtgtt gaccacagac tcgatgccta 240
cggcgaggtc taccgcagac tgaccggccg tgccgttgtc ttcgagttcc cccagag 297

<210> SEQ ID NO 375
<211> LENGTH: 297
<212> TYPE: RNA
<213> ORGANISM: Aspergillus glaucus

<400> SEQUENCE: 375
cgcucagcgc cgcauccucu cccgccccaa gcgcuccguc aacucgcgca ccaaccagac 60
ccagaagcgu ccccguuccc gcacucugac ugcuguccac gasuccaucc ucaccgaccu 120
cgucuacccc gucgagaucg uuggcaagcg uauccgcacc aaggaggacg gcagcaagac 180
caucaagguu guucucgacg agaaggagcg cgguggaguuu gaccacagac ucgaugccua 240
cggcgagguc uaccgcagac ugaccggccg ugccguuguc uucgaguucc cccagag 297

<210> SEQ ID NO 376
<211> LENGTH: 300
<212> TYPE: DNA
<213> ORGANISM: Aspergillus niger

<400> SEQUENCE: 376
cgttgctcag cgccgcatcc tgccccgccc caagcgctcc gccagctctc gttccaacca 60
gaagcagaag cgtccccgtt cccgcactct gactgctgtc cacgacgcca tcctcaccga 120
cctcgtctac cccgtcgaga tcgtcggcaa gcgtacccgc accaaggagg acggctccaa 180
gaccctcaag gtcatcctgg acgagaagga gcgtggtggt gttgaccacc gccttgatgc 240
ctacggcgag gtctaccgtc ggttgactgg ccgtgctgtt gtctttgaat tcccccaggg 300

<210> SEQ ID NO 377
<211> LENGTH: 300
<212> TYPE: RNA
<213> ORGANISM: Aspergillus niger

<400> SEQUENCE: 377
cguugcucag cgccgcaucc ugccccgccc caagcgcucc gccagcucuc guuccaacca 60
gaagcagaag cguccccguu cccgcacucu gacugcuguc cacgacgcca uccucaccga 120
ccucgucuac cccgucgaga ucgucggcaa gcguacccgc accaaggagg acggcuccaa 180
gacccucaag gucauccugg acgagaagga gcguggaguggu guugaccacc gccuugaugc 240
cuacggcgag gucuaccguc gguugacugg ccgugcuguu gucuuugaau ucccccaggg 300

<210> SEQ ID NO 378
<211> LENGTH: 27
<212> TYPE: DNA
<213> ORGANISM: Artificial Squence
<220> FEATURE:
<223> OTHER INFORMATION: Chemically Synthesized (Alb1)

<400> SEQUENCE: 378
attgtctacg atgttaaagg taaattc 27

<210> SEQ ID NO 379
<211> LENGTH: 27
<212> TYPE: DNA
<213> ORGANISM: Artificial Sequence
<220> FEATURE:
<223> OTHER INFORMATION: Chemically Synthesized (Alb1)

<400> SEQUENCE: 379
gaatttacct ttaacatcgt agacaat 27

<210> SEQ ID NO 380
<211> LENGTH: 25
<212> TYPE: DNA
<213> ORGANISM: Artificial Sequence
<220> FEATURE:
<223> OTHER INFORMATION: Chemically Synthesized (Alb2)

<400> SEQUENCE: 380
agaatttctg ctgaagaagc tgcct 25

<210> SEQ ID NO 381
<211> LENGTH: 25
<212> TYPE: DNA
<213> ORGANISM: Artificial Sequence
<220> FEATURE:
<223> OTHER INFORMATION: Chemically Synthesized (Alb2)

<400> SEQUENCE: 381
aggcagcttc ttcagcagaa attct 25

<210> SEQ ID NO 382
<211> LENGTH: 29
<212> TYPE: DNA
<213> ORGANISM: Artificial Sequence
<220> FEATURE:
<223> OTHER INFORMATION: Chemically Synthesized (Alb3a)

<400> SEQUENCE: 382
tcagattagt ctacgatgtt aaaggtaaa 29

<210> SEQ ID NO 383
<211> LENGTH: 29
<212> TYPE: DNA
<213> ORGANISM: Artificial Sequence
<220> FEATURE:
<223> OTHER INFORMATION: Chemically Synthesized (Alb3a)

<400> SEQUENCE: 383
tttaccttta acatcgtaga ctaatctga 29

<210> SEQ ID NO 384
<211> LENGTH: 32
<212> TYPE: DNA
<213> ORGANISM: Artificial Sequence
<220> FEATURE:
<223> OTHER INFORMATION: Chemically Synthesized (Alb3)

<400> SEQUENCE: 384
tcagattagt ctacgatgtt aaaggtaaat tc 32

<210> SEQ ID NO 385
<211> LENGTH: 32
<212> TYPE: DNA
<213> ORGANISM: Artificial Sequence
<220> FEATURE:
<223> OTHER INFORMATION: Chemically Synthesized (Alb3)

<400> SEQUENCE: 385
gaatttacct ttaacatcgt agactaatct ga 32

<210> SEQ ID NO 386
<211> LENGTH: 25
<212> TYPE: DNA
<213> ORGANISM: Artificial Sequence
<220> FEATURE:
<223> OTHER INFORMATION: Chemically Synthesized (kru2)

<400> SEQUENCE: 386
agctgcatac aagttatgta aggtc 25

<210> SEQ ID NO 387
<211> LENGTH: 25
<212> TYPE: DNA
<213> ORGANISM: Artificial Sequence
<220> FEATURE:
<223> OTHER INFORMATION: Chemically Synthesized (kru2)

<400> SEQUENCE: 387
gaccttacat aacttgtatg cagct 25

<210> SEQ ID NO 388
<211> LENGTH: 21
<212> TYPE: DNA
<213> ORGANISM: Artificial Sequence
<220> FEATURE:
<223> OTHER INFORMATION: Chemically Synthesized (kru1)

<400> SEQUENCE: 388
tcaccccaga agaagctgca t 21

<210> SEQ ID NO 389
<211> LENGTH: 21
<212> TYPE: DNA
<213> ORGANISM: Artificial Sequence
<220> FEATURE:
<223> OTHER INFORMATION: Chemically Synthesized (kru1)

<400> SEQUENCE: 389
atgcagcttc ttctggggtg a 21

<210> SEQ ID NO 390
<211> LENGTH: 20
<212> TYPE: DNA
<213> ORGANISM: Artificial Sequence
<220> FEATURE:
<223> OTHER INFORMATION: Chemically Synthesized (parap1)

<400> SEQUENCE: 390
aaagtagatt tgcttgccac 20

<210> SEQ ID NO 391
<211> LENGTH: 20
<212> TYPE: DNA
<213> ORGANISM: Artificial Sequence
<220> FEATURE:
<223> OTHER INFORMATION: Chemically Synthesized (parap1)

<400> SEQUENCE: 391
gtggcaagca aatctacttt 20

<210> SEQ ID NO 392
<211> LENGTH: 22
<212> TYPE: DNA
<213> ORGANISM: Artificial Sequence
<220> FEATURE:
<223> OTHER INFORMATION: Chemically Synthesized (parap2)

<400> SEQUENCE: 392
aagggaatcc catacgttgt ca 22

<210> SEQ ID NO 393
<211> LENGTH: 22
<212> TYPE: DNA
<213> ORGANISM: Artificial Sequence
<220> FEATURE:
<223> OTHER INFORMATION: Chemically Synthesized (parap2)

<400> SEQUENCE: 393
tgacaacgta tgggattccc tt 22

<210> SEQ ID NO 394
<211> LENGTH: 27
<212> TYPE: DNA
<213> ORGANISM: Artificial Sequence
<220> FEATURE:
<223> OTHER INFORMATION: Chemically Synthesized (Trop1)

<400> SEQUENCE: 394
taccaacgaa cacttcagat tgattta 27

<210> SEQ ID NO 395
<211> LENGTH: 27
<212> TYPE: DNA
<213> ORGANISM: Artificial Sequence
<220> FEATURE:
<223> OTHER INFORMATION: Chemically Synthesized (Trop1)

<400> SEQUENCE: 395
taaatcaatc tgaagtgttc gttggta 27

<210> SEQ ID NO 396
<211> LENGTH: 24
<212> TYPE: DNA
<213> ORGANISM: Artificial Sequence
<220> FEATURE:
<223> OTHER INFORMATION: Chemically Synthesized (Trop2)

<400> SEQUENCE: 396
ttctgctgaa gaagcttctt acaa 24

<210> SEQ ID NO 397
<211> LENGTH: 24
<212> TYPE: DNA
<213> ORGANISM: Artificial Sequence
<220> FEATURE:
<223> OTHER INFORMATION: Chemically Synthesized (Trop2)

<400> SEQUENCE: 397
ttgtaagaag cttcttcagc agaa 24

<210> SEQ ID NO 398
<211> LENGTH: 31
<212> TYPE: DNA
<213> ORGANISM: Artificial Sequence
<220> FEATURE:
<223> OTHER INFORMATION: Chemically Synthesized (Trop3)

<400> SEQUENCE: 398
acagaatttc tgctgaagaa gcttcttaca a 31

<210> SEQ ID NO 399
<211> LENGTH: 31
<212> TYPE: DNA
<213> ORGANISM: Artificial Sequence
<220> FEATURE:
<223> OTHER INFORMATION: Chemically Synthesized (Trop3)

<400> SEQUENCE: 399
ttgtaagaag cttcttcagc agaaattctg t 31

<210> SEQ ID NO 400
<211> LENGTH: 30
<212> TYPE: DNA
<213> ORGANISM: Artificial Sequence
<220> FEATURE:
<223> OTHER INFORMATION: Chemically Synthesized (Trop4)

<400> SEQUENCE: 400
cgaacacttc agattgattt acgatgttaa 30

<210> SEQ ID NO 401
<211> LENGTH: 31
<212> TYPE: DNA
<213> ORGANISM: Artificial Sequence
<220> FEATURE:
<223> OTHER INFORMATION: Chemically Synthesized (Trop4)

<400> SEQUENCE: 401
tttaacatcg taaatcaatc tgaagtgttc g 31

<210> SEQ ID NO 402
<211> LENGTH: 31
<212> TYPE: DNA
<213> ORGANISM: Artificial Sequence
<220> FEATURE:
<223> OTHER INFORMATION: Chemically Synthesized (Trop6)

<400> SEQUENCE: 402
tttaacatcg taaatgaatc tgaagtgttc g 31

<210> SEQ ID NO 403
<211> LENGTH: 31
<212> TYPE: DNA
<213> ORGANISM: Artificial Sequence
<220> FEATURE:
<223> OTHER INFORMATION: Chemically Synthesized (Trop6)

<400> SEQUENCE: 403
cgaacacttc agattcattt acgatgttaa a 31

<210> SEQ ID NO 404
<211> LENGTH: 41
<212> TYPE: DNA
<213> ORGANISM: Artificial Sequence
<220> FEATURE:
<223> OTHER INFORMATION: Chemically Synthesized (Trop9)

<400> SEQUENCE: 404
ttacctttaa catcgtaaat gaatctgaag tgttcgttgg t 41

<210> SEQ ID NO 405
<211> LENGTH: 41
<212> TYPE: DNA
<213> ORGANISM: Artificial Sequence
<220> FEATURE:
<223> OTHER INFORMATION: Chemically Synthesized (Trop9)

<400> SEQUENCE: 405
accaacgaac acttcagatt catttacgat gttaaaggta a 41

<210> SEQ ID NO 406

<211> LENGTH: 21
<212> TYPE: DNA
<213> ORGANISM: Artificial Sequence
<220> FEATURE:
<223> OTHER INFORMATION: Chemically Synthesized (Glab1)

<400> SEQUENCE: 406
tatcactgac gaagaagctt c 21

<210> SEQ ID NO 407
<211> LENGTH: 21
<212> TYPE: DNA
<213> ORGANISM: Artificial Sequence
<220> FEATURE:
<223> OTHER INFORMATION: Chemically Synthesized (Glab1)

<400> SEQUENCE: 407
gaagcttctt cgtcagtgat a 21

<210> SEQ ID NO 408
<211> LENGTH: 26
<212> TYPE: DNA
<213> ORGANISM: Artificial Sequence
<220> FEATURE:
<223> OTHER INFORMATION: Chemically Synthesized (Glab2)

<400> SEQUENCE: 408
ttgggtaagg tcaagaaggt ccaatt 26

<210> SEQ ID NO 409
<211> LENGTH: 26
<212> TYPE: DNA
<213> ORGANISM: Artificial Sequence
<220> FEATURE:
<223> OTHER INFORMATION: Chemically Synthesized (Glab2)

<400> SEQUENCE: 409
aattggacct tcttgacctt acccaa 26

<210> SEQ ID NO 410
<211> LENGTH: 27
<212> TYPE: DNA
<213> ORGANISM: Artificial Sequence
<220> FEATURE:
<223> OTHER INFORMATION: Chemically Synthesized (Glab3)

<400> SEQUENCE: 410
tatcactgac gaagaagctt cctacaa 27

<210> SEQ ID NO 411
<211> LENGTH: 27
<212> TYPE: DNA
<213> ORGANISM: Artificial Sequence
<220> FEATURE:
<223> OTHER INFORMATION: Chemically Synthesized (Glab3)

<400> SEQUENCE: 411
ttgtaggaag cttcttcgtc agtgata 27

<210> SEQ ID NO 412
<211> LENGTH: 22
<212> TYPE: DNA
<213> ORGANISM: Artificial Sequence
<220> FEATURE:
<223> OTHER INFORMATION: Chemically Synthesized (Glab5)

<400> SEQUENCE: 412
atacgttgtc actgacgatg gt 22

<210> SEQ ID NO 413
<211> LENGTH: 22
<212> TYPE: DNA
<213> ORGANISM: Artificial Sequence
<220> FEATURE:
<223> OTHER INFORMATION: Chemically Synthesized (Glab5)

<400> SEQUENCE: 413
accatcgtca gtgacaacgt at 22

<210> SEQ ID NO 414
<211> LENGTH: 17
<212> TYPE: DNA
<213> ORGANISM: Artificial Sequence
<220> FEATURE:
<223> OTHER INFORMATION: Chemically Synthesized (MycoSEQ AF1F)

<400> SEQUENCE: 414
gaccgccacg tcctctt 17

<210> SEQ ID NO 415
<211> LENGTH: 17
<212> TYPE: DNA
<213> ORGANISM: Artificial Sequence
<220> FEATURE:
<223> OTHER INFORMATION: Chemically Synthesized (MycoSEQ AF1R)

<400> SEQUENCE: 415
ctctggggga actcgaa 17

<210> SEQ ID NO 416
<211> LENGTH: 17
<212> TYPE: DNA
<213> ORGANISM: Artificial Sequence
<220> FEATURE:
<223> OTHER INFORMATION: Chemically Synthesized (MycoSEQ NIG1R)

<400> SEQUENCE: 416
ccctggggga attcaaa 17

<210> SEQ ID NO 417
<211> LENGTH: 17
<212> TYPE: DNA
<213> ORGANISM: Artificial Sequence
<220> FEATURE:
<223> OTHER INFORMATION: Chemically Synthesized (MycoSEQ NIG1F)

<400> SEQUENCE: 417
gaccgccacg ttctctt 17

<210> SEQ ID NO 418
<211> LENGTH: 18
<212> TYPE: DNA
<213> ORGANISM: Artificial Sequence
<220> FEATURE:
<223> OTHER INFORMATION: Chemically Synthesized (AF6 FOW)

<400> SEQUENCE: 418
agcaagactc tcaaggtc 18

<210> SEQ ID NO 419
<211> LENGTH: 20
<212> TYPE: DNA

<213> ORGANISM: Artificial Sequence
<220> FEATURE:
<223> OTHER INFORMATION: Chemically Synthesized (ASP2)

<400> SEQUENCE: 419
aggtttaccg ccgactaacc 20

<210> SEQ ID NO 420
<211> LENGTH: 20
<212> TYPE: DNA
<213> ORGANISM: Artificial Sequence
<220> FEATURE:
<223> OTHER INFORMATION: Chemically Synthesized (ASP2)

<400> SEQUENCE: 420
ggttagtcgg cggtaaacct 20

<210> SEQ ID NO 421
<211> LENGTH: 23
<212> TYPE: DNA
<213> ORGANISM: Artificial Sequence
<220> FEATURE:
<223> OTHER INFORMATION: Chemically Synthesized (AFUM1)

<400> SEQUENCE: 421
cgctgtccac gacgccatcc tca 23

<210> SEQ ID NO 422
<211> LENGTH: 23
<212> TYPE: DNA
<213> ORGANISM: Artificial Sequence
<220> FEATURE:
<223> OTHER INFORMATION: Chemically Synthesized (AFUM1)

<400> SEQUENCE: 422
tgaggatggc gtcgtggaca gcg 23

<210> SEQ ID NO 423
<211> LENGTH: 20
<212> TYPE: DNA
<213> ORGANISM: Artificial Sequence
<220> FEATURE:
<223> OTHER INFORMATION: Chemically Synthesized (AFUM2)

<400> SEQUENCE: 423
ccgactaacc ggccgctctg 20

<210> SEQ ID NO 424
<211> LENGTH: 20
<212> TYPE: DNA
<213> ORGANISM: Artificial Sequence
<220> FEATURE:
<223> OTHER INFORMATION: Chemically Synthesized (AFUM2)

<400> SEQUENCE: 424
cagagcggcc ggttagtcgg 20

<210> SEQ ID NO 425
<211> LENGTH: 24
<212> TYPE: DNA
<213> ORGANISM: Artificial Sequence
<220> FEATURE:
<223> OTHER INFORMATION: Chemically Synthesized (ACAN1)

<400> SEQUENCE: 425
cgtgcacgac aacatcctga ccga 24

<210> SEQ ID NO 426
<211> LENGTH: 24
<212> TYPE: DNA
<213> ORGANISM: Artificial Sequence
<220> FEATURE:
<223> OTHER INFORMATION: Chemically Synthesized (ACAN1)

<400> SEQUENCE: 426
tcggtcagga tgttgtcgtg cacg 24

<210> SEQ ID NO 427
<211> LENGTH: 25
<212> TYPE: DNA
<213> ORGANISM: Artificial Sequence
<220> FEATURE:
<223> OTHER INFORMATION: Chemically Synthesized (ACAN2)

<400> SEQUENCE: 427
cggcggcgtt gaccaccgcc tggac 25

<210> SEQ ID NO 428
<211> LENGTH: 25
<212> TYPE: DNA
<213> ORGANISM: Artificial Sequence
<220> FEATURE:
<223> OTHER INFORMATION: Chemically Synthesized (ACAN2)

<400> SEQUENCE: 428
gtccaggcgg tggtcaacgc cgccg 25

<210> SEQ ID NO 429
<211> LENGTH: 22
<212> TYPE: DNA
<213> ORGANISM: Artificial Sequence
<220> FEATURE:
<223> OTHER INFORMATION: Chemically Synthesized (ATERR1)

<400> SEQUENCE: 429
cggcggtgtc gaccaccgcc tc 22

<210> SEQ ID NO 430
<211> LENGTH: 22
<212> TYPE: DNA
<213> ORGANISM: Artificial Sequence
<220> FEATURE:
<223> OTHER INFORMATION: Chemically Synthesized (ATERR1)

<400> SEQUENCE: 430
gaggcggtgg tcgacaccgc cg 22

<210> SEQ ID NO 431
<211> LENGTH: 24
<212> TYPE: DNA
<213> ORGANISM: Artificial Sequence
<220> FEATURE:
<223> OTHER INFORMATION: Chemically Synthesized (ATERR2)

<400> SEQUENCE: 431
cgtctcaccg gccgtgccgt cgtc 24

<210> SEQ ID NO 432
<211> LENGTH: 24
<212> TYPE: DNA
<213> ORGANISM: Artificial Sequence
<220> FEATURE:

-continued

<223> OTHER INFORMATION: Chemically Synthesized (ATERR2)

<400> SEQUENCE: 432
gacgacggca cggccggtga gacg 24

<210> SEQ ID NO 433
<211> LENGTH: 25
<212> TYPE: DNA
<213> ORGANISM: Artificial Sequence
<220> FEATURE:
<223> OTHER INFORMATION: Chemically Synthesized (AVER1)

<400> SEQUENCE: 433
cttgacgacc tcgtctaccc cgttg 25

<210> SEQ ID NO 434
<211> LENGTH: 25
<212> TYPE: DNA
<213> ORGANISM: Artificial Sequence
<220> FEATURE:
<223> OTHER INFORMATION: Chemically Synthesized (AVER1)

<400> SEQUENCE: 434
caacggggta gacgaggtcg tcaag 25

<210> SEQ ID NO 435
<211> LENGTH: 29
<212> TYPE: DNA
<213> ORGANISM: Artificial Sequence
<220> FEATURE:
<223> OTHER INFORMATION: Chemically Synthesized (AVER2)

<400> SEQUENCE: 435
ctaccgtcgt ttgaccggtc gtgctgttg 29

<210> SEQ ID NO 436
<211> LENGTH: 29
<212> TYPE: DNA
<213> ORGANISM: Artificial Sequence
<220> FEATURE:
<223> OTHER INFORMATION: Chemically Synthesized (AVER2)

<400> SEQUENCE: 436
caacagcacg accggtcaaa cgacggtag 29

<210> SEQ ID NO 437
<211> LENGTH: 25
<212> TYPE: DNA
<213> ORGANISM: Artificial Sequence
<220> FEATURE:
<223> OTHER INFORMATION: Chemically Synthesized (ANID1)

<400> SEQUENCE: 437
gtaccctcac tgctgttcac gatgc 25

<210> SEQ ID NO 438
<211> LENGTH: 25
<212> TYPE: DNA
<213> ORGANISM: Artificial Sequence
<220> FEATURE:
<223> OTHER INFORMATION: Chemically Synthesized (ANID1)

<400> SEQUENCE: 438
gcatcgtgaa cagcagtgag ggtac 25

-continued

<210> SEQ ID NO 439
<211> LENGTH: 23
<212> TYPE: DNA
<213> ORGANISM: Artificial Sequence
<220> FEATURE:
<223> OTHER INFORMATION: Chemically Synthesized (ANID2)

<400> SEQUENCE: 439
gtcgtctgac gggtcgtgct gtc 23

<210> SEQ ID NO 440
<211> LENGTH: 23
<212> TYPE: DNA
<213> ORGANISM: Artificial Sequence
<220> FEATURE:
<223> OTHER INFORMATION: Chemically Synthesized (ANID2)

<400> SEQUENCE: 440
gacagcacga cccgtcagac gac 23

<210> SEQ ID NO 441
<211> LENGTH: 26
<212> TYPE: DNA
<213> ORGANISM: Artificial Sequence
<220> FEATURE:
<223> OTHER INFORMATION: Chemically Synthesized (AFLAV1)

<400> SEQUENCE: 441
gccgtttgac cggccgcaac gtcgtc 26

<210> SEQ ID NO 442
<211> LENGTH: 26
<212> TYPE: DNA
<213> ORGANISM: Artificial Sequence
<220> FEATURE:
<223> OTHER INFORMATION: Chemically Synthesized (AFLAV1)

<400> SEQUENCE: 442
gacgacgttg cggccggtca aacggc 26

<210> SEQ ID NO 443
<211> LENGTH: 21
<212> TYPE: DNA
<213> ORGANISM: Artificial Sequence
<220> FEATURE:
<223> OTHER INFORMATION: Chemically Synthesized (ACLAV1)

<400> SEQUENCE: 443
cgagatcgtc ggcaagcgca c 21

<210> SEQ ID NO 444
<211> LENGTH: 21
<212> TYPE: DNA
<213> ORGANISM: Artificial Sequence
<220> FEATURE:
<223> OTHER INFORMATION: Chemically Synthesized (ACLAV1)

<400> SEQUENCE: 444
gtgcgcttgc cgacgatctc g 21

<210> SEQ ID NO 445
<211> LENGTH: 22
<212> TYPE: DNA
<213> ORGANISM: Artificial Sequence
<220> FEATURE:
<223> OTHER INFORMATION: Chemically Synthesized (ACLAV2)

<400> SEQUENCE: 445
cggccgctcc gttgtcttcg ag 22

<210> SEQ ID NO 446
<211> LENGTH: 22
<212> TYPE: DNA
<213> ORGANISM: Artificial Sequence
<220> FEATURE:
<223> OTHER INFORMATION: Chemically Synthesized (ACLAV2)

<400> SEQUENCE: 446
ctcgaagaca acggagcggc cg 22

<210> SEQ ID NO 447
<211> LENGTH: 27
<212> TYPE: DNA
<213> ORGANISM: Artificial Sequence
<220> FEATURE:
<223> OTHER INFORMATION: Chemically Synthesized (CLAV3)

<400> SEQUENCE: 447
cgccgtttaa ccggccgctc cgttgtc 27

<210> SEQ ID NO 448
<211> LENGTH: 27
<212> TYPE: DNA
<213> ORGANISM: Artificial Sequence
<220> FEATURE:
<223> OTHER INFORMATION: Chemically Synthesized (ACLAV3)

<400> SEQUENCE: 448
gacaacggag cggccggtta aacggcg 27

<210> SEQ ID NO 449
<211> LENGTH: 185
<212> TYPE: DNA
<213> ORGANISM: Saccharomyces cerevisiae

<400> SEQUENCE: 449
catcactcta gatgccacca atgaaaactt cagattggtc tacgatgtca agggtagatt 60
cgctgtccac cgtatcaccg atgaagaagc ytcttacaar ttgggtaagg tcaagaaggt 120
ycaattaggt aagaagggtg ttccatacgt tgttacccac gatggtagaa ctatcagata 180
cccag 185

<210> SEQ ID NO 450
<211> LENGTH: 185
<212> TYPE: RNA
<213> ORGANISM: Saccharomyces cerevisiae

<400> SEQUENCE: 450
caucacucua gaugccacca augaaaacuu cagauugguc uacgauguca aggguagauu 60
cgcuguccac cguaucaccg augaagaagc yucuuacaar uuggguaagg ucaagaaggu 120
ycaauuaggu aagaagggug uuccauacgu uguuacccac gaugguagaa cuaucagaua 180
cccag 185

<210> SEQ ID NO 451
<211> LENGTH: 150
<212> TYPE: DNA
<213> ORGANISM: Candida neoformans

<400> SEQUENCE: 451

```
ggtgtacgat gtcaagggta gattcacyst scacagaatc accgcygagg agkctwccta     60

caagytsgsy aagrtcarga agrtcsmktt gggyaagagr rgtrtyccmt acgyygtcas    120

ccacgacggt agaactatca gatacccaga                                     150


<210> SEQ ID NO 452
<211> LENGTH: 150
<212> TYPE: RNA
<213> ORGANISM: Candida neoformans

<400> SEQUENCE: 452

gguguacgau gucaagggua gauucacysu scacagaauc accgcygagg agkcuwccua     60

caagyusgsy aagrucarga agrucsmkuu gggyaagagr rguruyccmu acgyygucas    120

ccacgacggu agaacuauca gauacccaga                                     150


<210> SEQ ID NO 453
<211> LENGTH: 300
<212> TYPE: DNA
<213> ORGANISM: Aspergillus fischeri

<400> SEQUENCE: 453

cgtcgctcag cgccgcatcc tgccccgccc caagcgctcc gtcaactccc gcaccaacca     60

gaagcagaag cgtcctcgct ctcgcaccct gaccgccgtc cacgacgcca tcctcaacga    120

cctcgtttac cccgtcgaga tcgtcggcaa gcgtacccgc accaaggaag acggcagcaa    180

gactctcaag gtcatcctcg acgagaagga gcgtggcggt gttgaccaca gactcgatgc    240

ctacggcgag gtctaccgcc gactgaccgg ccgctctgtt gtcttcgagt tcccccagag    300


<210> SEQ ID NO 454
<211> LENGTH: 300
<212> TYPE: RNA
<213> ORGANISM: Aspergillus fischeri

<400> SEQUENCE: 454

cgucgcucag cgccgcaucc ugccccgccc caagcgcucc gucaacuccc gcaccaacca     60

gaagcagaag cguccucgcu cucgcacccu gaccgccguc cacgacgcca uccucaacga    120

ccucguuuac cccgucgaga ucgucggcaa gcguacccgc accaaggaag acggcagcaa    180

gacucucaag gucauccucg acgagaagga gcguggcggu guugaccaca gacucgaugc    240

cuacggcgag gucuaccgcc gacugaccgg ccgcucuguu gucuucgagu ucccccagag    300


<210> SEQ ID NO 455
<211> LENGTH: 300
<212> TYPE: DNA
<213> ORGANISM: Aspergillus fischeri

<400> SEQUENCE: 455

cgtcgctcag cgccgcatcc tgccccgccc caagcgctct gtcaactccc gcaccaacca     60

gaagcagaag cgtcctcgct ctcgcaccct gaccgctgtc cacgatgcca tcctcaacga    120

cctcgtttac cccgtcgaga tcgtcggcaa gcgtatccgc accaaggagg acggcagcaa    180

gactctcaag gtcatcctgg acgagaagga gcgtggtggt gttgaccaca gactcgatgc    240

ctacggcgag gtttaccgcc gactaactgg ccgctctgtt gtcttcgagt tcccccagag    300


<210> SEQ ID NO 456
<211> LENGTH: 300
<212> TYPE: RNA
```

-continued

<213> ORGANISM: Aspergillus fischeri

<400> SEQUENCE: 456
cgucgcucag cgccgcaucc ugccccgccc caagcgcucu gucaacuccc gcaccaacca 60
gaagcagaag cguccucgcu cucgcacccu gaccgcuguc cacgaugcca uccucaacga 120
ccucguuuac cccgucgaga ucgucggcaa gcguauccgc accaaggagg acggcagcaa 180
gacucucaag gucauccugg acgagaagga gcgugguggu guugaccaca gacucgaugc 240
cuacggcgag guuuaccgcc gacuaacugg ccgcucuguu gucuucgagu ucccccagag 300

<210> SEQ ID NO 457
<211> LENGTH: 300
<212> TYPE: DNA
<213> ORGANISM: Aspergillus fischeri

<400> SEQUENCE: 457
cgtcgctcag cgccgcatcc tgccccgccc caagcgctct gtcaactccc gcaccaacca 60
gaagcagaag cgtcctcgct ctcgcaccct gaccgctgtc cacgatgcca tcctcaacga 120
cctcgtttac cccgtcgaga tcgtcggcaa gcgtatccgc accaaggagg acggcagcaa 180
gactctcaag gtcatcctgg acgagaagga gcgtggtggt gttgaccaca gactcgatgc 240
ctacggcgag gtttaccgcc gactaactgg ccgctctgtt gtcttcgagt tcccccagag 300

<210> SEQ ID NO 458
<211> LENGTH: 300
<212> TYPE: RNA
<213> ORGANISM: Aspergillus fischeri

<400> SEQUENCE: 458
cgucgcucag cgccgcaucc ugccccgccc caagcgcucu gucaacuccc gcaccaacca 60
gaagcagaag cguccucgcu cucgcacccu gaccgcuguc cacgaugcca uccucaacga 120
ccucguuuac cccgucgaga ucgucggcaa gcguauccgc accaaggagg acggcagcaa 180
gacucucaag gucauccugg acgagaagga gcgugguggu guugaccaca gacucgaugc 240
cuacggcgag guuuaccgcc gacuaacugg ccgcucuguu gucuucgagu ucccccagag 300

<210> SEQ ID NO 459
<211> LENGTH: 297
<212> TYPE: DNA
<213> ORGANISM: Neosartorya fischeri

<400> SEQUENCE: 459
cgctcagcgc cgcatcctgc cccgccccaa gcgctccgtc aactcccgca ccaaccagaa 60
gcagaagcgc cctcgctccc gcaccctgac cgctgtccac gacgccatcc tcaacgacct 120
cgtttacccc gtcgagatcg tcggcaagcg tatccgcacc aaggaggacg gcagcaagac 180
tctcaaggtc atcctggacg agaaggagcg tggcggtgtt gaccacagac tcgatgccta 240
cggcgaggtt taccgccgac taaccggccg ctctgttgtc ttcgagttcc cccagag 297

<210> SEQ ID NO 460
<211> LENGTH: 297
<212> TYPE: RNA
<213> ORGANISM: Neosartorya fischeri

<400> SEQUENCE: 460
cgcucagcgc cgcauccugc cccgccccaa gcgcuccguc aacucccgca ccaaccagaa 60
gcagaagcgc ccucgcuccc gcacccugac cgcuguccac gacgccaucc ucaacgaccu 120
cguuuacccc gucgagaucg ucggcaagcg uauccgcacc aaggaggacg gcagcaagac 180
ucucaagguc auccuggacg agaaggagcg uggcgguguu gaccacagac ucgaugccua 240
cggcgagguu uaccgccgac uaaccggccg cucuguuguc uucgaguucc cccagag 297

<210> SEQ ID NO 461
<211> LENGTH: 297
<212> TYPE: DNA
<213> ORGANISM: Neosartorya fischeri

<400> SEQUENCE: 461
tgctcagcgc cgcatcctgc cccgccccaa gcgctctgtc aactcccgca ccaaccagaa 60
gcagaagcgc cctcgctctc gcaccctgac cgctgtccac gacgccatcc tcaccgacct 120
cgtttacccc gtcgagatcg tcggcaagcg tatccgcacc aaggaggacg gcagcaagac 180
tctcaaggtc atcctggacg agaaggagcg tggcggtgtt gaccacagac tcgatgccta 240
cggcgaggtc taccgccgac taaccggccg ctctgttgtc ttcgagttcc cccagag 297

<210> SEQ ID NO 462
<211> LENGTH: 297
<212> TYPE: RNA
<213> ORGANISM: Neosartorya fischeri

<400> SEQUENCE: 462
ugcucagcgc cgcauccugc cccgccccaa gcgcucuguc aacucccgca ccaaccagaa 60
gcagaagcgc ccucgcucuc gcacccugac cgcuguccac gacgccaucc ucaccgaccu 120
cguuuacccc gucgagaucg ucggcaagcg uauccgcacc aaggaggacg gcagcaagac 180
ucucaagguc auccuggacg agaaggagcg uggcgguguu gaccacagac ucgaugccua 240
cggcgagguc uaccgccgac uaaccggccg cucuguuguc uucgaguucc cccagag 297

<210> SEQ ID NO 463
<211> LENGTH: 297
<212> TYPE: DNA
<213> ORGANISM: Neosartorya fischeri

<400> SEQUENCE: 463
tgctcagcgc cgcatcctgc cacgccccaa gcgctctgtc aactcccgca ccaaccagaa 60
gcagaagcgc cctcgctctc gcaccctgac cgccgtccac gacgccatcc tcgacgacct 120
cgtttacccc gtcgagatcg tcggcaagcg tatccgcacc aaggaggacg gcagcaagac 180
tctcaaggtc atcctggacg agaaggagcg tggcggtgtt gaccacagac tcgatgccta 240
cggcgaggtc taccgccgac taaccggccg tgctgttgtc ttcgagttcc cccagag 297

<210> SEQ ID NO 464
<211> LENGTH: 297
<212> TYPE: RNA
<213> ORGANISM: Neosartorya fischeri

<400> SEQUENCE: 464
ugcucagcgc cgcauccugc cacgccccaa gcgcucuguc aacucccgca ccaaccagaa 60
gcagaagcgc ccucgcucuc gcacccugac cgccguccac gacgccaucc ucgacgaccu 120
cguuuacccc gucgagaucg ucggcaagcg uauccgcacc aaggaggacg gcagcaagac 180
ucucaagguc auccuggacg agaaggagcg uggcgguguu gaccacagac ucgaugccua 240
cggcgagguc uaccgccgac uaaccggccg ugcuguuguc uucgaguucc cccagag 297

-continued

```
<210> SEQ ID NO 465
<211> LENGTH: 297
<212> TYPE: DNA
<213> ORGANISM: Neosartorya fischeri

<400> SEQUENCE: 465

tgctcagcgc cgcatcctgc cacgccccaa gcgctctgtc aactcccgca ccaaccagaa     60

gcagaagcgc cctcgctctc gcaccctgac cgccgtccac gacgccatcc tcgacgacct    120

cgtttacccc gtcgagatcg tcggcaagcg tatccgcacc aaggaggacg gcagcaagac    180

tctcaaggtc atcctggacg agaaggagcg tggcggtgtt gaccacagac tcgatgccta    240

cggcgaggtc taccgccgac taaccggccg tgctgttgtc ttcgagttcc cccagag       297


<210> SEQ ID NO 466
<211> LENGTH: 297
<212> TYPE: RNA
<213> ORGANISM: Neosartorya fischeri

<400> SEQUENCE: 466

ugcucagcgc cgcauccugc cacgccccaa gcgcucuguc aacucccgca ccaaccagaa     60

gcagaagcgc ccucgcucuc gcacccugac cgccguccac gacgccaucc ucgacgaccu    120

cguuuacccc gucgagaucg ucggcaagcg uauccgcacc aaggaggacg gcagcaagac    180

ucucaagguc auccuggacg agaaggagcg uggcgguguu gaccacagac ucgaugccua    240

cggcgagguc uaccgccgac uaaccggccg ugcuguuguc uucgaguucc cccagag       297
```